United States Patent
Gordon et al.

(10) Patent No.: US 11,180,500 B2
(45) Date of Patent: Nov. 23, 2021

(54) DERIVATIVES OF RELEBACTAM AND USES THEREOF

(71) Applicant: ARIXA PHARMACEUTICALS, INC., Palo Alto, CA (US)

(72) Inventors: Eric M. Gordon, Palo Alto, CA (US); Matthew A. J. Duncton, Palo Alto, CA (US); John Freund, Atherton, CA (US)

(73) Assignee: Arixa Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/589,498

(22) Filed: Oct. 1, 2019

(65) Prior Publication Data

US 2020/0102307 A1    Apr. 2, 2020

Related U.S. Application Data

(60) Provisional application No. 62/739,746, filed on Oct. 1, 2018.

(51) Int. Cl.
| | | |
|---|---|---|
| *A61K 31/439* | (2006.01) | |
| *A61P 31/04* | (2006.01) | |
| *C07D 471/08* | (2006.01) | |
| *C07D 401/12* | (2006.01) | |
| *A61K 9/00* | (2006.01) | |

(52) U.S. Cl.
CPC ............ *C07D 471/08* (2013.01); *A61P 31/04* (2018.01); *C07D 401/12* (2013.01); *A61K 9/0053* (2013.01)

(58) Field of Classification Search
CPC ...... A61K 31/439; A61P 31/04; C07D 471/08
See application file for complete search history.

(56) References Cited

U.S. PATENT DOCUMENTS

| | | | |
|---|---|---|---|
| 3,658,849 A | 4/1972 | Leffingwell | |
| 4,522,811 A | 6/1985 | Eppstein et al. | |
| 5,674,533 A | 10/1997 | Santus et al. | |
| 7,112,592 B2 | 9/2006 | Lampilas et al. | |
| 7,994,218 B2 | 8/2011 | Jandeleit et al. | |
| 8,168,617 B2 | 5/2012 | Jandeleit et al. | |
| 8,772,490 B2 | 7/2014 | Abe et al. | |
| 9,035,062 B2 | 5/2015 | Abe et al. | |
| 9,284,273 B2 | 3/2016 | Abe et al. | |
| 9,340,493 B2 | 5/2016 | Brown et al. | |
| 9,393,239 B2 | 7/2016 | Maiti et al. | |
| 10,085,999 B1 | 10/2018 | Gordon et al. | |
| 2009/0099253 A1 | 4/2009 | Li et al. | |
| 2011/0294777 A1 | 12/2011 | Blizzard et al. | |
| 2014/0045943 A1 | 2/2014 | Khan et al. | |
| 2015/0196559 A1 | 7/2015 | Wang et al. | |
| 2015/0225335 A1 | 8/2015 | Takashima et al. | |
| 2017/0165371 A1 | 6/2017 | Goldberg | |
| 2017/0290918 A1 | 10/2017 | Honda et al. | |
| 2017/0296503 A1 | 10/2017 | Eto et al. | |
| 2018/0148448 A1 | 5/2018 | Wu | |

FOREIGN PATENT DOCUMENTS

| | | |
|---|---|---|
| DE | 3045373 | 7/1982 |
| RU | 2445314 | 4/2013 |
| WO | 2007/116922 | 10/2007 |
| WO | 2009/033054 | 3/2009 |
| WO | 2009/033079 | 3/2009 |
| WO | 2009/091856 | 7/2009 |
| WO | 2009/092606 | 7/2009 |
| WO | 2010/126820 | 11/2010 |
| WO | 2011/046771 | 4/2011 |
| WO | 2011/150380 | 12/2011 |
| WO | 2012/086241 | 6/2012 |
| WO | 2012/165648 | 12/2012 |
| WO | 2016/116788 | 7/2016 |
| WO | 2017/045510 | 3/2017 |
| WO | 2018/208557 A1 | 11/2018 |

OTHER PUBLICATIONS

Search Report for Russia Application No. 2019135891, dated Feb. 6, 2020, 2 pages.
International Search Report and Written Opinion for Application No. PCT/US2019/053990, dated Dec. 4, 2019, 14 pages.
Beaudoin et al., "Bioanalytical method validation for the simultaneous determination of ceftazidime and avibactam in rat plasma," Bioanalysis, 2016, vol. 8, No. 2, p. 111-122.
Beaudoin et al., "Preparation of Unsymmetrical Sulfonyureas from N,N-Sulfuryldiimidazoles," the Journal of Organic Chemistry, 2003, vol. 68, No. 1, p. 115-119.
Boyd et al., "NMR spectroscopic studies of intermediary metabolites of cyclophosphamide. 2. Direct observation, characterization, and reactivity studies of iminocyclophosphamide and related species," The Journal of Medicinal Chemistry, 1987, vol. 30, No. 2, p. 366-374.
DeBergh et al., "Synthesis of Aryl Sulfonamides via Palladium-Catalyzed Chlorosulfonylation of Arylboronic Acids," Journal of the American Chemical Society, 2013, vol. 135, No. 29, p. 10638-10641.
Hecker et al., "Discovery of a Cyclic Boronic Acid β-Lactamase Inhibitor (RPX7009) with Utility vs Class A Serine Carbapenemases," Journal of Medicinal Chemistry, 2015, vol. 58, p. 3682-3692.
Illa et al., "Practical and Highly Selective Sulfur Ylide-Mediated Asymmetric Expoxidations and Aziridinations Using a Cheap and Readily Available Chiral Sulfide: Extensive Studies to Map Out Scope, Limitations, and Rationalization of Diastereo- and Enantioselectivities," Journal of the American Chemical Society, 2013, vol. 135, No. 32, p. 11951-11966.

(Continued)

*Primary Examiner* — Brenda L Coleman

(74) *Attorney, Agent, or Firm* — Jason G. Tebbutt

(57) ABSTRACT

Derivatives of relebactam, therapeutic methods of using the derivatives of relebactam, particularly in combination with β-lactam antibiotics and pharmaceutical compositions thereof are disclosed. The derivatives of relebactam are suitable for oral administration.

14 Claims, 1 Drawing Sheet

(56) References Cited

OTHER PUBLICATIONS

King et al., "Structural and Kinetic Characterization of Diazabicyclooctanes as Dual Inhibitors of Both Seratin-B-Lactamase and Penicillin-Binding Proteins," ACS Chemical Biology, 2016, vol. 11, No. 4, p. 864-868.
Oger et al., "Lipase-Catalyzed Regioselective Monoacetylation of Unsymmetrical 1,5-Primary Diols," The Journal of Organic Chemistry, 2010, vol. 75, No. 6, p. 1892-1897.
Levasseur et al., "In vitro antibacterial activity of the ceftazidime-avibactam combination against enterobacteriaceae, including strains with well-characterized β-lactamases," Antimicrobial Agents Chemotherapy, 2015, vol. 59, No. 4, p. 1931-1634.
Livermore et al., "Activity of OP0595/β-lactam combinations against Gram-negative bacteria with extended-spectrum, AmpC and carapenem—hydrolysing β-lactamases," Journal of Antimicrobial Chemotherapy, 2015, vol. 70, Issue 11, p. 3032-3041.
Rusha et al., "Design and application of esterase-labile sulfonate protecting groups," Chemical Communications, 2011, vol. 47, p. 2038-2040.
Shi et al., "The Rhodium-Catalyzed Carbene Cyclization Cycloaddition Cascade Reaction of Vinylsulfonates," Advanced Synthesis and Catalysis, 2009, vol. 351, p. 3128-3132.
Simpson et al., "A Comprehensive Approach to the Synthesis of Sulfate Esters," Journal of the American Chemical Society, 2006, vol. 128, No. 5, p. 1605-1610.
Soengas et al., "Convenient Procedure for the Indium-Mediated Hydroxymethylation of Active Bromo Compounds: Transformation of Ketones into a-Hydroxymethyl Nitroalkanes," Synlett, 2010, vol. 17, p. 2625-2627.
Zasowski et al., "The β-Lactams Strike Back: Ceftazidime-Avibactam," Pharmacotherapy, 2015, vol. 35, Issue 8, p. 755-770.
Zhang et al., "Enhanced Photoresponsive Ultrathin Graphitic-Phase C3N4 Nanosheets for Bioimaging," Journal of the American Chemical Society, 2013, vol. 135, No. 1, p. 18-21.
International Search Report and Written Opinion for Application No. PCT/US2018/030652, dated Aug. 29, 2018, 13 pages.
Caira, M., "Crystalline Polymorphism of Organic Compounds", Topics in Current Chemistry, 1998, vol. 198, p. 163-208.
Gordon et al., "Orally Absorbed Derivatives of the [beta]-Lactamase Inhibitor Avibactam. Design of Novel Prodrugs of Sulfate Containing Drugs." Journal of Medicinal Chemistry, 2018, vol. 61, No. 22, p. 10340-10344.
International Search Report and Written Opinion for Application No. PCT/US2020/021795, dated May 20, 2020, 15 pages.
Abdelraouf et al., "In Vivo Pharmacodynamic Profile of Ceftibuten/Clavulanate Combination against Extended Spectrum Beta-lactamase-Producing Enterobacteriaceae in the Murine Thigh Infection Model", Antimicrobial Agents and Chemotherapy, May 6, 2019, 34 pages.
Grupper et al., "In Vitro Pharmacodynamics of a Novel Ceftibuten-Clavulanate Combination Antibiotic against Enterobacteriaceae", Antimicrobial Agents and Chemotherapy, May 6, 2019, 33 pages.
Merdjan et al., "Safety, Single Dose Pharmacokinetics, and Pharmacodynamics of Beta-Lactamase Inhibitor NXL104 in Healthy Young Male Adults", 47th Interscience Conference on Antimicrobial Agents and Chemotherapy, 2007, 1 page.
Merdjan et al., "Safety and Pharmacokinetics of Single and Multiple Ascending Doses of Avibactam Alone and in Combination with Ceftazidime in Healthy Male Volunteers: Results of Two Randomized, Placebo-Controlled Studies", Clinical Drug Investigation, Mar. 2015, 11 pages.
VanScoy B. D., A. Mullarkey, H. Conde, N. Onufrak, J. Trias, C. Sable, S. M. Bhavnani, P. G. Ambrose. Evaluation of the Pharmacokinetics—Pharmacodynamics of Oral Avibactam in Combination with Ceftibuten Using a One-Compartment in Vitro Infection Model. Abstract T-07, 2019 ASM/ESCMID Conference on Drug Development to Meet the Challenge of Antimicrobial Resistance, Boston, Massachusetts Presented on Thursday Sep. 5, 2019.
Bush et al., "β-Lactams and β-Lactamase Inhibitors: An Overview", Cold Springs Harbor Perspectives in Medicine, 2016, vol. 6, 22 pages.
Haidar et al., "Identifying Spectra of Activity and Therapeutic Niches for Ceftazidime-Avibactam and Imipenem-Relebactam against Carbapenem-Resistant Enterobacteriaceae", Antimicrobial Agents and Chemotherapy, American Society for Microbiology, Sep. 2017, vol. 61, Issue 9, 8 pages.
Qin et al., "β-Lactam Antibiotics Renaissance", Antibiotics, 2014, vol. 3, p. 193-215.
Wong et al., "Novel Beta-lactamase Inhibitors: Unlocking Their Potential in Therapy", Drugs, Apr. 2017, vol. 77, No. 6, p. 615-628.

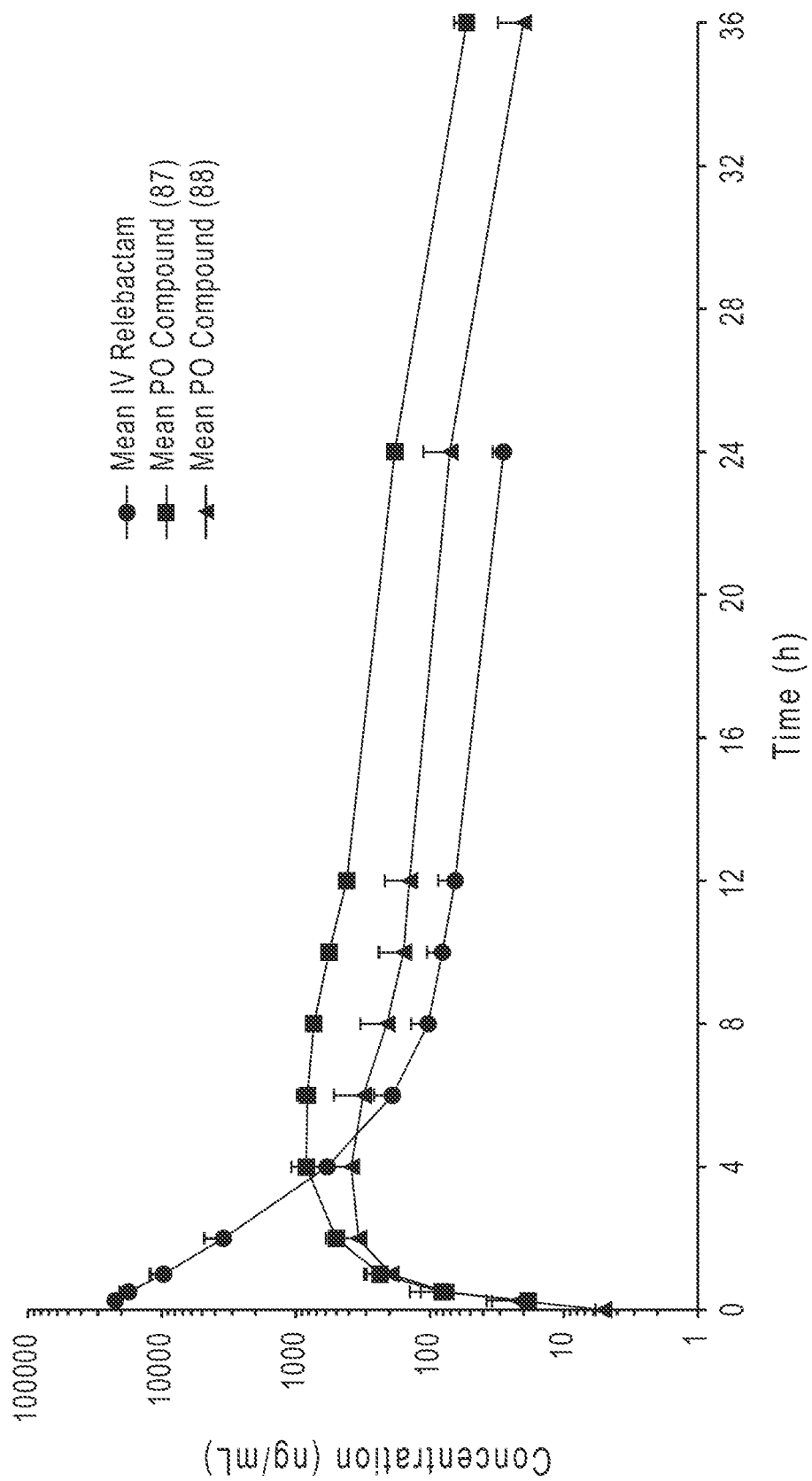

DERIVATIVES OF RELEBACTAM AND USES THEREOF

This application claims the benefit under 35 U.S.C. § 119(e) of U.S. Provisional Application No. 62/739,746 filed on Oct. 1, 2018, which is incorporated by reference in its entirety.

FIELD

The present disclosure relates to derivatives of relebactam, to pharmaceutical compositions thereof, and to the use of the derivatives of relebactam to treat bacterial infections. The compounds can be administered orally to provide relebactam.

BACKGROUND

Overuse, incorrect use, and agricultural use of antibiotics has led to the emergence of resistant bacteria that are refractory to eradication by conventional anti-infective agents, such as those based on β-lactams or fluoroquinolone architectures. Many of these resistant bacteria are responsible for common infections including, for example, pneumonia, and sepsis.

Development of resistance to commonly used β-lactam anti-infectives is related to expression of β-lactamases by the targeted bacteria. β-Lactamases typically hydrolyze the β-lactam ring, thus rendering the antibiotic ineffective against bacteria. Accordingly, inhibition of β-lactamases by a suitable substrate can prevent degradation of the β-lactam antibiotic, thereby increasing the effectiveness of the administered antibiotic and mitigating the emergence of resistance.

Relebactam is a known β-lactamase inhibitor that is currently marketed in combination with β-lactam antibiotics to treat gram negative bacterial infections. Relebactam must be administered intravenously, which limits its use to expensive clinical settings.

SUMMARY

According to the present invention, compounds have the structure of Formula (I):

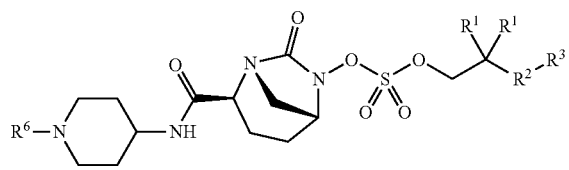

(1)

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;
$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and
$R^6$ is selected from a moiety of Formula (2), a moiety of Formula (3), a moiety of Formula (4), and a moiety of Formula (5):

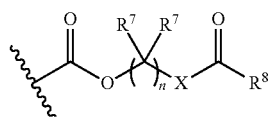

(2)

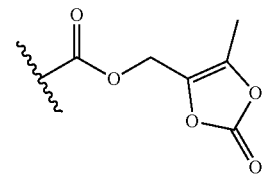

(3)

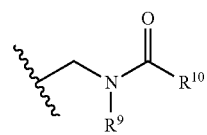

(3)

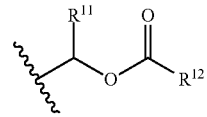

(4)

wherein,
each $R^7$ is independently selected from hydrogen and $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
n is an integer from 1 to 4;
X is selected from O and NH;
$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

According to the present invention, pharmaceutical compositions comprise a compound according to the present invention and a pharmaceutically acceptable vehicle.

According to the present invention, methods of treating a bacterial infection in a patient comprise administering to a patient in need of such treatment a therapeutically effective amount of a compound according to the present invention or a pharmaceutically acceptable salt thereof or a pharmaceutical composition of any of the foregoing; and a therapeutically effective amount of a β-lactam antibiotic.

According to the present invention, methods of inhibiting a β-lactamase enzyme in a patient comprise administering to the patient an effective amount of the compound according to the present invention or a pharmaceutically acceptable salt thereof or a pharmaceutical composition of any of the foregoing.

BRIEF DESCRIPTION OF THE DRAWINGS

The drawings described herein are for illustration purposes only. The drawings are not intended to limit the scope of the present disclosure.

The FIGURE shows the mean plasma concentration of relebactam following intravenous (IV) administration of relebactam or peroral administration of Compound (87) or Compound (88) to Beagle dogs.

DETAILED DESCRIPTION

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, and but-3-yn-1-yl, etc. The term "alkyl" is specifically intended to include groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl, or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy, or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, such as the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be, for example, $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of the fraction absorbed, the fraction escaping gut-wall elimination, and the fraction escaping hepatic elimination; and the factors that influence bioavailability can be divided into physiological, physicochemical, and biopharmaceutical factors.

"Compounds" and moieties disclosed herein include any specific compounds within these formula. Compounds may be identified either by their chemical structure and/or chemical name. Compounds are named using the ChemBioDraw Ultra Version 14.0.0.117 (CambridgeSoft, Cambridge, Mass.) nomenclature/structure program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, for example, the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl for example, the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—$CH_2$-cyclo-$C_3H_5$), cyclopentylmethyl (—$CH_2$-cyclo-$C_5H_9$), or cyclohexylmethyl (—$CH_2$-cyclo-$C_6H_{11}$). A cycloalkylalkyl group can be cyclopropylethenyl (—CH=CH-cyclo-$C_3H_5$), or cyclopentylethynyl (—C≡C-cyclo-$C_5H_9$).

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—$CH_3$)—, —SO—, and —$SO_2$—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be, or example, $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Fluoroalkyl" refers to an alkyl group as defined herein in which one or more of the hydrogen atoms is replaced with a fluoro. A fluoroalkyl group can be $C_{1-6}$ fluoroalkyl, $C_{1-5}$ fluoroalkyl, $C_{1-4}$ fluoroalkyl, or $C_{1-3}$ fluoroalkyl. A fluoroalkyl group can be pentafluoroethyl (—$CF_2CF_3$) or trifluoromethyl (—$CF_3$).

"Fluoroalkoxy" refers to an alkoxy group as defined herein in which one or more of the hydrogen atoms is replaced with a fluoro. A fluoroalkoxy group can be, for example, $C_{1-6}$ fluoroalkoxy, $C_{1-5}$ fluoroalkoxy, $C_{1-4}$ fluoroalkoxy $C_{1-3}$, fluoroalkoxy, —$OCF_2CF_3$ or —$OCF_3$.

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR—, —SO$_2$—, and —SO$_2$—, or the heteroatomic group can be selected from —O— and —NH—, or the heteroatomic group is —O— and —NH—. A heteroalkoxy group can be, for example, C$_{1-6}$ heteroalkoxy, C$_{1-5}$ heteroalkoxy, C$_{1-4}$ heteroalkoxy, or C$_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, =N—N=, —N=N—, —N=N—NR—, —PR—, —P(O)OR—, —P(O)R—, —POR—, —SO—, —SO$_2$—, —Sn(R)$_2$—, and the like, where each R is independently selected from hydrogen, C$_{1-6}$ alkyl, substituted C$_{1-6}$ alkyl, C$_{6-12}$ aryl, substituted C$_{6-12}$ aryl, C$_{7-18}$ arylalkyl, substituted C$_{7-18}$ arylalkyl, C$_{3-7}$ cycloalkyl, substituted C$_{3-7}$ cycloalkyl, C$_{3-7}$ heterocycloalkyl, substituted C$_{3-7}$ heterocycloalkyl, C$_{1-6}$ heteroalkyl, substituted C$_{1-6}$ heteroalkyl, C$_{6-12}$ heteroaryl, substituted C$_{6-12}$ heteroaryl, C$_{7-18}$ heteroarylalkyl, and substituted C$_{7-18}$ heteroarylalkyl. Each R can be independently selected from hydrogen and C$_{1-3}$ alkyl. Reference to, for example, a C$_{1-6}$ heteroalkyl, means a C$_{1-6}$ alkyl group in which at least one of the carbon atoms (and certain associated hydrogen atoms) is replaced with a heteroatom. For example, C$_{1-6}$ heteroalkyl includes, for example, groups having five carbon atoms and one heteroatom, groups having four carbon atoms and two heteroatoms. In a heteroalkyl, the heteroatomic group can be selected from —O—, —S—, —NH—, —N(~CH$_3$)—, —SO—, and —SO$_2$—, or the heteroatomic group can be selected from —O— and —NH—, or the heteroatomic group can be —O— or —NH—. A heteroalkyl group can be C$_{1-6}$ heteroalkyl, C$_{1-5}$ heteroalkyl, or C$_{1-4}$ heteroalkyl, or C$_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(~CH$_3$)—, —S(O)—, and —SO$_2$—, or the heteroatomic group can be selected from —O— and —NH—, or the heteroatomic group can be —O— or —NH—. A heteroaryl group can be selected from C$_{5-10}$ heteroaryl, C$_{5-9}$ heteroaryl, C$_{5-8}$ heteroaryl, C$_{5-7}$ heteroaryl, C$_{5-6}$ heteroaryl, C$_5$ heteroaryl, or C$_6$ heteroaryl.

Examples of suitable heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl group can be derived from thiophene, pyrrole, benzothiophene, benzofuran, indole, pyridine, quinoline, imidazole, oxazole, or pyrazine. For example, a heteroaryl can be C$_5$ heteroaryl and can be selected from furyl, thienyl, pyrrolyl, imidazolyl, pyrazolyl, isothiazolyl, or isoxazolyl. A heteroaryl can be C$_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be C$_{6-16}$ heteroarylalkyl, C$_{6-14}$ heteroarylalkyl, C$_{6-12}$ heteroarylalkyl, C$_{6-10}$ heteroarylalkyl, C$_{6-8}$ heteroarylalkyl, or C$_7$ heteroarylalkyl, or C$_6$ heteroarylalkyl. In a heteroarylalkyl, the heteroatomic group can be selected from —O—, —S—, —NH—, —N(~CH$_3$)—, —SO—, and —SO$_2$—, or the heteroatomic group can be selected from —O— and —NH—, or the heteroatomic group can be —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be C$_5$ heterocycloalkyl and can be selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be C$_6$ heterocycloalkyl and can be selected from piperidinyl, tetrahydropyranyl, piperizinyl, oxazinyl, dithianyl, and dioxanyl. A heterocycloalkyl group can be, for example, C$_{3-6}$ heterocycloalkyl, C$_{3-5}$ heterocycloalkyl, C$_{5-6}$ heterocycloalkyl, C$_5$ heterocycloalkyl, or C$_6$ heterocycloalkyl. In a heterocycloalkyl, the heteroatomic group can be selected from —O—, —S—, —NH—, —N(~CH$_3$)—, —SO—, and —SO$_2$—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be C$_{4-12}$ heterocycloalkylalkyl, C$_{4-10}$ heterocycloalkylalkyl, C$_{4-8}$ heterocycloalkylalkyl, C$_{4-6}$ heterocycloalkylalkyl, C$_{6-7}$ heterocycloalkylalkyl, or C$_6$ heterocycloalkylalkyl or C$_7$ heterocycloalkylalkyl. In a heterocycloalkylalkyl, the heteroatomic group can be selected from —O—, —S—, —NH—, —N(~CH$_3$)—, —SO—, and —SO$_2$—, or the heteroatomic group can be selected from —O— and —NH—, or the heteroatomic group can be —O— or —NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, and phenalene. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, and triphenylene, trinaphthalene.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Metabolic intermediate" refers to a compound that is formed in vivo by metabolism of a parent compound and that further undergoes reaction in vivo to release an active agent. Compounds of Formula (1) are protected sulfonate nucleophile prodrugs of non-β-lactam β-lactamase inhibitors that are metabolized in vivo to provide the corresponding metabolic intermediates such as relebactam ([(2S,5R)-7-oxo-2-(piperidin-4-ylcarbamoyl)-1,6-diazabicyclo[3.2.1] octan-6-yl] hydrogen sulfate). Metabolic intermediates undergo nucleophilic cyclization to release a non-β-lactam β-lactamase inhibitor such as relebactam and one or more reaction products. It is desirable that the reaction products or metabolites thereof not be toxic.

"Neopentyl" refers to a radical in which a methylene carbon is bonded to a carbon atom, which is bonded to three non-hydrogen substituents. Examples of non-hydrogen substituents include carbon, oxygen, nitrogen, and sulfur. Each of the three non-hydrogen substituents can be carbon. Two of the three non-hydrogen substituents can be carbon, and the third non-hydrogen substituent can be selected from oxygen and nitrogen. A neopentyl group can have the structure:

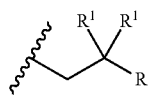

where each $R^1$ is defined as for Formula (1).

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, and xanthene. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine.

"Patient" refers to a mammal, for example, a human. The term "patient" is used interchangeably with "subject."

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, such as an alkali metal ion, an alkaline earth ion, or an aluminum ion, or combinations thereof; or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt such as a hydrochloride salt, is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as prophylaxis. Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for a compound of Formula (1), the promoiety can have the structure:

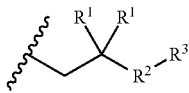

where $R^1$, $R^2$, and $R^3$ are defined as for Formula (1).

"Single bond" as in the expression "$R^2$ is selected from a single bond" refers to a moiety in which $R^2$ is a single bond. For example, in a moiety having the structure —$C(R^1)_2$—$R^2$—$R^3$, where $R^2$ is a single bond, —$R^2$— corresponds to a single bond, "-a", and the moiety has the structure —$C(R^1)_2$—$R^3$.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water. Solvates refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —$CF_3$, —$OCF_3$, =O, —$NO_2$, $C_{1-6}$ alkoxy, $C_{1-6}$ alkyl, —COOR, —$NR_2$, and —$CONR_2$; wherein each R can be independently selected from hydrogen and $C_{1-6}$ alkyl. Each substituent can be independently selected from deuterio, halogen, —$NH_2$, —OH, $C_{1-3}$ alkoxy, and $C_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, $C_{1-3}$ alkyl, =O, $C_{1-3}$ alkyl, $C_{1-3}$ alkoxy, and phenyl. Each substituent can be selected from deuterio, —OH, —$NH_2$, $C_{1-3}$ alkyl, and $C_{1-3}$ alkoxy.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or at least one or more symptoms thereof in a patient who may be exposed to or predisposed to a disease or disorder even though that patient does not yet experience or display symptoms of the disease.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. The "therapeutically effective amount" will vary depending, for example, on the compound, the disease and its severity and the age, weight, adsorption, distribution, metabolism and excretion, of the patient to be treated. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a subject. In some embodiments, the vehicle is pharmaceutically acceptable.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds provided by the present disclosure are amide and sulfonate ester prodrugs of non-β-lactam β-lactamase inhibitors. In the non-β-lactam β-lactamase inhibitor prodrugs a nucleophilic moiety is positioned proximate to the hydrogen sulfate group. In vivo, the nucleophilic moiety reacts to release the non-β-lactam β-lactamase inhibitor. Examples of non-β-lactam β-lactamase inhibitors include avibactam ([2S,5R]-2-carbamoyl-7-oxo-1,6-diazabicyclo [3.2.1]octan-6-yl hydrogen sulfate), relebactam ((1R,2S, 5R)-7-oxo-2-(piperidin-4-ylcarbamoyl)-1,6-diazabicyclo [3.2.1]octan-6-yl hydrogen sulfate), and nacubactam (1R, 2S,5R)-2-((2-aminoethoxy)carbamoyl)-7-oxo-1,6-diazabicyclo[3.2.1]octan-6-yl hydrogen sulfate, and derivatives and analogs of any of the foregoing. These compounds are inhibitors of class A, class C, and certain Class D β-lactamases and are useful in the treatment of bacterial infections when used in conjunction with β-lactam antibiotics. Compounds provided by the present disclosure are amide- and sulfonate ester-derivatives of relebactam.

Compounds provided by the present disclosure are double prodrugs of relebactam.

Compounds provided by the present disclosure include compounds of Formula (1):

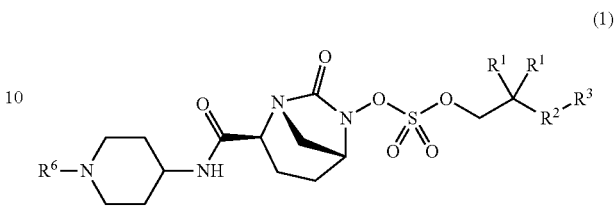

(1)

or a pharmaceutically acceptable salt thereof, wherein, each $R^1$ can be independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ can be selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ can be selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{6-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ can be selected from a moiety of Formula (2), a moiety of Formula (3), a moiety of Formula (4), and a moiety of Formula (5):

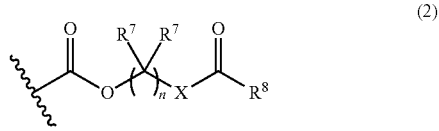

(2)

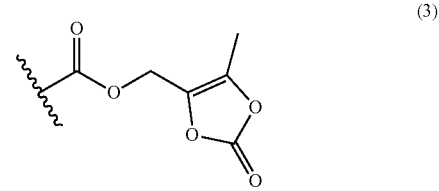 [SMILES: *C(=O)OCc1oc(=O)oc1C]

(3)

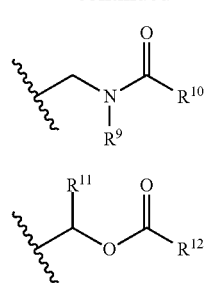

(4)

(5)

wherein, each $R^7$ can be independently selected from hydrogen and $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n can be an integer from 1 to 4;

X can be selected from O and NH;

$R^8$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ can be selected from hydrogen and $C_{1-6}$ alkyl;

$R^{10}$ can be selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^{11}$ can be selected from hydrogen and $C_{1-6}$ alkyl; and $R^{12}$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

In compounds of Formula (1), each substituent can be independently selected from deuterio, —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl, such has methyl, ethyl, n-propyl, isopropyl, n-butyl, tert-butyl, or iso-butyl.

In compounds of Formula (1), a substituent group can be a nucleophilic group. Nucleophilic groups are functional group having a reactive pair of electrons and having the ability of forming a chemical bond by donating electrons. Examples of suitable nucleophilic groups include esters, carboxylates, sulfonates, substituted or unsubstituted amines, alcohols (hydroxyl), thiols, sulfides, hydroxylamines, and imines. Other examples of suitable nucleophilic groups include —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each R$^4$ can be independently selected from hydrogen, $C_{1-6}$ alkyl, $C_{1-6}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{6-8}$ heteroaryl, $C_{5-10}$ arylalkyl, $C_{5-10}$ heteroarylalkyl, substituted $C_{1-6}$ alkyl, substituted $C_{1-6}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{6-8}$ heteroaryl, substituted $C_{5-10}$ arylalkyl, and substituted $C_{5-10}$ heteroarylalkyl.

In compounds of Formula (1), each substituent can independently be selected from —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, and —CH(—NH$_2$)(—R$^4$), wherein each R$^4$ can be selected from hydrogen, $C_{1-8}$ alkyl, and $C_{1-8}$ heteroalkyl.

In compounds of Formula (1), each R$^1$ can independently be $C_{1-6}$ alkyl.

In compounds of Formula (1), each R$^1$ can independently be methyl, ethyl, or n-propyl.

In compounds of Formula (1), each R$^1$ can be same and can be methyl, ethyl, or n-propyl.

In compounds of Formula (1), each R$^1$ can be methyl.

In compounds of Formula (1), each R$^1$ together with the geminal carbon atom to which they are bonded can form a $C_{3-6}$ cycloalkyl ring or a substituted $C_{3-6}$ cycloalkyl ring.

In compounds of Formula (1), each R$^1$ together with the geminal carbon atom to which they are bonded can form a $C_{3-6}$ cycloalkyl ring. For example, each R$^1$ together with the geminal carbon atom to which they are bonded can form a cyclopropyl ring, a cyclobutyl ring, a cyclopentyl ring, or a cyclohexyl ring.

In compounds of Formula (1), each R$^1$ together with the geminal carbon atom to which they are bonded can form a $C_{3-6}$ heterocycloalkyl ring or a substituted $C_{3-6}$ heterocycloalkyl ring.

In compounds of Formula (1), R$^2$ can be selected from a single bond, $C_{1-2}$ alkanediyl, and substituted $C_{1-2}$ alkanediyl.

In compounds of Formula (1), R$^2$ can be a single bond.

In compounds of Formula (1), R$^2$ can be a single bond; and R$^3$ can be $C_{1-6}$ alkyl.

In compounds of Formula (1), can be selected from $C_{1-2}$ alkanediyl and substituted $C_{1-2}$ alkanediyl.

In compounds of Formula (1), R$^2$ can be methanediyl, ethanediyl, substituted methanediyl, or substituted ethanediyl.

In compounds of Formula (1), R$^2$ can be substituted $C_{1-2}$ alkanediyl where the substituted group can be selected from —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl.

In compounds of Formula (1), R$^2$ can be substituted $C_{1-2}$ alkanediyl where the substituent group can be a nucleophilic group. For example, R$^2$ can be substituted $C_{1-2}$ alkanediyl where the substituent group can be selected from —OH, —CF$_3$, —O—CF$_3$, —NO$_2$, —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—(O)—S—R$^4$, —O—C(O)—NH—R$^4$, —S—S—R$^4$, —S—R$^4$, —NH—R$^4$, and —CH(—NH$_2$)(—R$^4$), where each R$^4$ can be defined as for Formula (1), or each R$^4$ can be selected from hydrogen and C$_{1-8}$ alkyl.

In compounds of Formula (1), R$^2$ can be substituted C$_{1-2}$ alkanediyl where the substituent group can be selected from —OH, —O—(O)—R$^4$, —S—C(O)—R$^4$, —NH—C(O)—R$^4$, —C(O)—O—R$^4$, —C(O)—S—R$^4$, —C(O)—NH—R$^4$, —S—S—R$^4$, —S—R$^4$, —NH—R$^4$, —CH(—NH$_2$)(—R$^4$), substituted C$_{5-6}$ aryl, —NHR$^4$, and —CH(—NH$_2$)(—R$^4$); and R$^4$ can be defined as for Formula (1), or each R$^4$ can be selected from hydrogen and C$_{1-8}$ alkyl.

In compounds of Formula (1), where R$^2$ can be substituted C$_{1-6}$ alkanediyl, substituted C$_{1-6}$ heteroalkanediyl, or substituted C$_{5-6}$ arenediyl, the stereochemistry of the carbon atom to which the substituent group can be bonded can be of the (S) configuration.

In compounds of Formula (1), where R$^2$ can be substituted C$_{1-6}$ alkanediyl, substituted C$_{1-6}$ heteroalkanediyl, or substituted C$_{5-6}$ arenediyl, the stereochemistry of the carbon atom to which the substituent group can be bonded can be of the (R) configuration.

In compounds of Formula (1), R$^2$ can be selected from C$_{5-6}$ cycloalkanediyl, C$_{5-6}$ heterocycloalkanediyl, C$_{5-6}$ arenediyl, and C$_{5-6}$ heterocycloalkanediyl.

In compounds of Formula (1), R$^2$ can be cyclopenta-1,3-diene-diyl, substituted cyclopenta-1,3-diene-diyl, benzene-diyl or substituted benzene-diyl. For example, R$^2$ can be 1,2-benzene-diyl or substituted 1,2-benzene-diyl.

In compounds of Formula (1), R$^3$ can be selected from —O—C(O)—R$^4$, —S—C(O)—R$^4$, —NH—C(O)—R$^4$, —O—C(O)—O—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—(O)—S—R$^4$, —O—C(O)—NH—R$^4$, —S—S—R$^4$, —S—R$^4$, —NH—R$^4$, and —CH(—NH$_2$)(—R$^4$); where R$^4$ can be defined as for Formula (1), or each R$^4$ can be selected from hydrogen and C$_{1-8}$ alkyl.

In compounds of Formula (1), R$^3$ can be selected from —O—C(O)—R$^4$, —C(O)—O—R$^4$, —S—C(O)—R$^4$, —C(O)—S—R$^4$, —S—S—R$^4$, —NH—R$^4$, and —CH(—NH$_2$)(—R$^4$); where R$^4$ can be defined as for Formula (1), or each R$^4$ can be selected from hydrogen and C$_{1-8}$ alkyl.

In compounds of Formula (1), R$^3$ can be —C(O)—O—R$^4$); where R$^4$ can be defined as for Formula (1), or each R$^4$ can be selected from hydrogen and C$_{1-8}$ alkyl.

In compounds of Formula (1), R$^4$ can be selected from hydrogen, C$_{1-3}$ alkyl, C$_{5-6}$ cycloalkyl, C$_{5-6}$ heterocycloalkyl, C$_{5-6}$ aryl, substituted C$_{1-3}$ alkyl, substituted C$_{5-6}$ cycloalkyl, substituted C$_{5-6}$ heterocycloalkyl, and substituted C$_{5-6}$ aryl.

In compounds of Formula (1), R$^4$ can be selected from methyl, ethyl, phenyl, and benzyl.

In compounds of Formula (1), R$^4$ can be selected from hydrogen and C$_{1-8}$ alkyl.

In compounds of Formula (1), R$^4$ can be selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

In compounds of Formula (1), R$^4$ can be selected from C$_{1-8}$ alkyl, C$_{1-8}$ heteroalkyl, C$_{7-9}$ arylalkyl, and C$_{5-7}$ heterocycloalkyl.

In compounds of Formula (1), R$^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1), R$^3$ can be —C(O)—O—R$^4$; and R$^4$ can be selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl, In compounds of Formula (1), R$^3$ can be —C(O)—O—R$^4$; and R$^4$ can be selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

In compounds of Formula (1), R$^3$ can be —C(O)—O—R$^4$; and R$^4$ can be selected from C$_{1-8}$ alkyl, C$_{1-8}$ heteroalkyl, C$_{7-9}$ arylalkyl, and C$_{5-7}$ heterocycloalkyl.

In compounds of Formula (1), R$^3$ can be selected from —O—C(O)—CH$_3$, —O—C(O)—CH$_2$—CH$_3$, —O—C(O)-phenyl, —O—C(O)—CH$_2$-phenyl, —S—C(O)—CH$_3$, —S—C(O)—CH$_2$—CH$_3$, —S—C(O)-phenyl, —S—C(O)—CH$_2$-phenyl, —NH—C(O)—CH$_3$, —NH—C(O)—CH$_2$—CH$_3$, —NH—C(O)-phenyl, —NH—C(O)—CH$_2$-phenyl, —O—C(O)—O—CH$_3$, —O—C(O)—O—CH$_2$—CH$_3$, —O—C(O)—O-phenyl, —O—C(O)—O—CH$_2$-phenyl, —S—C(O)—O—CH$_3$, —S—C(O)—O—CH$_2$—CH$_3$, —S—C(O)—O-phenyl, —S—C(O)—O—CH$_2$-phenyl, —NH—C(O)—O—CH$_3$, —NH—C(O)—O—CH$_2$—CH$_3$, —NH—C(O)—O-phenyl, —NH—C(O)—O—CH$_2$-phenyl, —C(O)—O—CH$_3$, —C(O)—O—CH$_2$—CH$_3$, —C(O)—O-phenyl, —C(O)—O—CH$_2$-phenyl, —C(O)—S—CH$_3$, —C(O)—S—CH$_2$—CH$_3$, —C(O)—S-phenyl, —C(O)—S—CH$_2$-phenyl, —C(O)—NH—CH$_3$, —C(O)—NH—CH$_2$—CH$_3$, —C(O)—NH-phenyl, —C(O)—NH—CH$_2$-phenyl, —O—C(O)—O—CH$_3$, —O—C(O)—O—CH$_2$—CH$_3$, —O—C(O)—O— phenyl, —O—C(O)—O—CH$_2$-phenyl, —O—C(O)—S—CH$_3$, —O—C(O)—S—CH$_2$—CH$_3$, —O—C(O)—S-phenyl, —O—C(O)—S—CH$_2$-phenyl, —O—C(O)—NH—CH$_3$, —O—C(O)—NH—CH$_2$—CH$_3$, —O—C(O)—NH-phenyl, —O—C(O)—NH—CH$_2$-phenyl, —S—SH, —S—S—CH$_3$, —S—S—CH$_2$—CH$_3$, —S—S-phenyl, —S—S—CH$_2$-phenyl, —SH, —S—CH$_3$, —S—CH$_2$—CH$_3$, —S-phenyl, —S—CH$_2$-phenyl, —NH$_2$, —NH—CH$_3$, —NH—CH$_2$—CH$_3$, —NH—phenyl, —NH—CH$_2$-phenyl, —CH(—NH$_2$)(~CH$_3$), —CH(—NH$_2$)(—CH$_2$~CH$_3$), —CH(—NH$_2$)(-phenyl), and —CH(—NH$_2$)(—CH$_2$-phenyl).

In compounds of Formula (1), R$^3$ can be selected from C$_{5-6}$ cycloalkyl, C$_{5-6}$ heterocycloalkyl, C$_{5-6}$ aryl, C$_{5-6}$ heteroaryl, substituted C$_{5-6}$ cycloalkyl, substituted C$_{5-6}$ heterocycloalkyl, substituted C$_{5-6}$ aryl, and substituted C$_{5-6}$ heteroaryl, comprising at least one nucleophilic group. For example, R$^3$ can have the structure of Formula (13a) or Formula (13b):

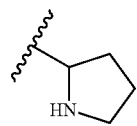

(13a)

(13b)

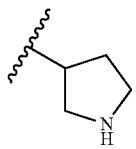

In compounds of Formula (1), $R^4$ can be selected from $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1), each $R^1$ together with the carbon atom to which they are bonded form a $C_{4-6}$ heterocycloalkyl ring comprising two adjacent S atoms or a substituted $C_{4-6}$ heterocycloalkyl ring comprising at least one heteroatom selected from O and S, and a carbonyl (=O) substituent group bonded to a carbon atom adjacent the at least one heteroatom.

In compounds of Formula (1), $R^2$ can be a bond; $R^3$ can be $C_{1-3}$ alkyl; and each $R^1$ together with the carbon atom to which they are bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In compounds of Formula (1) and Formula (2), each $R^1$ together with the carbon atom to which they are bonded can from a $C_4$-, $C_5$-, or $C_6$-heterocycloalkyl group. The heterocycloalkyl group can have two adjacent sulfur atoms. In compounds of Formula (1) and Formula (2) in each $R^1$ together with the carbon atom to which they are bonded can from a $C_4$-, $C_5$-, or $C_6$-heterocycloalkyl group, $R^2$ can be a single bond and $R^3$ can be $C_{1-6}$ alkyl, such as $C_{1-4}$ alkyl, such as methyl or ethyl.

In compounds of Formula (1) and Formula (2), each $R^1$ together with the carbon atom to which they are bonded can from a substituted $C_4$-, substituted $C_5$-, or substituted $C_6$-heterocycloalkyl group. The substituted heterocycloalkyl group can have a sulfur atom and an adjacent carbonyl (=O) group. The substituted heterocycloalkyl group can have am oxygen atom and an adjacent carbonyl (=O) group.

In compounds of Formula (1) and Formula (2), each $R^1$ together with the carbon atom to which they are bonded can from a substituted $C_4$-, substituted $C_5$-, or substituted $C_6$-heterocycloalkyl group, $R^3$ can be a single bond and $R^4$ can be $C_{1-6}$ alkyl, such as $C_{1-4}$ alkyl, such as methyl or ethyl.

In compounds of Formula (1), $R^2$ can be a single bond; $R^3$ can be $C_{1-3}$ alkyl; and each $R^1$ together with the carbon atom to which they are bonded can form a $C_{4-6}$ heterocycloalkyl ring or a substituted $C_{4-6}$ heterocycloalkyl ring.

In compounds of Formula (1), $R^2$ can be a single bond; $R^3$ can be $C_{1-3}$ alkyl; and each $R^1$ together with the carbon atom to which they are bonded can form a $C_{4-6}$ heterocycloalkyl ring comprising two adjacent S atoms or a substituted $C_{4-6}$ heterocycloalkyl ring comprising at least one heteroatom selected from O and S, and a carbonyl (=O) substituent group bonded to a carbon atom adjacent the heteroatom.

In compounds of Formula (1), $R^2$ can be a single bond; $R^3$ can be $C_{1-3}$ alkyl; and each $R^1$ together with the carbon atom to which they are bonded can form a 1,2-dithiolane, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

In compounds of Formula (1),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1),
each $R^1$ and the geminal carbon to which they are bonded can form a $C_{3-6}$ cycloalkyl ring;
$R^2$ can be selected from a bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In compounds of Formula (1),
$R^2$ can be a bond;
$R^3$ be $C_{1-3}$ alkyl; and
each $R^1$ together with the carbon atom to which they are bonded can form a 1,2-dithiolante, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

In compounds of Formula (1),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$);
wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$;
wherein $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$);
wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$;

wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In compounds of Formula (1),
each $R^1$ can be methyl;
$R^2$ can be a single bond; and
$R^3$ can be —C(O)—O—$R^4$;
wherein $R^4$ can be selected from $C_{1-10}$ alkyl, $C_{1-10}$ heteroalkyl, $C_{7-10}$ alkylarene, and $C_{5-10}$ heteroalkylcycloalkyl.

In compounds of Formula (1),
each $R^1$ can be independently selected from $C_{1-3}$ alkyl, or each $R^1$ together with the geminal carbon atom to which they are bonded form a $C_{3-6}$ cycloalkyl ring, a substituted $C_{3-6}$ cycloalkyl ring, a $C_{3-6}$ heterocycloalkyl ring, or a substituted $C_{3-6}$ heterocycloalkyl ring;
$R^2$ can be a single bond;
$R^3$ can be —C(O)—O—$R^4$; and
$R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1),
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1),
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1),
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1),
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of Formula (1),
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond; and
$R^3$ can be $C_{1-3}$ alkyl.

In compounds of Formula (1),
each $R^1$ can be independently selected from $C_{1-3}$ alkyl;
$R^2$ can be selected from a single bond and methanediyl; and
$R^3$ can be selected from —O—C(O)—$R^4$ and —C(O)—O—$R^4$, wherein $R^4$ can be selected from $C_{1-10}$ alkyl and substituted phenyl.

In compounds of Formula (1),
each $R^1$ can be independently selected from $C_{1-3}$ alkyl;
$R^2$ can be a single bond;
$R^3$ can be —CH═C($R^4$)$_2$, wherein each $R^4$ can be —C(O)—O—$R^8$, or each $R^4$ together with the carbon atom to which they are bonded from a substituted heterocyclohexyl ring; and
each $R^8$ can be $C_{1-4}$ alkyl.

In compounds of Formula (1),
each $R^1$ can be independently selected from $C_{1-3}$ alkyl;
$R^2$ can be selected from a single bond and methanediyl; and
$R^3$ can be substituted phenyl, wherein the one or more substituents can be independently selected from —CH$_2$—O—C(O)—$R^4$ and —O—C(O)—$R^4$, wherein $R^4$ can be selected from $C_{1-10}$ alkyl and phenyl.

In compounds of Formula (1),
each $R^1$ can be independently selected from $C_{1-3}$ alkyl;
$R^2$ can be selected from —C($R^8$)$_2$— and —CH$_2$—C($R^8$)$_2$—, wherein each $R^8$ can be independently selected from $C_{1-3}$ alkyl; and
$R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In compounds of Formula (1), each $R^1$ together with the carbon atom to which they are bonded form a substituted $C_{5-6}$ heterocyclic ring;
$R^2$ can be a single bond; and
$R^3$ can be $C_{1-3}$ alkyl.

In compounds of Formula (1), $R^6$ can be a moiety of Formula (2):

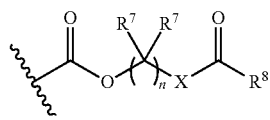

(2)

where n, X, each $R^7$, and $R^8$ are defined as in Formula (1).

In moieties of Formula (2), n can be selected from 1 and 2.

In moieties of Formula (2), n can be 1.

In moieties of Formula (2), n can be 2.

In moieties of Formula (2), each $R^7$ and the geminal carbon atom to which they are bonded can form a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring.

In moieties of Formula (2), each $R^7$ and the geminal carbon atom to which they are bonded can form a $C_{3-6}$ cycloalkyl ring or a substituted $C_{3-6}$ cycloalkyl ring.

In moieties of Formula (2), each $R^7$ can be independently selected from hydrogen and $C_{1-8}$ alkyl.

In moieties of Formula (2), each $R^7$ can be independently selected from hydrogen and $C_{1-3}$ alkyl.

In moieties of Formula (2), each $R^7$ can be hydrogen.

In moieties of Formula (2), each $R^7$ can be selected from methyl, ethyl, n-propyl, and iso-propyl.

In moieties of Formula (2), one $R^7$ can be hydrogen and the other $R^7$ can be selected from methyl, ethyl, n-propyl, and iso-propyl.

In moieties of Formula (2), the carbon atom to which $R^7$ is bonded can be in the (S) configuration.

In moieties of Formula (2), the carbon atom to which $R^7$ is bonded can be in the (R) configuration.

In moieties of Formula (2), X can be NH.

In moieties of Formula (2), X can be O.

In moieties of Formula (2), $R^8$ can be selected from hydrogen, $C_{1-8}$ alkyl, $C_{5-8}$ cycloalkyl, $C_{5-10}$ cycloalkylalkyl, $C_{6-8}$ aryl, $C_{7-10}$ arylalkyl, substituted $C_{1-8}$ alkyl, substituted $C_{5-8}$ cycloalkyl, substituted $C_{5-10}$ cycloalkylalkyl, substituted $C_{6-8}$ aryl, and substituted $C_{7-10}$ arylalkyl.

In moieties of Formula (2), $R^8$ can be selected from hydrogen, $C_{1-8}$ alkyl, $C_{5-8}$ cycloalkyl, $C_{5-10}$ cycloalkylalkyl, $C_{6-8}$ aryl, and $C_{7-10}$ arylalkyl.

In moieties of Formula (2), $R^8$ can be selected from hydrogen, $C_{1-8}$ alkyl, $C_{5-8}$ cycloalkyl, and $C_{6-8}$ aryl.

In moieties of Formula (2), $R^8$ can be selected from $C_{1-8}$ alkoxy, $C_{1-8}$ cycloalkoxy, substituted $C_{1-8}$ alkoxy, and substituted $C_{1-8}$ cycloalkoxy.

In moieties of Formula (2), $R^8$ can be selected from $C_{5-8}$ aryl, substituted $C_{5-8}$ aryl, $C_{5-8}$ heteroaryl, and substituted $C_{5-8}$ heteroaryl.

In moieties of Formula (2), $R^8$ can be selected from $C_{5-8}$ aryl and substituted $C_{5-8}$ aryl.

In moieties of Formula (2), $R^8$ can be $C_{1-8}$ alkoxy.

In moieties of Formula (2), $R^8$ can be selected from hydrogen, methyl, ethyl, propyl, isopropyl, butyl, isobutyl, sec-butyl, tert-cyclopropyl cyclobutyl, cyclopentyl cyclohexyl, and benzyl.

In moieties of Formula (2), $R^8$ can be selected from hydrogen, $C_{1-6}$ alkyl, and —CH(—$R^{13}$)—$NH_2$, wherein $R^{13}$ can be selected from $C_{1-6}$ alkyl, alkoxy, and cycloalkoxy.

In moieties of Formula (2), $R^8$ can be selected from hydrogen and $C_{1-6}$ alkyl.

In moieties of Formula (2), $R^8$ can be selected from hydrogen, methyl, ethyl, n-propyl, isopropyl, n-butyl, isobutyl, sec-butyl, and tert-butyl.

In moieties of Formula (2), $R^8$ can be —CH(—$R^{13}$)—$NH_2$, wherein $R^{13}$ can be selected from $C_{1-6}$ alkyl, $C_{1-6}$ alkoxy, and cycloalkoxy.

In moieties of Formula (2), the carbon atom to which $R^{13}$ is bonded can be of the (S) configuration.

In moieties of Formula (2), the carbon atom to which $R^{13}$ is bonded can be of the (R) configuration.

In compounds of Formula (1),
each $R^1$ can be $C_{1-6}$ alkyl;
$R^2$ can be a single bond;
$R^3$ can be —C(O)—O—;
$R^4$ can be $C_{1-6}$ alkyl;
n can be 1;
$R^6$ can be a moiety of Formula (2);
each $R^7$ can be selected from hydrogen and $C_{1-6}$ alkyl; and
$R^8$ can be selected from $C_{1-6}$ alkyl and —CH(—$R^{13}$)—$NH_2$, wherein $R^{13}$ can be selected from $C_{1-6}$ alkyl.

In compounds of Formula (1), $R^6$ can be a moiety of Formula (3):

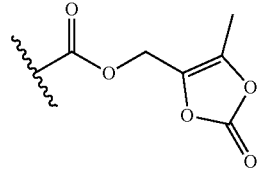

In moieties of Formula (3),
each $R^1$ can be $C_{1-6}$ alkyl;
$R^2$ can be a single bond;
$R^3$ can be —C(O)—O—; and
$R^4$ can be $C_{1-6}$ alkyl.

In compounds of Formula (1), $R^6$ can be a moiety of Formula (4):

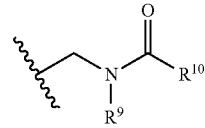

wherein $R^9$ and $R^{10}$ are defined as in Formula (1).

In moieties of Formula (4), $R^9$ can be selected from hydrogen, methyl, ethyl, and isopropyl.

In moieties of Formula (4), $R^9$ can be hydrogen.

In moieties of Formula (4), $R^9$ can be selected from methyl, ethyl, and isopropyl.

In moieties of Formula (4), $R^{10}$ can be selected from $C_{1-8}$ alkyl, $C_{5-8}$ cycloalkyl, $C_{5-10}$ cycloalkylalkyl, $C_{6-8}$ aryl, $C_{7-10}$ arylalkyl, substituted $C_{1-8}$ alkyl, substituted $C_{5-8}$ cycloalkyl, substituted $C_{5-10}$ cycloalkylalkyl, substituted $C_{6-8}$ aryl, and substituted $C_{7-10}$ arylalkyl.

In moieties of Formula (4), $R^{10}$ can be selected from $C_{1-8}$ alkyl, $C_{5-8}$ cycloalkyl, $C_{5-10}$ cycloalkylalkyl, $C_{6-8}$ aryl, and $C_{7-10}$ arylalkyl.

In moieties of Formula (4), $R^{10}$ can be selected from $C_{1-8}$ alkyl, $C_{5-8}$ cycloalkyl, and $C_{6-s}$ aryl.

In moieties of Formula (4), $R^{10}$ can be selected from methyl, ethyl, propyl, isopropyl, n-butyl, isobutyl, sec-butyl, tert-butyl, cyclopropyl, cyclobutyl, cyclopentyl, cyclohexyl, and benzyl.

In moieties of Formula (4), $R^{10}$ can be selected from cyclopentyl, substituted cyclopentyl, cyclohexyl, substituted cyclohexyl, benzyl, and substituted benzyl.

In moieties of Formula (4), $R^{10}$ can be selected from $C_{1-8}$ alkyl.

In moieties of Formula (4), $R^{10}$ can be selected from methyl, ethyl, n-propyl, isopropyl, n-butyl, iso-butyl, sec-butyl, and tert-butyl.

In moieties of Formula (4),
$R^9$ can be selected from hydrogen, methyl, ethyl, and isopropyl; and
$R^{10}$ can be selected from methyl, ethyl, n-propyl, isopropyl, n-butyl, iso-butyl, sec-butyl, and tert-butyl.

In compounds of Formula (1),
each $R^1$ can be $C_{1-6}$ alkyl;
$R^2$ can be a single bond;
$R^3$ can be —C(O)—O—;
$R^4$ can be $C_{1-6}$ alkyl;
$R^6$ can be a moiety of Formula (4);
$R^9$ can be selected from hydrogen, methyl, ethyl, and isopropyl; and $R^{10}$ can be selected from methyl, ethyl, n-propyl, isopropyl, n-butyl, iso-butyl, sec-butyl, and tert-butyl.

In compounds of Formula (1), $R^6$ can be a moiety of Formula (5):

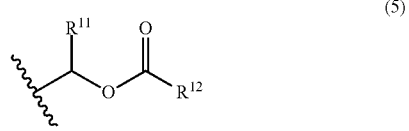

In moieties of Formula (5), $R^{11}$ can be selected from hydrogen, methyl, ethyl, and isopropyl.

In moieties of Formula (5), $R^{11}$ can be hydrogen.

In moieties of Formula (5), $R^{11}$ can be selected from methyl, ethyl, and isopropyl.

In moieties of Formula (5), the carbon atom to which $R^{11}$ is bonded can be of the (S) configuration.

In moieties of Formula (5), the carbon atom to which $R^{11}$ is bonded can be of the (R) configuration.

In moieties of Formula (5), $R^{12}$ can be selected from $C_{1-8}$ alkyl, $C_{5-8}$ cycloalkyl, $C_{5-10}$ cycloalkylalkyl, $C_{6-8}$ aryl, $C_{7-10}$ arylalkyl, substituted $C_{1-8}$ alkyl, substituted $C_{5-8}$ cycloalkyl, substituted $C_{5-10}$ cycloalkylalkyl, substituted $C_{6-8}$ aryl, and substituted $C_{7-10}$ arylalkyl.

In moieties of Formula (5), $R^{12}$ can be selected from $C_{1-8}$ alkyl, $C_{5-8}$ cycloalkyl, $C_{5-10}$ cycloalkylalkyl, $C_{6-8}$ aryl, and $C_{7-10}$ arylalkyl.

In moieties of Formula (5), $R^{12}$ can be selected from $C_{1-8}$ alkyl, $C_{5-8}$ cycloalkyl, and $C_{6-8}$ aryl.

In moieties of Formula (5), $R^{12}$ can be selected from methyl, ethyl, propyl, isopropyl, n-butyl, isobutyl, sec-butyl, tert-butyl, cyclopropyl, cyclobutyl, cyclopentyl, cyclohexyl, and benzyl.

In moieties of Formula (5), $R^{12}$ can be selected from cyclopentyl, substituted cyclopentyl, cyclohexyl, substituted cyclohexyl, benzyl, and substituted benzyl.

In moieties of Formula (5), $R^{12}$ can be selected from $C_{1-8}$ alkyl.

In moieties of Formula (5), $R^{12}$ can be selected from methyl, ethyl, n-propyl, isopropyl, n-butyl, iso-butyl, sec-butyl, and tert-butyl.

In moieties of Formula (5),
$R^{11}$ an be selected from hydrogen, methyl, ethyl, and isopropyl; and
$R^{12}$ can be selected from methyl, ethyl, n-propyl, isopropyl, n-butyl, iso-butyl, sec-butyl, and tert-butyl.

In compounds of Formula (1),
each $R^1$ can be $C_{1-6}$ alkyl;
$R^2$ can be a single bond;
$R^3$ can be —C(O)—O—;
$R^4$ can be $C_{1-6}$ alkyl;
$R^6$ can be a moiety of Formula (5);
$R^{11}$ can be selected from hydrogen, methyl, ethyl, and isopropyl; and
$R^{12}$ can be selected from methyl, ethyl, n-propyl, isopropyl, n-butyl, iso-butyl, sec-butyl, and tert-butyl.

In compounds of Formula (1), $R^6$ can be a moiety of Formula (2).

In compounds of Formula (1), $R^6$ can be a moiety of Formula (3).

In compounds of Formula (1), $R^6$ can be a moiety of Formula (4).

In compounds of Formula (1), $R^6$ can be a moiety of Formula (5).

In compounds of Formula (1), the compound can be selected from:
tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (5);
acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (6);
1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (7);
(pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (8);
(isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (9);
1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (10);
1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (11),
a pharmaceutically acceptable salt of any of the foregoing, and
a combination of any of the foregoing.

A compound of Formula (1) can be a compound of sub-genus (1A):

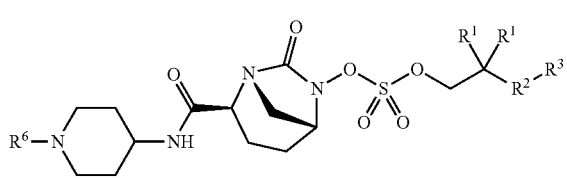

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

A compound of Formula (1) can be a compound of sub-genus (1A):

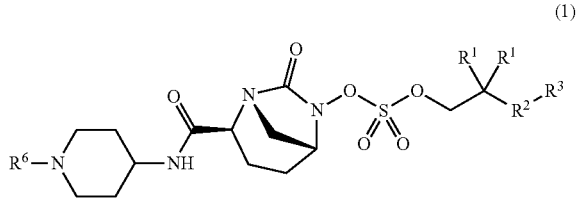

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl;
$R^3$ can be selected from —C(O)—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ can be selected from a moiety of Formula (2), a moiety of Formula (3), a moiety of Formula (4), and a moiety of Formula (5):

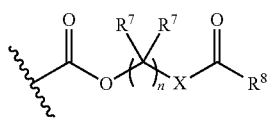

(2)

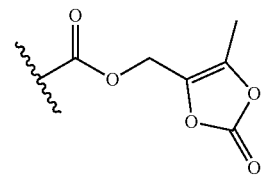

(3)

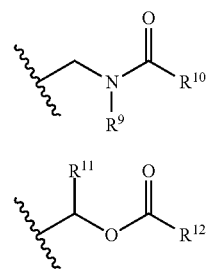

(4)

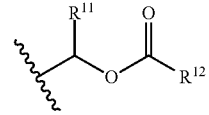

(5)

wherein,
each $R^7$ can be independently selected from hydrogen and $C_{1-6}$ alkyl
n can be selected from 1 and 2;
X can be O;
$R^8$ can be selected from hydrogen, $C_{1-6}$ alkyl and —CH(—$R^{13}$)—NH$_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1A), each $R^1$ can be independently selected from $C_{1-3}$ alkyl.

In compounds of subgenus (1A), each $R^1$ together with the carbon atom to which they are bonded can form a $C_{3-6}$ cycloalkyl ring.

In compounds of subgenus (1A), $R^2$ can be a single bond.
In compounds of subgenus (1A), $R^2$ can be methane-diyl.
In compounds of subgenus (1A), $R^2$ can be ethane-diyl.
In compounds of subgenus (1A), $R^3$ can be —C(O)—O—$R^4$.
In compounds of subgenus (1A), $R^3$ can be —S—C(O)—$R^4$.
In compounds of subgenus (1A), $R^4$ can be $C_{1-10}$ alkyl.
In compounds of subgenus (1A), $R^4$ can be $C_{1-10}$ heteroalkyl.

In compounds of subgenus (1A), $R^4$ can be $C_{5-10}$ arylalkyl.
In compounds of subgenus (1A), $R^4$ can be $C_{3-6}$ heterocycloalkyl.
In compounds of subgenus (1A), $R^4$ can be substituted $C_{4-10}$ heterocycloalkylalkyl.
In compounds of subgenus (1A), $R^6$ can be a moiety of Formula (2).
In compounds of subgenus (1A), $R^6$ can be a moiety of Formula (3).
In compounds of subgenus (1A), $R^6$ can be a moiety of Formula (4).
In compounds of subgenus (1A), $R^6$ can be a moiety of Formula (5).

A compound of Formula (1) can be a compound of sub-genus (1B):

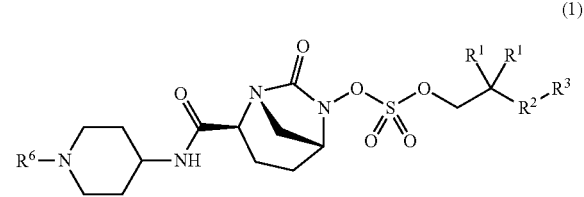

(1)

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

A compound of Formula (1) can be a compound of sub-genus (1B):

(1)

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be a single bond;
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ can be selected from a moiety of Formula (2), a moiety of Formula (3), a moiety of Formula (4), and a moiety of Formula (5):

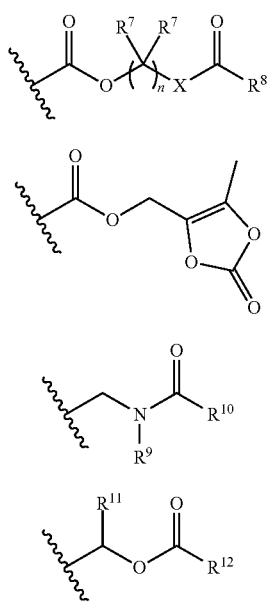

(2)

(3)

(4)

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and —CH(—$R^{13}$)—NH$_2$, wherein
$R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1B), each $R^1$ can be independently selected from $C_{1-3}$ alkyl.

In compounds of subgenus (1B), each $R^1$ together with the carbon atom to which they are bonded form a $C_{3-6}$ cycloalkyl ring.

In compounds of subgenus (1B), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, and —CH$_2$—$C_{3-6}$ substituted heterocycloalkyl, and —(CH$_2$)$_2$—$C_{3-6}$ substituted heterocycloalkyl.

In compounds of subgenus (1B), in the substituted $C_{3-6}$ heterocycloalkyl the one or more heteroatoms can be oxygen, and the one or more substituents can be independently selected from $C_{1-3}$ alkyl and =O.

In compounds of subgenus (1B), each $R^1$ can be methyl, or each $R^1$ together with the carbon atom to which they are bonded form a cyclohexyl ring or a cyclopentyl ring.

In compounds of subgenus (1B), $R^4$ can be selected from methyl, ethyl, n-propyl, iso-propyl, n-butyl, n-hexyl, n-heptyl, —CH$_2$—CH$_2$—O—CH$_3$, benzyl, 3-oxetanyl, and methyl-5-methyl-1,3-dioxol-2-one.

In compounds of subgenus (1B),
each $R^1$ can be methyl, or each $R^1$ together with the carbon atom to which they are bonded form a cyclohexyl ring or a cyclopentyl ring;

$R^2$ can be a single bond; and
$R^3$ can be —C(O)—O—$R^4$, wherein $R^4$ can be selected from methyl, ethyl, n-propyl, iso-propyl, n-butyl, n-hexyl, n-heptyl, —CH$_2$—CH$_2$—O—CH$_3$, —CH$_2$-phenyl (benzyl), β-oxetanyl, and methyl-5-methyl-1,3-dioxol-2-one.

In compounds of subgenus (1B), $R^6$ can be a moiety of Formula (2).

In compounds of subgenus (1B), $R^6$ can be a moiety of Formula (3).

In compounds of subgenus (1B), $R^6$ can be a moiety of Formula (4).

In compounds of subgenus (1B), $R^6$ can be a moiety of Formula (5).

A compound of Formula (1) can be a compound of sub-genus (1C):

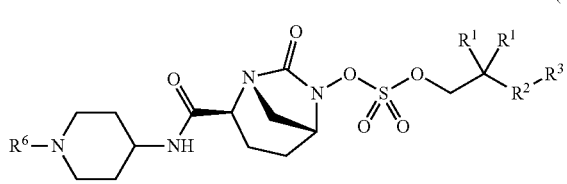

(1)

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

A compound of Formula (1) can be a compound of sub-genus (1C):

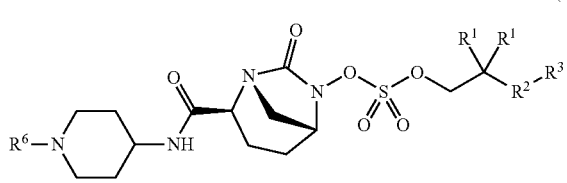

(1)

or a pharmaceutically acceptable salt thereof, wherein,
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—;
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ can be selected from a moiety of Formula (2), a moiety of Formula (3), a moiety of Formula (4), and a moiety of Formula (5):

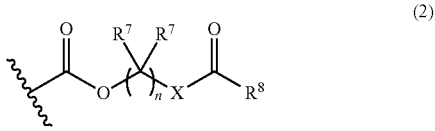

(2)

-continued

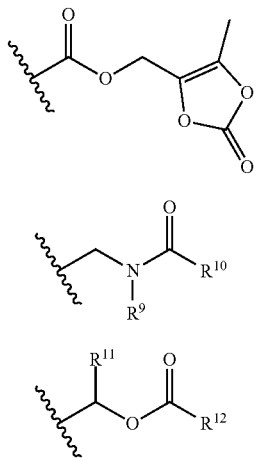

(3)

(4)

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and —CH(—$R^{13}$)—NH$_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1C), each $R^1$ can be independently selected from $C_{1-3}$ alkyl.

In compounds of subgenus (1C), each $R^1$ together with the carbon atom to which they are bonded form a $C_{3-6}$ cycloalkyl ring.

In compounds of subgenus (1C), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_3$-heterocycloalkyl wherein the one or more heteroatoms can be oxygen, —CH$_2$—$C_{3-6}$ substituted heterocycloalkyl, and —(CH$_2$)$_2$—$C_{3-6}$ substituted heterocycloalkyl.

In compounds of subgenus (1C), in the substituted $C_{3-6}$ heterocycloalkyl the one or more heteroatoms can be oxygen, and the one or more substituents can be independently selected from $C_{1-3}$ alkyl and =O.

In compounds of subgenus (1C), $R^4$ can be $C_{1-10}$ alkyl.

In compounds of subgenus (1C),
each $R^1$ can be methyl;
$R^2$ can be —(CH$_2$)$_2$—; and
$R^3$ can be —C(O)—O—$R^4$ wherein $R^4$ can be selected from n-hexyl and n-heptyl.

In compounds of subgenus (1C), $R^6$ can be a moiety of Formula (2).

In compounds of subgenus (1C), $R^6$ can be a moiety of Formula (3).

In compounds of subgenus (1C), $R^6$ can be a moiety of Formula (4).

In compounds of subgenus (1C), $R^6$ can be a moiety of Formula (5).

A compound of Formula (1) can be a compound of sub-genus (1D):

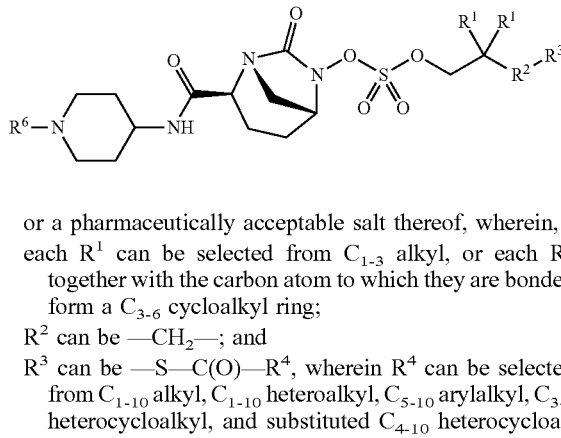

(1)

or a pharmaceutically acceptable salt thereof, wherein,
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

A compound of Formula (1) can be a compound of sub-genus (1D):

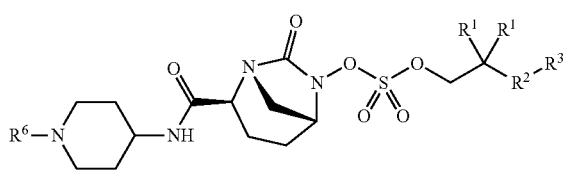

(1)

or a pharmaceutically acceptable salt thereof, wherein,
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—;
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ can be selected from a moiety of Formula (2), a moiety of Formula (3), a moiety of Formula (4), and a moiety of Formula (5):

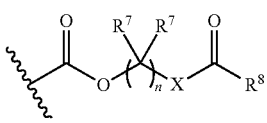

(2)

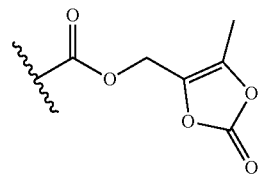

(3)

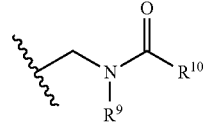

(4)

-continued

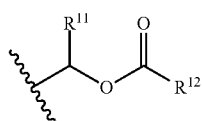

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and —CH(—$R^{13}$)—NH$_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1D), each $R^1$ can be independently selected from $C_{1-3}$ alkyl.

In compounds of subgenus (1D), each $R^1$ together with the carbon atom to which they are bonded form a $C_{3-6}$ cycloalkyl ring.

In compounds of subgenus (1D), $R^4$ can be selected from $C_{1-7}$ alkyl, $C_{1-10}$ heteroalkyl wherein the one or more heteroatoms can be oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms can be oxygen, —CH$_2$—$C_{3-6}$ substituted heterocycloalkyl, —(CH$_2$)$_2$—$C_{3-6}$ substituted heterocycloalkyl.

In compounds of subgenus (1D), in the substituted $C_{3-6}$ heterocycloalkyl the one or more heteroatoms can be oxygen, and the one or more substituents can be independently selected from $C_{1-3}$ alkyl and =O.

In compounds of subgenus (1D), $R^4$ can be $C_{1-10}$ alkyl.

In compounds of subgenus (1D),
each $R^1$ can be methyl;
$R^2$ can be —CH$_2$—; and
$R^3$ can be —S—C(O)—$R^4$, wherein $R^4$ can be methyl.

In compounds of subgenus (1D), $R^6$ can be a moiety of Formula (2).

In compounds of subgenus (1D), $R^6$ can be a moiety of Formula (3).

In compounds of subgenus (1D), $R^6$ can be a moiety of Formula (4).

In compounds of subgenus (1D), $R^6$ can be a moiety of Formula (5).

A compound of Formula (1) can be a compound of sub-genus (1E):

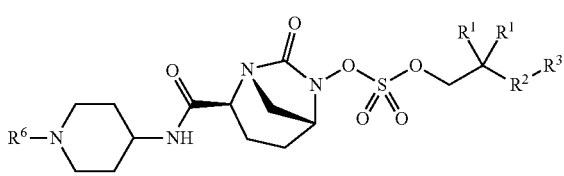

(1)

or a pharmaceutically acceptable salt thereof, wherein,
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond; and
$R^3$ can be $C_{1-3}$ alkyl.

A compound of Formula (1) can be a compound of sub-genus (1E):

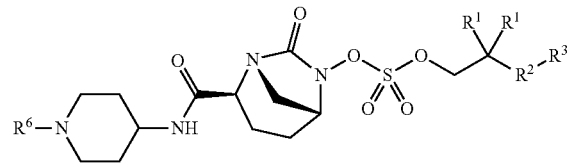

(1)

or a pharmaceutically acceptable salt thereof, wherein,
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond;
$R^3$ can be $C_{1-3}$ alkyl; and
$R^6$ can be selected from a moiety of Formula (2), a moiety of Formula (3), a moiety of Formula (4), and a moiety of Formula (5):

(2)

(3)

(4)

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and —CH(—$R^{13}$)—NH$_2$, wherein
$R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1E), each $R^1$ together with the carbon atom to which they are bonded form a $C_{3-6}$ heterocycloalkyl ring or a $C_{3-6}$ heterocycloalkyl ring;

In compounds of subgenus (1E), the one or more heteroatoms can be oxygen and the one or more substituents can be =O.

In compounds of subgenus (1E),
each $R^1$ together with the carbon atom to which they are bonded form a dihydrofuran-2(3H)-one ring;
$R^2$ can be a single bond; and
$R^3$ can be methyl.

In compounds of subgenus (1E), $R^6$ can be a moiety of Formula (2).

In compounds of subgenus (1E), $R^6$ can be a moiety of Formula (3).

In compounds of subgenus (1E), $R^6$ can be a moiety of Formula (4).

In compounds of subgenus (1E), $R^6$ can be a moiety of Formula (5).

A compound of Formula (1) can be a compound of sub-genus (1F):

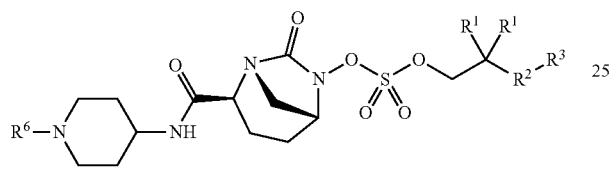

(1)

or a pharmaceutically acceptable salt thereof, wherein,
each $R^1$ can be independently selected from $C_{1-3}$ alkyl;
$R^2$ can be selected from a single bond and methanediyl; and
$R^3$ can be selected from —O—C(O)—$R^4$ and —C(O)—O—$R^4$, wherein $R^4$ can be selected from $C_{1-10}$ alkyl and substituted phenyl.

A compound of Formula (1) can be a compound of sub-genus (1F):

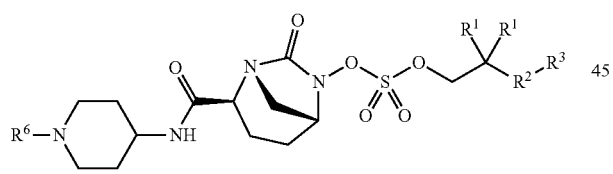

(1)

or a pharmaceutically acceptable salt thereof, wherein,
each $R^1$ can be independently selected from $C_{1-3}$ alkyl;
$R^2$ can be selected from a single bond and methanediyl;
$R^3$ can be selected from —O—C(O)—$R^4$ and —C(O)—O—$R^4$, wherein $R^4$ can be selected from $C_{1-10}$ alkyl and substituted phenyl; and
$R^6$ can be selected from a moiety of Formula (2), a moiety of Formula (3), a moiety of Formula (4), and a moiety of Formula (5):

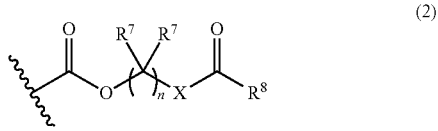

(2)

-continued

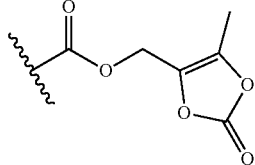

(3)

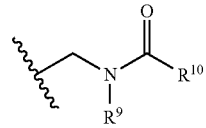

(4)

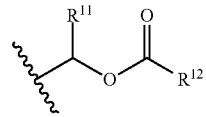

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and —CH(—$R^{13}$)—NH$_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1F), $R^2$ can be a single bond.
In compounds of subgenus (1F), $R^2$ can be methanediyl.
In compounds of subgenus (1F), $R^3$ can be —O—C(O)—$R^4$.
In compounds of subgenus (1F), $R^2$ can be methanediyl; and $R^3$ can be —O—C(O)—$R^4$.
In compounds of subgenus (1F), $R^3$ can be —C(O)—O—$R^4$.
In compounds of subgenus (1F), $R^2$ can be a single bond; and $R^3$ can be —C(O)—O—$R^4$.
In compounds of subgenus (1E), $R^2$ can be a single bond; $R^3$ can be —C(O)—O—$R^4$; and $R^4$ can be $C_{1-3}$ alkyl.
In compounds of subgenus (1F), $R^4$ can be $C_{1-10}$ alkyl.
In compounds of subgenus (1F), $R^4$ can be $C_{1-4}$ alkyl.
In compounds of subgenus (1F), $R^4$ can be substituted phenyl.
In compounds of subgenus (1F), $R^2$ can be methanediyl; $R^3$ can be —O—C(O)—$R^4$; and $R^4$ can be substituted phenyl.
In compounds of subgenus (1F), the one or more substituents can be independently selected from halogen, $C_{1-3}$ alkyl, and $C_{1-3}$ alkoxy.
In compounds of subgenus (1F), the substituted phenyl can be 2,6-substituted phenyl.
In compounds of subgenus (1F), each of the substituents can be selected from $C_{1-3}$ alkyl and $C_{1-3}$ alkoxy.
In compounds of subgenus (1F), the substituted phenyl can be 2,5,6-substituted phenyl.
In compounds of subgenus (1F), each of the substituents at the 2 and 6 positions can be independently selected from $C_{1-3}$ alkyl and $C_{1-3}$ alkoxy; and the substituent at the 5 position can be halogen.
In compounds of subgenus (1F), $R^6$ can be a moiety of Formula (2).

In compounds of subgenus (1F), $R^6$ can be a moiety of Formula (3).

In compounds of subgenus (1F), $R^6$ can be a moiety of Formula (4).

In compounds of subgenus (1F), $R^6$ can be a moiety of Formula (5).

A compound of Formula (1) can be a compound of sub-genus (1G):

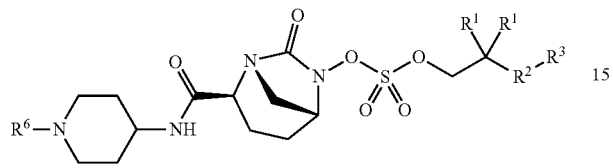

(1)

or a pharmaceutically acceptable salt thereof, wherein,
each $R^1$ can be independently selected from $C_{1-3}$ alkyl;
$R^2$ can be a single bond; and
$R^3$ can be $-CH=C(R^4)_2$, wherein each $R^4$ can be $-C(O)-O-R^8$, or each $R^4$ together with the carbon atom to which they are bonded from a substituted heterocyclohexyl ring.

A compound of Formula (1) can be a compound of sub-genus (1G):

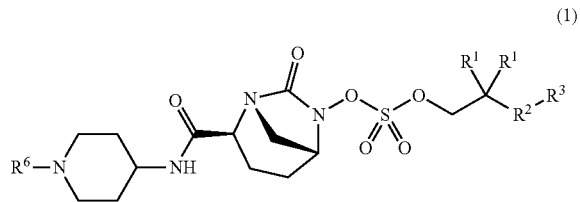

(1)

or a pharmaceutically acceptable salt thereof, wherein,
each $R^1$ can be independently selected from $C_{1-3}$ alkyl;
$R^2$ can be a single bond;
$R^3$ can be $-CH=C(R^4)_2$, wherein each $R^4$ can be $-C(O)-O-R^8$, or each $R^4$ together with the carbon atom to which they are bonded from a substituted heterocyclohexyl ring; and
$R^6$ can be selected from a moiety of Formula (2), a moiety of Formula (3), a moiety of Formula (4), and a moiety of Formula (5):

(2)

(3)

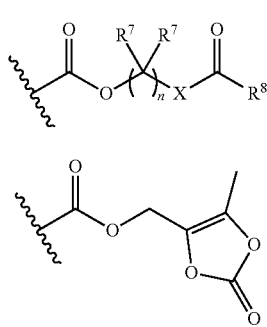

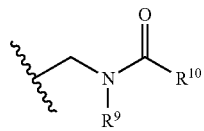

(4)

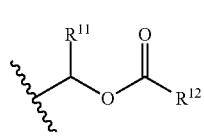

(5)

wherein,
each $R^7$ can be independently selected from hydrogen and $C_{1-6}$ alkyl;
n can be selected from 1 and 2;
X can be O;
$R^8$ can be selected from hydrogen, $C_{1-6}$ alkyl and $-CH(-R^{13})-NH_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1G), each $R^4$ can be $-C(O)-O-R^8$.

In compounds of subgenus (1G), each $R^4$ can be $-C(O)-O-R^8$, or each $R^4$ together with the carbon atom to which they are bonded from a substituted heterocyclohexyl ring.

In compounds of subgenus (1G), in the substituted heterocyclohexyl ring, the one or more heteroatoms can be oxygen.

In compounds of subgenus (1G), in the substituted heterocyclohexyl ring, the one or more substituents can be independently selected from $C_{1-3}$ alkyl and =O.

In compounds of subgenus (1G), the substituted heterocycloalkyl ring can be 2,2-dimethyl-5-yl-1,3-dioxane-4,6-dione.

In compounds of subgenus (1G), $R^6$ can be a moiety of Formula (2).

In compounds of subgenus (1G), $R^6$ can be a moiety of Formula (3).

In compounds of subgenus (1G), $R^6$ can be a moiety of Formula (4).

In compounds of subgenus (1G), $R^6$ can be a moiety of Formula (5).

A compound of Formula (1) can be a compound of sub-genus (1H):

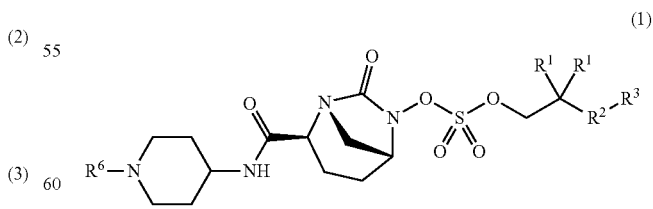

(1)

or a pharmaceutically acceptable salt thereof, wherein,
each $R^1$ can be independently selected from $C_{1-3}$ alkyl;
$R^2$ can be selected from a single bond and methanediyl;
$R^3$ can be substituted phenyl, wherein the one or more substituents can be independently selected from —CH$_2$—O—C(O)—R$^4$ and —O—C(O)—R$^4$, wherein R$^4$ can be selected from C$_{1-10}$ alkyl and phenyl; and R$^6$ can be selected from a moiety of Formula (2), a moiety of Formula (3), a moiety of Formula (4), and a moiety of Formula (5):

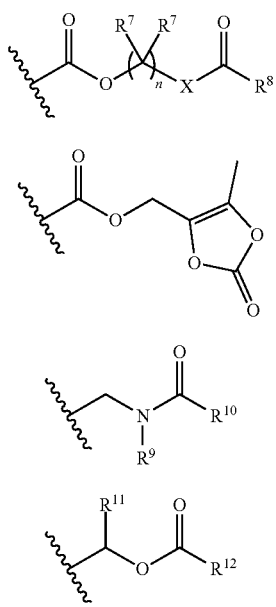

wherein,
each R$^7$ can be independently selected from hydrogen and C$_{1-6}$ alkyl;
n can be selected from 1 and 2;
X can be O;
R$^8$ can be selected from hydrogen, C$_{1-6}$ alkyl and —CH(—R$^{13}$)—NH$_2$, wherein R$^{13}$ can be selected from C$_{1-6}$ alkyl, alkoxy, and cycloalkoxy;
R$^9$ can be selected from hydrogen and C$_{1-6}$ alkyl;
R$^{10}$ can be selected from C$_{1-6}$ alkyl;
R$^{11}$ can be selected from hydrogen and C$_{1-6}$ alkyl; and
R$^{12}$ can be selected from C$_{1-6}$ alkyl.

In compounds of subgenus (1H), R$^2$ can be a single bond.

In compounds of subgenus (1H), R$^2$ can be 2-substituted phenyl.

In compounds of subgenus (1H), the one or more substituents can be —CH$_2$—O—C(O)—R$^4$.

In compounds of subgenus (1H), the one or more substituents can be —O—C(O)—R$^4$.

In compounds of subgenus (1H), R$^4$ can be C$_{1-10}$ alkyl.

In compounds of subgenus (1H), R$^4$ can be selected from methyl, ethyl, iso-propyl, pivalolyl, and phenyl.

In compounds of subgenus (1H), R$^6$ can be a moiety of Formula (2).

In compounds of subgenus (1H), R$^6$ can be a moiety of Formula (3).

In compounds of subgenus (1H), R$^6$ can be a moiety of Formula (4).

In compounds of subgenus (1H), R$^6$ can be a moiety of Formula (5).

A compound of Formula (1) can be a compound of sub-genus (1I):

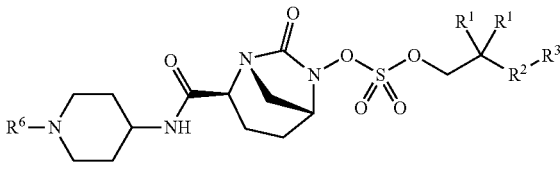

or a pharmaceutically acceptable salt thereof, wherein,
each R$^1$ can be independently selected from C$_{1-3}$ alkyl;
R$^2$ can be selected from —C(R$^8$)$_2$— and —CH$_2$—C(R$^8$)$_2$—, wherein each R$^8$ can be independently selected from C$_{1-3}$ alkyl;
R$^3$ can be selected from —C(O)—O—R$^4$ and —O—C(O)—R$^4$, wherein R$^4$ can be selected from C$_{1-10}$ alkyl, C$_{1-10}$ heteroalkyl, substituted C$_{1-10}$ alkyl, substituted C$_{1-10}$ heteroalkyl, and 4(yl-methyl)-5-methyl-1,3-dioxol-2-one; and
R$^6$ can be selected from a moiety of Formula (2), a moiety of Formula (3), a moiety of Formula (4), and a moiety of Formula (5):

wherein,
each R$^7$ can be independently selected from hydrogen and C$_{1-6}$ alkyl;
n can be selected from 1 and 2;
X can be O;
R$^8$ can be selected from hydrogen, C$_{1-6}$ alkyl and —CH(—R$^{13}$)—NH$_2$, wherein R$^{13}$ can be selected from C$_{1-6}$ alkyl, alkoxy, and cycloalkoxy;
R$^9$ can be selected from hydrogen and C$_{1-6}$ alkyl;
R$^{10}$ can be selected from C$_{1-6}$ alkyl;
R$^{11}$ can be selected from hydrogen and C$_{1-6}$ alkyl; and
R$^{12}$ can be selected from C$_{1-6}$ alkyl.

In compounds of subgenus (1I), each R$^1$ can be methyl.

In compounds of subgenus (1I), R$^2$ can be —C(R$^8$)$_2$—.

In compounds of subgenus (1I), R$^2$ can be —CH$_2$—C(R$^8$)$_2$—.

In compounds of subgenus (1I), each R$^8$ can be methyl.

In compounds of subgenus (1I), each $R^1$ can be methyl; and each $R^8$ can be methyl.

In compounds of subgenus (1I), $R^3$ can be —C(O)—O—$R^4$.

In compounds of subgenus (1I), $R^3$ can be —O—C(O)—$R^4$.

In compounds of subgenus (1I), $R^6$ can be a moiety of Formula (2).

In compounds of subgenus (1I), $R^6$ can be a moiety of Formula (3).

In compounds of subgenus (1I), $R^6$ can be a moiety of Formula (4).

In compounds of subgenus (1I), $R^6$ can be a moiety of Formula (5).

A compound of Formula (1) can be a compound of sub-genus (1J):

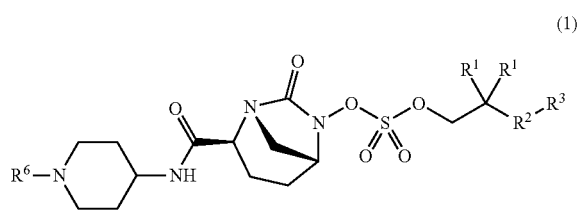

(1)

or a pharmaceutically acceptable salt thereof, wherein,
each $R^1$ together with the carbon atom to which they are bonded form a substituted $C_{5-6}$ heterocyclic ring;
$R^2$ can be a single bond;
$R^3$ can be $C_{1-3}$ alkyl; and
$R^6$ can be selected from a moiety of Formula (2), a moiety of Formula (3), a moiety of Formula (4), and a moiety of Formula (5):

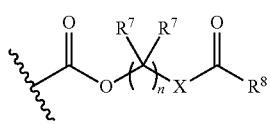

(2)

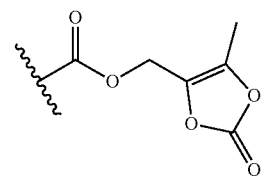

(3)

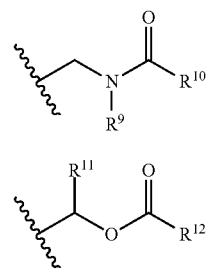

(4)

(5)

wherein,
each $R^7$ can be independently selected from hydrogen and $C_{1-6}$ alkyl;
n can be selected from 1 and 2;
X can be O;

$R^8$ can be selected from hydrogen, $C_{1-6}$ alkyl and —CH(—$R^{13}$)—NH$_2$, wherein $R^{13}$ can be selected from $C_{1-6}$ alkyl, alkoxy, and cycloalkoxy;
$R^9$ can be selected from hydrogen and $C_{1-6}$ alkyl;
$R^{10}$ can be selected from $C_{1-6}$ alkyl;
$R^{11}$ can be selected from hydrogen and $C_{1-6}$ alkyl; and
$R^{12}$ can be selected from $C_{1-6}$ alkyl.

In compounds of subgenus (1J), in the substituted $C_{5-6}$ heterocyclic ring, the one or more heteroatoms can be oxygen; and the one or more substituents can be independently selected from $C_{1-3}$ alkyl and =O.

In compounds of subgenus (1J), each $R^1$ together with the carbon atom to which they are bonded form a tetrahydro-2H-pyran-2-one ring.

In compounds of subgenus (1J),
each $R^1$ can be independently selected from $C_{1-3}$ alkyl;
$R^2$ can be selected from $C_{2-4}$ alkanediyl; and
$R^3$ can be substituted $C_{5-6}$ heterocycloalkyl, wherein the one or more heteroatoms can be independently selected from N and O; and the one or more substituents can be independently selected from $C_{1-3}$ alkyl and =O.

In compounds of subgenus (1J), $R^3$ can have the structure of Formula (6):

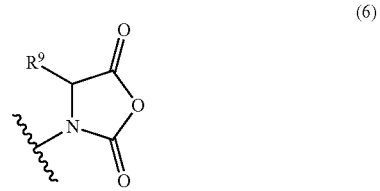

(6)

wherein $R^9$ can be selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

In compounds of subgenus (1J), $R^9$ can be selected from hydrogen and $C_{1-6}$ alkyl such as $C_{1-4}$ alkyl such as methyl or ethyl.

In compounds of subgenus (1J), $R^6$ can be a moiety of Formula (2).

In compounds of subgenus (1J), $R^6$ can be a moiety of Formula (3).

In compounds of subgenus (1J), $R^6$ can be a moiety of Formula (4).

In compounds of subgenus (1J), $R^6$ can be a moiety of Formula (5).

A compound of Formula (1) can have the structure of Formula (13):

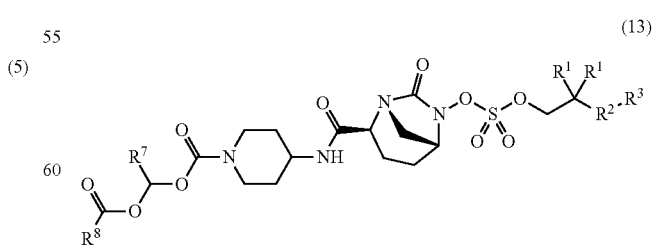

(13)

or a pharmaceutically acceptable salt thereof, wherein,
each $R^1$ can independently be selected from hydrogen and $C_{1-3}$ alkyl;

$R^2$ can be a single bond;

$R^3$ can be —C(O)—O—$R^4$, wherein $R^4$ can be $C_{1-4}$ alkyl;

$R^7$ can be selected from hydrogen and $C_{1-4}$ alkyl; and $R^8$ can be $C_{1-4}$ alkyl.

In compounds of Formula (13), each $R^1$ can independently be selected from hydrogen, methyl, ethyl, n-propyl, and iso-propyl.

In compounds of Formula (13), each $R^1$ can be methyl.

In compounds of Formula (13), $R^4$ can be selected from methyl, ethyl, n-propyl, and iso-propyl.

In compounds of Formula (13), $R^4$ can be ethyl.

In compounds of Formula (13), $R^7$ can be selected from hydrogen, methyl, ethyl, n-propyl, and iso-propyl.

In compounds of Formula (13), $R^7$ can be hydrogen.

In compounds of Formula (13), $R^7$ can be methyl.

In compounds of Formula (13), $R^8$ can be selected from methyl, ethyl, n-propyl, iso-propyl, n-butyl, iso-butyl, and tert-butyl.

In compounds of Formula (13), $R^8$ can be selected from n-butyl, iso-butyl, and tert-butyl.

In compounds of Formula (13), $R^8$ can be tert-butyl.

In compounds of Formula (13), each $R^8$ can be selected from methyl, ethyl, n-propyl, and iso-propyl.

A compound of Formula (13) can be selected from:

acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (6/86);

1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (7/87);

(pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (8/88);

(isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (9/89);

1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (10/90);

1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (11/91);

a pharmaceutically acceptable salt of any of the foregoing;

or a combination of any of the foregoing.

A compound of Formula (1) can be a solvate, a pharmaceutically acceptable salt, or a combination thereof.

In compounds of Formula (1), a pharmaceutically acceptable salt can be the hydrochloride salt.

In compounds of Formula (1), a pharmaceutically acceptable salt can be the dihydrochloride salt.

A compound of Formula (1) can be a pharmaceutically acceptable salt of a compound of Formula (1), a hydrate thereof, or a solvate of any of the foregoing.

The compound described herein may be synthesized using methods known in the art. The synthesis of the various diazabicyclo[3.2.1]octane structures described herein are conventional and are well known to those of skill in the art (Tandiparthi et al., PCT International Application Publication No. WO 2016/116788; Lampilas et al., U.S. Pat. No. 7,112,592; King et al., ACS Chemical Biology 2016; 11, 864; and Bush et al., Cold Spring Harb Perspect Med 2016; 6:a025247). Formation of sulfate esters are also well-known in the art (Simpson et al., J. Am. Chem. Soc. 2006, 128, 1605; Li et al., U.S. Application Publication No. 2009/0099253; Jandeleit et al., PCT International Application Publication No. WO 2009/033054; Jandeleit et al., PCT International Application Publication No. WO 2009/033079; and Jandeleit et al., PCT International Application Publication No. WO 2011/150380).

Sulfate monoester analogs of sulfate-containing compounds can be prepared by reacting a hydroxyl-substituted sulfate-containing compound with a chlorosulfate monoester to provide the corresponding sulfate monoester analog. The methods can be useful in preparing prodrugs of sulfate-containing pharmaceutical compounds.

Prodrugs are derivatized forms of drugs that following administration are converted or metabolized to an active form of the parent drug in vivo. Prodrugs are used to modify one or more aspects of the pharmacokinetics of a drug in a manner that enhances the therapeutic efficacy of a parent drug. For example, prodrugs are often used to enhance the oral bioavailability of a drug. To be therapeutically effective, drugs exhibiting poor oral bioavailability may require frequent dosing, large administered doses, or may need to be administered by other than oral routes, such as intravenously. In particular, many drugs with sulfate groups exhibit poor oral bioavailability.

Intramolecular cyclization prodrug strategies have been used to modify the pharmacokinetics of drugs. Intramolecular cyclization release prodrug strategies have been applied to drugs containing sulfonic acid functional groups. For example, prodrugs comprising a substituted neopentyl sulfonate ester derivative in which the neopentyl group is removed in vivo by unmasking a nucleophilic heteroatom bonded to a substituted neopentyl moiety followed by intramolecular cyclization to generate the parent drug in the sulfonic acid or sulfonic salt form have been described, for example, in U.S. Pat. Nos. 7,994,218 and 8,168,617. In such prodrugs the nucleophilic heteroatom can be nitrogen or oxygen and the nitrogen or oxygen nucleophile can be masked with an amine or alcohol protecting group, respectively, capable of being deprotected in vivo.

Sulfate monoester analogs of a sulfate-containing compound can be prepared by reacting a hydroxyl-substituted analog of the sulfate-containing compound with a chlorosulfate monoester under basic conditions, to provide the corresponding sulfate monoester analog. A chlorosulfate monoester can be prepared by reacting sulfuryl chloride with an alcohol having the desired promoiety. Neopentyl alcohols having neopentyl promoieties can be prepared by standard synthetic methods such as those described in U.S. Pat. Nos. 7,994,218 and 8,168,617.

For example, sulfate monoester analogs of relebactam can be synthesized by reacting tert-butyl 4-((2S,5R)-6-hydroxy-7-oxo-1,6-diazabicyclo[3.2.1]octane-2-carboxamido)piperidine-1-carboxylate hydrate with a chlorosulfate monoester having a desired promoiety in the presence of a base to provide the corresponding tert-butyl 4-((2S,5R)-6-hydroxy-7-oxo-1,6-diazabicyclo[3.2.1]octane-2-carboxamido)piperidine-1-yl sulfate monoester. The compound can then be deprotected in the presence of an acid to provide the sulfate monoester analog of relebactam.

tert-Butyl 4-((2S,5R)-6-hydroxy-7-oxo-1,6-diazabicyclo[3.2.1]octane-2-carboxamido)piperidine-1-carboxylate hydrate can be prepared by hydrogenating tert-butyl 4-((2S,5R)-6-(benzyloxy)-7-oxo-1,6-diazabicyclo[3.2.1]octane-2-carboxamido)piperidine-1-carboxylate using the methods described, for example, in U.S. Pat. Nos. 8,772,490; 9,035,062; and 9,284,273.

For example, a relebactam sulfate monoester analog of a sulfate monoester of Formula (7a) can be synthesized by reacting a cyclic hydroxamic acid of Formula (7b) with a chlorosulfonate monoester of Formula (7c) under basic conditions:

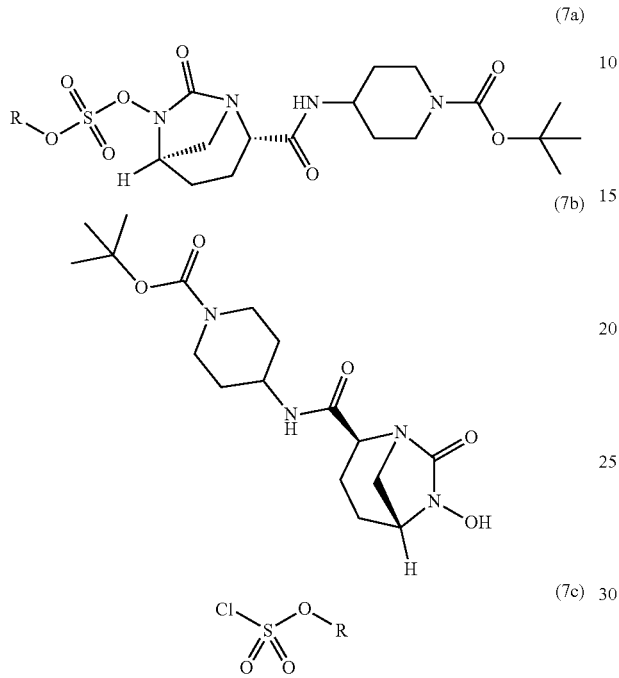

where,

R can be selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

The chlorosulfate monoester can comprise a chlorosulfate neopentyl ester, such as a chlorosulfate neopentyl ester of Formula (8):

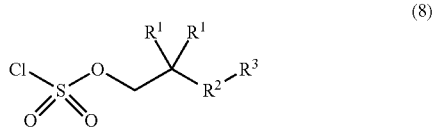

wherein, each $R^1$ can be independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ can be selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ can be selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

The chlorosulfate monoester can be synthesized by reacting an alcohol such as a neopentyl alcohol with sulfuryl chloride.

The method can be used to bond any suitable chlorosulfonate ester to a cyclic hydroxamic acid such as, for example, a chlorosulfonate ester of Formula (7c) and a cyclic hydroxamic acid of Formula (9) to provide the corresponding sulfate monoester analog of Formula (10):

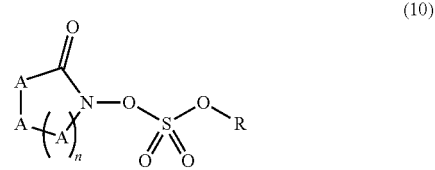

where,

R can be selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

n can be an integer from 1 to 6;

each A can be independently selected from —(CH$_2$)—, —(CHR)—, —(CR$_2$)—, —NH—, —NR—, O, and S, where R can be independently selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; or one A can be bonded to another A through a group -L-, where L can be selected from $C_{1-8}$ alkyl, $C_{1-8}$ heteroalkyl, substituted $C_{1-8}$ alkyl, and substituted $C-s_8$ heteroalkyl.

R can further include any of the promoieties disclosed herein, such as a promoiety having the structure:

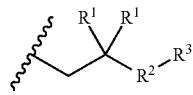

where $R^1$, $R^2$, and $R^3$ are defined as in Formula (1).

The amine group of relebactam can be derivatized by reacting the corresponding chlorosulfonate ester of (11) with a nitrophenol carbonate of Formula (12) in the presence of a base such as triethylamine:

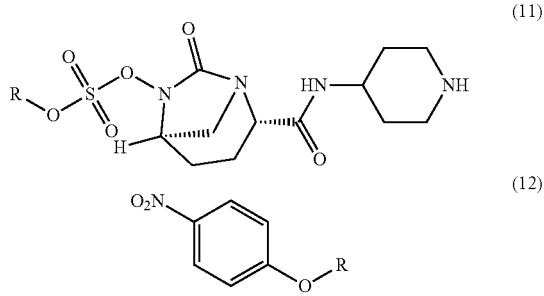

where R can be a carbonate such as a moiety of Formula (2)-(5) as disclosed herein.

Compounds of Formula (1) or pharmaceutically acceptable salts thereof may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. Pharmaceutical compositions provided by the present disclosure can be injectable formulations. Pharmaceutical compositions provided by the present disclosure can be injectable intravenous formulations. In certain embodiments, pharmaceutical compositions provided by the present disclosure are oral formulations. Oral formulations may be oral dosage forms.

Pharmaceutical compositions provided by the present disclosure may comprise a therapeutically-effective amount of a compound of Formula (1) or a pharmaceutically acceptable salt thereof together with a suitable amount of one or more pharmaceutically acceptable vehicles so as to provide a composition for proper administration to a patient. Suitable pharmaceutical vehicles and methods of preparing pharmaceutical compositions are described in the art.

Compounds of Formula (1) or pharmaceutically acceptable salts thereof or pharmaceutical composition thereof may be administered by intravenous injection. Suitable forms for injection include sterile aqueous solutions or dispersions of a compound of Formula (1) or a pharmaceutical composition thereof may be formulated in a physiological buffer solution.

Prior to administration, a compound of Formula (1) or a pharmaceutically acceptable salt thereof or a pharmaceutical composition thereof may be sterilized by any art recognized the technique, including addition of antibacterial or antifungal agents, for example, paraben, chlorobutanol, phenol, sorbic acid, thimersol, and the like. A compound of Formula (1) or a pharmaceutically acceptable salt thereof may be sterilized by filtration before administration to a subject thereby minimizing or eliminating the need for additional sterilization agents. An injectable dosage of a compound of Formula (1) may include from about 0.01 mL to about 10 mL, from about 0.1 mL to about 10 mL, from about 0.1 mL to about 5 mL, and in certain embodiments, from about 1 mL to about 5 mL.

Pharmaceutical compositions may comprise a therapeutically effective amount of one or more compounds of Formula (1), preferably in purified form, together with a suitable amount of a pharmaceutically acceptable vehicle, so as to provide a form for proper administration to a patient. When administered to a patient, the compounds and pharmaceutically acceptable vehicles are preferably sterile. Water is a preferred vehicle when the compound is administered intravenously. Saline solutions and aqueous dextrose and glycerol solutions may also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Pharmaceutical compositions may also contain minor amounts of wetting or emulsifying agents, or pH buffering agents. In addition, auxiliary, stabilizing, thickening, lubricating and coloring agents may be used.

Pharmaceutical compositions comprising a compound may be manufactured by means of conventional mixing, dissolving, granulating, levitating, emulsifying, encapsulating, entrapping or lyophilizing processes. Pharmaceutical compositions may be formulated in a conventional manner using one or more physiologically acceptable carriers, diluents; excipients or auxiliaries, which facilitate processing of compounds into preparations which can be used pharmaceutically. Proper formulation is dependent upon the route of administration chosen.

Pharmaceutical compositions provided by the present disclosure may take the form of solutions, suspensions, emulsion, or any other form suitable for use. Examples of suitable pharmaceutical vehicles are described in the art.

For parenteral administration, compounds of Formula (1) may be incorporated into a solution or suspension. Parenteral administration refers to the administration by injection, for instance by intravenous, intracapsular, intrathecal, intrapleural, intratumoral, or intraperitoneal injection or intravesically. In certain embodiments, a compound of Formula (1) can be administered intravenously.

A solution or suspension may also comprise at least one of the following adjuvants: sterile diluents such as water for injection, saline, fixed oils, polyethylene glycols, glycerol, propylene glycol or other synthetic solvents, antioxidants such as ascorbic acid or sodium bisulfite, buffers such as acetates, citrates or phosphates, and agents for adjustment of the tonicity such as sodium chloride or dextrose. A parenteral preparation may be enclosed into ampoules, disposable syringes or multiple dosage vessels made of glass or plastic.

When a compound is acidic or basic it may be included in any of the above-described formulations as the free acid or free base, a pharmaceutically acceptable salt, a solvate of any of the foregoing, or a hydrate of any of the foregoing. Pharmaceutically acceptable salts substantially retain the activity of the free acid or base, may be prepared by reaction with bases or acids, and tend to be more soluble in aqueous and other protic solvents than the corresponding free acid or base form.

Pharmaceutical compositions provided by the present disclosure comprise a compound of Formula (1) together with a suitable amount of one or more pharmaceutically acceptable vehicles so as to provide a composition for proper administration to a patient. Examples of suitable pharmaceutical vehicles are known in the art.

Pharmaceutical compositions comprising a compound of Formula (1) may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (1) or crystalline form thereof and one or more pharmaceutically acceptable vehicles into formulations that can be used pharmaceutically. Proper formulation is dependent upon the route of administration chosen. In certain embodiments, a pharmaceutical composition comprising a compound of Formula (1) or crystalline form thereof may be formulated for oral administration, and in certain embodiments for sustained release oral administration. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of at least one compound of Formula (1) calculated to produce an intended therapeutic effect. A unit dosage form may be for a single daily dose, for administration 2 times per day, or one of multiple daily doses, e.g., 3 or more times per day. When multiple daily doses are used, a unit dosage may be the same or different for each dose. One or more dosage forms may comprise a dose, which may be administered to a patient at a single point in time or during a time interval.

A compound of Formula (1) may be incorporated into pharmaceutical compositions to be administered orally. Oral administration of such pharmaceutical compositions may result in uptake of a compound of Formula (1) throughout the intestine and entry into the systemic circulation. Such oral compositions may be prepared in a manner known in the pharmaceutical art and comprise at least one compound of Formula (1) and at least one pharmaceutically acceptable vehicle. Oral pharmaceutical compositions may include a therapeutically effective amount of at least one compound of Formula (1) and a suitable amount of a pharmaceutically acceptable vehicle, so as to provide an appropriate form for administration to a patient.

Pharmaceutical compositions comprising at least one compound of Formula (1) may be formulated for immediate release for parenteral administration, oral administration, or for any other appropriate route of administration.

Controlled drug delivery systems may be designed to deliver a drug in such a way that the drug level is maintained within a therapeutically effective window and effective and safe blood levels are maintained for a period as long as the system continues to deliver the drug at a particular rate. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution-controlled systems, diffusion-controlled systems, ion exchange resins, osmotically controlled systems, erodable matrix systems, pH independent formulations, gastric retention systems, and the like.

An oral dosage form provided by the present disclosure may be a controlled release dosage form. Controlled delivery technologies can improve the absorption of a drug in a particular region or regions of the gastrointestinal tract.

The appropriate oral dosage form for a particular pharmaceutical composition provided by the present disclosure may depend, at least in part, on the gastrointestinal absorption properties of a compound of Formula (1), the stability of a compound of Formula (1) in the gastrointestinal tract, the pharmacokinetics of a compound of Formula (1), and the intended therapeutic profile. An appropriate controlled release oral dosage form may be selected for a particular compound of Formula (1). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

Gastric retention dosage forms, i.e., dosage forms that are designed to be retained in the stomach for a prolonged period of time, may increase the bioavailability of drugs that are most readily absorbed by the upper gastrointestinal tract. For example, certain compounds of Formula (1) may exhibit limited colonic absorption and be absorbed primarily from the upper gastrointestinal tract. Thus, dosage forms that release a compound of Formula (1) in the upper gastrointestinal tract and/or retard transit of the dosage form through the upper gastrointestinal tract will tend to enhance the oral bioavailability of the compound of Formula (1). The residence time of a conventional dosage form in the stomach is about 1 to about 3 hours. After transiting the stomach, there is approximately a 3-hour to 5-hour window of bioavailability before the dosage form reaches the colon. However, if the dosage form is retained in the stomach, the drug may be released before it reaches the small intestine and will enter the intestine in solution in a state in which it can be more readily absorbed. Another use of a gastric retention dosage form is to improve the bioavailability of a drug that is unstable to the basic conditions of the intestine.

Pharmaceutical compositions provided by the present disclosure may be practiced with dosage forms adapted to provide sustained release of a compound of Formula (1) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Sustained release oral dosage forms may be in any appropriate form for oral administration, such as, for example, in the form of tablets, pills, or granules. Granules can be filled into capsules, compressed into tablets, or included in a liquid suspension. Sustained release oral dosage forms may additionally include an exterior coating to provide, for example, acid protection, ease of swallowing, flavor, identification, and the like.

Sustained release oral dosage forms may comprise a therapeutically effective amount of a compound of Formula (1) and at least one pharmaceutically acceptable vehicle. In certain embodiments, a sustained release oral dosage form may comprise less than a therapeutically effective amount of a compound of Formula (1) and a pharmaceutically effective vehicle. Multiple sustained release oral dosage forms, each dosage form comprising less than a therapeutically effective amount of a compound of Formula (1) may be administered at a single time or over a period of time to provide a therapeutically effective dose or regimen for treating a disease in a patient. In certain embodiments, a sustained release oral dosage form comprises more than one compound of Formula (1).

Sustained release oral dosage forms provided by the present disclosure can release a compound of Formula (1) from the dosage form to facilitate the ability of the compound of Formula (1) to be absorbed from an appropriate region of the gastrointestinal tract, for example, in the small intestine or in the colon. Sustained release oral dosage forms may release a compound of Formula (1) from the dosage form over a period of at least about 4 hours, at least about 8 hours, at least about 12 hours, at least about 16 hours, at least about 20 hours, and in certain embodiments, at least about 24 hours. In certain embodiments, sustained release oral dosage forms may release a compound of Formula (1) from the dosage form in a delivery pattern, for example, corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 24 hours; where wt % refers to the percent of the total weight of the compound in the dosage form. Sustained release oral dosage forms may release a compound of Formula (1) from the dosage form in a delivery pattern, for example, corresponding to about 0 wt % to about 20 wt % in about 0 to about 4 hours; about 20 wt % to about 50 wt % in about 0 to about 8 hours; about 55 wt % to about 85 wt % in about 0 to about 14 hours; and about 80 wt % to about 100 wt % in about 0 to about 20 hours. In certain embodiments, sustained release oral dosage forms may release a compound of Formula (1) from the dosage form in a delivery pattern corresponding to about 0 wt % to about 20 wt % in about 0 to about 2 hours; about 20 wt % to about 50 wt % in about 0 to about 4 hours; about 55 wt % to about 85 wt % in about 0 to about 7 hours; and about 80 wt % to about 100 wt % in about 0 to about 8 hours.

Sustained release oral dosage forms comprising a compound of Formula (1) may provide a concentration of the corresponding drug in the plasma, blood, cerebrospinal fluid, or tissue of a patient over time, following oral administration to the patient. The concentration profile of the drug may exhibit an AUC that is proportional to the dose of the corresponding compound of Formula (1).

Regardless of the specific type of controlled release oral dosage form used, a compound of Formula (1) may be released from an orally administered dosage form over a sufficient period of time to provide prolonged therapeutic concentrations of the compound of Formula (1) in the plasma and/or blood of a patient. Following oral administration, a dosage form comprising a compound of Formula (1) may provide a therapeutically effective concentration of the corresponding drug in the plasma and/or blood of a patient for a continuous time period of at least about 4 hours, of at least about 8 hours, for at least about 12 hours, for at least about 16 hours, and in certain embodiments, for at least about 20 hours following oral administration of the dosage form to the patient. The continuous time periods during which a therapeutically effective concentration of the drug is maintained may be the same or different. The continuous period of time during which a therapeutically effective plasma concentration of the drug is maintained may begin shortly after oral administration or following a time interval.

An appropriate dosage of a compound of Formula (1) or pharmaceutical composition comprising a compound of Formula (1) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

A compound of Formula (1) and/or pharmaceutical composition thereof can generally be used in an amount effective to achieve the intended purpose. For use to treat a disease such as a bacterial infection, a compound of Formula (1) and/or pharmaceutical compositions thereof, may be administered or applied in a therapeutically effective amount.

The amount of a compound of Formula (1) and/or pharmaceutical composition thereof that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1) and/or pharmaceutical composition thereof administered will depend on, among other factors, the subject being treated, the weight of the subject, the severity of the affliction, the manner of administration and the judgment of the prescribing physician.

A compound of Formula (1) may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

In certain embodiments, a therapeutically effective dose of a compound of Formula (1) and/or pharmaceutical composition thereof will provide therapeutic benefit without causing substantial toxicity. Toxicity of compounds of Formula (1) and/or pharmaceutical compositions thereof may be determined using standard pharmaceutical procedures and may be readily ascertained by the skilled artisan. The dose ratio between toxic and therapeutic effect is the therapeutic index. In certain embodiments, a compound of Formula (1) and/or pharmaceutical composition thereof exhibits a particularly high therapeutic index in treating disease and disorders. In certain embodiments, a dose of a compound of Formula (1) and/or pharmaceutical composition thereof will be within a range of circulating concentrations that include an effective dose with minimal toxicity.

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. In certain embodiments, a kit for use in treating cancer in a patient comprises a compound of Formula (1) or a pharmaceutically acceptable salt thereof, a pharmaceutically acceptable vehicle for administering the compound, and instructions for administering the compound to a patient.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

The amount of a compound of Formula (1) that will be effective in the treatment of a cancer will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

In certain embodiments, pharmaceutical compositions comprising a compound of Formula (1) may be administered once per day, twice per day, and in certain embodiments at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1) contained within each of the multiple dosage forms may be the same or different.

Suitable daily dosage ranges for administration may range from about 2 µg to about 20 mg of a compound of Formula (1) per kilogram body weight.

Suitable daily dosage ranges for administration may range from about 1 µg to about 50 mg of a compound of Formula (1) per square meter ($m^2$) of body surface.

In certain embodiments, a compound of Formula (1) may be administered to treat cancer in a subject in an amount from about 1 mg to about 2,000 mg per day, from about 100 µg to about 1,500 mg per day, from about 20 µg to about 1,000 mg per day, or in any other appropriate daily dose.

In certain embodiments, pharmaceutical compositions comprising a compound of Formula (1) may be administered to treat cancer in a subject so as to provide a therapeutically effective concentration of a compound of Formula (1) in the blood or plasma of the subject. In certain embodiments, a therapeutically effective concentration of a compound of Formula (1) in the blood or plasma of a subject is from about 1 µg/mL to about 60 µg/mL, from about 2 µg/mL to about 50 µg/mL, from about 5 µg/mL to about 40 µg/mL, from about 5 µg/mL to about 20 µg/mL, and in certain embodiments, from about 5 µg/mL to about 10 µg/mL. In certain embodiments, a therapeutically effective concentration of a compound of Formula (1) in the blood or plasma of a subject is at least about 2 µg/mL, at least about 5 µg/mL, at least about 10 µg/mL, at least about 15 µg/mL, at least about 25 µg/mL, and in certain embodiments, at least about 30 µg/mL. In certain embodiments, a therapeutically effective concentration of a compound of Formula (1) in the blood or plasma of a subject is less than an amount that causes unacceptable adverse effects including adverse effects to homeostasis. In certain embodiments, a therapeutically effective concentration of a compound of Formula (1) in the blood or plasma of a subject is an amount sufficient to restore and/or maintain homeostasis in the subject.

In certain embodiments, pharmaceutical compositions comprising a compound of Formula (1) may be administered to treat cancer in a subject so as to provide a therapeutically effective concentration of a compound of Formula (1) in the blood or plasma of a subject for an extended period of time such as, for example, for at least about 4 hours, for at least about 6 hours, for at least about 8 hours, for at least about 10 hours, and in certain embodiments, for at least about 12 hours.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided to treat the cancer being treated with the compound of Formula (1) or to treat a disease, disorder, or condition other than the cancer being treated with the compound of Formula (1).

In certain embodiments, a compound of Formula (1) may be used in combination with at least one other therapeutic agent. In certain embodiments, a compound of Formula (1) may be administered to a patient together with another compound for treating cancer in the subject. In certain embodiments, the at least one other therapeutic agent may be a different compound of Formula (1). A compound of Formula (1) and the at least one other therapeutic agent may act additively or, and in certain embodiments, synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating cancer or a different disease, disorder or condition than cancer. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

In certain embodiments, pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

In certain embodiments, pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a subject. In certain embodiments, a pharmaceutical composition comprising a compound of Formula (1) may be co-administered with an active agent having pharmacological effects that enhance the therapeutic efficacy of the compound of Formula (1).

In certain embodiments, a compound of Formula (1) or a pharmaceutical composition comprising a compound of Formula (1) may be administered in conjunction with an agent known or believed to be effective in treating cancer in a patient.

In certain embodiments, a compound of Formula (1) or a pharmaceutical composition comprising a compound of Formula (1) may be administered in conjunction with an agent known or believed to interfere with proliferation. In certain embodiments, a compound of Formula (1) or a pharmaceutical composition comprising a compound of Formula (1) may be administered in conjunction with an agent known or believed to interfere with mitosis. In certain embodiments, a compound of Formula (1) or a pharmaceutical composition comprising a compound of Formula (1) may be administered in conjunction with an agent known or believed to interfere with DNA replication. In certain embodiments, a compound of Formula (1) or a pharmaceutical composition comprising a compound of Formula (1) may be administered in conjunction with an agent known or believed to interfere with DNA repair.

For use to treat or prevent infectious disease, the compounds or compositions described herein, or pharmaceutical compositions thereof, can be administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from 1 microgram per kilogram to 50 milligrams per kilogram, from 10 micrograms per kilogram to 30 milligrams per kilogram, from 100 micrograms per kilogram to 10 milligrams per kilogram, or from 100 micrograms per kilogram to 5 milligrams per kilogram).

In some embodiments, a therapeutically effective dosage should produce a serum concentration of active ingredient of from 0.001 ng/mL to 50 µg/mL to 200 µg/mL. The compositions, in other embodiments, should provide a dosage of from 0.0001 mg to 70 mg of compound per kilogram of body weight per day. Dosage unit forms are prepared to provide from 0.01 mg to 0.1 mg, form 1 mg to 500 mg, or from 1,000 mg 5,000 mg, and in some embodiments from 10 mg to 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial sulfonamide derivative that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known antimicrobial agents by comparing the $IC_{50}$, MIC and/or $I_{100}$ of the specific compound disclosed herein with that of a known antimicrobial agent and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: *The Pharmacological Basis of Therapeutics*, Ch. 1, p. 1).

The therapy may be repeated intermittently while infections are detectable, or even when they are not detectable. Administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

A compound of Formula (1) and/or pharmaceutical composition thereof can generally be used in an amount effective to achieve the intended purpose. For use to treat a disease such as a bacterial infection, a compound of Formula (1) and/or pharmaceutical compositions thereof, may be administered or applied in a therapeutically effective amount.

The amount of a compound of Formula (1) and/or pharmaceutical composition thereof that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1) and/or pharmaceutical composition thereof administered will depend on, among other factors, the subject being treated, the weight of the subject, the severity of the affliction, the manner of administration and the judgment of the prescribing physician.

A compound of Formula (1) may be assayed in vitro and in vivo, for the desired therapeutic activity, prior to use in humans. For example, in vitro assays may be used to determine whether administration of a specific compound or a combination of compounds is preferred. The compounds may also be demonstrated to be effective and safe using animal model systems.

A therapeutically effective dose of a compound of Formula (1) and/or pharmaceutical composition thereof will provide therapeutic benefit without causing substantial toxicity. Toxicity of compounds of Formula (1) and/or pharmaceutical compositions thereof may be determined using standard pharmaceutical procedures and may be readily ascertained by the skilled artisan. The dose ratio between toxic and therapeutic effect is the therapeutic index. A compound of Formula (1) and/or pharmaceutical composition thereof exhibits a particularly high therapeutic index in treating disease and disorders. A dose of a compound of Formula (1) and/or pharmaceutical composition thereof will be within a range of circulating concentrations that include an effective dose with minimal toxicity.

A compound of Formula (1), a pharmaceutically acceptable salt thereof, or a pharmaceutical composition of any of the foregoing may be included in a kit that may be used to administer the compound to a patient for therapeutic purposes. A kit may include a pharmaceutical composition comprising a compound of Formula (1) suitable for administration to a patient and instructions for administering the pharmaceutical composition to the patient. A kit for use in treating a bacterial infection in a patient comprises a compound of Formula (1) or a pharmaceutically acceptable salt thereof, a pharmaceutically acceptable vehicle for administering the compound, and instructions for administering the compound to a patient. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

The amount of a compound of Formula (1) that will be effective in the treatment of a bacterial infection will depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of compound of Formula (1) administered may depend on, among other factors, the subject being treated, the weight of the subject, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of compound of Formula (1) and appropriate dosing intervals may be selected to maintain a sustained therapeutically effective concentration of the compound of Formula (1) in the blood of a patient, and in certain embodiments, without exceeding a minimum adverse concentration.

Pharmaceutical compositions comprising a compound of Formula (1) may be administered once per day, twice per day, or at intervals of more than once per day. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of compound of Formula (1) contained within each of the multiple dosage forms may be the same or different.

Suitable daily dosage ranges for administration may range from 2 µg to 20 mg of a compound of Formula (1) per kilogram body weight.

Suitable daily dosage ranges for administration may range from 1 µg to 50 mg of a compound of Formula (1) per square meter ($m^2$) of body surface.

A compound of Formula (1) may be administered to treat a bacterial infection in a patient in an amount from 1 mg to 2,000 mg per day, from 100 µg to 1,500 mg per day, from 20 µg to 1,000 mg per day, or in any other appropriate daily dose.

A pharmaceutical composition comprising a compound of Formula (1) may be administered to treat a bacterial infection in a subject to provide a therapeutically effective concentration of a compound of Formula (1) in the blood or plasma of the subject. A therapeutically effective concentration of a compound of Formula (1) in the blood or plasma of a subject is from 1 µg/mL to 60 µg/mL, from 2 µg/mL to 50 µg/mL, from 5 µg/mL to 40 µg/mL, from 5 µg/mL to 20 µg/mL, or from 5 µg/mL to 10 µg/mL. A therapeutically effective concentration of a compound of Formula (1) in the blood or plasma of a subject is at least 2 µg/mL, at least 5 µg/mL, at least 10 µg/mL, at least 15 µg/mL, at least 25 µg/mL, or at least 30 µg/mL. A therapeutically effective concentration of a compound of Formula (1) in the blood or plasma of a subject is less than an amount that causes unacceptable adverse effects including adverse effects to homeostasis. A therapeutically effective concentration of a compound of Formula (1) in the blood or plasma of a subject is an amount sufficient to restore and/or maintain homeostasis in the subject.

A pharmaceutical composition comprising a compound of Formula (1) may be administered to treat a bacterial infection in a patient so as to provide a therapeutically effective concentration of a compound of Formula (1) in the blood or plasma of a subject for an extended period of time such as, for example, for at least 4 hours, for at least 6 hours, for at least 8 hours, for at least 10 hours, or for at least 12 hours.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided to treat the bacterial infection being treated with the compound of Formula (1) or to treat a disease, disorder, or condition other than a bacterial infection being treated with the compound of Formula (1).

The compounds and compositions described herein can be used in a wide variety of applications to treat infectious diseases in a subject. The methods generally involve administering a therapeutically effective amount of a compound of Formula (1) or a pharmaceutical composition thereof to the subject or administering a therapeutically effective amount of a compound of Formula (1) and an antibiotic, or a pharmaceutical composition thereof to the subject.

Compounds provided by the present disclosure are prodrugs of β-lactamase inhibitors. Compounds and compositions provided by the present disclosure can be used to treat a disease in which the etiology of the disease is associated with the expression of β-lactamases. For example, certain bacterial infections are resistant to β-lactamase antibiotics because β-lactamases produced by the bacteria hydrolyze the β-lactam ring of the β-lactam antibiotic.

Compounds and compositions provided by the present disclosure can be used to treat a bacterial disease in a patient.

Compounds and compositions provided by the present disclosure can be used to treat a bacterial infection. For example, compounds and composition provided by the present disclosure can be used to treat a bacterial infection associated with bacteria such as obligate aerobic bacteria, obligate anaerobic bacteria, faculatitive anaerobic bacteria, and microaerophilic bacteria.

Examples of obligate aerobic bacteria include gram-negative cocci such as *Moraxella catarrhalis, Neisseria gonorrhoeae*, and *N. meningitidi*; gram-positive bacilli such as *Corynebacterium jeikeium*; acid-fast bacilli such as *Mycobacterium avium* complex, *M. kansasii, M. leprae, M. tuberculosis*, and *Nocardia* sp; nonfermentative, non-enterobacteriaceae such as *Acinetobacter calcoaceticus, Elizabethkingia meningoseptica* (previously *Flavobacterium meningosepticum*), *Pseudomonas aeruginosa, P. alcaligenes*, other *Pseudomonas* sp, and *Stenotrophomonas maltophilia*; fastidious gram-negative coccobacilli and bacilli such as *Brucella, Bordetella, Francisella*, and *Legionella* spp; and treponemataceae (spiral bacteria) such as *Leptospira* sp.

Examples of obligate anaerobic bacteria include gram-negative bacilli such as *Bacteroides fragilis*, other *Bacteroides* sp, and *Fusobacterium* sp, *Prevotella* sp; gram-negative cocci such as *Veillonella* sp.; gram-positive cocci such as *Peptococcus niger*, and *Peptostreptococcus* sp.; non-spore-forming gram-positive bacilli such as *Clostridium botulinum, C. perfringens, C. tetani*, other *Clostridium* sp; and endospore-forming gram-positive bacilli such as *Clostridium botulinum, C. perfringens, C. tetani*, and other *Clostridium* sp.

Examples of facultative anaerobic bacteria include gram-positive cocci, catalase-positive such as *Staphylococcus aureus* (coagulase-positive), *S. epidermidis* (coagulase-negative), and other coagulase-negative staphylococci; gram-positive cocci, catalase-negative such as *Enterococcus faecalis, E. faecium, Streptococcus agalactiae* (group *B. streptococcus*), *S. bovis, S. pneumoniae, S. pyogenes* (group A *streptococcus*), viridans group streptococci (*S. mutans, S. mitis, S. salivarius, S. sanguis*), *S. anginosus* group (*S. anginosus, S. milleri, S. constellatus*), and *Gemella morbillorum*; gram-positive bacilli such as *Bacillus anthracis, Erysipelothrix rhusiopathiae*, and *Gardnerella vaginalis* (gram-variable); gram-negative bacilli such as Enterobacteriaceae (*Citrobacter* sp, *Enterobacter aerogenes, Escherichia coli, Klebsiella* sp, *Morganella morganii, Proteus* sp,

*Plesiomonas shigelloides, Providencia rettgeri, Salmonella typhi*, other *Salmonella* sp, *Serratia marcescens*, and *Shigella* sp, *Yersinia enterocolitica, Y. pestis*); fermentative, non-Enterobacteriaceae such as *Aeromonas hydrophila, Chromobacterium violaceum*, and *Pasteurella multocida*; fastidious gram-negative coccobacilli and bacilli such as *Actinobacillus actinomycetemcomitans, Bartonella bacilliformis, B. henselae, B. quintana, Eikenella corrodens, Haemophilus influenzae*, and other *Haemophilus* sp; mycoplasma such as *Mycoplasma pneumoniae*; and treponemataceae (spiral bacteria) such as *Borrelia burgdorferi*, and *Treponema pallidum*.

Examples of microaerophilic bacteria include curved bacilli such as *Campylobacter jejuni, Helicobacter pylori, Vibrio cholerae*, and *V. vulnificus*; obligate intracellular parasitic; chlamydiaceae such as *Chlamydia trachomatis, Chlamydophila pneumoniae*, and *C. psittaci*; coxiellaceae such as *Coxiella burnetii*; and rickettsiales such as *Rickettsia prowazekii, R. rickettsii, R. typhi, R. tsutsugamushi, Ehrlichia chaffeensis*, and *Anaplasma phagocytophilum*.

Compounds and compositions provided by the present disclosure can be used to treat a bacterial disease in which the bacteria produce a β-lactamase. Examples of bacteria that produce a β-lactamase include *Mycobacterium tuberculosis*, methicillin-resistant *Staphylococcus aureus, Staphyloccus, Enterobacteriaceae, Pseudomonas aeruginosa, Haemophilus influenzae, Klebsiella pneumoniae, Citrobacter*, and *Morganella*.

Compounds and compositions provided by the present disclosure can be used to treat a bacterial disease in which a β-lactamase inhibitor is effective in treating the bacterial disease such as a bacterial infection.

An infectious disease can be a bacterial infection. A bacterial infection can be an infection of a gram-positive bacteria. A bacterial infection can be an infection of a gram-negative bacteria. Examples of gram-negative bacteria include *Acinetobacter, Aeromonas, Bacteroides, Burkholderia, Citrobacter, Enterobacter, Escherichia, Fusobacterium, Haemophilus, Klebsiella, Moraxella, Morganella, Mycoplasma, Neisseria, Pantoea, Pasteurella, Plesiomonas, Porphyromonas, Prevotella, Proteus, Providencia, Pseudomonas, Salmonella, Serratia, Shigella, Spirillum, Stenotrophomonas, Streptobacillus, Treponema*, or *Yersinia*. Examples of gram-negative bacteria include *Acinetobacter baumannii, Aeromonas hydrophila, Arizona hinshawii, Bacteroidesfragilis, Branhamella catarrhalis, Burkholderia cepacia, Citrobacter diversus, Citrobacterfreundii, Enterobacter aerogenes, Enterobacter cloacae, Escherichia coli, Fusobacterium nucleatum, Haemophilus influenzae, Haemophilus parainfluenzae, Klebsiella oxytoca, Klebsiella pneumoniae, Moraxella catarrhalis, Morganella morganii, Neisseria gonorrhoeae, Neisseria meningitidis, Pantoea agglomerans, Pasteurella multocida, Plesiomonas shigelloides, Prevotella melaninogenica, Proteus mirabilis, Proteus rettgeri, Proteus vulgaris, Pseudomonas aeruginosa, Pseudomonas diminuta, Pseudomonas fluorescens, Pseudomonas stutzeri, Salmonella enterica, Salmonella enteritidis, Salmonella typhi, Serratia marcescens, Spirillum minus, Stenotrophomonas maltophilia, Streptobacillus moniliformis, Treponema pallidum*, or *Yersinia enterocolitica*.

The development of antibiotic resistance continues to grow as a problem facing patients and clinicians. Accordingly, the U.S. Food and Drug Administration has identified the following pathogens as presenting a potentially serious threat to public health: *Acinetobacter* species, *Aspergillus* species, *Burkholderia cepacia* complex, *Campylobacter* species, *Candida* species, *Clostridium difficile, Coccidioides* species, *Cryptococcus* species, Enterobacteriaceae (e.g., *Klebsiella pneumoniae*), *Enterococcus* species, *Helicobacter pylori, Mycobacterium tuberculosis* complex, *Neisseria gonorrhoeae, N. meningitidis*, non-tuberculous mycobacteria species, *Pseudomonas* species, *Staphylococcus aureus, Streptococcus agalactiae, S. pneumoniae, S. pyogenes*, and *Vibrio cholerae*. The FDA has designated these organisms "qualifying pathogens" for purposes of the Generating Antibiotic Incentives Now (GAIN) Act, intended to encourage development of new antibacterial and antifungal drugs for the treatment of serious or life-threatening infections. Other types of bacteria can be added or subtract from the list of "qualifying pathogens" and the methods provided by the present disclosure encompass any newly added bacteria. Compounds, compositions, methods, and kits provided by the present disclosure are useful for the treatment of diseases, infections caused by many of these organisms as well.

The compounds and compositions described herein may be used treat or prevent various diseases caused by the above bacteria. These include, but are not limited to, venereal disease, pneumonia, complicated urinary tract infections, urinary tract infections, complicated intra-abdominal infections and intra-abdominal infections.

Methods provided by the present disclosure can also be administered to a patient to inhibit a β-lactamase. Compounds and compositions provided by the present disclosure can be administered to a patient to inhibit any suitable type of β-lactamase. Examples of types of β-lactamases include extended-spectrum β-lactamases such as TEM β-lactamases (Class A), SHV β-lactamases (Class A), CTX-M β-lactamases (Class A), OXA β-lactamases (Class D), and other extended spectrum β-lactamases such as PER, VEB, GES, and IBC β-lactamases; inhibitor-resistant β-lactamases; AmpC-type-β lactamases (Class C); carbapenemases such as IMP-type carbapenemases (metallo-β-lactamases) (Class B), VIM (verona integron-encoded metallo-β-lactamase (Class B), OXA (oxcillinase) group β-lactamases (Class D), KPC (*K. pneumoniae* carbapenemase) (Class A), CMY (Class C), SME, IMI, NMC, and CcrA, and NDM-1 (New Delhi metallo-β-lactamase) (Class B).

Examples of types of β-lactamases include cephalosporinases, penicillinases, cephalosporinases, broad-spectrum β-lactamases, extended-spectrum β-lactamases, inhibitor-resistant β-lactamases, carbenicillinase, cloxicillinases, oxacillinases, carbapenemases, and metalloenzymes.

Types of β-lactamases include Class A, Class B, Class C, and Class D β-lactamases.

Compounds and compositions provided by the present disclosure can be administered orally.

Compounds provided by the present disclosure, when orally administered, provide an enhanced oral bioavailability of the β-lactamase inhibitor compared to the oral bioavailability of the parent B-lactamase inhibitor. For example, compounds of Formula (1) can exhibit an oral bioavailability (F %) of the parent compound, relebactam, of at least 10%, at least 20%, at least 30%, at least 40%, at least 50%, or at least 60%.

Pharmaceutical compositions provided by the present disclosure may further comprise one or more pharmaceutically active compounds in addition to a compound of Formula (1). Such compounds may be provided to treat a bacterial infection being treated with the compound of Formula (1) or to treat a disease, disorder, or condition other than the bacterial infection being treated with the compound of Formula (1).

A compound of Formula (1) may be used in combination with at least one other therapeutic agent. A compound of Formula (1) may be administered to a patient together with another compound for treating a bacterial infection in the patient. The at least one other therapeutic agent may be a different compound of Formula (1). A compound of Formula (1) and the at least one other therapeutic agent may act additively or synergistically. The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating a bacterial infection or a different disease, disorder or condition than a bacterial infection. Methods provided by the present disclosure include administration of a compound of Formula (1) and one or more other therapeutic agents provided that the combined administration does not inhibit the therapeutic efficacy of a compound of Formula (1) and/or does not produce adverse combination effects.

Pharmaceutical compositions comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain embodiments of combination therapy, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

Pharmaceutical compositions comprising a compound of Formula (1) may be administered with one or more substances to enhance, modulate and/or control release, bioavailability, therapeutic efficacy, therapeutic potency, stability, and the like of a compound of Formula (1). For example, to enhance the therapeutic efficacy of a compound of Formula (1), a compound of Formula (1) or a pharmaceutical composition comprising a compound of Formula (1) may be co-administered with one or more active agents to increase the absorption or diffusion of the compound of Formula (1) from the gastrointestinal tract to the systemic circulation, or to inhibit degradation of the compound of Formula (1) in the blood of a subject. A pharmaceutical composition comprising a compound of Formula (1) may be co-administered with an active agent having pharmacological effects that enhance the therapeutic efficacy of the compound of Formula (1).

A compound of Formula (1) may be administered together with another therapeutic compound, where the compound of Formula (1) enhances the efficacy of the other therapeutic compound. For example, the other therapeutic compound can be an antibiotic such as a β-lactam antibiotic, and the compound of Formula (1), which provides a systemic β-lactamase inhibitor, can enhance the efficacy of the β-lactam antibiotic by inhibiting the hydrolysis of the β-lactam ring by β-lactamases.

Compounds and compositions provided by the present disclosure can be administered in combination with an antibiotic such as a β-lactam antibiotic.

Antibiotics include, for example, aminoglycosides such as amikacin, gentamicin, neomycin, streptomycin, and tobramycin; β-lactams (cephalosporins, first generation) such as cefadroxil, cefazolin, cephalexin; β-lactams (cephalosporins, second generation) such as cefaclor, cefotetan, cefoxitin, cefprozil, and cefuroxime; β-lactams (cephalosporins, third generation) such as cefotaxime, cefpodoxime, ceftazidime, ceftibuten, and ceftriaxone; β-lactams (cephalosporins, sixth generation) such as cefepime; β-lactams (cephalosporins, fifth generation) such as ceftaroline; β-lactams (penicillins) such as amoxicillin, ampicillin, dicloxacillin, nafcillin, and oxacillin, penicillin G, penicillin G benzathine, penicillin G procaine, piperacillin, and ticarcillin; β-lactam monobactams such as aztreonam; β-lactam carbapenems such as ertapenem, imipenem, meropenem, and doripenem; fluoroquiniolones such as ciprofloxacin, gemifloxacin, levofloxacin, moxifloxacin, norfloxacin, and ofloxacin; macrolides such as azithromycin, clarithromycin, erythromycin, fidaxomicin, lactobionate, gluceptate, and telithromycin; sulfonamides such as sulfisoxazole, sulfamethizole, sulfamethoxazole, and trimethoprim; tetracyclines such as doxycycline, minocycline, tetracycline, and tigecycline; and other antibiotics such as clindamycin, chlorramphenicol, colistin (poloymyxin E), dalbavancin, daptomycin, fosfomycin, linezolid, metronidazole, nitrofurantoin, oritavancin, quinupristin, dalfoprisin, rifampin, rifapentine, tedizolid, telavancin, and vancomycin. The antibiotic can be ceftazidime.

Other examples of antibiotics include penicillins such as aminopenicillins including amoxicillin and ampicillin, antipseudomonal penicillins including carbenicillin, peperacillin, and ticarcillin, β-lactamase inhibitors including amoxicillin, ampicillin, piperacillin, and clavulanate, natural penicillins including penicillin g benzathine, penicillin v potassium, and procaine penicillin, and penicillinase resistant penicillin including oxacillin, dicloxacillin, and nafcillin; tetracyclines; cephalosporins such as avibactam, tazobactam, cefadroxil, defazolin, cephalexin, and cefazolin; quinolones such as lomefloxacin, ofloxacin, norfloxacin, gatifloxacin, ciprofloxacin, moxifloxacin, levofloxacin, gemifloxacin, delafoxacin, cinoxacin, nalidixic acid, trovafloxacin, and sparfloxacin; lincomycins such as lincomycin and clindamycin; macrolides such as detolides including telithromycin and macrolides such as erythromycin, azithromycin, clarithromycin, and fidaxomicin; sulfonamides such as sulfamethoxazole/trimethoprim, sulfisoxazole; glycopeptides; aminoglycosides such as paromomycin, tobramycin, gentamycin, amikacin, kanamycin, and neomycin; and carbapenems such as doripenem, meropenem, ertapenem, and cilastatin/imipenem. Examples of suitable β-lactam antibiotics include penams such as β-lactamase-sensitive penams such as benzathine penicillin, benzylpenicillin, phenoxymethyl pencillin, and procain penicillin; β-lactamase-resistant penams such as cloxacillin, dicloxacillin, flucloxacillin, methicillin, nafcillin, oxacillin, and temocillin; broad spectrum penams such as amoxicillin and ampicillin; extended-spectrum penams such as mecillanam; carboxypenicillins such as carbenicillin and ticarcillin, and ureidopenicillins such as azlocillin, mezlocillin, and peperacillin.

Examples of suitable β-lactam antibiotics include cephams such as first generation cephams including cefazolin, cephalexin, cephalosporin C, cephalothin; second generation cephams such as cefaclor, cefamoandole, cefuroxime, cefotetan, and cefoxitin; third generation cephams such as cefixime, cefotaxime, cefpodoxime, ceflazidime, and ceftriaxone; fourth generation cephams such as cefipime and cefpirome; and fifth generation cephams such as ceftaroline.

Examples of suitable β-lactam antibiotics include carbapenems and penems such as biapenem, doripenem, ertapenem, faropenem, imipenem, meropenem, panipernem, razupenem, tebipenem, and thienamycin.

Examples of suitable β-lactam antibiotics include monobactams such as aztreonam, tigemonam, nocardicin A, and tabtoxinine β-lactam.

Compounds of Formula (1) can be co-administered with orally bioavailable antibiotics such as orally available aztreonam. Derivatives of aztreonam that following oral administration can provide a therapeutically effective amount of aztreonam in the systemic circulation are disclosed in U.S. Application Publication No. 2019/0100516, which is incorporated by reference in its entirety.

Derivatives of aztreonam include compounds having the structure of Formula (14):

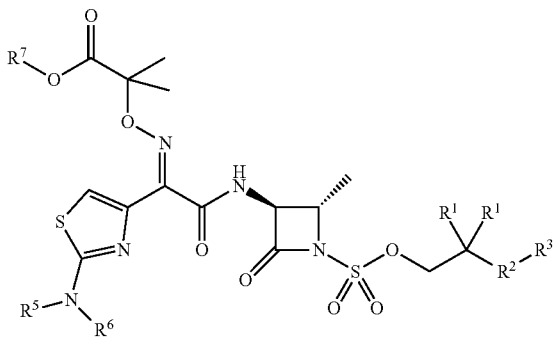

(14)

wherein, each $R^1$ can be independently selected from $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ can be selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ can be selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ can be selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^7$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

In compounds of Formula (14):

each $R^1$ can be selected from $C_{1-6}$ alkyl;

$R^4$ can be selected from $C_{1-6}$ alkyl, $C_{1-6}$ heteroalkyl, $C_{5-6}$ cycloalkyl, and $C_{5-6}$ heterocycloalkyl;

each of $R^5$ and $R^6$ can be hydrogen; and $R^7$ can be selected from hydrogen, $C_{1-6}$ alkyl, $C_{1-6}$ heteroalkyl, and 4-(yl-methyl)-5-methyl-1,3-dioxol-2-one.

In compounds of Formula (30), each $R^1$ can be selected from $C_{1-3}$ alkyl; $R^4$ can be selected from $C_{1-6}$ alkyl and $C_{5-6}$ cycloalkyl; each of $R^5$ and $R^6$ can be hydrogen; and $R^7$ can be selected from hydrogen and $C_{1-6}$ alkyl.

Compounds and pharmaceutical compositions provided by the present disclosure can be administered with β-lactamase inhibitors and/or carbapenemase inhibitors or pharmaceutical compositions thereof. Examples of suitable β-lactamase inhibitors and/or carbapenemase inhibitors include clavulanic acid, sulbactam, avibactam, tazobactam, relebactam, nacubactam, vaborbactam, ETX 2514, RG6068 (i.e., OP0565) (Livermore et al., *J AntiMicrob Chemother* 2015, 70: 3032) and RPX7009 (Hecker et al., *J Med Chem* 2015 58: 3682-3692).

Compounds of Formula (1) can be coadministered with other orally bioavailable β-lactamase inhibitors such as the avibactam, relebactam, and nacubactam derivatives disclosed in U.S. Pat. No. 10,085,999.

Compounds and compositions provided by the present disclosure be used in combination with one or more other active ingredients. A compound may be administered in combination, or sequentially, with another therapeutic agent. Such other therapeutic agents include those known for treatment, prevention, or amelioration of infectious disease.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided by the present disclosure are administered prior to or subsequent to the one or more additional active ingredients.

ASPECTS OF THE INVENTION

The invention is further defined by the following aspects.

Aspect 1. A compound of Formula (1):

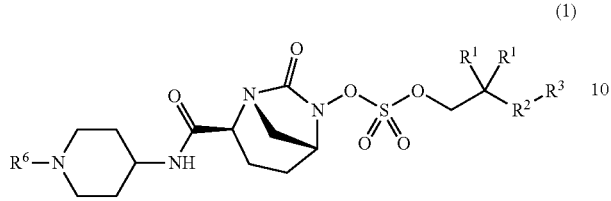
(1)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—(O)—O—$R^4$, —NH—C(O)—O—$R^4$, —C(O)—O—$R^4$, —C(O)—S—$R^4$, —C(O)—NH—$R^4$, —O—(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH═C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (2), a moiety of Formula (3), a moiety of Formula (4), and a moiety of Formula (5):

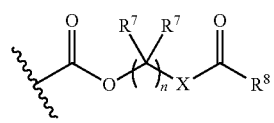
(2)

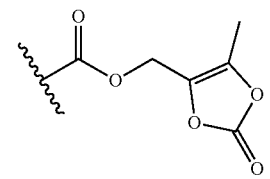
(3)

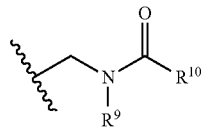
(3)

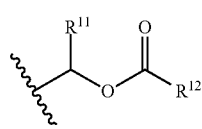
(4)

wherein, each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 2. The compound of aspect 1, wherein each substituent is independently selected from —OH, —CN, —CF$_3$, —OCF$_3$, ═O, —NO$_2$, $C_{1-6}$ alkoxy, $C_{1-6}$ alkyl, —COOR, —NR$_2$, and —CONR$_2$; wherein each R is independently selected from hydrogen and $C_{1-6}$ alkyl.

Aspect 3. The compound of aspect 1, wherein each substituent is independently selected from —OH, —CF$_3$, —O—CF$_3$, —NO$_2$, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—R$^4$, —NH—R$^4$, —CH(—NH$_2$)(—R$^4$), wherein each R$^4$ is selected from hydrogen, C$_{1-8}$ alkyl, and C$_{1-8}$ heteroalkyl.

Aspect 4. The compound of any one of aspects 1 to 3, wherein each R$^1$ is independently C$_{1-6}$ alkyl.

Aspect 5. The compound of any one of aspects 1 to 3, wherein each R$^1$ is methyl.

Aspect 6. The compound of any one of aspects 1 to 3, wherein each R$^1$ together with the geminal carbon atom to which they are bonded form a C$_{3-6}$ cycloalkyl ring or a substituted C$_{3-6}$ cycloalkyl ring.

Aspect 7. The compound of any one of aspects 1 to 3, wherein each R$^1$ together with the geminal carbon atom to which they are bonded form a C$_{3-6}$ cycloalkyl ring.

Aspect 8. The compound of any one of aspects 1 to 3, wherein each R$^1$ together with the geminal carbon atom to which they are bonded form a cyclopropyl ring, a cyclobutyl ring, a cyclopentyl ring, or a cyclohexyl ring.

Aspect 9. The compound of any one of aspects 1 to 3, wherein each R$^1$ together with the geminal carbon atom to which they are bonded form a C$_{3-6}$ heterocycloalkyl ring or a substituted C$_{3-6}$ heterocycloalkyl ring.

Aspect 10. The compound of any one of aspects 1 to 9, wherein R$^2$ is a single bond.

Aspect 11. The compound of any one of aspects 1 to 9, wherein R$^2$ is a single bond; and R$^3$ is C$_{1-6}$ alkyl.

Aspect 12. The compound of any one of aspects 1 to 9, wherein R$^2$ is selected from C$_{1-2}$ alkanediyl and substituted C$_{1-2}$ alkanediyl.

Aspect 13. The compound of aspect 12, wherein the substituent group is selected from —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl.

Aspect 14. The compound of aspect 12, wherein the substituent group is selected from —OH, —O—C(O)—R$^4$, —S—C(O)—R$^4$, —NH—C(O)—R$^4$, —C(O)—O—R$^4$, —(O)—S—R$^4$, —C(O)—NH—R$^4$, —S—S—R$^4$, —S—R$^4$, —NH—R$^4$, —CH(—NH$_2$)(—R$^4$), and —CH(—NH$_2$)(—R$^4$); and R$^4$ is selected from hydrogen and C$_{1-6}$ alkyl.

Aspect 15. The compound of any one of aspects 1 to 9, wherein R$^2$ is substituted C$_{1-2}$ alkanediyl; and the stereochemistry of the carbon atom to which the substituent group is bonded is of the (S) configuration.

Aspect 16. The compound of any one of aspects 1 to 9, wherein R$^2$ is substituted C$_{1-2}$ alkanediyl; and the stereochemistry of the carbon atom to which the substituent group is bonded is of the (R) configuration.

Aspect 17. The compound of any one of aspects 1 to 9, wherein R$^2$ is selected from C$_{5-6}$ cycloalkanediyl, C$_{5-6}$ heterocycloalkanediyl, C$_6$ arenediyl, and C$_{5-6}$ heterocycloalkanediyl.

Aspect 18. The compound of any one of aspects 1 to 17, wherein R$^3$ is selected from —O—C(O)—R$^4$, —C(O)—O—R$^4$, —S—(O)—R$^4$, —(O)—S—R$^4$, —S—S—R$^4$, —NH—R$^4$, and —CH(—NH$_2$)(—R$^4$).

Aspect 19. The compound of any one of aspects 1 to 17, wherein R$^3$ is —(O)—O—R$^4$.

Aspect 20. The compound of any one of aspects 1 to 19, wherein R$^4$ is selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

Aspect 21. The compound of any one of aspects 1 to 19, wherein R$^4$ is selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

Aspect 22. The compound of any one of aspects 1 to 19, wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 23. The compound of any one of aspects 1 to 19, wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 24. The compound of any one of aspects 1 to 17, wherein,
R$^3$ is —(O)—O—R$^4$; and
R$^4$ is selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

Aspect 25. The compound of any one of aspects 1 to 17, wherein,
R$^3$ is —(O)—O—R$^4$; and
R$^4$ is selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

Aspect 26. The compound of any one of aspects 1 to 17, wherein,
R$^3$ is —C(O)—O—R$^4$; and
R$^4$ is selected from C$_{1-8}$ alkyl, C$_{1-8}$ heteroalkyl, C$_{7-9}$ arylalkyl, and C$_{5-7}$ heterocycloalkyl.

Aspect 27. The compound of any one of aspects 1 and 10 to 26, wherein each R$^1$ together with the carbon atom to which they are bonded form a C$_{4-6}$ heterocycloalkyl ring comprising two adjacent S atoms or a substituted C$_{4-6}$ heterocycloalkyl ring comprising at least one heteroatom selected from O and S, and a =O substituent group bonded to a carbon atom adjacent the at least one heteroatom.

Aspect 28. The compound of aspect 1, wherein,
R$^2$ is a single bond; R$^3$ is C$_{1-3}$ alkyl; and
each R$^1$ together with the carbon atom to which they are bonded form a C$_{4-6}$ heterocycloalkyl ring or a substituted C$_{4-6}$ heterocycloalkyl ring.

Aspect 29. The compound of aspect 1, wherein,
R$^2$ is a single bond;
R$^3$ is C$_{1-3}$ alkyl; and
each R$^1$ together with the carbon atom to which they are bonded form a C$_{4-6}$ heterocycloalkyl ring comprising two adjacent S atoms or a substituted C$_{4-6}$ heterocycloalkyl ring comprising at least one heteroatom selected from O and S, and a =O substituent group bonded to a carbon atom adjacent the heteroatom.

Aspect 30. The compound of aspect 1, wherein,
R$^2$ is a single bond;
R$^3$ is C$_{1-3}$ alkyl; and
each R$^1$ together with the carbon atom to which they are bonded form a 1,2-dithiolante, 1,2-dithane ring, thietan-2-one ring, dihydrothiophen-2(3H)-one ring, tetrahydro-2H-thipyran-2-one ring, oxetan-2-one ring dihydrofuran-2(3H)-one ring, or tetrahydro-2H-pyran-2-one ring.

Aspect 31. The compound of aspect 1, wherein,
each R$^1$ is methyl;
R$^2$ is selected from a single bond, methanediyl, ethanediyl, —CH(—OH)—, —CH(—O—C(O)—CH$_2$CH$_3$)—, and 1,2-benzene-diyl; and
R$^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$); wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 32. The compound of aspect 1, wherein,
each R$^1$ is methyl;
R$^2$ is selected from a single bond, methanediyl, ethanediyl, —CH(—OH)—, —CH(—O—C(O)—CH$_2$CH$_3$)—, and 1,2-benzene-diyl; and
R$^3$ is selected from —C(O)—O—R$^4$; wherein R$^4$ is selected from C$_{1-8}$ alkyl, C$_{1-8}$ heteroalkyl, C$_{7-9}$ arylalkyl, and C$_{5-7}$ heterocycloalkyl.

Aspect 33. The compound of aspect 1, wherein,
each R$^1$ is methyl;
R$^2$ is selected from a single bond, methanediyl, ethanediyl, —CH(—OH)—, —CH(—O—C(O)—CH$_2$CH$_3$)—, and 1,2-benzene-diyl; and
R$^3$ is selected from —O—C(O)—R$^4$, —C(O)—O—R$^4$, —S—C(O)—R$^4$, —C(O)—S—R$^4$, —S—S—R$^4$, —NHR$^4$, and —CH(—NH$_2$)(—R$^4$); wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 34. The compound of aspect 1, wherein,
each R$^1$ is methyl;
R$^2$ is selected from a single bond, methanediyl, ethanediyl, —CH(—OH)—, —CH(—O—C(O)—CH$_2$CH$_3$)—, and 1,2-benzene-diyl; and
R$^3$ is selected from —C(O)—O—R$^4$; wherein R$^4$ is selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

Aspect 35. The compound of aspect 1, wherein,
each R$^1$ is methyl;
R$^2$ is a single bond; and
R$^3$ is —C(O)—O—R$^4$; wherein R$^4$ is selected from C$_{1-10}$ alkyl, C$_{1-10}$ heteroalkyl, C$_{7-9}$ alkylarene, and C$_{5-10}$ heteroalkylcycloalkyl.

Aspect 36. The compound of aspect 1, wherein,
each R$^1$ is methyl;
R$^2$ is a single bond; and
R$^3$ is —C(O)—O—R$^4$; wherein R$^4$ is selected from C$_{1-10}$ alkyl, C$_{1-10}$ heteroalkyl, C$_{7-10}$ alkylarene, and C$_{5-10}$ heteroalkylcycloalkyl.

Aspect 37. The compound of aspect 1, wherein each R$^1$ is independently C$_{1-6}$ alkyl, or each R$^1$ together with the geminal carbon atom to which they are bonded form a C$_{3-6}$ cycloalkyl ring, a substituted C$_{3-6}$ cycloalkyl ring, a C$_{3-6}$ heterocycloalkyl ring, or a substituted C$_{3-6}$ heterocycloalkyl ring.

Aspect 38. The compound of aspect 1, wherein R$^2$ is independently selected from a single bond, C$_{1-2}$ alkanediyl, and substituted C$_{1-2}$ alkanediyl.

Aspect 39. The compound of aspect 1, wherein R$^3$ is —C(O)—O—R$^4$, wherein R$^4$ is selected from C$_{1-8}$ alkyl, C$_{1-8}$ heteroalkyl, C$_{5-7}$ cycloalkyl, C$_{5-7}$ heterocycloalkyl, C$_6$ aryl, C$_{7-9}$ arylalkyl, substituted C$_{1-8}$ alkyl, substituted C$_{1-8}$ heteroalkyl, substituted C$_{5-6}$ cycloalkyl, substituted C$_{5-6}$ heterocycloalkyl, substituted C$_6$ aryl, and C$_{7-9}$ arylalkyl.

Aspect 40. The compound of aspect 1, wherein,
each R$^1$ is independently selected from C$_{1-3}$ alkyl, or each R$^1$ together with the geminal carbon atom to which they are bonded form a C$_{3-6}$ cycloalkyl ring, a substituted C$_{3-6}$ cycloalkyl ring, a C$_{3-6}$ heterocycloalkyl ring, or a substituted C$_{3-6}$ heterocycloalkyl ring;
R$^2$ is a single bond;
R$^3$ is —C(O)—O—R$^4$; and R$^4$ is selected from C$_{1-8}$ alkyl, C$_{1-8}$ heteroalkyl, C$_{7-9}$ arylalkyl, C$_{5-7}$ heterocycloalkyl, substituted C$_{1-8}$ alkyl, substituted C$_{1-8}$ heteroalkyl, substituted C$_{7-9}$ arylalkyl, and substituted C$_{5-7}$ heterocycloalkyl.

Aspect 41. The compound of any one of aspects 1 to 40, wherein R$^6$ is a moiety of Formula (2):

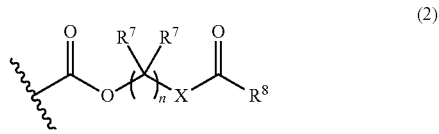

(2)

Aspect 42. The compound of aspect 41, wherein n is selected from 1 and 2.

Aspect 43. The compound of aspect 41, wherein n is 1.

Aspect 44. The compound of aspect 41, wherein n is 2.

Aspect 45. The compound of any one of aspects 41 to 44, wherein each R$^7$ and the geminal carbon atom to which they are bonded forms a C$_{3-6}$ cycloalkyl ring, a C$_{3-6}$ heterocycloalkyl ring, a substituted C$_{3-6}$ cycloalkyl ring, or a substituted C$_{3-6}$ heterocycloalkyl ring.

Aspect 46. The compound of any one of aspects 41 to 44, wherein each R$^7$ and the geminal carbon atom to which they are bonded forms a C$_{3-6}$ cycloalkyl ring or a substituted C$_{3-6}$ cycloalkyl ring.

Aspect 47. The compound of any one of aspects 41 to 44, wherein each R$^7$ is independently selected from hydrogen and C$_{1-8}$ alkyl.

Aspect 48. The compound of claim 41, wherein each R$^7$ is independently selected from hydrogen and C$_{1-3}$ alkyl.

Aspect 49. The compound of any one of aspects 41 to 44, wherein each R$^7$ is hydrogen.

Aspect 50. The compound of any one of aspects 41 to 44, wherein each R$^7$ is selected from methyl, ethyl, n-propyl, and iso-propyl.

Aspect 51. The compound of any one of aspects 41 to 44, wherein one R$^7$ is hydrogen and the other R$^7$ is selected from methyl, ethyl, n-propyl, and iso-propyl.

Aspect 52. The compound of any one of aspects 41 to 51, wherein the carbon atom to which R$^7$ is bonded is in the (S) configuration.

Aspect 53. The compound of any one of aspects 41 to 51, wherein the carbon atom to which R$^7$ is bonded is in the (R) configuration.

Aspect 54. The compound of any one of aspects 41 to 53, wherein X is NH.

Aspect 55. The compound of any one of aspects 41 to 53, wherein X is O.

Aspect 56. The compound of any one of aspects 41 to 55, wherein R$^8$ is selected from hydrogen, C$_{1-8}$ alkyl, C$_{5-8}$ cycloalkyl, C$_{5-10}$ cycloalkylalkyl, C$_{6-8}$ aryl, C$_{7-10}$ arylalkyl, substituted C$_{1-8}$ alkyl, substituted C$_{5-8}$ cycloalkyl, substituted C$_{5-10}$ cycloalkylalkyl, substituted C$_{6-8}$ aryl, and substituted C$_{7-10}$ arylalkyl.

Aspect 57. The compound of any one of aspects 41 to 55, wherein R$^8$ is selected from hydrogen, C$_{1-8}$ alkyl, C$_{5-8}$ cycloalkyl, C$_{5-10}$ cycloalkylalkyl, C$_{6-8}$ aryl, and C$_{7-10}$ arylalkyl.

Aspect 58. The compound of any one of aspects 41 to 55, wherein R$^8$ is selected from hydrogen, C$_{1-8}$ alkyl, C$_{5-8}$ cycloalkyl, and C$_{6-8}$ aryl.

Aspect 59. The compound of any one of aspects 41 to 55, wherein R$^8$ is selected from C$_{1-8}$ alkoxy, C$_{1-8}$ cycloalkoxy, substituted C$_{1-8}$ alkoxy, and substituted C$_{1-8}$ cycloalkoxy.

Aspect 60. The compound of any one of aspects 41 to 55, wherein $R^8$ is selected from $C_{5-8}$ aryl, substituted $C_{5-8}$ aryl, $C_{5-8}$ heteroaryl, and substituted $C_{5-8}$ heteroaryl.

Aspect 61. The compound of any one of aspects 41 to 55, wherein $R^8$ is selected from $C_{5-8}$ aryl and substituted $C_{5-8}$ aryl.

Aspect 62. The compound of any one of aspects 41 to 55, wherein $R^8$ is $C_{1-8}$ alkoxy.

Aspect 63. The compound of any one of aspects 41 to 55, wherein $R^8$ is selected from hydrogen, methyl, ethyl, propyl, isopropyl, butyl, isobutyl, sec-butyl, tert-cyclopropyl cyclobutyl, cyclopentyl cyclohexyl, and benzyl.

Aspect 64. The compound of any one of aspects 41 to 55, wherein $R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy.

Aspect 65. The compound of any one of aspects 41 to 55, wherein $R^8$ is selected from hydrogen and $C_{1-6}$ alkyl.

Aspect 66. The compound of any one of aspects 41 to 55, wherein $R^8$ is selected from hydrogen, methyl, ethyl, n-propyl, isopropyl, n-butyl, iso-butyl, sec-butyl, and tert-butyl.

Aspect 67. The compound of any one of aspects 41 to 55, wherein $R^8$ is —CH(—$R^{13}$)—NH$_2$, wherein $R^{13}$ is selected from $C_{1-6}$ alkyl, $C_{1-6}$ alkoxy, and cycloalkoxy.

Aspect 68. The compound of any one of aspects 41 to 67, wherein the carbon atom to which $R^{13}$ is bonded is of the (S) configuration.

Aspect 69. The compound of any one of aspects 41 to 67, wherein the carbon atom to which $R^{13}$ is bonded is of the (R) configuration.

Aspect 70. The compound of aspect 41, wherein,
each $R^1$ is $C_{1-6}$ alkyl;
$R^2$ is a single bond;
$R^3$ is —C(O)—O—;
$R^4$ is $C_{1-6}$ alkyl;
n is 1;
each $R^7$ is selected from hydrogen and $C_{1-6}$ alkyl; and
$R^8$ is selected from $C_{1-6}$ alkyl and —CH(—$R^{13}$)—NH$_2$, wherein $R^{13}$ is selected from $C_{1-6}$ alkyl.

Aspect 71. The compound of any one of aspects 1 to 40, wherein $R^6$ is a moiety of Formula (3):

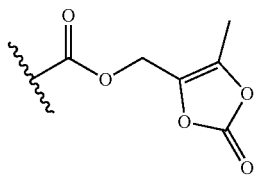
(3)

Aspect 72. The compound of aspect 71, wherein,
each $R^1$ is $C_{1-6}$ alkyl;
$R^2$ is a single bond;
$R^3$ is —C(O)—O—; and
$R^4$ is $C_{1-6}$ alkyl.

Aspect 73. The compound of any one of aspects 1 to 40, wherein $R^6$ is a moiety of Formula (4):

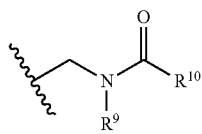
(4)

Aspect 74. The compound of aspect 73, wherein $R^9$ is selected from hydrogen, methyl, ethyl, and isopropyl.

Aspect 75. The compound of aspect 73, wherein $R^9$ is hydrogen.

Aspect 76. The compound of aspect 73, wherein $R^9$ is selected from methyl, ethyl, and isopropyl.

Aspect 77. The compound of any one of aspects 73 to 76, wherein $R^{10}$ is selected from $C_{1-8}$ alkyl, $C_{5-8}$ cycloalkyl, $C_{5-10}$ cycloalkylalkyl, $C_{6-8}$ aryl, $C_{7-10}$ arylalkyl, substituted $C_{1-8}$ alkyl, substituted $C_{5-8}$ cycloalkyl, substituted $C_{5-10}$ cycloalkylalkyl, substituted $C_{6-8}$ aryl, and substituted $C_{7-10}$ arylalkyl.

Aspect 78. The compound of any one of aspects 73 to 76, wherein $R^{10}$ is selected from $C_{1-8}$ alkyl, $C_{5-8}$ cycloalkyl, $C_{5-10}$ cycloalkylalkyl, $C_{6-8}$ aryl, and $C_{7-10}$ arylalkyl.

Aspect 79. The compound of any one of aspects 73 to 76, wherein $R^{10}$ is selected from $C_{1-8}$ alkyl, $C_{5-8}$ cycloalkyl, and $C_{6-8}$ aryl.

Aspect 80. The compound of claim 73, wherein $R^{10}$ is selected from methyl, ethyl, propyl, isopropyl, n-butyl, isobutyl, sec-butyl, tert-butyl, cyclopropyl, cyclobutyl, cyclopentyl, cyclohexyl, and benzyl.

Aspect 81. The compound of any one of aspects 73 to 76, wherein $R^{10}$ is selected from cyclopentyl, substituted cyclopentyl, cyclohexyl, substituted cyclohexyl, benzyl, and substituted benzyl.

Aspect 82. The compound of any one of aspects 73 to 76, wherein $R^{10}$ is selected from $C_{1-8}$ alkyl.

Aspect 83. The compound of any one of aspects 73 to 76, wherein $R^{10}$ is selected from methyl, ethyl, n-propyl, isopropyl, n-butyl, iso-butyl, sec-butyl, and tert-butyl.

Aspect 84. The compound of aspect 73, wherein,
$R^9$ is selected from hydrogen, methyl, ethyl, and isopropyl; and
$R^{10}$ is selected from methyl, ethyl, n-propyl, isopropyl, n-butyl, iso-butyl, sec-butyl, and tert-butyl.

Aspect 85. The compound of aspect 73, wherein,
each $R^1$ is $C_{1-6}$ alkyl;
$R^2$ is a single bond;
$R^3$ is —C(O)—O—;
$R^4$ is $C_{1-6}$ alkyl;
$R^9$ is selected from hydrogen, methyl, ethyl, and isopropyl; and
$R^{10}$ is selected from methyl, ethyl, n-propyl, isopropyl, n-butyl, iso-butyl, sec-butyl, and tert-butyl.

Aspect 86. The compound of any one of aspects 1 to 40, wherein $R^6$ is a moiety of Formula (5):

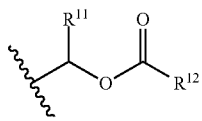
(5)

Aspect 87. The compound of aspect 86, wherein $R^{11}$ is selected from hydrogen, methyl, ethyl, and isopropyl.

Aspect 88. The compound of aspect 86, wherein $R^{11}$ is hydrogen.

Aspect 89. The compound of aspect 86, wherein $R^{11}$ is selected from methyl, ethyl, and isopropyl.

Aspect 90. The compound of any one of aspects 86 to 89, wherein the carbon atom to which $R^{11}$ is bonded is of the (S) configuration.

Aspect 91. The compound of any one of aspects 86 to 89, wherein the carbon atom to which $R^{11}$ is bonded is of the (R) configuration.

Aspect 92. The compound of any one of aspects 86 to 91, wherein $R^{12}$ is selected from $C_{1-8}$ alkyl, $C_{5-8}$ cycloalkyl, $C_{5-10}$ cycloalkylalkyl, $C_{6-8}$ aryl, $C_{7-10}$ arylalkyl, substituted $C_{1-8}$ alkyl, substituted $C_{5-8}$ cycloalkyl, substituted $C_{5-10}$ cycloalkylalkyl, substituted $C_{6-8}$ aryl, and substituted $C_{7-10}$ arylalkyl.

Aspect 93. The compound of any one of aspects 86 to 91, wherein $R^{12}$ is selected from $C_{1-8}$ alkyl, $C_{5-8}$ cycloalkyl, $C_{5-10}$ cycloalkylalkyl, $C_{6-8}$ aryl, and $C_{7-10}$ arylalkyl.

Aspect 94. The compound of any one of aspects 86 to 91, wherein $R^{12}$ is selected from $C_{1-8}$ alkyl, $C_{5-8}$ cycloalkyl, and $C_{6-8}$ aryl.

Aspect 95. The compound of any one of aspects 86 to 91, wherein $R^{12}$ is selected from methyl, ethyl, propyl, isopropyl, n-butyl, isobutyl, sec-butyl, tert-butyl, cyclopropyl, cyclobutyl, cyclopentyl, cyclohexyl, and benzyl.

Aspect 96. The compound of any one of aspects 86 to 91, wherein $R^{12}$ is selected from cyclopentyl, substituted cyclopentyl, cyclohexyl, substituted cyclohexyl, benzyl, and substituted benzyl.

Aspect 97. The compound of any one of aspects 86 to 91, wherein $R^{12}$ is selected from $C_{1-8}$ alkyl.

Aspect 98. The compound of any one of aspects 86 to 91, wherein $R^{12}$ is selected from methyl, ethyl, n-propyl, isopropyl, n-butyl, iso-butyl, sec-butyl, and tert-butyl.

Aspect 99. The compound of aspect 86, wherein, $R^{11}$ is selected from hydrogen, methyl, ethyl, and isopropyl; and $R^{12}$ is selected from methyl, ethyl, n-propyl, isopropyl, n-butyl, iso-butyl, sec-butyl, and tert-butyl.

Aspect 100. The compound of aspect 86, wherein,
each $R^1$ is $C_{1-6}$ alkyl;
$R^2$ is a single bond;
$R^3$ is —C(O)—O—;
$R^4$ is $C_{1-6}$ alkyl;
$R^{11}$ is selected from hydrogen, methyl, ethyl, and isopropyl; and
$R^{12}$ is selected from methyl, ethyl, n-propyl, isopropyl, n-butyl, iso-butyl, sec-butyl, and tert-butyl.

Aspect 101. The compound of any one of aspects 1 to 40, wherein $R^6$ is a moiety of Formula (2).

Aspect 102. The compound of any one of aspects 1 to 40, wherein $R^6$ is a moiety of Formula (3).

Aspect 103. The compound of any one of aspects 1 to 40, wherein $R^6$ is a moiety of Formula (4).

Aspect 104. The compound of any one of aspects 1 to 40, wherein $R^6$ is a moiety of Formula (5).

Aspect 105. The compound of aspect 1, wherein the compound is selected from:
tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate,
a pharmaceutically acceptable salt of any of the foregoing, and
a combination of any of the foregoing.

Aspect 106. A compound of Formula (1):

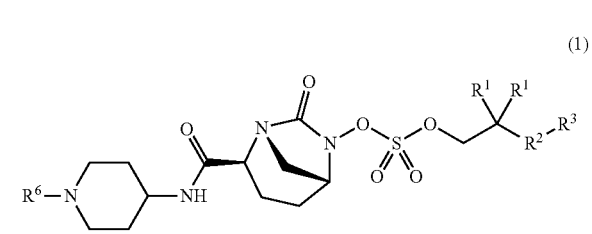

(1)

or a pharmaceutically acceptable salt thereof, wherein,
each $R^1$ is independently selected from $C_{1-3}$ alkyl, or each $R^1$ together with the carbon atom to which they are bonded form a $C_{3-6}$ cycloalkyl ring;
$R^2$ is selected from single bond, methane-diyl, and ethane-diyl;
$R^3$ is selected from —C(O)—O—$R^4$ and —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ is selected from a moiety of Formula (2), a moiety of Formula (3), a moiety of Formula (4), and a moiety of Formula (5):

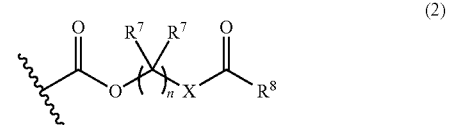

(2)

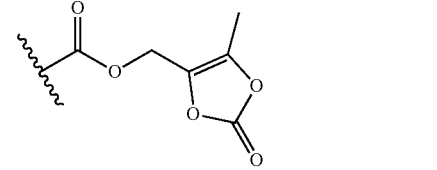

(3)

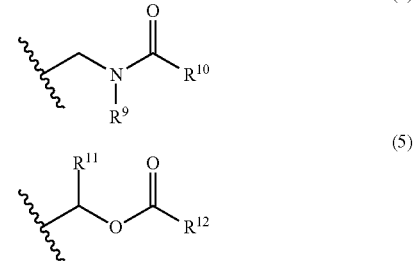

(4)

(5)

wherein,
each $R^7$ is independently selected from hydrogen and $C_{1-6}$ alkyl;

n is selected from 1 and 2;

X is O;

$R^8$ is selected from hydrogen, $C_{1-6}$ alkyl and —CH(—$R^{13}$)—NH$_2$,
wherein $R^{13}$ is selected from $C_{1-6}$ alkyl, alkoxy, and cycloalkoxy;

$R^9$ is selected from hydrogen and $C_{1-6}$ alkyl;

$R^{10}$ is selected from $C_{1-6}$ alkyl;

$R^{11}$ is selected from hydrogen and $C_{1-6}$ alkyl; and $R^{12}$ is selected from $C_{1-6}$ alkyl.

Aspect 107. The compound of aspect 106, wherein each $R^1$ is independently selected from $C_{1-3}$ alkyl.

Aspect 108. The compound of aspect 106, wherein each $R^1$ together with the carbon atom to which they are bonded form a $C_{3-6}$ cycloalkyl ring.

Aspect 109. The compound of any one of aspects 106 to 108, wherein $R^2$ a single bond.

Aspect 110. The compound of any one of aspects 106 to 108, wherein $R^2$ is methane-diyl.

Aspect 111. The compound of any one of aspects 106 to 108, wherein $R^2$ is ethane-diyl.

Aspect 112. The compound of any one of aspects 106 to 111, wherein $R^3$ is —C(O)—O—$R^4$.

Aspect 113. The compound of any one of aspects 106 to 111, wherein $R^3$ is —S—C(O)—$R^4$.

Aspect 114. The compound of any one of aspects 106 to 113, wherein $R^4$ is $C_{1-10}$ alkyl.

Aspect 115. The compound of any one of aspects 106 to 113, wherein $R^4$ is $C_{1-10}$ heteroalkyl.

Aspect 116. The compound of any one of aspects 106 to 113, wherein $R^4$ is $C_{5-10}$ arylalkyl.

Aspect 117. The compound of any one of aspects 106 to 113, wherein $R^4$ is $C_{3-6}$ heterocycloalkyl.

Aspect 118. The compound of any one of aspects 106 to 113, wherein $R^4$ is substituted $C_{4-10}$ heterocycloalkylalkyl.

Aspect 119. The compound of any one of aspects 106 to 118, wherein $R^6$ is a moiety of Formula (2).

Aspect 120. The compound of any one of aspects 106 to 118, wherein $R^6$ is a moiety of Formula (3).

Aspect 121. The compound of any one of aspects 106 to 118, wherein $R^6$ is a moiety of Formula (4).

Aspect 122. The compound of any one of aspects 106 to 118, wherein $R^6$ is a moiety of Formula (5).

Aspect 123. A compound of Formula (1):

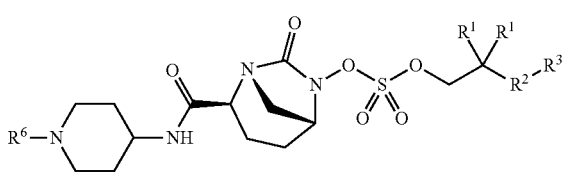

(1)

or a pharmaceutically acceptable salt thereof, wherein, each $R^1$ is independently selected from $C_{1-3}$ alkyl, or each $R^1$ together with the carbon atom to which they are bonded form a $C_{3-6}$ cycloalkyl ring;

$R^2$ is a single bond;

$R^3$ is —C(O)—O—$R^4$, where $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and $R^6$ is selected from a moiety of Formula (2), a moiety of Formula (3), a moiety of Formula (4), and a moiety of Formula (5):

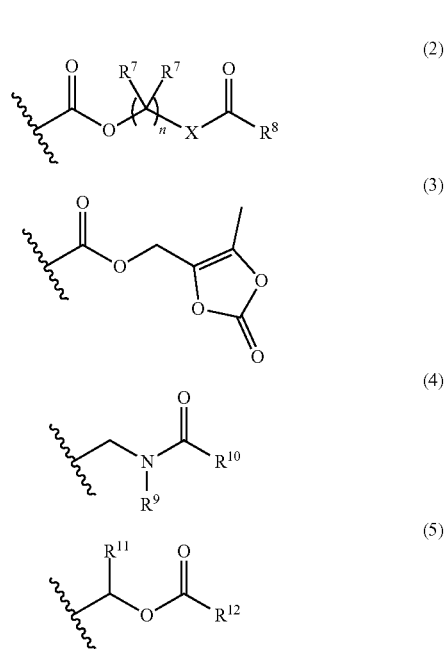

wherein, each $R^7$ is independently selected from hydrogen and $C_{1-6}$ alkyl;

n is selected from 1 and 2;

X is O;

$R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy;

$R^9$ is selected from hydrogen and $C_{1-6}$ alkyl;

$R^{10}$ is selected from $C_{1-6}$ alkyl;

$R^{11}$ is selected from hydrogen and $C_{1-6}$ alkyl; and $R^{12}$ is selected from $C_{1-6}$ alkyl.

Aspect 124. The compound of aspect 123, wherein each $R^1$ is independently selected from $C_{1-3}$ alkyl.

Aspect 125. The compound of aspect 123, wherein each $R^1$ together with the carbon atom to which they are bonded form a $C_{3-6}$ cycloalkyl ring.

Aspect 126. The compound of any one of aspects 123 to 125, wherein $R^4$ is selected from $C_{1-7}$ alkyl, $C_{1-10}$ heteroalkyl wherein the one or more heteroatoms is oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms is oxygen, and —CH$_2$—$C_{3-6}$ substituted heterocycloalkyl, and —(CH$_2$)$_2$—$C_{3-6}$ substituted heterocycloalkyl.

Aspect 127. The compound of aspect 123, wherein in the substituted $C_{3-6}$ heterocycloalkyl the one or more heteroatoms is oxygen, and the one or more substituents is independently selected from $C_{1-3}$ alkyl and =O.

Aspect 128. The compound of aspect 123, wherein each $R^1$ is methyl, or each $R^1$ together with the carbon atom to which they are bonded form a cyclohexyl ring or a cyclopentyl ring.

Aspect 129. The compound of aspect 123, wherein $R^4$ is selected from methyl, ethyl, n-propyl, iso-propyl, n-butyl, n-hexyl, n-heptyl, —CH$_2$—CH$_2$—O—CH$_3$, benzyl, 3-oxetanyl, and methyl-5-methyl-1,3-dioxol-2-one.

Aspect 130. The compound of aspect 123, wherein, each $R^1$ is methyl, or each $R^1$ together with the carbon atom to which they are bonded form a cyclohexyl ring or a cyclopentyl ring;

$R^2$ is a single bond; and $R^3$ is —C(O)—O—$R^4$, wherein $R^4$ is selected from methyl, ethyl, n-propyl, iso-propyl, n-butyl, n-hexyl, n-heptyl, —CH$_2$—CH$_2$—O—CH$_3$, —CH$_2$-phenyl (benzyl), 3-oxetanyl, and methyl-5-methyl-1,3-dioxol-2-one.

Aspect 131. The compound of any one of aspects 123 to 131, wherein $R^6$ is a moiety of Formula (2).

Aspect 132. The compound of any one of aspects 123 to 131, wherein $R^6$ is a moiety of Formula (3).

Aspect 133. The compound of any one of aspects 123 to 131, wherein $R^6$ is a moiety of Formula (4).

Aspect 134. The compound of any one of aspects 123 to 131, wherein $R^6$ is a moiety of Formula (5).

Aspect 135. A compound of Formula (1):

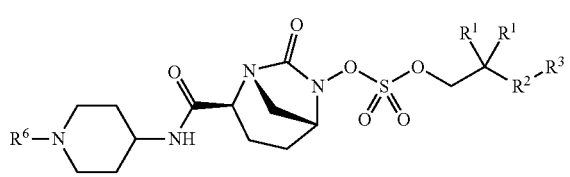

(1)

or a pharmaceutically acceptable salt thereof, wherein,
each $R^1$ is independently selected from $C_{1-3}$ alkyl, or each $R^1$ together with the carbon atom to which they are bonded form a $C_{3-6}$ cycloalkyl ring;
$R^2$ is —(CH$_2$)$_2$—;
$R^3$ is —C(O)—O—$R^4$ wherein $R^4$ is selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl; and
$R^6$ is selected from a moiety of Formula (2), a moiety of Formula (3), a moiety of Formula (4), and a moiety of Formula (5):

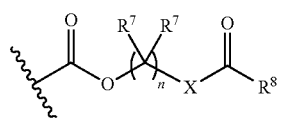

(2)

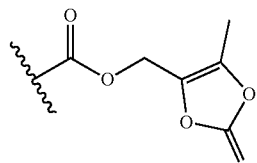

(3)

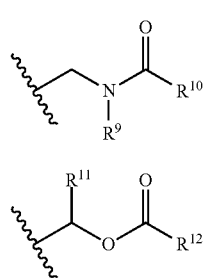

(4)

(5)

wherein,
each $R^7$ is independently selected from hydrogen and $C_{1-6}$ alkyl;
n is selected from 1 and 2;

X is O;
$R^8$ is selected from hydrogen, $C_{1-6}$ alkyl and —CH(—$R^{13}$)—NH$_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 136. The compound of aspect 135, wherein each $R^1$ is independently selected from $C_{1-3}$ alkyl.

Aspect 137. The compound of aspect 135, wherein each $R^1$ together with the carbon atom to which they are bonded form a $C_{3-6}$ cycloalkyl ring.

Aspect 138. The compound of any one of aspects 135 to 137, wherein $R^4$ is selected from $C_{1-7}$ alkyl, $C_{1-10}$ heteroalkyl wherein the one or more heteroatoms is oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms is oxygen, —CH$_2$—$C_{3-6}$ substituted heterocycloalkyl, and —(CH$_2$)$_2$—$C_{3-6}$ substituted heterocycloalkyl.

Aspect 139. The compound of any one of aspects 135 to 138, wherein in the substituted $C_{3-6}$ heterocycloalkyl the one or more heteroatoms is oxygen, and the one or more substituents is independently selected from $C_{1-3}$ alkyl and =O.

Aspect 140. The compound of any one of aspects 135 to 139, wherein $R^4$ is $C_{1-10}$ alkyl.

Aspect 141. The compound of aspect 135, wherein,
each $R^1$ is methyl;
$R^2$ is —(CH$_2$)$_2$—; and
$R^3$ is —C(O)—O—$R^4$ where $R^4$ is selected from n-hexyl and n-heptyl.

Aspect 142. The compound of any one of aspects 135 to 141, wherein $R^6$ is a moiety of Formula (2).

Aspect 143. The compound of any one of aspects 135 to 141, wherein $R^6$ is a moiety of Formula (3).

Aspect 144. The compound of any one of aspects 135 to 141, wherein $R^6$ is a moiety of Formula (4).

Aspect 145. The compound of any one of aspects 135 to 141, wherein $R^6$ is a moiety of Formula (5).

Aspect 146. A compound of Formula (1):

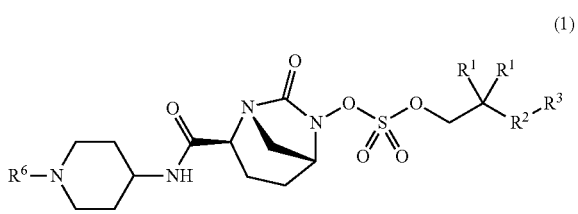

(1)

or a pharmaceutically acceptable salt thereof, wherein,
each $R^1$ is selected from $C_{1-3}$ alkyl, or each $R^1$ together with the carbon atom to which they are bonded form a $C_{3-6}$ cycloalkyl ring;
$R^2$ is —CH$_2$—;
$R^3$ is —S—C(O)—$R^4$, wherein $R^4$ is selected from $C_{1-10}$ alkyl, $C_{1-10}$ heteroalkyl, $C_{5-10}$ arylalkyl, $C_{3-6}$ heterocycloalkyl, substituted $C_{4-10}$ heterocycloalkylalkyl; and
$R^6$ is selected from a moiety of Formula (2), a moiety of Formula (3), a moiety of Formula (4), and a moiety of Formula (5):

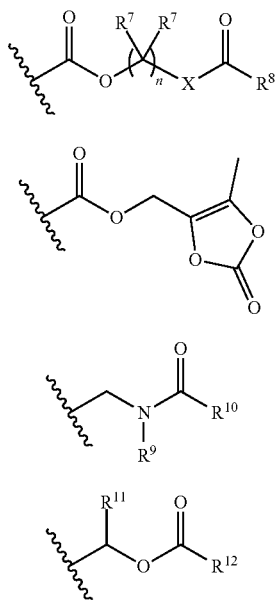

(2)

(3)

(4)

(5)

wherein,
each $R^7$ is independently selected from hydrogen and $C_{1-6}$ alkyl;
n is selected from 1 and 2;
X is O;
$R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 147. The compound of aspect 146, wherein each $R^1$ is independently selected from $C_{1-3}$ alkyl.

Aspect 148. The compound of aspect 146, wherein each $R^1$ together with the carbon atom to which they are bonded form a $C_{3-6}$ cycloalkyl ring.

Aspect 149. The compound of any one of aspects 146 to 148, wherein $R^4$ is selected from $C_{1-7}$ alkyl, $C_{1-10}$ heteroalkyl wherein the one or more heteroatoms is oxygen, —CH$_2$—$C_{4-6}$ cycloalkyl, —(CH$_2$)$_2$—$C_{4-6}$ cycloalkyl, $C_{3-6}$ heterocycloalkyl wherein the one or more heteroatoms is oxygen, —CH$_2$—$C_{3-6}$ substituted heterocycloalkyl, and —(CH$_2$)$_2$—$C_{3-6}$ substituted heterocycloalkyl.

Aspect 150. The compound of any one of aspects 146 to 149, wherein in the substituted $C_{3-6}$ heterocycloalkyl the one or more heteroatoms is oxygen, and the one or more substituents is independently selected from $C_{1-3}$ alkyl and =O.

Aspect 151. The compound of any one of aspects 146 to 150, wherein $R^4$ is $C_{1-10}$ alkyl.

Aspect 152. The compound of aspect 146, wherein,
each $R^1$ is methyl;
$R^2$ is —CH$_2$—; and
$R^3$ is —S—C(O)—$R^4$, wherein $R^4$ is methyl.

Aspect 153. The compound of any one of aspects 146 to 152, wherein $R^6$ is a moiety of Formula (2).

Aspect 154. The compound of any one of aspects 146 to 152, wherein $R^6$ is a moiety of Formula (3).

Aspect 155. The compound of any one of aspects 146 to 152, wherein $R^6$ is a moiety of Formula (4).

Aspect 156. The compound of any one of aspects 146 to 152, wherein $R^6$ is a moiety of Formula (5).

Aspect 157. A compound of Formula (1):

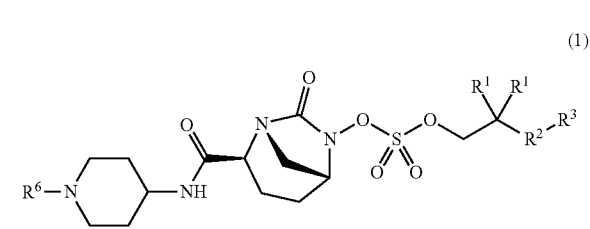

(1)

or a pharmaceutically acceptable salt thereof, wherein,
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ is a single bond;
$R^3$ is $C_{1-3}$ alkyl; and
$R^6$ is selected from a moiety of Formula (2), a moiety of Formula (3), a moiety of Formula (4), and a moiety of Formula (5):

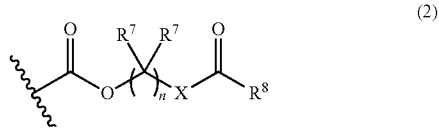

(2)

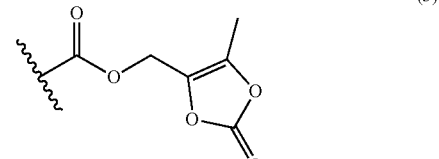

(3)

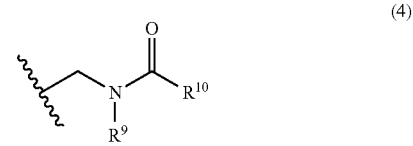

(4)

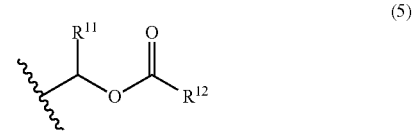

(5)

wherein,
each $R^7$ is independently selected from hydrogen and $C_{1-6}$ alkyl;
n is selected from 1 and 2;
X is O;
$R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 158. The compound of aspect 157, wherein each $R^1$ together with the carbon atom to which they are bonded form a $C_{3-6}$ heterocycloalkyl ring or a $C_{3-6}$ heterocycloalkyl ring.

Aspect 159. The compound of any one of aspects 157 to 158, wherein the one or more heteroatoms is oxygen and the one or more substituents is =O.

Aspect 160. The compound of aspect 157, wherein, each R¹ together with the carbon atom to which they are bonded form a dihydrofuran-2(3H)-one ring; R² is a single bond; and R³ is methyl.

Aspect 161. The compound of any one of aspects 157 to 160, wherein R⁶ is a moiety of Formula (2).

Aspect 162. The compound of any one of aspects 157 to 160, wherein R⁶ is a moiety of Formula (3).

Aspect 163. The compound of any one of aspects 157 to 160, wherein R⁶ is a moiety of Formula (4).

Aspect 164. The compound of any one of aspects 157 to 160, wherein R⁶ is a moiety of Formula (5).

Aspect 165. A compound of Formula (1):

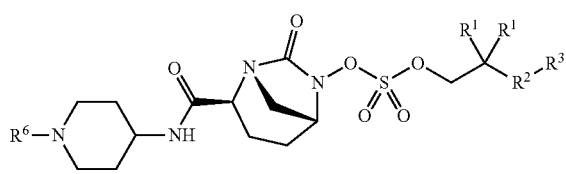
(1)

or a pharmaceutically acceptable salt thereof, wherein,
each R¹ is independently selected from $C_{1-3}$ alkyl;
R² is selected from a single bond and methanediyl;
R³ is selected from —O—C(O)—R⁴ and —C(O)—O—R⁴, wherein R⁴ is selected from $C_{1-10}$ alkyl and substituted phenyl; and
R⁶ is selected from a moiety of Formula (2), a moiety of Formula (3), a moiety of Formula (4), and a moiety of Formula (5):

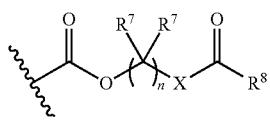
(2)

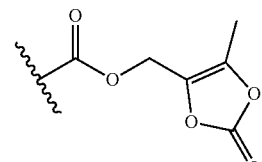
(3)

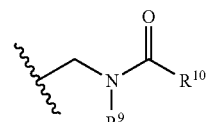
(4)

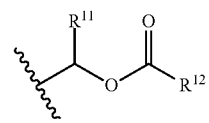
(5)

wherein,
each R⁷ is independently selected from hydrogen and $C_{1-6}$ alkyl;

n is selected from 1 and 2;
X is O;
R⁸ is selected from hydrogen, $C_{1-6}$ alkyl, and —CH(—R¹³)—NH₂, wherein R¹³ is selected from $C_{1-6}$ alkyl, alkoxy, and cycloalkoxy;
R⁹ is selected from hydrogen and $C_{1-6}$ alkyl;
R¹⁰ is selected from $C_{1-6}$ alkyl;
R¹¹ is selected from hydrogen and $C_{1-6}$ alkyl; and
R¹² is selected from $C_{1-6}$ alkyl.

Aspect 166. The compound of aspect 165, wherein R² is a single bond.

Aspect 167. The compound of aspect 165, wherein R² is methanediyl.

Aspect 168. The compound of any one of aspects 165 to 167, wherein R³ is —O—C(O)—R⁴.

Aspect 169. The compound of aspect 165, wherein R² is methanediyl; and R³ is —O—C(O)—R⁴.

Aspect 170. The compound of aspect 165, wherein R³ is —C(O)—O—R⁴.

Aspect 171. The compound of aspect 165, wherein R² is a single bond; and R³ is —C(O)—O—R⁴.

Aspect 172. The compound of aspect 165, wherein R² is a single bond; R³ is —C(O)—O—R⁴; and R⁴ is $C_{1-3}$ alkyl.

Aspect 173. The compound of any one of aspects 165 to 172, wherein R⁴ is $C_{1-10}$ alkyl.

Aspect 174. The compound of any one of aspects 165 to 172, wherein R⁴ is $C_{1-4}$ alkyl.

Aspect 175. The compound of any one of aspects 165 to 172, wherein R⁴ is substituted phenyl.

Aspect 176. The compound of aspect 165, wherein R² is methanediyl; R³ is —O—C(O)—R⁴; and R⁴ is substituted phenyl.

Aspect 177. The compound of any one of aspects 165 to 176, wherein the one or more substituents is independently selected from halogen, $C_{1-3}$ alkyl, and $C_{1-3}$ alkoxy.

Aspect 178. The compound of any one of aspects 165 to 177, wherein the substituted phenyl is 2,6-substituted phenyl.

Aspect 179. The compound of aspect 178, wherein each of the substituents is selected from $C_{1-3}$ alkyl and $C_{1-3}$ alkoxy.

Aspect 180. The compound of aspect 178, wherein the substituted phenyl is 2,5,6-substituted phenyl.

Aspect 181. The compound of any one of aspects 165 to 180, wherein each of the substituents at the 2 and 6 positions is independently selected from $C_{1-3}$ alkyl and $C_{1-3}$ alkoxy; and the substituent at the 5 position is halogen.

Aspect 182. The compound of any one of aspects 165 to 181, wherein R⁶ is a moiety of Formula (2).

Aspect 183. The compound of any one of aspects 165 to 181, wherein R⁶ is a moiety of Formula (3).

Aspect 184. The compound of any one of aspects 165 to 181, wherein R⁶ is a moiety of Formula (4).

Aspect 185. The compound of any one of aspects 165 to 181, wherein R⁶ is a moiety of Formula (5).

Aspect 186. A compound of Formula (1):

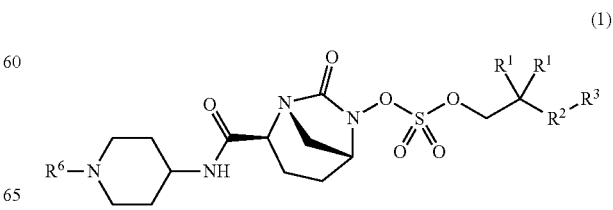
(1)

or a pharmaceutically acceptable salt thereof, wherein,
each $R^1$ is independently selected from $C_{1-3}$ alkyl;
$R^2$ is a single bond;
$R^3$ is —CH=C($R^4$)$_2$, wherein each $R^4$ is —C(O)—O—$R^8$, or each $R^4$ together with the carbon atom to which they are bonded from a substituted heterocyclohexyl ring; and
$R^6$ is selected from a moiety of Formula (2), a moiety of Formula (3), a moiety of Formula (4), and a moiety of Formula (5):

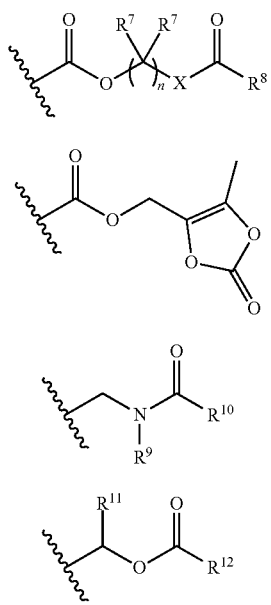

wherein,
each $R^7$ is independently selected from hydrogen and $C_{1-6}$ alkyl
n is selected from 1 and 2;
X is O;
$R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 187. The compound of aspect 186, wherein each $R^4$ is —C(O)—O—$R^8$.

Aspect 188. The compound of aspect 186, wherein each $R^4$ is —C(O)—O—$R^8$, or each $R^4$ together with the carbon atom to which they are bonded from a substituted heterocyclohexyl ring.

Aspect 189. The compound of aspect 188, wherein in the substituted heterocyclohexyl ring, the one or more heteroatoms is oxygen.

Aspect 190. The compound of aspect 188, wherein in the substituted heterocyclohexyl ring, the one or more substituents is independently selected from $C_{1-3}$ alkyl and =O.

Aspect 191. The compound of aspect 188, wherein the substituted heterocycloalkyl ring is 2,2-dimethyl-5-yl-1,3-dioxane-4,6-dione.

Aspect 192. The compound of any one of aspects 186 to 191, wherein $R^6$ is a moiety of Formula (2).

Aspect 193. The compound of any one of aspects 186 to 191, wherein $R^6$ is a moiety of Formula (3).

Aspect 194. The compound of any one of aspects 186 to 191, wherein $R^6$ is a moiety of Formula (4).

Aspect 195. The compound of any one of aspects 186 to 191, wherein $R^6$ is a moiety of Formula (5).

Aspect 196. A compound of Formula (1):

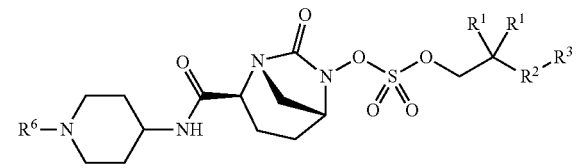

or a pharmaceutically acceptable salt thereof, wherein,
each $R^1$ is independently selected from $C_{1-3}$ alkyl;
$R^2$ is selected from a single bond and methanediyl;
$R^3$ is substituted phenyl, wherein the one or more substituents is independently selected from —CH$_2$—O—C(O)—$R^4$ and —O—C(O)—$R^4$, wherein $R^4$ is selected from $C_{1-10}$ alkyl and phenyl; and
$R^6$ is selected from a moiety of Formula (2), a moiety of Formula (3), a moiety of Formula (4), and a moiety of Formula (5):

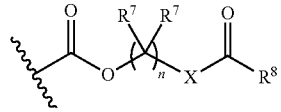

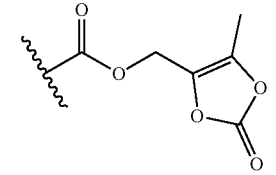

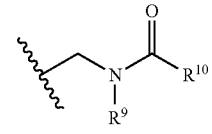

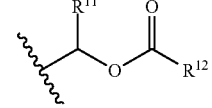

wherein,
each $R^7$ is independently selected from hydrogen and $C_{1-6}$ alkyl;
n is selected from 1 and 2;
X is O;
$R^8$ is selected from hydrogen, $C_{1-6}$ alkyl, and —CH(—$R^{13}$)—NH$_2$, wherein $R^{13}$ is selected from $C_{1-6}$ alkyl, alkoxy, and cycloalkoxy;
$R^9$ is selected from hydrogen and $C_1$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 197. The compound of aspect 196, wherein $R^2$ is a single bond.

Aspect 198. The compound of aspect 196, wherein $R^2$ is methanediyl.

Aspect 199. The compound of aspect 196, wherein $R^2$ is 2-substituted phenyl.

Aspect 200. The compound of any one of aspects 196 to 199, wherein the one or more substituents is —$CH_2$—O—C(O)—$R^4$.

Aspect 201. The compound of any one of aspects 196 to 199, wherein the one or more substituents is —O—C(O)—$R^4$.

Aspect 202. The compound of any one of aspects 196 to 201, wherein $R^4$ is $C_{1-10}$ alkyl.

Aspect 203. The compound of any one of aspects 196 to 202, wherein $R^4$ is selected from methyl, ethyl, iso-propyl, pivalolyl, and phenyl.

Aspect 204. The compound of any one of aspects 196 to 203, wherein $R^6$ is a moiety of Formula (2).

Aspect 205. The compound of any one of aspects 196 to 203, wherein $R^6$ is a moiety of Formula (3).

Aspect 206. The compound of any one of aspects 196 to 203, wherein $R^6$ is a moiety of Formula (4).

Aspect 207. The compound of any one of aspects 196 to 203, wherein $R^6$ is a moiety of Formula (5).

Aspect 208. A compound of Formula (1):

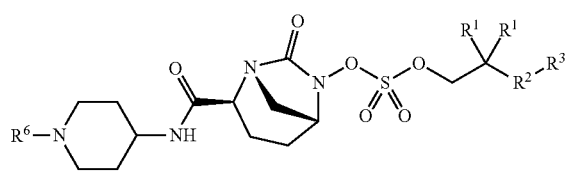

(1)

or a pharmaceutically acceptable salt thereof, wherein,
each $R^1$ is independently selected from $C_{1-3}$ alkyl;
$R^2$ is selected from —$C(R^8)_2$— and —$CH_2$—$C(R^8)_2$—, wherein each $R^8$ is independently selected from $C_{1-3}$ alkyl;
$R^3$ is selected from —C(O)—O—$R^4$ and —O—C(O)—$R^4$, wherein $R^4$ is selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one; and
$R^6$ is selected from a moiety of Formula (2), a moiety of Formula (3), a moiety of Formula (4), and a moiety of Formula (5):

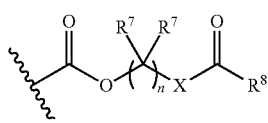

(2)

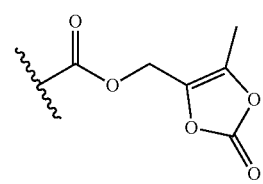

(3)

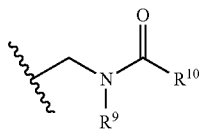

(4)

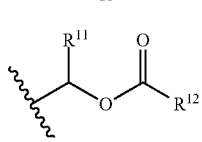

(5)

wherein,
each $R^7$ is independently selected from hydrogen and $C_{1-6}$ alkyl;
n is selected from 1 and 2;
X is O;
$R^8$ is selected from hydrogen, $C_{1-6}$ alkyl, and —CH(—$R^{13}$)—$NH_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 209. The compound of aspect 208, wherein each $R^1$ is methyl.

Aspect 210. The compound of any one of aspects 208 to 209, wherein $R^2$ is —$C(R^8)_2$—.

Aspect 211. The compound of any one of aspects 208 to 209, wherein $R^2$ is —$CH_2$—$C(R^8)_2$—.

Aspect 212. The compound of any one of aspects 208 to 211, wherein each $R^8$ is methyl.

Aspect 213. The compound of aspect 208, wherein each $R^1$ is methyl; and each $R^8$ is methyl.

Aspect 214. The compound of any one of aspects 208 to 213, wherein $R^3$ is —C(O)—O—$R^4$.

Aspect 215. The compound of any one of aspects 208 to 213, wherein $R^3$ is —O—C(O)—$R^4$.

Aspect 216. The compound of any one of aspects 208 to 215, wherein $R^6$ is a moiety of Formula (2).

Aspect 217. The compound of any one of aspects 208 to 215, wherein $R^6$ is a moiety of Formula (3).

Aspect 218. The compound of any one of aspects 208 to 215, wherein $R^6$ is a moiety of Formula (4).

Aspect 219. The compound of any one of aspects 208 to 215, wherein $R^6$ is a moiety of Formula (5).

Aspect 220. A compound of Formula (1):

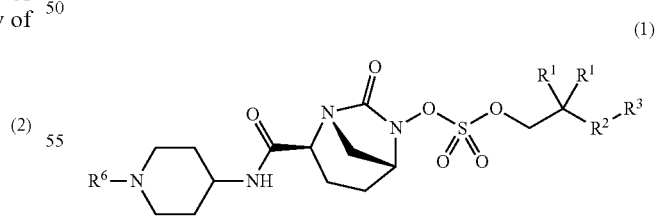

(1)

or a pharmaceutically acceptable salt thereof, wherein,
each $R^1$ together with the carbon atom to which they are bonded form a substituted $C_{5-6}$ heterocyclic ring;
$R^2$ is a single bond;
$R^3$ is $C_1$-3 alkyl; and
$R^6$ is selected from a moiety of Formula (2), a moiety of Formula (3), a moiety of Formula (4), and a moiety of Formula (5):

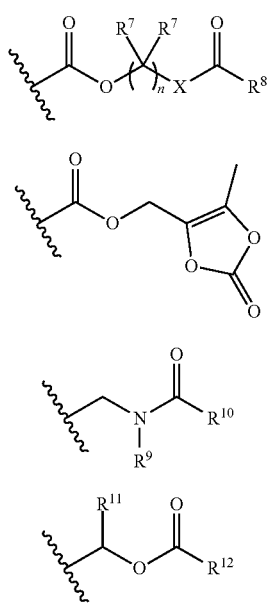

wherein,
each $R^7$ is independently selected from hydrogen and $C_{1-6}$ alkyl;
n is selected from 1 and 2;
X is O;
$R^8$ is selected from hydrogen, $C_{1-6}$ alkyl, and —CH(—$R^{13}$)—$NH_2$, wherein $R^{13}$ is selected from $C_{1-6}$ alkyl, alkoxy, and cycloalkoxy;
$R^9$ is selected from hydrogen and $C_{1-6}$ alkyl;
$R^{10}$ is selected from $C_{1-6}$ alkyl;
$R^{11}$ is selected from hydrogen and $C_{1-6}$ alkyl; and
$R^{12}$ is selected from $C_{1-6}$ alkyl.

Aspect 221. The compound of aspect 220, wherein in the substituted $C_{5-6}$ heterocyclic ring, the one or more heteroatoms is oxygen; and the one or more substituents is independently selected from $C_{1-3}$ alkyl and =O.

Aspect 222. The compound of any one of aspects 220 to 221, wherein each $R^1$ together with the carbon atom to which they are bonded form a tetrahydro-2H-pyran-2-one ring.

Aspect 223. The compound of aspect 220, wherein,
each $R^1$ is independently selected from $C_{1-3}$ alkyl;
$R^2$ is selected from $C_{2-4}$ alkanediyl; and
$R^3$ is substituted $C_{5-6}$ heterocycloalkyl, wherein the one or more heteroatoms is independently selected from N and O; and the one or more substituents is independently selected from $C_{1-3}$ alkyl and =O.

Aspect 224. The compound of any one of aspects 220 to 223, wherein $R^4$ has the structure of Formula (6):

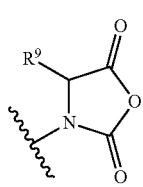

wherein $R^9$ is selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

Aspect 225. The compound of any one of aspects 220 to 224, wherein $R^6$ is a moiety of Formula (2).

Aspect 226. The compound of any one of aspects 220 to 224, wherein $R^6$ is a moiety of Formula (3).

Aspect 227. The compound of any one of aspects 220 to 224, wherein $R^6$ is a moiety of Formula (4).

Aspect 228. The compound of any one of aspects 220 to 224, wherein $R^6$ is a moiety of Formula (5).

Aspect 229. A pharmaceutical composition comprising the compound of any one of aspects 1 to 228 and a pharmaceutically acceptable vehicle.

Aspect 230. The pharmaceutical composition of aspect 229, further comprising an antibiotic.

Aspect 231. The pharmaceutical composition of any one of aspects 220 to 230, wherein the antibiotic comprises a β-lactam antibiotic.

Aspect 232. The pharmaceutical composition of any one of aspects 220 to 231, wherein the pharmaceutical composition comprises an oral dosage formulation.

Aspect 233. The pharmaceutical composition of any one of aspects 220 to 232, wherein the pharmaceutical composition comprises an oral dosage form.

Aspect 234. A method of treating a bacterial infection in a patient comprising administering to a patient in need of such treatment: a therapeutically effective amount of the compound of any one of aspects 1 to 228 or a pharmaceutically acceptable salt thereof; and a therapeutically effective amount of a β-lactam antibiotic.

Aspect 235. The method of aspect 234, wherein administering comprises orally administering.

Aspect 236. The method of any one of aspects 234 to 235, wherein bacteria causing the bacterial infection produce a β-lactamase enzyme.

Aspect 237. The method of any one of aspects 234 to 236, wherein the bacterial infection is selected from a gram-negative bacterial infection, a gram-positive bacterial infection, an anaerobic bacterial infection, an aerobic bacterial infection, and a mecoraerophilic bacterial infection.

Aspect 238. The method of any one of aspects 234 to 237, wherein, the bacterial infection is capable of being treated with a therapeutically effective amount of the (-lactam antibiotic when co-administered with a therapeutically effective amount of relebactam.

Aspect 239. A method of inhibiting a β-lactamase enzyme in a patient comprising administering to the patient an effective amount of the compound of any one of aspects 1 to 228.

Aspect 240. The method of aspect 239, wherein administering comprises orally administering.

Aspect 241. The method of any one of aspects 239 to 240, wherein administering comprises administering an oral dosage form.

Aspect 242. The method of any one of aspects 239 to 241, wherein the β-lactamase enzyme comprises a Class A β-lactamase enzyme, a Class B β-lactamase enzyme, or a Class C β-lactamase enzyme.

Aspect 243. The method of any one of aspects 239 to 242, wherein the β-lactamase enzyme is inhibited by relebactam.

Aspect 244. A compound having the structure of Formula (13):

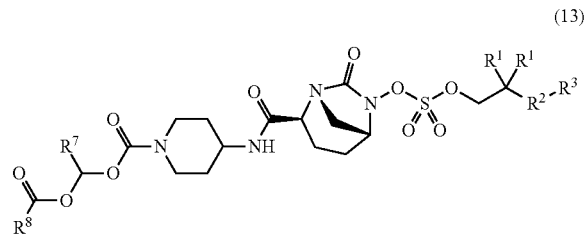

(13)

or a pharmaceutically acceptable salt thereof, wherein,
each $R^1$ is independently selected from hydrogen and $C_{1-3}$ alkyl;
$R^2$ is a single bond;
$R^3$ is —C(O)—O—$R^4$, wherein $R^4$ is $C_{1-4}$ alkyl;
$R^7$ is selected from hydrogen and $C_{1-4}$ alkyl; and
$R^8$ is $C_{1-4}$ alkyl.

Aspect 245. The compound of aspect 244, wherein each R1 is independently selected from hydrogen, methyl, ethyl, n-propyl, and iso-propyl.

Aspect 246. The compound of aspect 244, wherein each R1 is methyl.

Aspect 247. The compound of any one of aspects 244 to 246, wherein R4 is selected from methyl, ethyl, n-propyl, and iso-propyl.

Aspect 248. The compound of any one of aspects 244 to 246, wherein R4 is ethyl.

Aspect 249. The compound of any one of aspects 244 to 248, wherein R7 is selected from hydrogen, methyl, ethyl, n-propyl, and iso-propyl.

Aspect 250. The compound of any one of aspects 244 to 248, wherein R7 is hydrogen.

Aspect 251. The compound of any one of aspects 244 to 248, wherein R7 is methyl.

Aspect 252. The compound of any one of aspects 244 to 251, wherein R8 is selected from methyl, ethyl, n-propyl, iso-propyl, n-butyl, iso-butyl, and tert-butyl.

Aspect 253. The compound of any one of aspects 244 to 251, wherein R8 is selected from n-butyl, iso-butyl, and tert-butyl.

Aspect 254. The compound of any one of aspects 244 to 251, wherein R8 is tert-butyl.

Aspect 255. The compound of any one of aspects 244 to 251, wherein R8 is selected from methyl, ethyl, n-propyl, and iso-propyl.

Aspect 256. The compound of aspect 244, wherein the compound is selected from:
acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (6/86);
1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (7/87);
(pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (8/88);
(isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (9/89);
1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (10/90);
1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (11/91);
or a pharmaceutically acceptable salt of any of the foregoing;
or a combination of any of the foregoing.

Aspect 257. A pharmaceutical composition comprising the compound of any one of aspects 244 to 256 and a pharmaceutically acceptable vehicle.

Aspect 258. The pharmaceutical composition of aspect 257, further comprising an antibiotic.

Aspect 259. The pharmaceutical composition of aspect 258, wherein the antibiotic comprises a β-lactam antibiotic.

Aspect 260 The pharmaceutical composition of any one of aspects 257 to 259, wherein the pharmaceutical composition comprises an oral dosage formulation.

Aspect 261. The pharmaceutical composition of any one of aspects 257 to 260, wherein the pharmaceutical composition comprises an oral dosage form.

Aspect 262. A method of treating a bacterial infection in a patient comprising administering to a patient in need of such treatment: a therapeutically effective amount of the compound of any one of aspects 244 to 256 or a pharmaceutically acceptable salt thereof; and a therapeutically effective amount of a β-lactam antibiotic.

Aspect 263. The method of aspect 262, wherein administering comprises orally administering.

Aspect 264. The method of any one of aspects 262 to 263, wherein bacteria causing the bacterial infection produce a β-lactamase enzyme.

Aspect 265. The method of any one of aspects 262 to 264, wherein the bacterial infection is selected from a gram-negative bacterial infection, a gram-positive bacterial infection, an anaerobic bacterial infection, an aerobic bacterial infection, and a mecoraerophilic bacterial infection.

Aspect 266. The method of any one of aspects 262 to 265, wherein, the bacterial infection is capable of being treated with a therapeutically effective amount of the β-lactam antibiotic when co-administered with a therapeutically effective amount of relebactam.

Aspect 267. A method of inhibiting a β-lactamase enzyme in a patient comprising administering to the patient an effective amount of the compound of any one of aspects 244 to 256.

Aspect 268. The method of aspect 267, wherein administering comprises orally administering.

Aspect 269. The method of any one of aspects 267 to 268, wherein administering comprises administering an oral dosage form.

Aspect 270. The method of any one of aspects 262 to 266, wherein the β-lactamase enzyme comprises a Class A β-lactamase enzyme, a Class B β-lactamase enzyme, or a Class C β-lactamase enzyme.

Aspect 271. The method of any one of aspects 264 to 266, wherein the β-lactamase enzyme is inhibited by relebactam.

EXAMPLES

The following examples describe in detail the synthesis of compounds of Formula (1), characterization of compounds of Formula (1), and uses of compounds of Formula (1). It will be apparent to those skilled in the art that many modifications, both to materials and methods, may be practiced without departing from the scope of the disclosure.

Example 1

Synthesis of tert-butyl 4-((2S,5R)-6-(benzyloxy)-7-oxo-1,6-diazabicyclo[3.2.1]octane-2-carboxamido)piperidine-1-carboxylate (1)

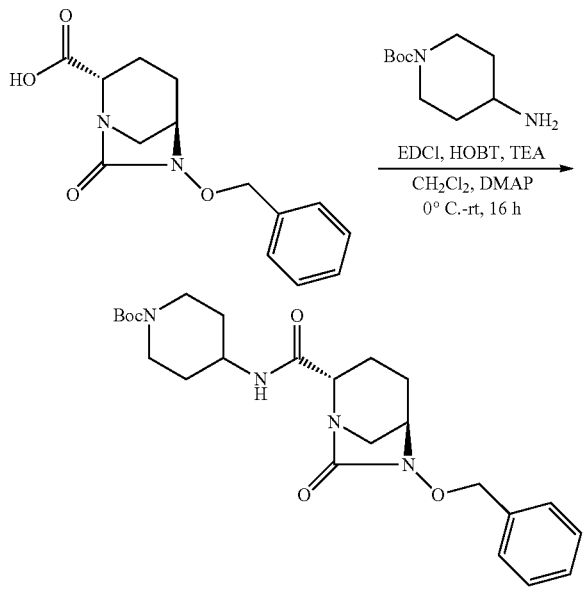

Step 1: Synthesis of (2S,5R)-6-(benzyloxy)-7-oxo-1,6-diazabicyclo[3.2.1]octane-2-carboxylic acid (1a)

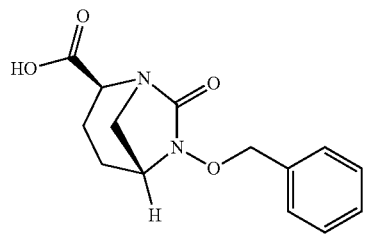 [SMILES: O=C(O)[C@@H]1CC[C@@H]2CN1C(=O)N2OCc1ccccc1]

A solution of distilled sulfuryl chloride (0.61 mL, 7.5 mmol) in Et₂O (10 mL) was cooled to −78° C. under nitrogen. A solution of ethyl 3-hydroxy-2,2-dimethylpropanoate (2a) (1.0 g, 6.8 mmol) and pyridine (0.55 mL, 6.8 mmol) in Et₂O (2.0 mL) was then added dropwise over 1 h via a syringe. The reaction was stirred at −78° C. for 1 h, and the mixture was allowed to warm to room temperature and stirred for additional 2 h. After the mixture was filtered, the filtrate was concentrated under vacuum to give the product (20a) as a colorless liquid (1.46 g, yield 87%). ¹H NMR (300 MHz, CDCl₃): δ 4.50 (s, 2H), 4.19 (q, J=6.9 Hz, 2H), 1.31 (s, 6H), 1.28 (t, J=6.9 Hz, 3H).

Step 2: Synthesis of tert-butyl 4-((2S,5R)-6-(benzyloxy)-7-oxo-1,6-diazabicyclo[3.2.1]octane-2-carboxamido)piperidine-1-carboxylate (1)

(2S,5R)-6-(Benzyloxy)-7-oxo-1,6-diazabicyclo[3.2.1]octane-2-carboxylic acid (1a) (32.0 g, 113 mmol), Et₃N (50 mL, 359 mmol) and 1-hydroxybenzotriazole (24.4 g, 181 mmol) in DCM (500 mL) was cooled to 0° C., and the resulting solution was stirred at 0° C. for 30 min. Tert-butyl 4-aminopiperidine-1-carboxylate (25.2 g, 120 mmol) and N,N-4-dimethylaminopyridine (3.0 g, 25 mmol) were added to the reaction mixture, warmed to 25° C., and stirred for 16 h. The mixture was washed with H₂O (2×300 mL), 10% aqueous citric acid solution (2×300 mL), saturated Na₂CO₃ solution (2×250 mL), H₂O (2×300 mL), dried (Na₂SO₄), and concentrated to give a pale foam. The solid was stirred with ether (300 mL) for 2 h and filtered to give the title compound (1) as a solid. The filtrate was concentrated and purified by column chromatography on silica gel using EtOAc/hexanes (1:1 to 6:4) as eluent to give additional product. Combined yield: 43.1 g, 83%. LC-MS: m/z=459.2 [M+H]⁺; ¹H-NMR (300 MHz, CDCl₃): δ 7.43-7.36 (m, 5H), 6.55 (d, J=8.1 Hz, 1H), 5.06 (d, J=11.1 Hz, 1H), 4.91 (d, J=11.4 Hz, 1H), 4.01-3.93 (m, 2H), 3.89 (d, J=7.2 Hz, 2H), 3.29 (br. s, 1H), 3.00 (d, J=8.7 Hz, 1H), 2.86 (t, J=12.0 Hz, 2H), 2.64 (d, J=11.1 Hz, 1H), 2.41-2.34 (m, 1H), 2.01-1.85 (m, 4H), 1.45 (s, 9H), 1.35-1.28 (m, 2H).

Example 2

Synthesis of tert-butyl 4-((2S,5R)-6-hydroxy-7-oxo-1,6-diazabicyclo[3.2.1]octane-2-carboxamido)piperidine-1-carboxylate hydrate (2)

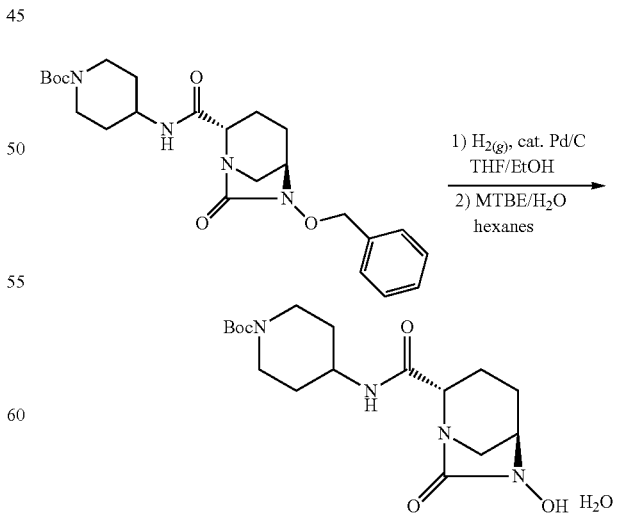

A round bottom flask purged with nitrogen was charged with tert-butyl 4-((2S,5R)-6-(benzyloxy)-7-oxo-1,6-diazabicyclo[3.2.1]octane-2-carboxamido)piperidine-1-carboxylate (1) (5.0 g, 11 mmol), palladium on carbon (10 wt % loading dry basis; ~50% wet; 750 mg, 0.7 mmol), followed by EtOH (30 mL), and THF (60 mL). The round bottom flask was charged with hydrogen, and the reaction mixture was stirred at 25° C. for 90 min. The hydrogenation flask and a receiving vessel were cooled to −10 C (dry ice/brine bath). The catalyst was filtered-off over a pad of Celite® into a receiving vessel, and the pad was rinsed with 3:1 THF/EtOH (20 mL). The filtrate was charged with tert-butyl methyl ether (100 mL) followed by distilled $H_2O$ (8 mL) and the mixture was stirred at −10° C. for several min. The mixture was charged with hexanes 100 mL and stirred at −10° C. for 1 h under an inert atmosphere of nitrogen. The suspension was concentrated, the residue was sonicated for several minutes in hexanes (50 mL), and the mixture concentrated. This was repeated once more to give the title compound (2) (3.9 g, 93%) as a solid. Note: This solid appeared to be stable to prolonged storage at 25° C. LC-MS: m/z=369.1 [M+H]$^+$; $^1$H-NMR (300 MHz, CDCl$_3$): δ 6.69 (d, J=8.1 Hz, 1H), 4.04-3.91 (m, 3H), 3.85 (d, J=7.8 Hz, 1H), 3.74 (s, 1H), 3.16 (d, J=11.1 Hz, 1H), 2.87 (t, J=12.2 Hz, 2H), 2.78 (d, J=11.1 Hz, 1H), 2.41 (dd, J=14.7, 6.6 Hz, 1H), 2.10 (m, 1H), 1.99-1.88 (m, 3H), 1.76-1.65 (m, 1H), 1.44 (s, 9H), 1.40-1.31 (m, 2H); $^1$H-NMR (300 MHz, d$_6$-DMSO): δ 9.70 (s, 1H), 7.87 (d, J=8.1 Hz, 1H), 3.87-3.72 (m, 3H), 3.64 (d, J=6.6 Hz, 1H), 3.56 (s, 1H), 2.98-2.94 (m, 1H), 2.87-2.83 (m, 1H), 2.77 (m, 2H), 2.06-2.00 (m, 1H), 1.86 (m, 1H), 1.77-1.60 (m, 4H), 1.37-1.27 (m, 11H); $^{13}$C-NMR (75 MHz, d$_6$-DMSO): δ 168.8, 167.0, 153.9, 78.6, 58.8, 58.7, 46.8, 46.1, 31.1, 31.0, 28.1, 20.3, 18.2.

Example 3

Synthesis of ethyl 3-((chlorosulfonyl)oxy)-2,2-dimethylpropanoate (3)

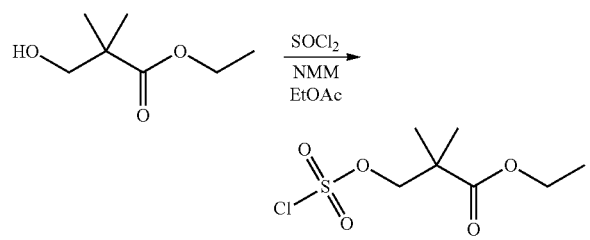

A round bottom flask was charged with 17.6 g of ethyl 3-hydroxy-2,2-dimethylpropanoate. $H_2O$ was removed by co-evaporating the alcohol with hexanes (4×100 mL). The residue of ethyl 3-hydroxy-2,2-dimethylpropanoate (16.1 g, 110 mmol) was dissolved in anhydrous EtOAc (80 mL) and stirred at 0° C. for 10 min. 4-Methylmorpholine (13.5 mL, 121 mmol) was added dropwise to the mixture and stirred at 0° C. for 10 min. Sulfuryl chloride (10.1 mL, 121 mmol) in anhydrous EtOAc (40 mL) was added dropwise over the course of 10 min, and the reaction mixture was stirred at 0° C. for 40 min. The solids were removed by filtration, and the filtrate was recovered in a receiving vessel that was cooled to 0° C. The filter cake was then rinsed with EtOAc (2×50 mL) giving the title compound (3) as a solution in EtOAc. This was used in the next step without further purification or concentration. The yield was assumed to be quantitative. $^1$H-NMR (300 MHz, CDCl$_3$): δ 4.50 (s, 2H), 4.19 (q, J=7.1 Hz, 2H), 1.31-1.25 (m, 9H).

Example 4

Synthesis of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4)

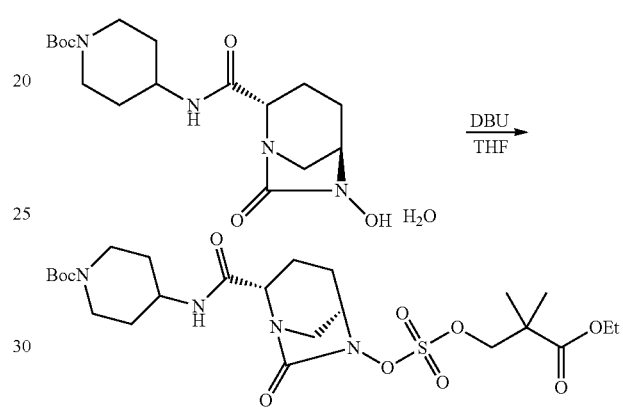

A flask was charged with tert-butyl 4-((2S,5R)-6-hydroxy-7-oxo-1,6-diazabicyclo[3.2.1]octane-2-carboxamido)piperidine-1-carboxylate hydrate (2) (3.7 g, 9.6 mmol) dissolved in THF (150 mL) and cooled to −78° C. A solution of ethyl 3-((chlorosulfonyl)oxy)-2,2-dimethylpropanoate (ca. 0.67 M, 29 mL, 19 mmol) in EtOAc was added dropwise to the reaction mixture at a rate such that the reaction temperature did not exceed −55° C., and this was stirred for 15 min. 1,8-Diazabicyclo[5.4.0]undec-7-ene (4.4 mL, 29 mmol) was added dropwise to the reaction mixture at such a rate that the reaction temperature did not exceed −58° C., and this was stirred for 10 min. The mixture was warmed to 0° C. at a rate not exceeding 20° C. per min. The reaction mixture was stirred at 0° C. (ice/water bath) until the starting material was consumed (within 1 h; reaction was followed by HPLC at 196 nm). The mixture was poured into ice cold $H_2O$ (300 mL), extracted with EtOAc (200 mL), and the organic layer was washed with brine (200 mL), dried (Na$_2$SO$_4$), and concentrated under vacuum. The residue was purified by column chromatography on silica gel using EtOAc/hexanes (0:1 to 7:3) as eluent to give the title compound (4) (4.4 g, 80%) as a white foam. LC-MS: m/z=577.1 [M+H]$^+$; $^1$H-NMR (300 MHz, CDCl$_3$): δ 6.43 (d, J=8.7 Hz, 1H), 4.71 (d, J=9.3 Hz, 1H), 4.60 (d, J=8.7 Hz, 1H), 4.21-3.93 (m, 7H), 3.29-3.26 (m, 1H), 2.92-2.83 (m, 3H), 2.48-2.41 (m, 1H), 2.17-2.14 (m, 1H), 1.94-1.83 (m, 4H), 1.46 (s, 9H), 1.40-1.25 (m, 11H); $^{13}$C-NMR (75 MHz, CDCl$_3$): δ 174.1, 167.9, 167.1, 154.7, 80.4, 79.9, 62.0, 61.3, 60.1, 47.1, 46.8, 42.8, 42.6, 32.1, 31.9, 28.5, 22.1, 21.7, 20.8, 17.6, 14.1.

Example 5

Synthesis of (5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (5)

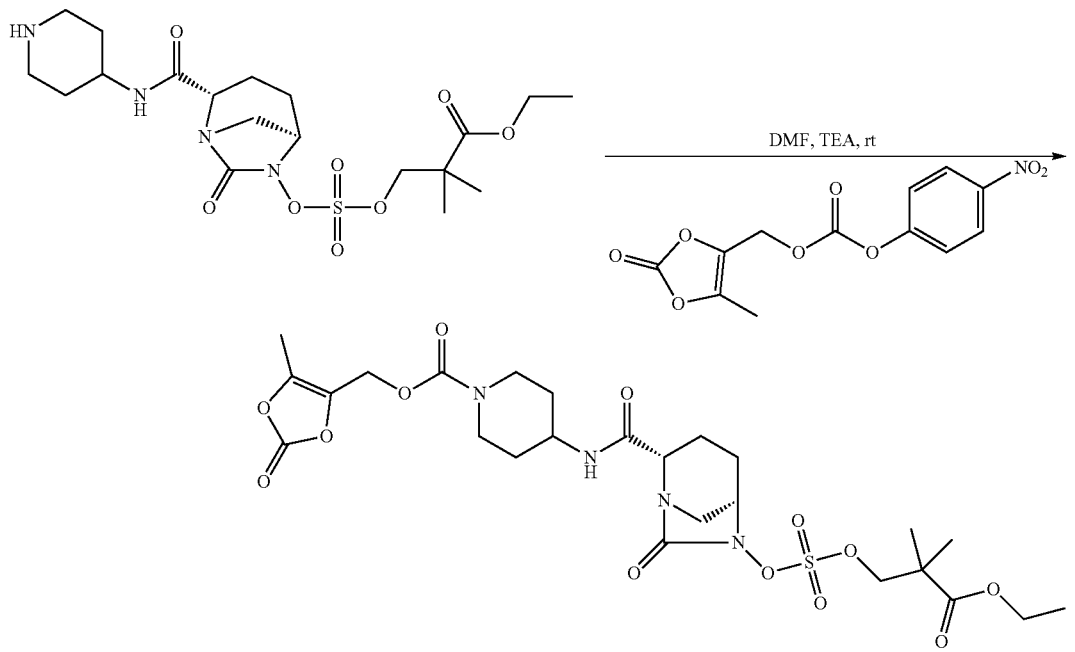

Step 1: Synthesis of (5-methyl-2-oxo-1,3-dioxol-4-yl)methyl (4-nitrophenyl) carbonate (5a)

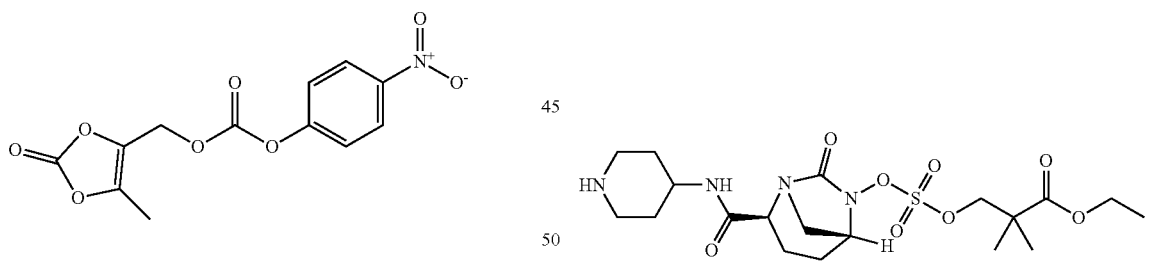

To a stirred mixture of 4-nitrophenyl chloroformate (3.0 g, 14.9 mmol) in DCM (30 mL) at 0° C. was added pyridine (1.4 mL, 16.4 mmol). 4-(Hydroxymethyl)-5-methyl-1,3-dioxol-2-one (2.03 g, 15.6 mmol) in DCM (15 mL) was then added to the mixture. The mixture was stirred at 0° C. for 30 min, then allowed to warm to room temperature and stirred for 18 h. Additional DCM was added, and the mixture was washed with $H_2O$ (1×), 0.5 N NaOH (1×), $H_2O$ (2×), and brine (1×), then dried ($Na_2SO_4$), filtered and concentrated under vacuum. The residue was purified by column chromatography on silica gel (40 g column) using EtOAc/hexanes as eluent (0:1 to 3:2) to give the title compound (5a) as an off-white solid (3.7 g). $^1$H-NMR (300 MHz, $CDCl_3$) δ 8.30 (d, J=8.7 Hz, 2H), 7.40 (d, J=8.7 Hz, 2H), 5.03 (s, 2H), 2.22 (s, 3H); $^{13}$C-NMR (75 MHz, $CDCl_3$), δ 155.1, 152.3, 151.7, 145.7, 141.5, 132.2, 125.4, 121.7, 58.1, 9.5.

Step 2: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (5b)

TFA (5.8 mL, 76.2 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (1.0 g, 1.7 mmol) in DCM (10 mL) at −10° C. The reaction mixture was stirred at −10° C. for 30 min. LC-MS indicated that the starting material was completely consumed (m/z=477.3 [M+H]$^+$ for desired product). The mixture was concentrated under vacuum to give the crude title compound (5b) containing a small amount of TFA. The compound was used directly in the next step without further purification. m/z=477.3 [M+H]$^+$ Step 3: Synthesis of (5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (5)

To a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (5b) (0.82 g, 1.7 mmol) in DMF (20 mL) was added Et₃N (2.9 mL, 20.6 mmol), followed by (5-methyl-2-oxo-1,3-dioxol-4-yl)methyl (4-nitrophenyl) carbonate (0.61 g, 2.1 mmol). The reaction mixture was stirred at 25° C. overnight, then diluted with EtOAc and washed with H₂O. The organic layer was dried (Na₂SO₄), filtered and concentrated under vacuum. The residue was purified by column chromatography on silica gel (40 g column) using EtOAc/hexanes as eluent (0:1 to 1:0) to give the desired product (100 mg) as a solid (foam). Also obtained from the column was the title compound (5) with a little bit impurity (130 mg). Data for pure product m/z=633.3 [M+H]⁺; ¹H-NMR (300 MHz, CDCl₃) δ 6.46 (d, J=7.8 Hz, 1H), 4.84 (s, 2H), 4.71 (d, J=8.7 Hz, 1H), 4.60 (d, J=9.3 Hz, 1H), 4.21-3.98 (m, 7H), 3.27 (d, J=11.7 Hz, 1H), 2.95-2.87 (m, 3H), 2.44-2.40 (m, 1H), 2.18 (s, 3H), 2.15-2.14 (m, 1H), 1.96-1.85 (m, 4H), 1.40-1.24 (m, 11H); ¹³C-NMR (75 MHz, CDCl₃) δ 174.4, 168.3, 167.3, 154.6, 140.3, 134.3, 80.8, 62.2, 61.6, 60.4, 55.2, 47.1, 43.3, 43.1, 32.0, 22.4, 22.0, 21.0, 17.8, 14.4, 9.8.

Example 6

Synthesis of acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (6)

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (6a)

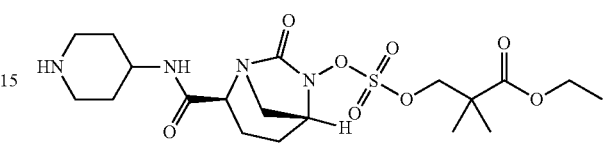

TFA (5.8 mL, 76.2 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (1.0 g, 1.7 mmol) in DCM (10 mL) at −10° C. The reaction mixture was stirred at −10° C. for 30 min. LC-MS indicated that the starting material was completely consumed (m/z=477.3 [M+H]⁺ for desired product). The mixture was concentrated under vacuum to give the crude title compound (6a) containing a small amount of TFA. The compound was used directly in the next step without further purification. m/z=477.3 [M+H]⁺

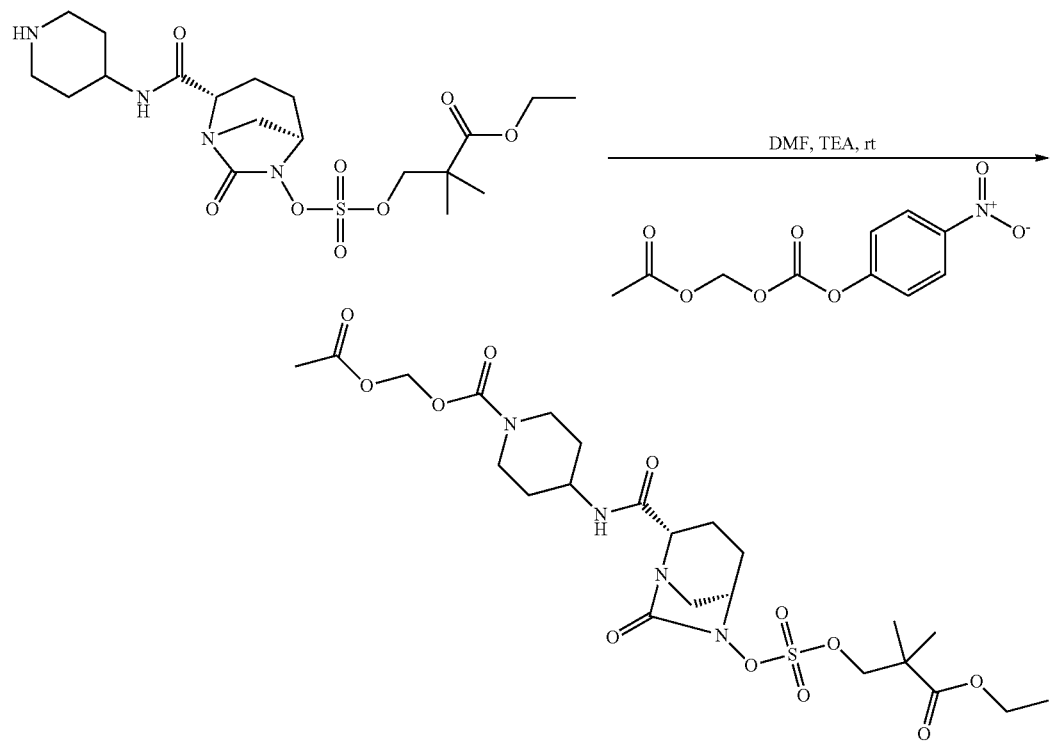

Step 2: Synthesis of acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (6)

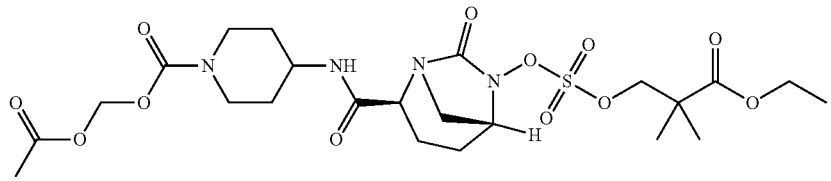 [SMILES: CCOC(=O)C(C)(C)COS(=O)(=O)ON1C(=O)N2C[C@H]1CC[C@H]2C(=O)NC1CCN(C(=O)OCOC(C)=O)CC1]

Et$_3$N (2.9 mL, 20.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (6a) (0.82 g, 1.7 mmol) in DMF (20 mL) under an atmosphere of nitrogen. (((4-Nitrophenoxy)carbonyl)oxy)methyl acetate (prepared according to PCT International Publication No. WO 2009/151392) (527 mg, 2.1 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give the product (300 mg) as a white foam. NMR and LCMS indicated that the product was pure, but HPLC showed the presence of an unknown impurity. A portion of the white foam (90 mg) was purified again by reverse phase HPLC using MeCN/H$_2$O (1:9 to 95:5) as eluent to give the title compound (6) (70 mg) as a solid. m/z=593.1 [M+H]$^+$; $^1$H-NMR (300 MHz, CDCl$_3$) δ 6.44 (d, J=8.1 Hz, 1H), 5.75 (s, 2H), 4.71 (d, J=9.0 Hz, 1H), 4.60 (d, J=8.7 Hz, 1H), 4.21-3.97 (m, 7H), 3.27 (d, J=11.7 Hz, 1H), 3.10-2.87 (m, 3H), 2.46-2.41 (m, 1H), 2.17-2.11 (m, 4H), 2.00-1.88 (m, 4H), 1.38-1.25 (m, 11H); $^{13}$C-NMR (75 MHz, CDCl$_3$) δ 174.0, 169.9, 168.0, 166.9, 153.4, 80.4, 61.9, 61.2, 60.0, 46.8, 42.9, 42.9, 42.8, 32.0, 31.8, 31.5, 22.1, 21.6, 20.9, 20.7, 17.4, 14.1.

Example 7

Synthesis of 1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (7)

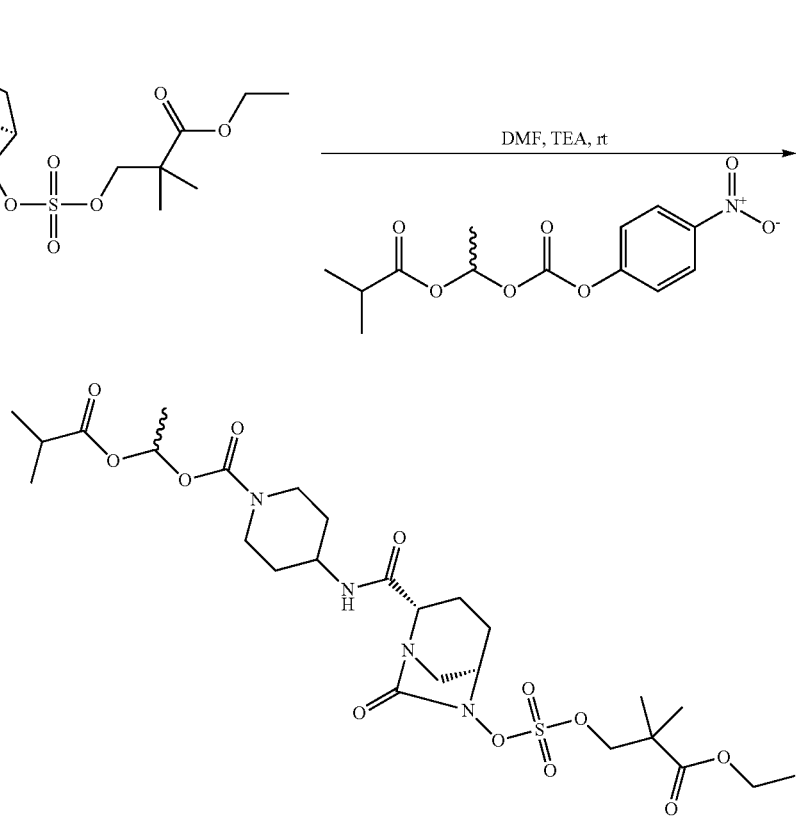

Step 1: Synthesis of ethyl 2,2-dimethyl-3-(((((2S, 5R)-7-oxo-2-(piperidin-4-ylcarbamoyl)-1,6-diazabicyclo[3.2.1]octan-6-yl)oxy)sulfonyl)oxy)propanoate (7a)

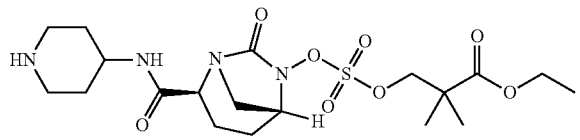 [SMILES: CCOC(=O)C(C)(C)COS(=O)(=O)ON1C(=O)N2C[C@H]1CC[C@H]2C(=O)NC1CCNCC1]

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (0.8 g, 1.4 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude title compound (7a) containing a small amount of TFA. The compound was used directly in the next step without further purification. m/z=477.3 [M+H]$^+$ Step 2: Synthesis of 1-(isobutyryloxy)ethyl 4-((2S, 5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (7)

Et$_3$N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (7a) (0.66 g, 1.4 mmol) in DMF (20 mL) under an atmosphere of nitrogen. 1-(((4-Nitrophenoxy)carbonyl)oxy)ethyl isobutyrate (ex-ChemScene catalog no. CS-B0942) (494 mg, 1.7 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give the product (290 mg) as a white foam. NMR and LCMS indicated that the title compound (7) was pure, but HPLC showed the presence of an unknown impurity. The white foam was purified again by reverse phase HPLC using MeCN/H$_2$O (1:9 to 95:5) as eluent to give the product (220 mg) as a white foam. m/z=635.1 [M+H]$^+$; $^1$H-NMR (300 MHz, CDCl$_3$) δ 6.82-6.76 (q, 1H), 6.45 (d, J=7.5 Hz, 1H), 4.71 (d, J=8.7 Hz, 1H), 4.60 (d, J=9.3 Hz, 1H), 4.23-3.97 (m, 7H), 3.27 (d, J=11.7 Hz, 1H), 2.94-2.87 (m, 3H), 2.56-2.41 (m, 2H), 2.17-2.14 (m, 1H), 2.00-1.77 (m, 4H), 1.48 (d, J=5.1 Hz, 3H), 1.47-1.24 (m, 11H), 1.16 (d, J=7.2 Hz, 6H); $^{13}$C-NMR (75 MHz, CDCl$_3$) δ 175.2, 174.1, 167.9, 166.9, 153.0, 90.0, 80.4, 61.9, 61.2, 60.0, 46.8, 46.7, 42.8, 42.8, 33.8, 31.8, 22.1, 21.6, 20.7, 19.8, 18.7, 18.7, 17.5, 14.1.

Example 8

Synthesis of (pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (8)

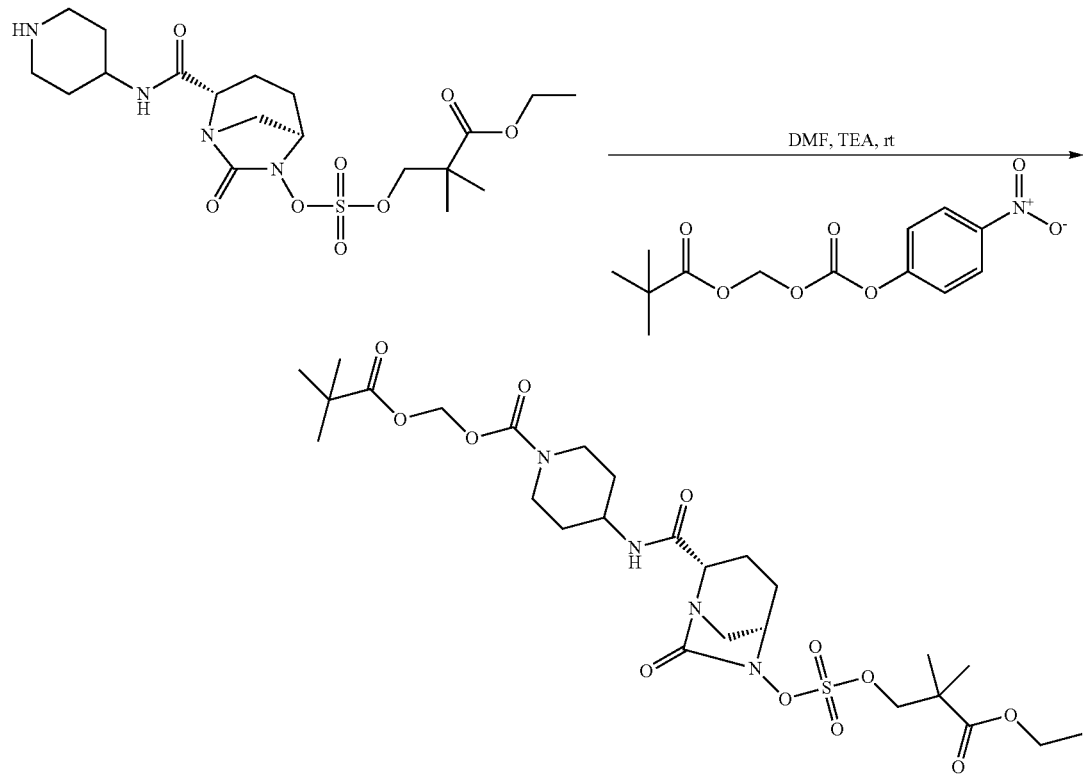

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (8a)

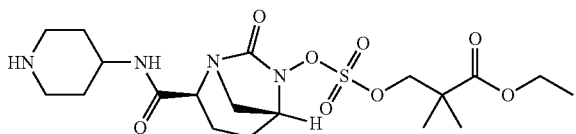

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (0.8 g, 1.4 mmol) in DCM (10 mL) at −10° C. The reaction mixture was stirred at −10° C. for 60 min. LC-MS indicated that the starting material was completely consumed (m/z=477.3 [M+H]+ for desired product). The mixture was concentrated under vacuum to give the crude title compound (8a) containing a small amount of TFA. The compound was used directly in the next step without further purification. m/z=477.3 [M+H]+. Note: excess TFA present.

Step 2: Synthesis of (pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (8)

Et₃N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (8a) (0.66 g, 1.4 mmol) in DMF (20 mL) under an atmosphere of nitrogen. (((4-Nitrophenoxy)carbonyl)oxy)methyl pivalate (494 mg, 1.7 mmol) was added and the mixture was stirred at 25° C. overnight. The reaction mixture was diluted with EtOAc and H₂O, and the aqueous and organic layers were partitioned. The organic layer was dried (Na₂SO₄), filtered and concentrated under vacuum to leave a crude residue. The residue was purified by column chromatography on silica gel (40 g column) using EtOAc/hexanes (0:1 to 1:0) as eluent to give impure product. The impure product was purified again by reverse phase HPLC using MeCN/H₂O (1:9 to 95:5) as eluent to give the title compound (8) (100 mg) as a white foam. LC/MS: m/z=635.2 [M+H]+; ¹H-NMR (300 MHz, CDCl₃): δ 6.43 (d, J=7.5 Hz, 1H), 5.77 (s, 2H), 4.71 (d, J=8.7 Hz, 1H), 4.60 (d, J=8.7 Hz, 1H), 4.22-3.97 (m, 7H), 3.27 (d, J=11.7 Hz, 1H), 2.97-2.87 (m, 3H), 2.46-2.40 (m, 1H), 2.18-2.14 (m, 1H), 1.97-1.83 (m, 4H), 1.42-1.24 (m, 11H), 1.22 (s, 9H); ¹³C-NMR (75 MHz, CDCl₃): δ 177.5, 174.0, 167.9, 166.9, 153.4, 80.6, 80.4, 61.9, 61.2, 60.0, 46.8, 46.7, 42.9, 42.9, 42.8, 38.8, 31.8, 31.6, 26.9, 22.1, 21.6, 20.7, 17.4, 14.1.

Example 9

Synthesis of (isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (9)

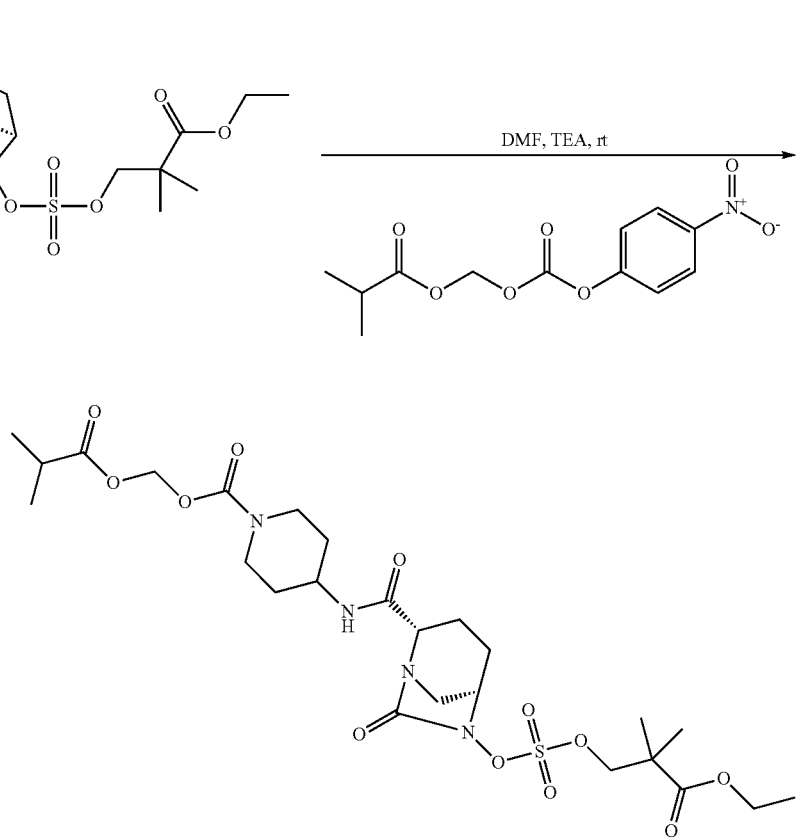

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (9a)

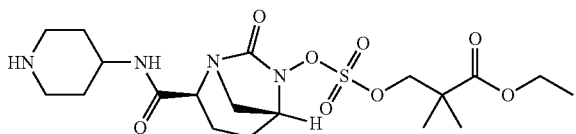

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (0.8 g, 1.4 mmol) in DCM (10 mL) at −10° C. The reaction mixture was stirred at −10° C. for 60 min. LC-MS indicated that the starting material was completely consumed (m/z=477.3 [M+H]+ for desired product). The mixture was concentrated under vacuum to give the crude title compound (9a) containing a small amount of TFA. The compound was used directly in the next step without further purification. m/z=477.3 [M+H]+ Note: excess TFA present.

Step 2: Synthesis of (isobutyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (9)

Et₃N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (9a) (0.66 g, 1.4 mmol) in DMF (20 mL) under an atmosphere of nitrogen. (((4-Nitrophenoxy)carbonyl)oxy)methyl isobutyrate (471 mg, 1.7 mmol) was added and the mixture was stirred at 25° C. overnight. The reaction mixture was diluted with EtOAc and H₂O, and the aqueous and organic layers were partitioned. The organic layer was dried (Na₂SO₄), filtered and concentrated under vacuum to leave a crude residue. The residue was purified by column chromatography on silica gel (40 g column) using EtOAc/hexanes (0:1 to 1:0) as eluent to give impure product. The impure product was purified again by reverse phase HPLC using MeCN/H₂O (1:9 to 95:5) as eluent to give the title compound (9) (100 mg) as a white foam. LC/MS: m/z=621.2 [M+H]+; ¹H-NMR (300 MHz, CDCl₃): δ 6.43 (d, J=8.1 Hz, 1H), 5.77 (s, 2H), 4.71 (d, J=8.7 Hz, 1H), 4.60 (d, J=8.7 Hz, 1H), 4.22-3.97 (m, 7H), 3.27 (d, J=11.1 Hz, 1H), 2.96-2.87 (m, 3H), 2.64-2.55 (m, 1H), 2.46-2.41 (m, 1H), 2.18-2.14 (m, 1H), 1.99-1.78 (m, 4H), 1.37-1.25 (m, 11H), 1.18 (d, J=6.9 Hz, 6H); ¹³C-NMR (75 MHz, CDCl₃): δ 176.7, 174.7, 168.6, 167.5, 154.1, 81.0, 62.5, 61.9, 60.6, 47.4, 47.4, 43.6, 43.5, 43.4, 34.4, 32.4, 22.7, 22.2, 21.3, 19.3, 18.1, 14.7.

Example 10

Synthesis of 1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (10)

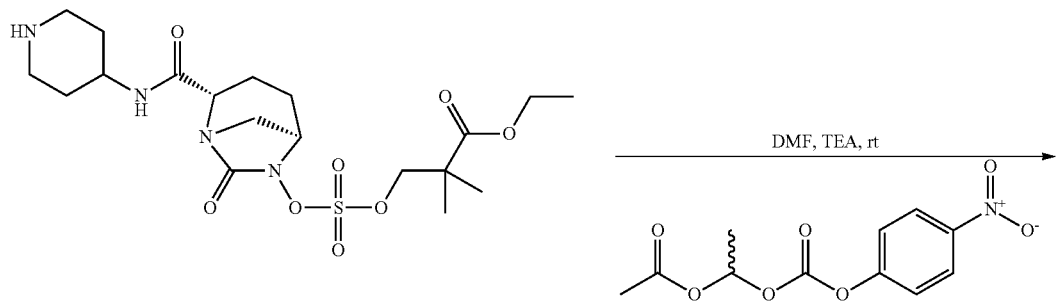

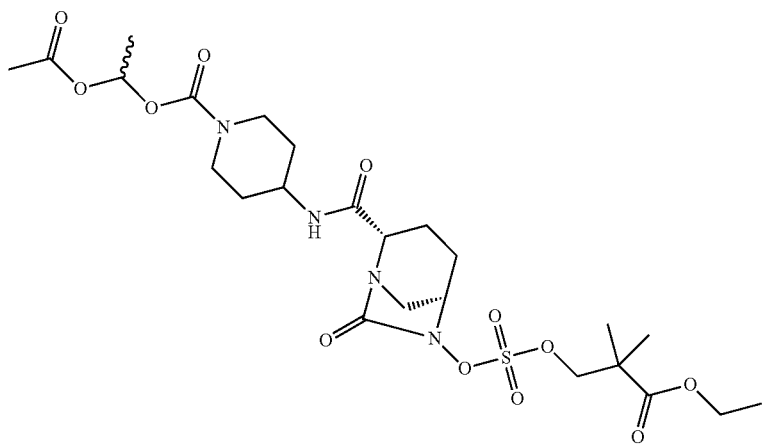

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (10a)

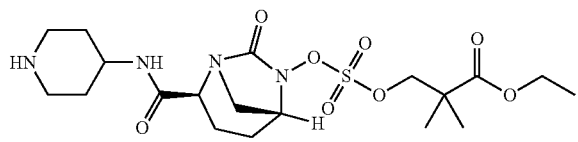 [SMILES: CCOC(=O)C(C)(C)COS(=O)(=O)ON1C(=O)N2C[C@H]1CC[C@H]2C(=O)NC1CCNCC1]

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (0.8 g, 1.4 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude title compound (10a) containing a small amount of TFA. The compound was used directly in the next step without further purification. m/z=477.3. [M+H]$^+$. Note: excess TFA present.

Step 2: Synthesis of 1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (10)

Et$_3$N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (10a) (0.66 g, 1.4 mmol) in DMF (20 mL) under a nitrogen atmosphere. 1-(((4-Nitrophenoxy)carbonyl)oxy)ethyl acetate (450 mg, 1.7 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give impure product. The impure product was purified again by reverse phase HPLC using MeCN/H$_2$O (1:9 to 95:5) as eluent to give the title compound (10) (160 mg) as a white gel. LC/MS: m/z=607.1 [M+H]$^+$; $^1$H-NMR (300 MHz, CDCl$_3$): δ 6.82-6.76 (m, 1H), 6.45 (d, J=8.1 Hz, 1H), 4.70 (d, J=9.6 Hz, 1H), 4.58 (d, J=9.3 Hz, 1H), 4.22-3.96 (m, 7H), 3.26 (d, J=12.0 Hz, 1H), 3.01-2.87 (m, 3H), 2.46-2.39 (m, 1H), 2.16-2.11 (m, 1H), 2.05 (s, 3H), 2.03-1.77 (m, 4H), 1.47 (d, J=5.1 Hz, 3H), 1.38-1.24 (m, 11H); $^{13}$C-NMR (75 MHz, CDCl$_3$): δ 174.0, 169.0, 167.9, 166.9, 152.9, 90.0, 80.4, 61.9, 61.2, 60.0, 46.8, 46.7, 42.8, 31.6, 22.0, 21.6, 21.0, 20.6, 19.8, 17.5, 14.1.

Example 11

Synthesis of 1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (11)

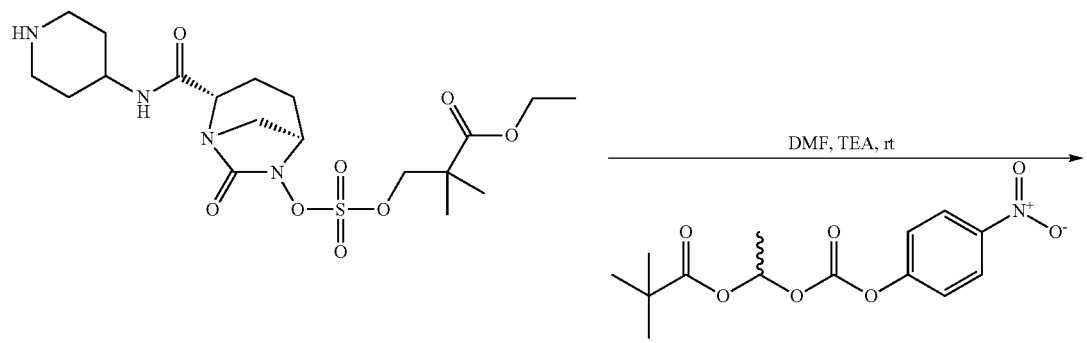

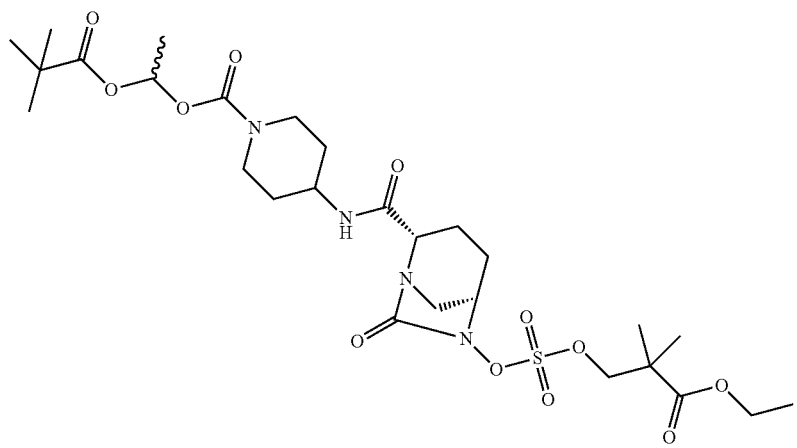

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (11a)

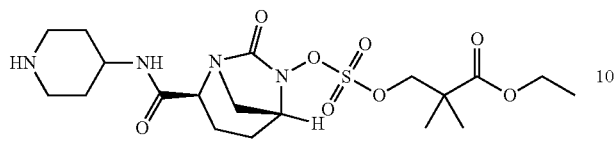

TFA (4.1 mL, 53.3 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (4) (0.7 g, 1.2 mmol) in DCM (10 mL) at −10° C. The reaction mixture was stirred at −10° C. for 60 min. LC-MS indicated that the starting material was completely consumed (m/z=477.3 [M+H]+ for desired product). The mixture was concentrated under vacuum to give the crude title compound (11a) containing a small amount of TFA. The compound was used directly in the next step without further purification. m/z=477.3 [M+H]+. Note: excess TFA present.

Step 2: Synthesis of 1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (11)

Et$_3$N (2.0 mL, 14.4 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (11a) (0.57 g, 1.2 mmol) in DMF (20 mL) under an atmosphere of nitrogen. 1-(((4-Nitrophenoxy)carbonyl)oxy)ethyl pivalate (450 mg, 1.4 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give impure product. The impure product was purified again by reverse phase HPLC using MeCN/H$_2$O (1:9 to 95:5) as eluent to give the product (115 mg) as a white gel. LC/MS: m/z=649.1 [M+H]+; $^1$H-NMR (300 MHz, CDCl$_3$): δ 6.79-6.74 (q, 1H), 6.45 (d, J=8.1 Hz, 1H), 4.71 (d, J=8.7 Hz, 1H), 4.59 (d, J=9.0 Hz, 1H), 4.21-3.91 (m, 7H), 3.26 (d, J=12.3 Hz, 1H), 3.00-2.87 (m, 3H), 2.48-2.40 (m, 1H), 2.17-2.12 (m, 1H), 1.97-1.80 (m, 4H), 1.48 (d, J=5.4 Hz, 3H), 1.42-1.26 (m, 11H), 1.24 (s, 9H); $^{13}$C-NMR (75 MHz, CDCl$_3$): δ $^{13}$C-NMR (75 MHz, CDCl$_3$): δ 176.6, 174.1, 167.89, 166.9, 153.0, 110.0, 90.1, 80.4, 61.9, 61.2, 60.0, 46.9, 46.7, 42.8, 42.8, 38.7, 31.7, 26.9, 22.1, 21.6, 20.7, 19.7, 17.4, 14.1.

Example 12

Synthesis of Relebactam Derivatives

Other derivatives of relebactam can be synthesized using the chlorosulfonyls of Examples 13-74 and adapting the methods of Examples 4 and 5.

Example 13

Synthesis of 2-methoxyethyl 3-((chlorosulfonyl)oxy)-2,2-dimethylpropanoate (13)

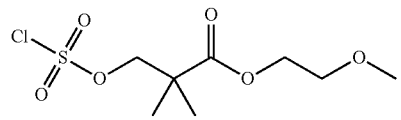

A solution of distilled sulfuryl chloride (0.51 mL, 6.2 mmol) in Et$_2$O (10 mL) was cooled to −78° C. under nitrogen. A solution of 2-methoxyethyl 3-hydroxy-2,2-dimethylpropanoate (15a) (1.0 g, 5.68 mmol) and pyridine (0.46 mL, 5.68 mmol) in Et$_2$O (2.0 mL) was then added dropwise over 1 h via a syringe. The reaction was stirred at −78° C. for 1 h, and then the mixture was allowed to warm to room temperature and stirred for 2 h. After the mixture was filtered, the filtrate was concentrated under vacuum to give the product (13) as a colorless liquid (1.5 g, yield 96%). $^1$H-NMR (300 MHz, CDCl$_3$): δ 4.40 (s, 2H), 4.29 (t, 3H), 3.59 (t, 3H), 3.37 (s, 3H), 1.32 (s, 6H).

Example 14

Synthesis of hexyl 3-((chlorosulfonyl)oxy)-2,2-dimethylpropanoate (14)

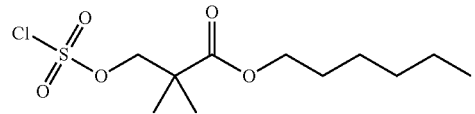 [SMILES: CCCCCCOC(=O)C(C)(C)COS(=O)(=O)Cl]

Step 1: Synthesis of hexyl 3-hydroxy-2,2-dimethylpropanoate (14a)

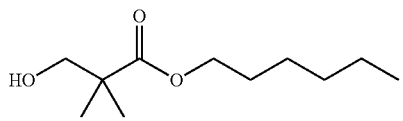

A mixture of 3-hydroxy-2,2-dimethylpropionic acid (4.7 g, 40 mmol), 1-hexanol (70 mL) and concentrated sulfuric acid (or fuming sulfuric acid, 1 mL) was heated to 80° C. and stirred overnight. After allowing to cool, the mixture was concentrated under vacuum (high vacuum pump required) and the residue was then partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried over anhydrous Na$_2$SO$_4$, filtered and concentrated under vacuum to provide the product as an oil. The product was difficult to purify using silica gel chromatography; and therefore the product was distilled under high vacuum at 47° C. to provide 4.92 g of the pure ester product (14a) (yield 61%). $^1$H-NMR (300 MHz, CDCl$_3$) δ 4.10 (td, J=6.7, 1.3 Hz, 2H), 3.55 (d, J=5.1 Hz, 2H), 2.42 (s, 1H), 1.64 (s, 1H), 1.72-1.56 (m, 1H), 1.35 (s, 1H), 1.31 (s, 6H), 1.27-1.11 (m, 6H), 0.95-0.84 (m, 3H). MS (ESI) C$_{11}$H$_{22}$O$_3$=203 (M+1)$^+$.

Step 2: Synthesis of hexyl 3-((chlorosulfonyl)oxy)-2,2-dimethylpropanoate (14b)

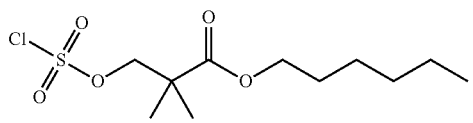 [SMILES: CCCCCCOC(=O)C(C)(C)COS(=O)(=O)Cl]

A solution of freshly distilled sulfuryl chloride (0.60 mL, 7.4 mmol) in Et$_2$O (10 mL) was cooled to −78° C. under an atmosphere of N$_2$. A solution of hexyl 3-hydroxy-2,2-dimethylpropanoate (14a) (1.0 g, 4.94 mmol) and pyridine (0.48 mL, 5.93 mmol) in Et$_2$O (5 mL) was added dropwise to the sulfuryl chloride solution over the course of 20 min. The flask was rinsed with Et$_2$O (3×1 mL) and the rinse added to the reaction mixture. The mixture was stirred at −78° C. until completion by TLC (30 min; 30% EA/hexane). The precipitate was filtered, and the filtrate was concentrated under vacuum to afford the crude product (14) as a solid foam and was used in the next step without further purification. $^1$H-NMR (300 MHz, CDCl$_3$): δ 4.50 (s, 2H), 4.13 (t, J=6.8 Hz, 2H), 1.69-1.60 (m, 2H), 1.40-1.27 (m, 12H), 0.91-0.87 (m, 3H).

Example 15

Synthesis of heptyl 3-((chlorosulfonyl)oxy)-2,2-dimethylpropanoate (15)

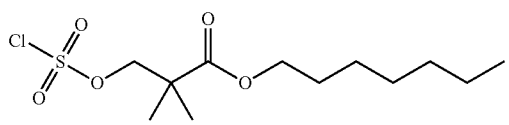 [SMILES: CCCCCCCOC(=O)C(C)(C)COS(=O)(=O)Cl]

Step 1: Synthesis of heptyl 3-hydroxy-2,2-dimethylpropanoate (15a)

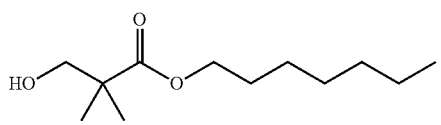

A mixture of 3-hydroxy-2,2-dimethylpropionic acid (4.7 g, 40 mmol), 1-heptanol (70 mL) and concentrated sulfuric acid (1 mL) was heated to 80° C. and stirred overnight. After allowing to cool, the mixture was concentrated under vacuum (high vacuum pump required) and the residue partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried (Na$_2$SO$_4$), filtered and concentrated under vacuum to provide the product as an oil. The product was distilled under high vacuum at 65° C. to provide the title compound (15a) as an oil (6.7 g, 77% yield). $^1$H-NMR (300 MHz, CDCl$_3$) δ 4.09 (td, J=6.7, 0.9 Hz, 2H), 3.55 (d, J=6.1 Hz, 2H), 2.43 (t, J=6.7 Hz, 1H), 1.60 (d, J=22.8 Hz, 4H), 1.3-1.58 (m, 6H), 1.27-1.14 (m, 6H), 0.92-0.83 (m, 3H).

Step 2: Synthesis of heptyl 3-((chlorosulfonyl)oxy)-2,2-dimethylpropanoate (22)

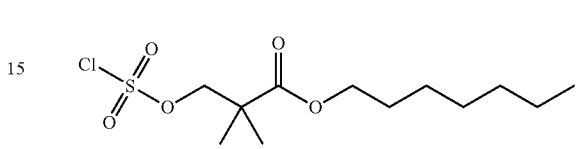

A solution of sulfuryl chloride (0.6 mL, 7.4 mmol) in Et$_2$O (15 mL) was cooled to −78° C. under an atmosphere of N$_2$. A solution of heptyl 3-hydroxy-2,2-dimethylpropanoate (15a) (1.0 g, 4.94 mmol) and pyridine (479 μL, 5.93 mmol) in Et$_2$O (1 mL) was added dropwise to the sulfuryl chloride solution over the course of 30 min. The flask was rinsed with Et$_2$O (3×1 mL) and the rinse added to the reaction mixture. The mixture was stirred at −78° C. until completion as monitored by TLC (30 min; 30% EA/hexane). The precipitate was filtered, and the filtrate was concentrated under vacuum to afford heptyl 3-((chlorosulfonyl)oxy)-2,2-dimethylpropanoate (15b) (1.37 g, yield 92%). The mixture was stored at −78° C. and used in the next step without further purification. $^1$H-NMR (300 MHz, CDCl$_3$) δ 4.50 (s, 2H), 4.20-4.02 (m, 2H), 1.68 (m, 2H), 1.31 (d, J=3.1 Hz, 13H), 1.23 (s, 1H), 0.95-0.83 (m, 3H).

Example 16

Synthesis of ethyl 1-(((chlorosulfonyl)oxy)methyl)cyclohexanecarboxylate (16)

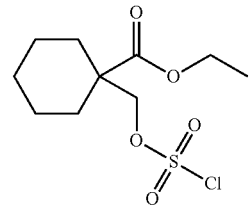 [SMILES: CCOC(=O)C1(COS(=O)(=O)Cl)CCCCC1]

Step 1: Synthesis of ethyl 1-(hydroxymethyl)cyclohexanecarboxylate (16a)

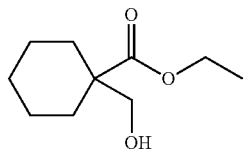

Diethyl cyclohexane-1,1-dicarboxylate (2.12 g, 9.29 mmol) was dissolved in THF (50 mL) and to which was added LiAl(OtBu)₃ (5.9 g, 23.2 mmol) in portions. The reaction mixture was stirred at reflux overnight. The reaction was cooled in an ice bath and treated carefully with 10% $KHSO_4$ aq. solution (30 mL) with stirring for 10 min. The precipitate formed was filtered out through a pad of Celite®. The filtrate was extracted with EtOAc (3×40 mL) and the organic phase was combined and washed with brine (50 mL), dried over $NaSO_4$, filtered and concentrated in vacuo. The residue was purified with CombiFlash ($SiO_2$) in 0-5% MeOH/DCM to obtain the desired product (16a) as an oil (1.23 g, 71% yield). ¹H-NMR (300 MHz, $CDCl_3$) δ 4.19 (qd, J=7.1, 0.8 Hz, 2H), 3.62 (d, J=6.4 Hz, 2H), 3.46 (s, 1H), 2.00 (dt, J=11.5, 6.4 Hz, 4H), 1.57-1.22 (m, 9H).

Step 2: Synthesis of ethyl 1-(((chlorosulfonyl)oxy)methyl)cyclohexanecarboxylate (16)

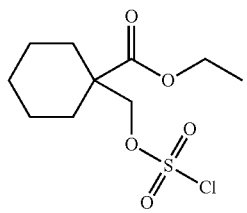 [SMILES: CCOC(=O)C1(COS(=O)(=O)Cl)CCCCC1]

A solution of freshly distilled sulfuryl chloride (294 µL, 3.63 mmol) in $Et_2O$ (10 mL) was cooled to −78° C. under an atmosphere of nitrogen. A solution of ethyl 1-(hydroxymethyl)cyclohexanecarboxylate (16a) (0.615 g, 3.3 mmol) and pyridine (294 µL, 3.63 mmol) in $Et_2O$ (6 mL) was added dropwise to the sulfuryl chloride solution during 15 min. The flask was rinsed with $Et_2O$ (3×1 mL) and the rinse added to the reaction. The mixture was stirred at −78° C. until completion (ca. 30 min; monitored by TLC, 30% EtOAc/hexane). The precipitate was filtered, and the filtrate was concentrated under vacuum to afford the title compound (16) as an oil, 0.94 g in quantitative yield, which was used directly in the next step without purification. ¹H-NMR (300 MHz, $CDCl_3$): δ 4.52 (s, 2H), 4.21 (q, J=7.1 Hz, 2H), 2.04 (s, 2H), 1.53-1.39 (m, 8H), 1.39-1.21 (m, 3H).

Example 17

Synthesis of (5-methyl-2-oxo-1,3-dioxol-4-yl)methyl 3-((chlorosulfonyl)ox)-2,2-dimethylpropanoate (17)

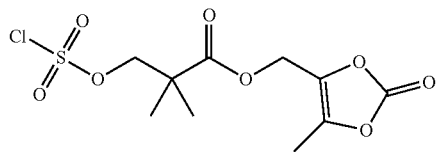 [SMILES: Cc1oc(=O)oc1COC(=O)C(C)(C)COS(=O)(=O)Cl]

Step 1: Synthesis of (5-methyl-2-oxo-1,3-dioxol-4-yl)methyl 3-hydroxy-2,2-dimethylpropanoate (17a)

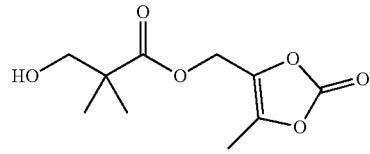 [SMILES: Cc1oc(=O)oc1COC(=O)C(C)(C)CO]

To a stirred solution of 3-hydroxy-2,2-dimethylpropanoic acid (4.0 g, 33.9 mmol) and potassium carbonate (4.68 g, 33.9 mmol) in DMF (45 mL) at 0° C. was added 4-(hydroxymethyl)-5-methyl-1,3-dioxol-2-one (5.03 g, 33.9 mmol) in DMF (5 mL) dropwise over 1 h. The reaction was stirred at room temperature overnight. The reaction mixture was diluted with EtOAc and washed with water and brine. The organic layer was dried with anhydrous $Na_2SO_4$, filtered, and concentrated under vacuum to give a crude residue. The residue was purified by silica gel column chromatography using EtOAc/hexane (1:4 to 2:3) as eluent to give the product (17a) as a yellow liquid (1.6 g, yield 21%). ¹H-NMR (300 MHz, $CDCl_3$): δ 4.86 (s, 2H), 3.58 (s, 2H), 2.18 (s, 3H), 1.20 (s, 6H).

Step 2: Synthesis of (5-methyl-2-oxo-1,3-dioxol-4-yl)methyl 3-((chlorosulfonyl)oxy)-2,2-dimethylpropanoate (17)

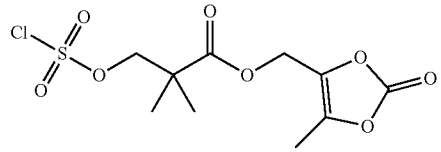 [SMILES: Cc1oc(=O)oc1COC(=O)C(C)(C)COS(=O)(=O)Cl]

A solution of distilled sulfuryl chloride (0.61 mL, 7.53 mmol) in $Et_2O$ (15 mL) was cooled to −78° C. under nitrogen. A solution of (5-methyl-2-oxo-1,3-dioxol-4-yl)methyl 3-hydroxy-2,2-dimethylpropanoate (17a) (1.48 g, 6.43 mmol) in $Et_2O$ (1 mL) was added. Subsequently, a solution of pyridine (0.55 mL, 6.86 mmol) in $Et_2O$ (1 mL) was added over a period of 1 h. The reaction was stirred at −78° C. for 1 h. After the mixture was filtered, the filtrate was concentrated under vacuum to give the product (17) as a yellow oil (1.6 g, yield 76%). ¹H-NMR (300 MHz, $CDCl_3$): δ 4.90 (s, 2H), 4.49 (s, 2H), 2.19 (s, 3H), 1.33 (s, 6H).

Example 18

Synthesis of 3-((chlorosulfonyl)oxy)-2,2-dimethylpropyl benzoate (18)

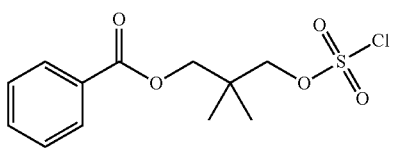 [SMILES: CC(C)(COC(=O)c1ccccc1)COS(=O)(=O)Cl]

Step 1: Synthesis of 3-hydroxy-2,2-dimethylpropyl benzoate (18a)

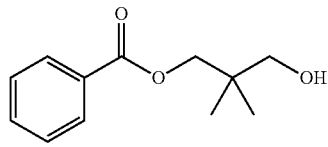

Benzoyl chloride (4.0 mL, 34.5 mmol) was added dropwise to a stirred solution of 2,2-dimethylpropane-1,3-diol (10.8 g, 103.4 mmol), pyridine (5.8 mL, 71.6 mmol) and N,N-4-dimethylaminopyridine (840 mg, 6.9 mmol) in dichloromethane (207 mL) at ca. 0° C. The mixture was stirred overnight with gradual warming to room temperature, quenched by addition of 1N HCl (100 mL) at 0° C. and extracted twice with dichloromethane. The combined organic extracts were washed with saturated aqueous NaHCO$_3$ (100 mL), brine (100 mL), dried (Na$_2$SO$_4$), filtered and the solvent concentrated under vacuum to leave a crude residue. The residue was split into two batches and purified by column chromatography on silica gel using EtOAc/hexanes (0:1 to 1:4) as eluent to give the product (18a) (5.95 g, 99%) as a colorless oil (note: oil dried under vacuum for 2 days). LC-MS: m/z=209.0 [M+H]$^+$. $^1$H-NMR (300 MHz, CDCl$_3$): 8.05 (m, 2H), 7.58 (m, 1H), 7.45 (m, 2H), 4.19 (s, 2H), 3.38 (d, J=6.3 Hz, 2H), 2.29 (t, J=6.3 Hz, 1H), 1.02 (s, 6H).

Step 2: Synthesis of 3-((chlorosulfonyl)oxy)-2,2-dimethylpropyl benzoate (18)

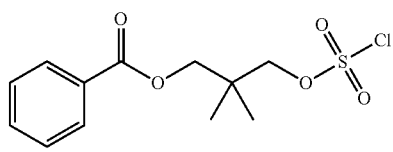 [SMILES: CC(C)(COC(=O)c1ccccc1)COS(=O)(=O)Cl]

Reference is made to *J. Am. Chem. Soc.* 2006, 128, 1605-1610. A solution of distilled sulfuryl chloride (1.2 mL, 15.8 mmol) in Et$_2$O (15 mL) was cooled to -78° C. under an atmosphere of argon. A solution of 3-hydroxy-2,2-dimethylpropyl benzoate (18a) (3.0 g, 14.4 mmol) and pyridine (1.2 mL, 14.4 mmol) in Et$_2$O (3.0 mL) was then added dropwise over 1 h via a syringe. The syringe was rinsed with Et$_2$O (3×1 mL), each rinse being added to the reaction mixture. The acetone/CO$_2$ bath was removed, and the mixture allowed to warm to room temperature, then stirred at room temperature for 4 h. TLC analysis (EtOAc/hexanes; 3:7) did not indicate complete reaction, so re-cooled to -78° C. and added more SO$_2$Cl$_2$ (0.1 mL), then allowed to warm to 25° C., and stirred for an additional 2 h. The mixture was filtered and the filtrate was concentrated under vacuum to give the product (18) (3.97 g, 89%) as an oil. $^1$H-NMR (300 MHz, CDCl$_3$): 8.03 (m, 2H), 7.61-7.57 (m, 1H), 7.49-7.44 (m, 2H), 4.41 (s, 2H), 4.18 (s, 2H), 1.16 (s, 6H).

Example 19

Synthesis of ethyl 3-((chlorosulfonyl)oxy)-2,2-dimethylpropanoate (19)

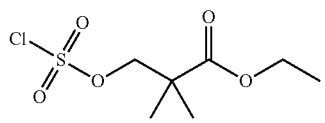

A solution of distilled sulfuryl chloride (0.55 mL, 7.5 mmol) in Et$_2$O (10 mL) was cooled to -78° C. under an atmosphere of argon. A solution of ethyl 3-hydroxy-2,2-dimethylpropanoate (2a) (1.0 g, 6.8 mmol) and pyridine (0.55 mL, 6.8 mmol) in Et$_2$O (1.0 mL) was then added dropwise over 1 h via a syringe. The syringe was rinsed with Et$_2$O (3×1 mL), each rinse being added to the reaction mixture. The acetone/CO$_2$ bath was removed, and the mixture was allowed to warm to room temperature, then stirred at room temperature for 4 h. TLC analysis (EtOAc/hexanes; 3:7) did not indicate that the reaction was complete. The mixture was re-cooled to -78° C. and more SO$_2$Cl$_2$ (0.11 mL) was added, and the mixture allowed to warm to room temperature and stirred for an additional 2 h. The mixture was filtered and the filtrate was concentrated under vacuum to give the product (19) (yield assumed quantitative). $^1$H-NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Example 20

Synthesis of benzyl 3-((chlorosulfonyl)oxy)-2,2-dimethylpropanoate (20)

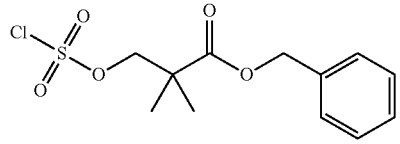 [SMILES: CC(C)(COS(=O)(=O)Cl)C(=O)OCc1ccccc1]

A solution of distilled sulfuryl chloride (0.77 mL, 10.6 mmol) in Et$_2$O (10 mL) was cooled to -78° C. under an atmosphere of argon. A solution of ethyl 3-hydroxy-2,2-dimethylpropanoate (2a) (Sigma-Aldrich; 2.0 g, 9.6 mmol) and pyridine (0.85 mL, 10.6 mmol) in Et$_2$O (2.0 mL) was then added dropwise over 1 h via a syringe. The syringe was rinsed with Et$_2$O with each rinse being added to the reaction mixture. The acetone/CO$_2$ bath was removed and the mixture allowed to warm to room temperature, then stirred at room temperature for 30 min. TLC analysis (EtOAc/hexanes; 3:7) did not indicate complete reaction, so re-cooled to -78° C. and added more SO$_2$Cl$_2$ (0.07 mL), then allowed to warm to room temperature and stirred for an additional 1 h. Et$_2$O (5 mL) was added and the mixture stirred for a few min, then filtered and the filtrate concentrated under vacuum to give the product (20) (2.19 g, 75%). $^1$H-NMR (300 MHz, CDCl$_3$): δ 7.41-7.32 (m, 4H), 5.18 (s, 2H), 4.52 (s, 2H), 1.34 (s, 6H).

Example 21

Synthesis of Phenyl Sulfochloridate (21)

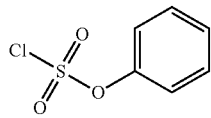 [SMILES: O=S(=O)(Cl)Oc1ccccc1]

Reference is made to *J. Am. Chem. Soc.* 2013, 135, 10638-10641. A solution of distilled sulfuryl chloride (2.6 mL, 35.1 mmol) in Et₂O (30 mL) was cooled to −78° C. under an atmosphere of argon. A solution of phenol (3.0 g, 31.9 mmol) in Et₂O (3.0 mL) and pyridine (2.6 mL, 31.9 mmol) were then added concurrently, but from different syringes, dropwise over 1 h. The syringes were each rinsed with Et₂O and each rinse was added to the reaction mixture. The mixture was allowed to warm to room temperature slowly and stirred at room temperature overnight. The mixture was filtered, and the filtrate concentrated under vacuum to give the product (4.65 g), contaminated with other products and phenol starting material. The phenyl sulfochloridate product (21) was not purified further and was used directly in the next step.

Example 22

Synthesis of 4-((chlorosulfonyl)oxy)-3,3-dimethylbutyl benzoate (22)

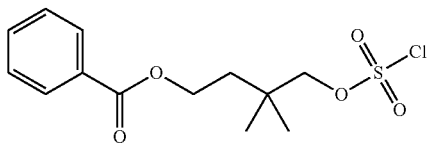 [SMILES: CC(C)(CCOC(=O)c1ccccc1)COS(=O)(=O)Cl]

Step 1: Synthesis of 2,2-dimethylbutane-1,4-diol (22a)

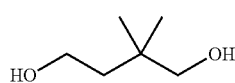

A solution of 2,2-dimethylsuccinic acid (10.0 g, 68.4 mmol) in THF (150 mL) was added dropwise to a suspension of lithium aluminum hydride (8.3 g, 219.0 mmol) in THF (80 mL) at 0° C. (ice bath). The mixture was warmed to room temperature over 20 min and then heated at reflux for 1.5 h. Upon completion (reaction monitored by TLC using MeOH/CH₂Cl₂ 5:95 as eluent) the reaction was quenched very carefully and dropwise by the addition of water (10 mL), 3 M NaOH (15 mL), and water (20 mL). The mixture was stirred at room temperature for 20 min, and the solids filtered over a pad of Celite®. The filter cake was rinsed thoroughly with THF. The filtrate was concentrated under vacuum giving a mixture of the title compound and unidentified by-products as a crude oil. The oil was purified by column chromatography on silica gel using MeOH/CH₂Cl₂ (0:1 to 1:9) as eluent to afford the product (22a) (4.649 g, 57%) as an oil. ¹H-NMR (300 MHz, CDCl₃): δ 4.11 (s, 2H), 3.66 (t, J=5.9 Hz, 2H), 3.30 (s, 2H), 1.52 (t, J=5.6 Hz, 2H), 0.89 (s, 6H).

Step 2: Synthesis of 4-hydroxy-3,3-dimethylbutyl benzoate (22b)

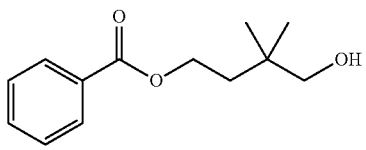 [SMILES: CC(C)(CO)CCOC(=O)c1ccccc1]

To a stirred solution of 2,2-dimethylbutane-1,4-diol (22a) (0.30 g, 2.5 mmol) in anhydrous dichloromethane (9 mL) was added benzoyl chloride (0.30 mL, 2.5 mmol), Et₃N (0.71 mL, 5.1 mmol), and a catalytic amount of N,N-4-dimethylaminopyridine at 0° C. (ice bath). The mixture was gradually warmed to room temperature and stirred overnight. After the starting material was completely consumed (reaction monitored by TLC using EtOAc/hexanes 2:8 as eluent), the reaction was quenched by the addition of 1N HCl (20 mL) at 0° C. (ice bath), and the mixture was extracted twice with dichloromethane. The combined organic layers were washed with saturated aqueous NaHCO₃, brine, dried (Na₂SO₄), filtered and the solvent concentrated to yield a mixture, of at least two products, as a clear and colorless oil. The oil was purified by column chromatography on silica gel using EtOAc/hexanes (0:1 to 4:6) as eluent to give the product (22b) (0.29 g, 51%) as an oil (which was dried under high vacuum for 2 d). ¹H-NMR (300 MHz, CDCl₃): δ 8.04-8.01 (m, 2H), 7.58-7.53 (m, 1H), 7.46-7.41 (m, 2H), 4.41 (t, J=7.4 Hz, 2H), 3.41 (s, 2H), 1.78 (t, J=7.4 Hz, 2H), 1.70 (s, 1H), 0.99 (s, 6H).

Step 3: Synthesis of 4-((chlorosulfonyl)oxy)-3,3-dimethylbutyl benzoate (22)

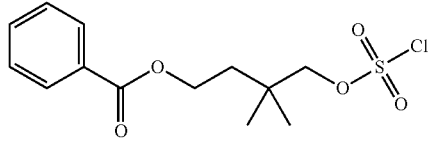 [SMILES: CC(C)(CCOC(=O)c1ccccc1)COS(=O)(=O)Cl]

A solution of freshly distilled sulfuryl chloride (0.11 mL, 1.5 mmol) in Et₂O (3 mL) was cooled to −78° C. under an atmosphere of Ar. A solution of 4-hydroxy-3,3-dimethylbutyl benzoate (22b) (0.28 g, 1.3 mmol) and pyridine (0.10 ml, 1.3 mmol) in Et₂O (2 mL) was added dropwise (over 1 h) to the cooled solution. The mixture was warmed to room temperature and stirred for 30 min (reaction was monitored by TLC using EtOAc/hexanes 2:8 as eluent). The mixture was re-cooled to −78° C. and sulfuryl chloride (0.02 mL) was added. The mixture was allowed to warm to room temperature, and stirred for 30 min. Et₂O (5 mL) was added and the mixture stirred for a few minutes. The mixture was filtered and the filtrate concentrated under vacuum to give the product (22) (0.305 g, 75%). ¹H-NMR (300 MHz, CDCl$_3$): δ 8.03 (d, J=8.1 Hz, 2H), 7.60-7.54 (m, 1H), 7.47-7.42 (m, 2H), 4.44-4.38 (m, 2H), 4.29 (s, 2H), 1.89-1.85 (m, 2H), 1.13 (s, 6H).

Example 23

Synthesis of 4-((chlorosulfonyl)oxy)-3,3-dimethylbutyl propionate (23)

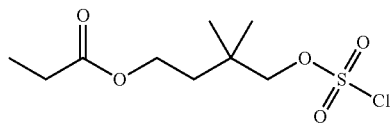 [SMILES: CCC(=O)OCCC(C)(C)COS(=O)(=O)Cl]

Step 1: Synthesis of 4-hydroxy-3,3-dimethylbutyl propionate (23a)

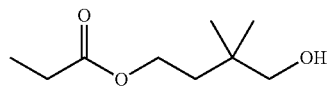

A solution of propionyl chloride (0.74 mL, 8.5 mmol) in anhydrous dichloromethane (5 mL) was added to a stirred solution of 2,2-dimethylbutane-1,4-diol (6a) (1.00 g, 8.5 mmol), Et$_3$N (2.4 mL, 16.9 mmol), and 4-N,N-dimethylaminopyridine (52 mg) in anhydrous dichloromethane (20 mL) at −78° C. under an atmosphere of argon. The mixture was stirred for 10 min and then allowed to warm to room temperature, stirred at room temperature for 1 h, then re-cooled to −78° C., and allowed to warm to room temperature slowly by allowing the mixture to stay in the cold bath and letting the dry ice sublime (recommended to allow warming to room temperature from −78° C. after addition of all the reagents). After the starting material was completely consumed (TLC 50% EtOAc/hexanes), the reaction was quenched by the addition of 0.5 N HCl (10 mL) at 0° C. The organic and aqueous layers were partitioned, and the aqueous layer was extracted with dichloromethane (2×20 mL). The combined organic layers were washed with saturated aqueous NaHCO$_3$ (20 mL), brine (20 mL), then dried (Na$_2$SO$_4$), filtered and the solvent concentrated under vacuum to leave a crude oil. The oil was purified by column chromatography on silica gel using EtOAc/hexanes (0:1 to 4:1) as eluent to give the product (23a) (463 mg, 22%) as an oil, contaminated with significant EtOAc solvent residues. $^1$H-NMR (300 MHz, CDCl$_3$): δ 4.14 (t, J=7.4 Hz, 2H), 3.32 (s, 2H), 2.30 (q, J=7.6 Hz, 2H), 1.88 (s, 1H), 1.61 (t, J=7.7 Hz, 2H), 1.13 (t, J=7.5 Hz, 3H), 0.91 (fd, J=1.2 Hz, 6H).

Step 2: Synthesis of 4-((chlorosulfonyl)oxy)-3,3-dimethylbutyl propionate (23)

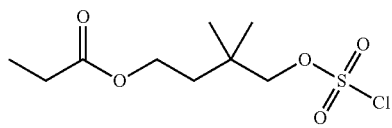 [SMILES: CCC(=O)OCCC(C)(C)COS(=O)(=O)Cl]

A solution of freshly distilled sulfuryl chloride (0.15 mL, 2.0 mmol) in Et$_2$O (3.5 mL) was cooled to −78° C. under an atmosphere of argon. A solution of 4-hydroxy-3,3-dimethylbutyl propionate (23a) (73% purity, the remainder being EtOAc; 441 mg, 1.8 mmol) and pyridine (0.15 mL, 1.8 mmol) in Et$_2$O (2.5 mL) was added dropwise over 1 h to the cooled solution. The mixture was allowed to warm to room temperature and was stirred for 30 min (monitored by TLC, 30% EtOAc/hexanes), re-cooled to −78° C. and sulfuryl chloride (0.03 mL) and pyridine (0.03 mL) was added, warmed to room temperature, and stirred for 30 min. Again, the mixture was re-cooled to −78° C. and another portion of sulfuryl chloride (0.15 mL) was added. The mixture was allowed to warm to room temperature, and stirred for 30 min. Et$_2$O (5 mL) was added and the mixture stirred for a few min. The mixture was filtered and the filtrate was concentrated under vacuum to give the product (23) (401 mg, 79%). $^1$H-NMR: (300 MHz, CDCl$_3$): 4.22 (s, 2H), 4.14 (t, J=6.8 Hz, 2H), 2.30 (q, J=7.6 Hz, 2H), 1.70 (t, J=6.8 Hz, 2H), 1.11 (t, J=7.7 Hz, 3H), 1.05 (s, 6H).

Example 24

Synthesis of benzyl (4-((chlorosulfonyl)oxy)-3,3-dimethylbutyl) adipate (24)

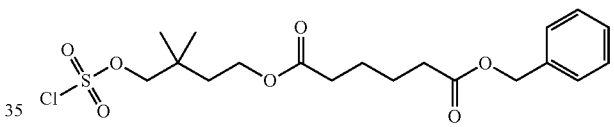

Step 1: Synthesis of benzyl (perfluorophenyl) adipate (24a)

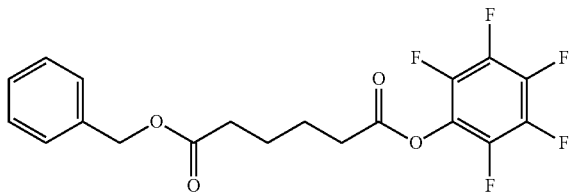 [SMILES: O=C(CCCCC(=O)Oc1c(F)c(F)c(F)c(F)c1F)OCc1ccccc1]

To a stirring solution of adipic acid monobenzyl ester (1.03 g, 4.3 mmol) and pentafluorophenol (0.87 g, 4.7 mmol) in EtOAc (18.7 mL) at 0° C. was added N,N'-dicyclohexylcarbodiimide (0.97 g, 4.7 mmol). The mixture was allowed to warm to room temperature and then stirred overnight. The resulting solid was removed by vacuum filtration through a pad of Celite®. The filter cake was washed with EtOAc. The filtrate was dry-loaded on to silica gel and purified by column chromatography on silica gel using EtOAc/hexanes (0:1 to 4:6) as eluent, to give the product (24a) (1.59 g, 93%) as a solid. $^1$H-NMR (300 MHz, CDCl$_3$): δ 7.37-7.35 (m, 5H), 5.13 (s, 2H), 2.68 (t, J=6.8 Hz, 2H), 2.44 (t, J=6.5 Hz, 2H), 1.82-1.78 (m, 4H).

Step 2: Synthesis of benzyl (4-hydroxy-3,3-dimethylbutyl) adipate (24b)

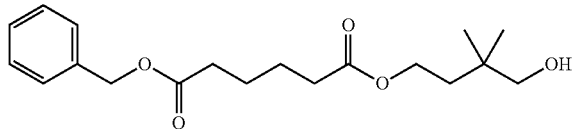 [SMILES: CC(C)(CO)CCOC(=O)CCCCC(=O)OCc1ccccc1]

To a stirred solution of 2,2-dimethylbutane-1,4-diol (24a) (0.22 g, 1.8 mmol) in anhydrous dichloromethane (4 mL) at ca. 0° C. (ice bath), under an atmosphere of argon, was added benzyl (perfluorophenyl) adipate (8a) (0.36 g, 0.9 mmol), Et₃N (0.25 mL, 1.8 mmol), and a catalytic amount of 4-N,N-dimethylaminopyridine (small unweighed amount). The mixture was gradually warmed to room temperature, and then at room temperature overnight. The mixture was dry-loaded on to silica gel and purified by column chromatography on silica gel using EtOAc/hexanes (0:1 to 3:7) as eluent to give the product contaminated with regio-isomeric product. This mixture was re-purified by column chromatography on silica gel using EtOAc/hexanes (0:1 to 3:7) as eluent to give pure product (24b) (113 mg 38%). ¹H-NMR (300 MHz, CDCl₃): 7.36-7.34 (m, 5H), 5.11 (s, 2H), 4.14 (t, J=7.2 Hz, 2H), 3.34 (d, J=5.7 Hz, 2H), 2.38-2.31 (m, 4H), 1.68-1.59 (m, 6H), 0.92 (s, 6H). The reaction could be repeated to give larger amounts of material.

Step 3: Synthesis of benzyl (4-((chlorosulfonyl)oxy)-3,3-dimethylbutyl) adipate (24)

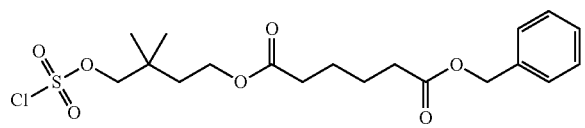 [SMILES: CC(C)(CCOC(=O)CCCCC(=O)OCc1ccccc1)COS(=O)(=O)Cl]

A solution of freshly distilled sulfuryl chloride (0.12 ml, 1.6 mmol) in Et₂O (5 mL) was cooled to −78° C. under an atmosphere of argon. A solution of benzyl (4-hydroxy-3,3-dimethylbutyl) adipate (24b) (446 mg, 1.3 mmol) and pyridine (0.11 mL, 1.3 mmol) in Et₂O (3.5 mL) was added dropwise over 1 h to the cooled solution. The mixture was allowed to warm to room temperature and was stirred for 30 min (monitored by TLC, 30% EA/hex). The reaction was not complete, so the mixture was recooled to −78° C., then sulfuryl chloride (0.05 mL) and pyridine (0.05 mL) were added. The mixture was allowed to warm to room temperature, and stirred for 30 min. Et₂O (5 mL) was added, and the mixture was stirred for a few mins. The mixture was filtered and the filtrate was concentrated under vacuum to give the product (24) (446 mg, 77%). ¹H-NMR (300 MHz, CDCl₃): δ 7.39-7.29 (m, 5H), 5.11 (s, 2H), 4.22 (s, 2H), 4.15 (t, J=6.8 Hz, 2H), 2.40-2.29 (m, 4H), 1.73-1.59 (m, 6H), 1.06 (s, 6H).

Example 25

Synthesis of methyl 3-((chlorosulfonyl)oxy)-2,2-dimethylpropanoate (25)

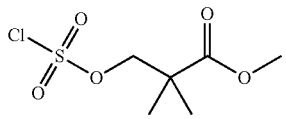

A solution of freshly distilled sulfuryl chloride (3.3 mL, 45.4 mmol) in Et₂O (45 mL) was cooled to −78° C. under an atmosphere of Ar. A solution of methyl 2,2-dimethyl-3-hydroxypropionate (3.0 g, 22.7 mmol) and pyridine (2.2 mL, 27.2 mmol) in Et₂O (20 mL) was added dropwise to the sulfuryl chloride solution over 30 min. The flask was rinsed with Et₂O (3×5 mL) and the rinse was added to the reaction mixture. The mixture was stirred at −78° C. until completion (monitored by TLC, 30% EA/hex, 30 min). The precipitate was filtered, and the filtrate was concentrated under vacuum to afford methyl 3-((chlorosulfonyl)oxy)-2,2-dimethylpropanoate (25) (5.6 g, 70% yield). ¹H-NMR (300 MHz, CDCl₃) δ 4.50 (s, 2H), 3.74 (s, 3H), 1.31 (s, 6H).

Example 26

Synthesis of isopropyl 3-((chlorosulfonyl)oxy)-2,2-dimethylpropanoate (26)

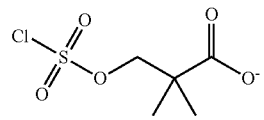

Step 1: Synthesis of isopropyl 3-hydroxy-2,2-dimethylpropanoate (26a)

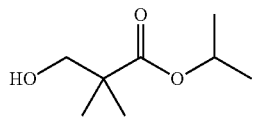

Reference is made to German Application Publication No. DE3045373. A mixture of 3-hydroxy-2,2-dimethylpropionic acid (4.7 g, 40 mmol), isopropanol (70 mL) and concentrated sulfuric acid (or fuming sulfuric acid; 1 mL) was heated to reflux and stirred overnight. After allowing to cool, the mixture was concentrated under vacuum and the residue partitioned between EtOAc (100 mL) and saturated aqueous NaHCO₃ (100 mL). The aqueous mixture was washed with H₂O (50 mL), saturated NaHCO₃ (50 mL) and brine (50 mL), then dried (Na₂SO₄), filtered and concentrated under vacuum to leave provide the product as an oil. The product (26a) was used directly in the next step without further purification. ¹H-NMR (300 MHz, CDCl₃): δ 5.08-4.95 (m, 1H), 3.53 (fd, 3=1.8 Hz, 2H), 2.49 (s, 1H), 1.25 (fd, J=2.4 Hz, 3H), 1.22 (fd, J=2.4 Hz, 3H), 1.17 (s, 3H), 1.16 (s, 3H).

Step 2: Synthesis of isopropyl 3-((chlorosulfonyl)oxy)-2,2-dimethylpropanoate (26)

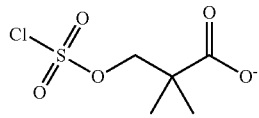

A solution of sulfuryl chloride (2.7 mL, 37.5 mmol) in Et$_2$O (45 mL) was cooled to −78° C. under an atmosphere of Ar. A solution of isopropyl 3-hydroxy-2,2-dimethylpropanoate (26a) (3.0 g, 18.7 mmol) and pyridine (1.82 mL, 22.5 mmol) in Et$_2$O (20 mL) was added dropwise to the sulfuryl chloride solution over the course of 30 min. The flask was rinsed with Et$_2$O (3×5 mL) and the rinse added to the reaction mixture. The mixture was stirred at −78° C. until completion by TLC (30 min; 30% EA/hex). The precipitate was filtered, and the filtrate was concentrated under vacuum to afford isopropyl 3-((chlorosulfonyl)oxy)-2,2-dimethylpropanoate (26) (4.1 g, 85% yield). The mixture was stored at −78° C. and was used immediately for the next step without further purification. $^1$H-NMR (300 MHz, CDCl$_3$): δ 5.10-4.98 (m, 1H), 4.49 (s, 2H), 1.29 (s, 6H), 1.26 (s, 3H), 1.24 (s, 3H).

Example 27

Synthesis of hexyl 3-((chlorosulfonyl)oxy)-2,2-dimethylpropanoate (27)

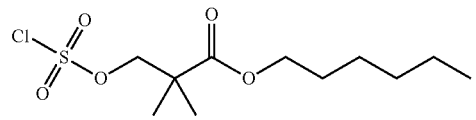 [SMILES: CCCCCCOC(=O)C(C)(C)COS(=O)(=O)Cl]

Step 1: Synthesis of hexyl 3-hydroxy-2,2-dimethylpropanoate (27a)

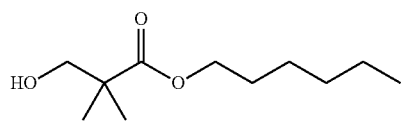

Reference is made to German Application Publication No. DE3045373. A mixture of 3-hydroxy-2,2-dimethylpropionic acid (4.7 g, 40 mmol), 1-hexanol (70 mL) and concentrated sulfuric acid (or fuming sulfuric acid; 1 mL) was heated to 80° C. and stirred overnight. After allowing to cool, the mixture was concentrated under vacuum (high vacuum pump required) and the residue partitioned between EtOAc (100 mL) and saturated aqueous NaHCO$_3$ (100 mL). The aqueous mixture was washed with H$_2$O (50 mL), saturated NaHCO$_3$ (50 mL) and brine (50 mL), then dried (Na$_2$SO$_4$), filtered and concentrated under vacuum to provide the product (27a) as an oil. $^1$H-NMR (300 MHz, CDCl$_3$): δ 4.04-3.98 (m, 2H), 3.47-3.45 (m, 2H), 2.26 (s, 1H). 1.58-1.32 (m, 2H), 1.32-1.23 (m, 6H), 1.12 (s, 3H), 1.11 (s, 3H).

Step 2: Synthesis of hexyl 3-((chlorosulfonyl)oxy)-2,2-dimethylpropanoate (27)

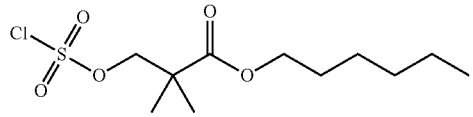 [SMILES: CCCCCCOC(=O)C(C)(C)COS(=O)(=O)Cl]

A solution of sulfuryl chloride (2.1 mL, 29.7 mmol) in Et$_2$O (40 mL) was cooled to −78° C. under an atmosphere of argon. A solution of hexyl 3-hydroxy-2,2-dimethylpropanoate (27a) (3.0 g, 14.8 mmol) and pyridine (1.4 mL, 17.8 mmol) in Et$_2$O (15 mL) was added dropwise to the sulfuryl chloride solution over the course of 30 min. The flask was rinsed with Et$_2$O (3×5 mL) and the rinse added to the reaction mixture. The mixture was stirred at −78° C. until completion by TLC (30 min; 30% EA/hex). The precipitate was filtered, and the filtrate was concentrated under vacuum to afford the product (27) (3.7 g, 83% yield). The mixture was stored at −78° C. and was used immediately for the next step without further purification. $^1$H-NMR (300 MHz, CDCl$_3$): 4.50 (s, 2H), 4.13 (t, J=6.8 Hz, 2H), 1.69-1.60 (m, 2H), 1.40-1.27 (m, 12H), 0.91-0.87 (m, 3H).

Example 28

Synthesis of heptyl 3-((chlorosulfonyl)oxy)-2,2-dimethylpropanoate (28)

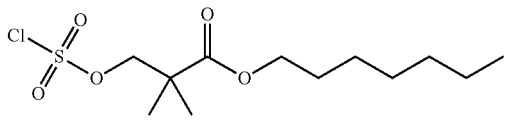 [SMILES: CCCCCCCOC(=O)C(C)(C)COS(=O)(=O)Cl]

Step 1: Synthesis of heptyl 3-hydroxy-2,2-dimethylpropanoate (28a)

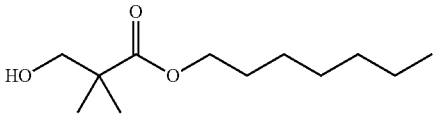

Reference is made to German Application Publication No. DE3045373. A mixture of 3-hydroxy-2,2-dimethylpropionic acid (4.7 g, 40 mmol), 1-heptanol (70 mL) and concentrated sulfuric acid (or fuming sulfuric acid; 1 mL) was heated to 80° C. and stirred overnight. After allowing the mixture to cool, the mixture was concentrated under vacuum (high vacuum pump required) and the residue partitioned between EtOAc (100 mL) and saturated aqueous NaHCO$_3$ (100 mL). The aqueous was washing with H$_2$O (50 mL), saturated NaHCO$_3$ (50 mL) and brine (50 mL), then dried (Na$_2$SO$_4$), filtered and concentrated under vacuum to provide the product (28a) as an oil. The product was used directly in the next step without further purification. $^1$H-NMR (300 MHz, CDCl$_3$): δ 4.31 (t, J=6.5 Hz, 2H), 3.77 (s, 2H), 1.87-1.81 (m, 2H), 1.53-1.50 (m, 8H), 1.41 (s, 6H), 1.12-1.08 (m, 3H).

Step 2: Synthesis of heptyl 3-((chlorosulfonyl)oxy)-2,2-dimethylpropanoate (28)

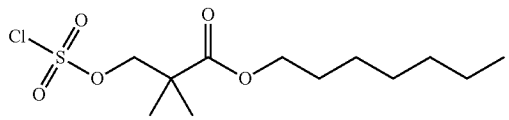 [SMILES: CCCCCCCOC(=O)C(C)(C)COS(=O)(=O)Cl]

A solution of sulfuryl chloride (2.0 mL, 27.7 mmol) in Et$_2$O (40 mL) was cooled to −78° C. under an atmosphere of argon. A solution of heptyl 3-hydroxy-2,2-dimethylpropanoate (28a) (3.0 g, 13.9 mmol) and pyridine (1.4 mL, 16.6 mmol) in Et$_2$O (15 mL) was added dropwise to the sulfuryl chloride solution over the course of 30 min. The flask was rinsed with Et$_2$O (3×5 mL) and the rinse added to the reaction mixture. The mixture was stirred at −78° C. until completion as monitored by TLC (30 min; 30% EA/hex). The precipitate was filtered, and the filtrate was concentrated under vacuum to afford heptyl 3-((chlorosulfonyl)oxy)-2,2-dimethylpropanoate (28) (3.3 g, 75%). The mixture was stored at −78° C. and was used immediately for the next step without further purification. $^1$H-NMR (300 MHz, CDCl$_3$): δ 4.46 (s, 2H), 4.11-4.00 (m, 2H), 1.64-1.55 (m, 2H), 1.26-1.24 (m, 8H), 0.85-0.81 (m, 3H).

Example 29

Synthesis of tert-butyl 3-((chlorosulfonyl)oxy)-2,2-dimethylpropanoate (29)

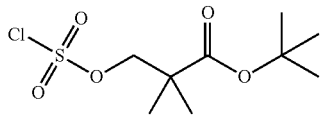 [SMILES: CC(C)(C)OC(=O)C(C)(C)COS(=O)(=O)Cl]

Step 1 and Step 2: Synthesis of tert-butyl 3-hydroxy-2,2-dimethylpropanoate (29a)

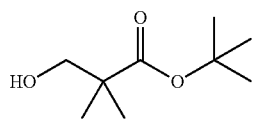

The compound was synthesized in accordance with PCT International Application Publication No. WO 2007116922. Sodium hydride (60% in mineral oil; 2.0 g) was added to a cooled solution of tert-butyl methyl malonate (4 g) in THF (100 mL) at 0° C. under an atmosphere of Ar. The mixture was stirred at 0° C. for 10 min. MeI (3.2 mL) was added to the mixture and the stirring was continued for 3 h (by this time the mixture was at room temperature). Brine and EtOAc were added to the mixture, and the organic layer was separated, dried (Na$_2$SO$_4$), filtered and concentrated under vacuum to give the product (ca. 4.5 g), which was used directly in the next step.

Solid lithium tri-tert-butoxy-aluminohydride (7.1 g, 28 mmol) was added portion-wise over 15 min to a solution of tert-butyl methyl 2,2-dimethyl-malonate (2.2 g) in THF (100 mL) under an atmosphere of Ar. The mixture was then heated to reflux and stirred overnight. After cooling to room temperature, a saturated solution of NH$_4$Cl and EtOAc were added, and the aqueous and organic layers were separated. The organic layer was washed with H$_2$O and brine, then dried (Na$_2$SO$_4$), filtered and concentrated under vacuum to provide a crude residue. The residue was purified by column chromatography on silica gel using EtOAc/hexanes (0:1 to 3:7) as eluent to give the product (29a) (900 mg) as an oil. $^1$H-NMR (300 MHz, CDCl$_3$): δ 3.50 (d, J=5.1 Hz, 2H), 2.53 (t, J=6.5 Hz, 1H), 1.45 (s, 9H), 1.14 (s, 6H)

Step 3: Synthesis of tert-butyl 3-((chlorosulfonyl)oxy)-2,2-dimethylpropanoate (29)

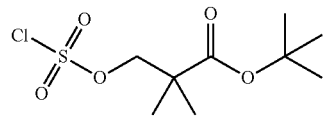 [SMILES: CC(C)(C)OC(=O)C(C)(C)COS(=O)(=O)Cl]

A solution of sulfuryl chloride (0.31 mL, 4.2 mmol) in Et$_2$O (6 mL) was cooled to −78° C. under an atmosphere of Ar. A solution of tert-butyl 3-hydroxy-2,2-dimethylpropanoate (29a) (0.49 g, 2.8 mmol) and pyridine (0.25 ml, 3.1 mmol) in Et$_2$O (6 mL) was added dropwise to the sulfuryl chloride solution over the course of 10 min. The mixture was stirred at −78° C. for 90 min and allowed to warm to 23° C. after TLC revealed that the reaction had not proceeded to completion (10% EtOAc/hexanes). The mixture was re-cooled to −78° C. and an additional 1 equivalent of sulfuryl chloride was added, stirred for 10 min, and the mixture allowed to warm to 23° C. (note: the mixture was allowed to stir for a total of 1 h after the addition and during the warming period). The precipitate was filtered, and the filtrate was concentrated under vacuum to give tert-butyl 3-((chlorosulfonyl)oxy)-2,2-dimethylpropanoate (29) (961 mg, yield assumed quantitative) as a clear, oil. $^1$H-NMR (300 MHz, CDCl$_3$): δ 4.46 (fd, J=1.5 Hz, 2H), 1.47 (fd, J=1.2 Hz, 9H), 1.27 (s, 6H).

Example 30

Synthesis of 2-methoxyethyl 3-((chlorosulfonyl)oxy)-2,2-dimethylpropanoate (30)

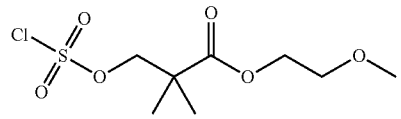 [SMILES: COCCOC(=O)C(C)(C)COS(=O)(=O)Cl]

Step 1: Synthesis of 2-methoxyethyl 3-hydroxy-2,2-dimethylpropanoate (30a)

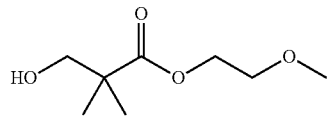

3-Hydroxy-2,2-dimethylpropanoic acid (1.2 g, 10.3 mmol) and Cs$_2$CO$_3$ (3.4 g, 10.4 mmol) were suspended in DMF (25 mL) at 23° C., then 2-bromoethyl methyl ether (1.0 mL, 10.4 mmol) was added. The resulting mixture was stirred at 70° C. overnight. After cooling, the mixture was filtered through a pad of Celite®. The filtrate was diluted with EtOAc (150 mL), and the mixture washed with water (3×100 mL) and brine, then dried (Na$_2$SO$_4$), filtered and concentrated to leave a crude residue. The residue was purified by column chromatography on silica gel using EtOAc/hexanes (1:4 to 4:1) as eluent to provide the product (30a) (1.3 g, crude weight) as an oil. $^1$H-NMR (300 MHz, CDCl$_3$): δ 4.28 (t, J=4.8 Hz, 2H), 3.62-3.55 (m, 4H), 3.38 (s, 3H), 2.65 (t, J=6.0 Hz, 1H), 1.21 (s, 6H).

Step 2: Synthesis of 2-methoxyethyl 3-((chlorosulfonyl)oxy)-2,2-dimethylpropanoate (30)

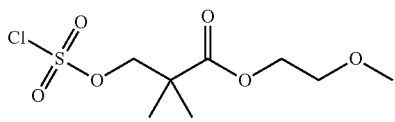 [SMILES: COCCOC(=O)C(C)(C)COS(=O)(=O)Cl]

A solution of freshly distilled sulfuryl chloride (0.2 mL, 2.8 mmol) in Et$_2$O (7.0 mL) was cooled to −78° C. under an atmosphere of Ar. A solution of 2-methoxyethyl 3-hydroxy-2,2-dimethylpropanoate (30a) (0.48 g, 2.7 mmol) and pyridine (0.24 mL, 3.0 mmol) in Et$_2$O (1 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (30) (0.5 g, 67%) as an oil, which was used directly in the next step without further purification [Note: $^1$HNMR indicated desired product with residue of pyridine and along with starting material].

Example 31

Synthesis of oxetan-3-yl 3-((chlorosulfonyl)oxy)-2,2-dimethylpropanoate (31)

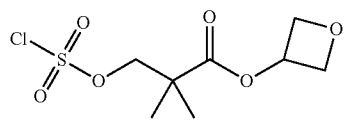 [SMILES: CC(C)(COS(=O)(=O)Cl)C(=O)OC1COC1]

Step 1: Synthesis of oxetan-3-yl 3-hydroxy-2,2-dimethylpropanoate (31a)

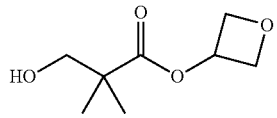

3-Hydroxy-2,2-dimethylpropanoic acid (4.7 g, 40 mmol) and Cs$_2$CO$_3$ (13.0 g, 40 mmol) were suspended in DMF (100 mL) at 23° C., then 3-iodooxetane (7.4 g, 40 mmol) was added. The resulting mixture was stirred at 70° C. overnight. After cooling, the mixture was diluted with EtOAc (150 mL), and the mixture washed with water (3×100 mL) and brine, then dried (Na$_2$SO$_4$), filtered and concentrated to provide a crude residue. The residue was purified by column chromatography on silica gel using EtOAc/hexanes as eluent to give the product (31a) (3.6 g, 51%) as an oil.

Step 2: Synthesis of oxetan-3-yl 3-((chlorosulfonyl)oxy)-2,2-dimethylpropanoate (31)

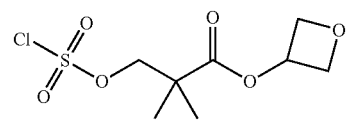 [SMILES: CC(C)(COS(=O)(=O)Cl)C(=O)OC1COC1]

A solution of freshly distilled sulfuryl chloride (0.2 mL, 2.7 mmol) in Et$_2$O (3 mL) was cooled to −78° C. under an atmosphere of Ar. A solution of oxetan-3-yl 3-hydroxy-2,2-dimethylpropanoate (31a) (0.46 g, 2.6 mmol) and pyridine (0.2 mL, 2.7 mmol) in Et$_2$O (2 mL) was added dropwise to the sulfuryl chloride solution over the course of 11 min. The flask was rinsed with Et$_2$O (3×1 mL) which was also added to the reaction mixture. The mixture was stirred at −78° C. until completion (monitored by TLC, 30% EtOAc/hex, 30 min). The precipitate was filtered, and the filtrate was concentrated under vacuum to afford the product (31) (0.5 g, 69%) as an oil, which was used directly in the next step without further purification. $^1$H-NMR (300 MHz, CDCl$_3$): δ 5.50-5.46 (m, 1H), 4.94-4.89 (m, 2H), 4.65-4.60 (m, 2H), 4.52 (s, 2H), 1.72 (br. s, 1H), 1.36 (s, 6H).

Example 32

Synthesis of ethyl 1-(((chlorosulfonyl)oxy)methyl)cyclohexanecarboxylate (32)

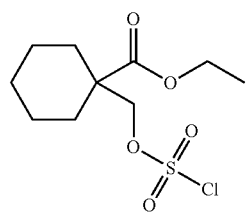 [SMILES: CCOC(=O)C1(COS(=O)(=O)Cl)CCCCC1]

A solution of freshly distilled sulfuryl chloride (77 μL, 1.1 mmol) in Et₂O (3 mL) was cooled to −78° C. under an atmosphere of Ar. A solution of ethyl 1-(hydroxymethyl) cyclohexanecarboxylate (0.2 g, 1.0 mmol) and pyridine (85 μL, 1.1 mmol) in Et₂O (2 mL) was added dropwise to the sulfuryl chloride solution over 11 min. The flask was rinsed with Et₂O (3×1 mL) and the rinse added to the reaction. The mixture was stirred at −78° C. until completion (ca. 30 min; monitored by TLC, 30% EtOAc/hex). The precipitate was filtered, and the filtrate was concentrated under vacuum to afford the title compound (32) as an oil, which was used directly in the next step without purification. A second batch using 476 mg of the starting alcohol, afforded 600 mg of the product (32) (approximately, 85% purity by ¹H-NMR).

Example 33

Step 1: Synthesis of ethyl 1-(((chlorosulfonyl)oxy)methyl)cyclopentane-1-carboxylate (33)

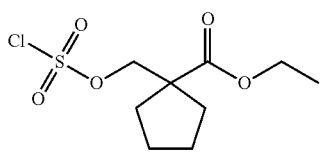 [SMILES: CCOC(=O)C1(COS(=O)(=O)Cl)CCCC1]

A solution of freshly distilled sulfuryl chloride (200 μL, 2.7 mmol) in Et₂O (3 mL) was cooled to −78° C. under an atmosphere of Ar. A solution of ethyl 1-(hydroxymethyl) cyclopentanecarboxylate (0.48 g, 2.7 mmol) and pyridine (222 μL, 2.7 mmol) in Et₂O (2 mL) was added dropwise to the sulfuryl chloride solution over 7 min. The flask was rinsed with Et₂O (2×1 mL) and both rinses were added to the reaction mixture. The mixture was stirred at −78° C. for 1.5 h. The precipitate was filtered, and the filter-cake washed with Et₂O (4 mL). The filtrate was concentrated under vacuum to afford the title compound (33) as an oil, which was used directly in the next step without further purification.

Example 34

Synthesis of ethyl 1-(((chlorosulfonyl)oxy)methyl)cyclobutanecarboxylate (34)

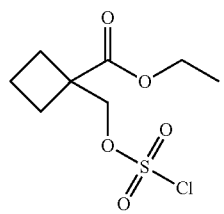

A solution of freshly distilled sulfuryl chloride (451 μL, 6.2 mmol) in Et₂O (5 mL) was cooled to −78° C. under an atmosphere of Ar. A solution of ethyl 1-(hydroxymethyl) cyclobutanecarboxylate (1.0 g, 6.1 mmol) and pyridine (500 μL, 6.2 mmol) in Et₂O (10 mL) was added dropwise to the sulfuryl chloride solution over the course of 11 min. The flask was rinsed with Et₂O (3×1 mL), which was also added to the reaction mixture. The mixture was stirred at −78° C., which was allowed to warm to ambient temp. within 4 h. The precipitate was filtered, and the filtrate was concentrated under vacuum to afford the title compound (34) (1.2 g, 76%) as an oil, which was used directly in the next step without further purification. Note: ¹HNMR indicated desired product (19a), together with starting material.

Example 35

Synthesis of ethyl 5-((chlorosulfonyl)oxy)-4,4-dimethylpentanoate (35)

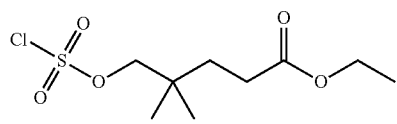 [SMILES: CCOC(=O)CCC(C)(C)COS(=O)(=O)Cl]

Step 1: Synthesis of ethyl 5-hydroxy-4,4-dimethylpentanoate (35a)

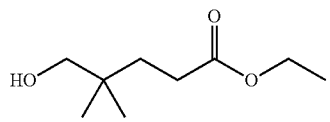

To a suspension of sodium 5-ethoxy-2,2-dimethyl-5-oxopentanoate (3.77 g, 17.9 mmol) in a mixture of tetrahydrofuran (39 mL) and DMF (13 mL) was added a solution of isopropyl chloroformate, 1.0M in toluene (27.0 mL, 27.0 mmol) at 0° C. The mixture was stirred at 0° C. for 10 min, and then allowed to warm to room temperature, and stirred for 2 h. The solution was cooled to 0° C. and sodium borohydride (1.21 g, 35.9 mmol) was added. The mixture was stirred for 20 min then methanol (6.5 mL) was added to the solution. After 10 min of stirring, ethyl acetate (25 mL) modified with a few drops of triethylamine and a saturated aqueous solution of NH₄Cl (25 mL) were added. The layers were separated, and the aqueous layer was extracted with EtOAc (2×40 mL). The combined organic layers were washed with brine, dried (MgSO₄), filtered and the filtrate was concentrated under vacuum. The residue was purified by column chromatography on silica gel using EtOAc/hexanes modified with 0.1% TEA (5:95 to 4:6) to give the product (35a) (2.01 g, 64% crude) as a colorless oil. One drop of triethylamine was added to the product to suppress lactonization.

Step 2: Synthesis of ethyl 5-((chlorosulfonyl)oxy)-4,4-dimethylpentanoate (35)

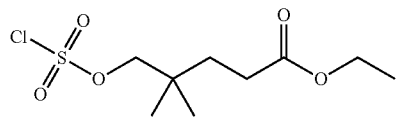 [SMILES: CCOC(=O)CCC(C)(C)COS(=O)(=O)Cl]

A solution of sulfuryl chloride (0.64 mL, 8.7 mmol) in Et₂O (10 mL) was cooled to −78° C. under an atmosphere of nitrogen. A solution of ethyl 5-hydroxy-4,4-dimethylpentanoate (35a) (0.76 g, 4.4 mmol) and pyridine (0.39 mL, 4.8 mmol) in Et$_2$O (10 mL) was added dropwise to the sulfuryl chloride solution over the course of 10 min. The syringe was rinsed with Et$_2$O (3×1 mL) and this was also added to the mixture. The mixture was stirred at −78° C. for 1.5 h, additional pyridine (0.9 equiv.) was added, and the mixture was filtered through a pad of Celite®. The filtrate was concentrated under vacuum to give the product (35) (0.897 g) as a colorless oil. This was used in the next step without further purification.

Example 36

Synthesis of hexyl 5-((chlorosulfonyl)oxy)-4,4-dimethylpentanoate (36)

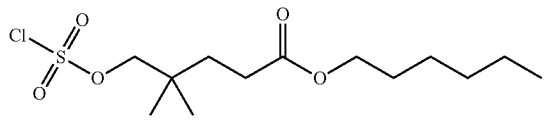 [SMILES: CCCCCCOC(=O)CCC(C)(C)COS(=O)(=O)Cl]

Step 1: Synthesis of sodium-5-(hexyloxy)-2,2-dimethyl-5-oxopentanoate (36a)

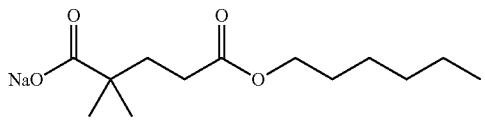

To a solution of 2,2-dimethylglutaric anhydride (5.0 g. 35.2 mmol) in 1-hexanol (50 mL) was added a solution of sodium hexan-1-olate (5.4 g, 43.5 mmol) in 1-hexanol. After 20 h of stirring, the solvent was evaporated and the resulting solid was suspended in diethyl ether (80 mL). The mixture was filtered and the solid was washed with diethyl ether (2×40 mL). The solid was dried under high vacuum to afford the product (36a) (3.84 g, 41%) as a solid. $^1$H-NMR (300 MHz, D$_2$O): δ 4.14 (t, J=6.5 Hz, 2H), 2.38-2.33 (m, 2H), 1.82-1.77 (m, 2H), 1.75-1.63 (m, 2H), 1.43-1.28 (m, 6H), 1.12 (s, 6H), 0.92-0.88 (m, 3H). The spectrum revealed that the product was contaminated with a small amount of an unidentified substance.

Step 2: Synthesis of hexyl 5-hydroxy-4,4-dimethylpentanoate (36b)

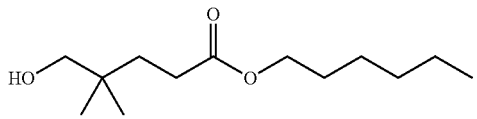 [SMILES: CCCCCCOC(=O)CCC(C)(C)CO]

To a suspension of sodium 5-(hexyloxy)-2,2-dimethyl-5-oxopentanoate (36a) (3.84 g, 14.4 mmol) in a mixture of THF (31 mL) and DMF (10 mL) was added isopropyl chloroformate, 1.0M in toluene (21.6 mL, 21.6 mmol) at 0° C. and the mixture was stirred for 10 min. After 3.3 h of stirring at room temperature, the solution was cooled to 0° C. and sodium borohydride (0.98 g, 28.8 mmol) was added. The mixture was stirred for 20 min and MeOH (5.2 mL) was added to the solution (reaction monitored by TLC using 2:8 ethyl acetate/hexanes as eluent). After 15 min, a few drops of triethylamine were added. After another 15 min of stirring, ethyl acetate (25 mL) and a solution of saturated aqueous NH$_4$Cl was added (25 mL). The organic and aqueous layers were separated, and the aqueous layer was extracted with EtOAc (2×40 mL). The combined organic layers were washed with brine, dried (MgSO$_4$), and filtered, and the filtrate was concentrated in vacuo. The residue was purified by column chromatography on silica gel using EtOAc/hexanes modified with 0.1% Et$_3$N (5:95 to 3:7) to give the product (36b) (2.16 g, 65%) as a colorless oil. One drop of Et$_3$N was added to suppress lactonization.

Step 3: Synthesis of hexyl 5-((chlorosulfonyl)oxy)-4,4-dimethylpentanoate (36)

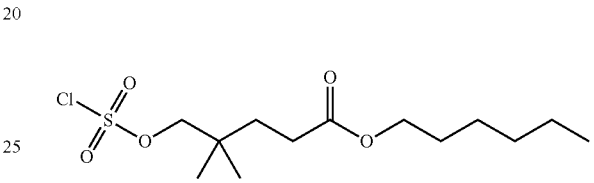

A solution of sulfuryl chloride (0.38 mL, 5.2 mmol) in Et$_2$O (8.5 mL) was cooled to −78° C. under a nitrogen atmosphere. A solution of hexyl 5-hydroxy-4,4-dimethylpentanoate (36b) (0.60 g, 2.6 mmol) and pyridine (0.42 mL, 5.2 mmol) in Et$_2$O (8.5 mL) was added dropwise to the sulfuryl chloride solution over the course of 10 min. The syringe was rinsed with Et$_2$O (3×1 mL) and the rinse was also added to the mixture. The mixture was stirred for 4.5 h (reaction monitored by TLC using 2:8 EtOAc/hexanes as eluent). The solids were filtered off and the solvent was concentrated in vacuo to give the product (36) as a colorless oil with a quantitative yield. To this was added 3 mL of THF and the solution was stored at −78° C. This was used in the next step without further purification.

Example 37

Synthesis of heptyl 5-((chlorosulfonyl)oxy)-4,4-dimethylpentanoate (37)

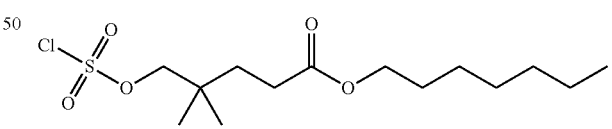

Step 1: Synthesis of sodium 5-(heptyloxy)-2,2-dimethyl-5-oxopentanoate (37a)

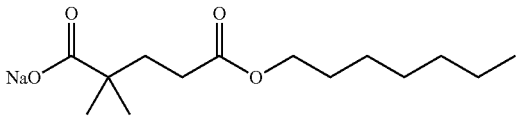

To a solution of 2,2-dimethylglutaric anhydride (5.0 g, 35.2 mmol) in 1-heptanol (40 mL) was added a solution of sodium heptan-1-olate (6.01 g, 43.5 mmol) in 1-heptanol (30 mL). After stirring overnight the solvent was evaporated and the resulting solid was suspended in Et$_2$O (80 mL). The mixture was filtered and the solid was washed with Et$_2$O (2×40 mL). The solid was dried under high vacuum to afford the product (37a) (7.89 g, 80%) as a solid. $^1$H-NMR (300 MHz, D$_2$O): δ 4.14 (t, J=6.5 Hz, 2H), 2.36-2.32 (m, 2H), 1.82-1.77 (m, 2H), 1.74-1.63 (m, 2H), 1.40-1.31 (m, 8H), 1.11 (s, 6H), 0.92-0.87 (m, 3H). The spectrum revealed that the product was contaminated with a small amount of an unidentified substance.

Step 2: Synthesis of heptyl 5-hydroxy-4,4-dimethylpentanoate (37b)

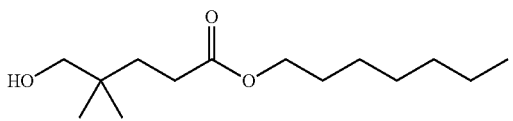 [SMILES: CCCCCCCOC(=O)CCC(C)(C)CO]

To a suspension of sodium 5-(heptyloxy)-2,2-dimethyl-5-oxopentanoate (44a) (7.89 g, 28.1 mmol) in a mixture of THF (61 mL) and DMF (20 mL) was added isopropyl chloroformate, 1.0M in toluene (42.2 mL, 42.2 mmol) at 0° C. and the mixture was stirred for 10 min. After 4 h of stirring at room temperature, the suspension was cooled to 0° C. and sodium borohydride (1.9 g, 56.3 mmol) was added. The mixture was stirred for 20 min and then MeOH (10 mL) was added to the solution (reaction monitored by TLC using 2:8 ethyl acetate/hexanes). After 30 min of stirring, EtOAc (50 mL), a few drops of Et$_3$N, and a saturated aqueous solution of NH$_4$Cl were added (50 mL). The aqueous and organic layers were separated, and the aqueous layer was extracted with EtOAc (2×80 mL). The combined organic layers were washed with brine (80 mL), and the filtrate was concentrated in vacuo. The residual solution was washed with H$_2$O (3×100 mL), brine (100 mL), and dried (Na$_2$SO$_4$), and concentrated. During all extractions, several drops of Et$_3$N were added to the organic layer to suppress lactonization. The residue was purified by column chromatography on silica gel using EtOAc/hexanes modified with 0.1% Et$_3$N (0:1 to 3:7) as eluent to give the product (37b) (3.35 g, 49% crude) as a colorless oil.

Step 3: Synthesis of heptyl 5-((chlorosulfonyl)oxy)-4,4-dimethylpentanoate (37)

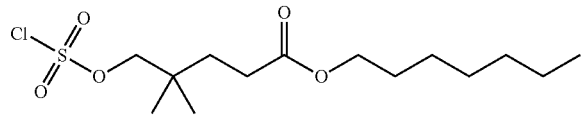 [SMILES: CCCCCCCOC(=O)CCC(C)(C)COS(=O)(=O)Cl]

A solution of sulfuryl chloride (0.60 mL, 8.2 mmol) in Et$_2$O (13 mL) was cooled to −78° C. under a nitrogen atmosphere. A solution of heptyl 5-hydroxy-4,4-dimethylpentanoate (37b) (1.0 g, 4.1 mmol) and pyridine (0.66 mL, 8.2 mmol) in Et$_2$O (13 mL) was added dropwise to the sulfuryl chloride solution over the course of 10 min. The syringe was rinsed with diethyl ether (3×1 mL) and this was also added to the mixture. The mixture was stirred for 4.5 h (reaction monitored by TLC using 2:8 ethyl acetate/hexanes as eluent). The solids were filtered-off, and the filtrate concentrated in vacuo to give the product (37) (1.13 g) as a colorless oil. To this was added 3 mL of THF and the solution stored at −78° C. This was used in the next step without further purification.

Example 38

Synthesis of 2-methoxyethyl 5-((chlorosulfonyl)oxy)-4,4-dimethylpentanoate (38)

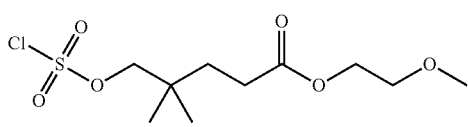 [SMILES: COCCOC(=O)CCC(C)(C)COS(=O)(=O)Cl]

Step 1: Synthesis of sodium 5-(2-methoxyethoxy)-2,2-dimethyl-5-oxopentanoate (38a)

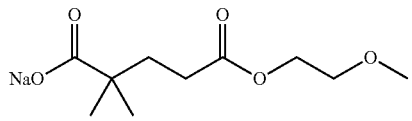

To a solution of 2,2-dimethylglutaric anhydride (5.0 g, 35.2 mmol) in 2-methoxyethanol (30 mL) was added a solution sodium 2-methoxyethanolate (4.27 g, 43.5 mmol) in 2-methoxyethanol (30 mL). After 20 h of stirring, the solvent was evaporated and the resulting solid was suspended in Et$_2$O (80 mL). The mixture was filtered and the solid was washed with Et$_2$O (2×40 mL). The solid was dried under high vacuum to afford the product (38a) (6.44 g, 76%) as a solid. $^1$H-NMR (300 MHz, D$_2$O): δ 4.30-4.27 (m, 2H), 3.75-3.72 (m, 2H), 3.42 (s, 3H), 2.41-2.36 (m, 2H), 1.83-1.78 (m, 2H), 1.12 (s, 6H). The spectrum revealed that the product was contaminated with a small amount of an unidentified substance.

Step 2: Synthesis of 2-methoxyethyl 5-hydroxy-4,4-dimethylpentanoate (38b)

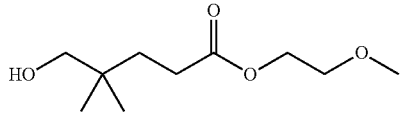

To a suspension of sodium 5-(2-methoxyethoxy)-2,2-dimethyl-5-oxopentanoate (38a) (6.44 g, 26.8 mmol) in a mixture of THF (58 mL) and DMF (19 mL) was added isopropyl chloroformate, 1.0M in toluene (40.2 mL, 40.2 mmol) at 0° C. and stirred for 10 min. After 4 h of stirring at room temperature, the mixture was stored at −78° C. overnight. The suspension was cooled to 0° C. and sodium borohydride (1.81 g, 53.6 mmol) was added. The mixture was stirred for 20 min and then MeOH (9.6 mL) was added to the solution (reaction monitored by TLC using 3:7 EtOAc/hexanes as eluent). After 30 min of stirring, EtOAc (50 mL) with a few drops of Et$_3$N followed by a saturated aqueous solution of NH$_4$Cl (50 mL) were added. The layers were separated and the aqueous layer was extracted with EtOAc (2×80 mL). The combined organic layers were washed with brine, dried (MgSO$_4$), filtered, and the filtrate was concentrated in vacuo. The residue was purified by column chromatography on silica gel to give the product (38b) (2.54 g, 46% crude).

Step 3: Synthesis of 2-methoxyethyl 5-((chlorosulfonyl)oxy)-4,4-dimethylpentanoate (38)

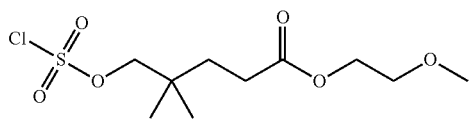 [SMILES: COCCOC(=O)CCC(C)(C)COS(=O)(=O)Cl]

A solution of sulfuryl chloride (0.36 mL, 4.9 mmol) in Et$_2$O (8 mL) was cooled to −78° C. under a nitrogen atmosphere. A solution of 2-methoxyethyl 5-hydroxy-4,4-dimethylpentanoate (38b) (0.50 g, 2.4 mmol) and pyridine (0.40 mL, 4.9 mmol) in Et$_2$O (8 mL) was added dropwise to the sulfuryl chloride solution over the course of 10 min. The syringe was rinsed with Et$_2$O (3×1 mL) and the rinse was also added to the mixture. The mixture was stirred for 4.5 h (reaction monitored by TLC using 2:8 EtOAc/hexanes as eluent). The solids were filtered-off and the filtrate concentrated in vacuo to give the product (38) (0.60 g, 2.0 mmol) as a colorless oil. To this was added 3 mL of THF and the solution was stored at −78° C. This was used in the next step without further purification.

Example 39

Synthesis of 5-((chlorosulfonyl)oxy)-2,2,4,4-tetramethylpentyl propionate (39)

Step 1: Synthesis of 5,5-dimethyltetrahydro-2H-pyran-2-one (39a)

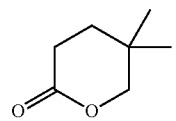

To a solution of ethyl 5-hydroxy-4,4-dimethylpentanoate (35a) (26.5 g, 152.1 mmol) in dichloromethane (683 mL) was added trifluoroacetic acid (1.75 mL, 22.8 mmol). The mixture was stirred at room temperature for 3 d. The reaction was quenched with a saturated aqueous sodium bicarbonate solution (150 mL), stirred rapidly for 30 min, and the layers were separated. The organic layer was washed with brine (150 mL), dried (Na$_2$SO$_4$), and concentrated under vacuum. The residue was purified by column chromatography on silica gel flash using EtOAc/hexanes (0:1 to 45:55) as eluent to give the product (39a) (8.79 g, 45%) as a colorless oil. The product was used in the next step without further purification and was contaminated with small amounts of unidentified byproducts. $^1$H-NMR (300 MHz, CDCl$_3$): δ 3.97 (s, 2H), 2.56 (t, J=7.4 Hz, 2H), 1.69 (t, J=7.4 Hz, 2H), 1.05 (s, 6H).

Step 2: Synthesis of 3,3,5,5-tetramethyltetrahydro-2H-pyran-2-one (39b)

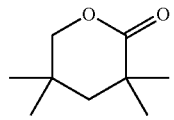

5,5-Dimethyltetrahydro-2H-pyran-2-one (39a) (8.79 g, 68.6 mmol) was dissolved in anhydrous DMF (150 mL) and the resulting solution was cooled to 0° C. under an inert atmosphere of argon. Sodium hydride, 60% in mineral oil (8.23 g, 205.7 mmol) was added in one portion and the mixture stirred for 20 min. This was followed by the drop-wise addition of MeI (17.1 mL, 274.3 mmol). The resulting solution was stirred at 0° C. for 20 min and then at room temperature for 3 d. The mixture was diluted with EtOAc (350 mL) and then quenched at 0° C. via the careful dropwise addition of a saturated aqueous solution of NH$_4$Cl (100 mL). The aqueous and organic layers were separated, and the aqueous layer was extracted with EtOAc (350 mL). The combined organic layers were washed with H$_2$O (6×300 mL), brine (300 mL), dried (Na$_2$SO$_4$), and concentrated under vacuum. The residue was purified by column chromatography on silica using EtOAc/hexanes (1:9) as eluent to give the product (39b) (3.42 g, 32%). The product was used in the next step without further purification and was contaminated with small amounts of various unidentified byproducts. $^1$H-NMR (300 MHz, CDCl$_3$): δ 4.01 (s, 2H), 1.62 (s, 2H), 1.30 (s, 6H), 1.02 (s, 6H).

Step 3: Synthesis of 2,2,4,4-tetramethylpentane-1,5-diol (39c)

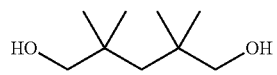

A necked round bottom flask containing a stirring slurry of 95% LiAlH$_4$ (0.87 g, 21.6 mmol) in Et$_2$O (126 mL) was cooled to 0° C. under an atmosphere of argon. To this slurry was added a solution of 3,3,5,5-tetramethyltetrahydro-2H-pyran-2-one (39b) (2.94 g, 18.8 mmol) in Et$_2$O (50 mL) under an inert atmosphere of argon. This was warmed to room temperature and stirred overnight. The mixture was cautiously quenched with H$_2$O (80 mL) then 3M NaOH (120 mL) and stirred for 30 min. The mixture was filtered through a pad of Celite®, and the pad was rinsed thoroughly with Et$_2$O. The aqueous and organic layers were separated, and the aqueous layer was extracted with Et$_2$O (3×100 mL). The combined organic layers were concentrated under vacuum and the residue was purified by column chromatography on silica gel using EtOAc/hexanes (2:8 to 6:4) as eluent to give the product (39c) (2.59 g, 86%) as a solid. $^1$H-NMR (300 MHz, CDCl$_3$): δ 3.41 (s, 4H), 2.55 (s, 2H), 1.34 (s, 2H), 0.95 (s, 12H)

Step 4: Synthesis of 5-hydroxy-2,2,4,4-tetramethylpentyl propionate (39d)

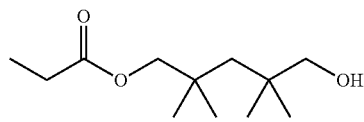

To a stirring solution of 2,2,4,4-tetramethylpentane-1,5-diol (39c) (0.48 g, 3.0 mmol) and pyridine (0.24 mL, 3.0 mmol) in DCM (20 mL) was added propionyl chloride (0.26 mL, 3.0 mmol) dropwise over the course of 30 min at ca. 0° C. (ice bath). The reaction mixture was stirred overnight at room temperature. The mixture was diluted with H$_2$O (20 mL), and the layers were separated. The aqueous layer was extracted with DCM (2×20 mL), and the combined organic layers were washed with brine (20 mL), dried (Na$_2$SO$_4$), and concentrated under vacuum. The residue was purified by column chromatography on silica gel EtOAc/hexanes (5:95 to 6:4) as eluent to give the product (39d) (411 mg, 63%). $^1$H-NMR (300 MHz, CDCl$_3$): δ 3.85 (s, 2H), 3.32 (s, 2H), 2.37 (q, J=7.7 Hz, 2H), 1.50 (s, 1H), 1.36 (s, 2H), 1.16 (t, J=7.5 Hz, 3H), 1.03 (s, 6H), 0.99 (s 6H).

Step 5: Synthesis of 5-((chlorosulfonyl)oxy)-2,2,4,4-tetramethylpentyl propionate (39)

A solution of sulfuryl chloride (0.136 mL, 1.9 mmol) in Et$_2$O (6.4 mL) was cooled to −78° C. under an atmosphere of argon. A solution of 5-hydroxy-2,2,4,4-tetramethylpentyl propionate (39d) (404 mg, 1.9 mmol) and pyridine (0.15 mL, 1.9 mmol) in Et$_2$O (6.4 mL) was added dropwise to the sulfuryl chloride solution over the course of 10 min. The mixture was warmed to room temperature and stirred for 70 min. The solids were filtered to give a solution of the product (39) in Et$_2$O as the filtrate. The yield was assumed quantitative, and the mixture was used in the next step without further purification.

Example 40

Synthesis of 5-((chlorosulfonyl)oxy)-2,2,4,4-tetramethylpentyl benzoate (40)

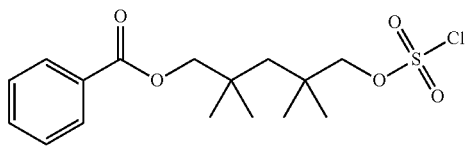 [SMILES: CC(C)(COC(=O)c1ccccc1)CC(C)(C)COS(=O)(=O)Cl]

Step 1: Synthesis of 5-hydroxy-2,2,4,4-tetramethylpentyl benzoate (40a)

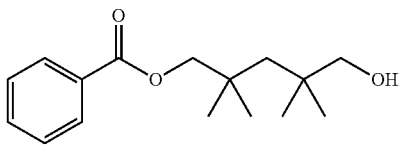 [SMILES: CC(C)(CO)CC(C)(C)COC(=O)c1ccccc1]

To a stirred solution of 2,2,4,4-tetramethylpentane-1,5-diol (39c) (0.48 g, 3.0 mmol) and pyridine (0.24 mL, 3.0 mmol) in DCM (20 mL) was added benzoyl chloride (0.37 mL, 3.0 mmol) dropwise over the course of 30 min at ca. 0° C. (ice bath) under an atmosphere of argon. The reaction mixture was stirred overnight at room temperature. The mixture was diluted with H$_2$O (20 mL), and the layers were separated. The aqueous layer was extracted with DCM (2×20 mL), and the combined organic layers were washed with brine (20 mL), dried (Na$_2$SO$_4$), and concentrated under vacuum. The residue was purified by column chromatography on silica gel using EtOAc/hexanes (5:95 to 1:1) as eluent to give the product (40a) (548 mg, 69%) as an oil. $^1$H-NMR (300 MHz, CDCl$_3$): δ 8.06 (d, J=8.4 Hz, 2H), 7.59-7.55 (m, 1H), 7.48-7.43 (m, 2H), 4.09 (s, 2H), 3.35 (s, 2H), 1.48 (s, 2H), 1.13 (s, 6H), 1.02 (s, 6H).

Step 2: Synthesis of 5-((chlorosulfonyl)oxy)-2,2,4,4-tetramethylpentyl benzoate (40)

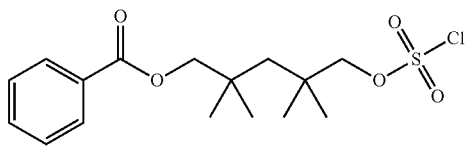 [SMILES: CC(C)(COC(=O)c1ccccc1)CC(C)(C)COS(=O)(=O)Cl]

A solution of sulfuryl chloride (0.15 mL, 2.0 mmol) in Et$_2$O (8.5 mL) was cooled to −78° C. under an atmosphere of argon. A solution of 5-hydroxy-2,2,4,4-tetramethylpentyl benzoate (40a) (541 mg, 2.0 mmol) and pyridine (0.17 mL, 2.0 mmol) in Et$_2$O (8.5 mL) was added dropwise to the sulfuryl chloride solution over the course of 10 min. The mixture was stirred at 0° C. for 20 min, then at room temperature for 90 min. The mixture was filtered and the filtrate used to provide a solution of the product (40) in Et$_2$O (ca. 20 mL). The yield was assumed quantitative and the product was used in the next step without further purification.

Example 41

Synthesis of 5-((chlorosulfonyl)oxy)-2,2,4,4-tetramethylpentyl 2,6-dimethylbenzoate (41)

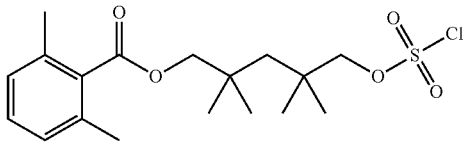 [SMILES: Cc1cccc(C)c1C(=O)OCC(C)(C)CC(C)(C)COS(=O)(=O)Cl]

Step 1: Synthesis of 5-hydroxy-2,2,4,4-tetramethylpentyl 2,6-dimethylbenzoate (41a)

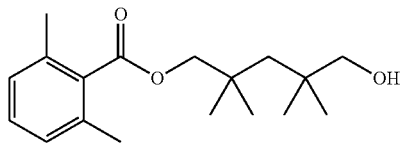 [SMILES: Cc1cccc(C)c1C(=O)OCC(C)(C)CC(C)(C)CO]

To a stirred solution of 2,2,4,4-tetramethylpentane-1,5-diol (39c) (0.48 g, 3.0 mmol) and pyridine (0.24 mL, 3.0 mmol) in DCM (20 mL) was added 2,6-dimethylbenzoyl chloride (0.45 mL, 3.0 mmol) dropwise over the course of 30 min at 0° C. (ice bath) under an atmosphere of argon. The reaction mixture was stirred overnight at room temperature. The mixture was diluted with $H_2O$ (20 mL), and the layers were separated. The aqueous layer was extracted with DCM (2×20 mL), and the combined organic layers were washed with brine (20 mL), dried ($Na_2SO_4$), and concentrated under vacuum. The residue was purified by column chromatography on silica gel using EtOAc/hexanes (5:95 to 1:1) as eluent to give the product (41a) (462 mg, 53%) as an oil. $^1$H-NMR (300 MHz, $CDCl_3$): δ 7.22-7.17 (m, 1H), 7.04 (d, J=7.5 Hz, 2H), 4.10 (s, 2H), 3.32 (s, 2H), 2.33 (s, 6H), 1.41 (s, 2H), 1.10 (s, 6H), 1.00 (s, 6H).

Step 2: Synthesis of 5-((chlorosulfonyl)oxy)-2,2,4,4-tetramethylpentyl 2,6-dimethylbenzoate (41)

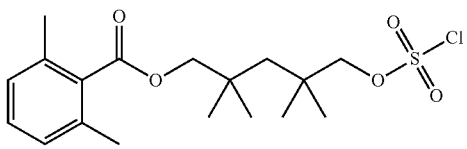 [SMILES: Cc1cccc(C)c1C(=O)OCC(C)(C)CC(C)(C)COS(=O)(=O)Cl]

A solution of sulfuryl chloride (0.11 mL, 1.5 mmol) in $Et_2O$ (7 mL) was cooled to −78° C. under an atmosphere of argon. A solution of 5-hydroxy-2,2,4,4-tetramethylpentyl 2,6-dimethylbenzoate (41a) (453 mg, 1.5 mmol) and pyridine (0.13 mL, 1.5 mmol) in $Et_2O$ (7 mL) was added dropwise to the sulfuryl chloride solution over the course of 10 min. The mixture was stirred in an ice bath for 20 min, then at room temperature for 90 min. The mixture was filtered and the filtrate stored to give a solution of the product (41) in $Et_2O$ (ca. 20 mL). The yield assumed quantitative. This mixture was used in the next step without further purification (a small quantity was concentrated under vacuum and the NMR taken of the residue). $^1$H-NMR (300 MHz, $CDCl_3$): δ 7.21 (t, J=7.7 Hz, 1H), 7.05 (d, J=7.2 Hz, 2H), 4.20 (s, 2H), 4.07 (s, 2H), 2.32 (s, 6H), 1.50 (s, 2H), 1.14 (s, 6H), 1.12 (s, 6H).

Example 42

Synthesis of (3-methyl-2-oxotetrahydrofuran-3-yl)methyl sulfochloridate (42)

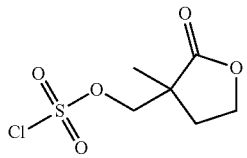

Pyridine (0.28 mL, 3.5 mmol) was added to a stirred mixture of 3-(hydroxymethyl)-3-methyldihydrofuran-2(3H)-one (prepared according to Synlett 2010, 2625-2627) (0.30 g, 2.3 mmol) and $Et_2O$ (8 mL) under an atmosphere of argon. The solution was cooled to −78° C. and sulfuryl chloride (0.28 mL, 3.5 mmol) in $Et_2O$ (3 mL) was slowly added at −78° C. The mixture was stirred at −78° C. for 1 h and then warmed to room temperature and stirred for 1 h. The reaction mixture was filtered to remove the pyridine salt, and the filtrate was concentrated under vacuum to give the product (42) as an oil, that was used directly in the next step without further purification (yield assumed quantitative).

Example 43

Synthesis of 3-((chlorosulfonyl)oxy)-2,2-dimethylpropyl pivalate (43)

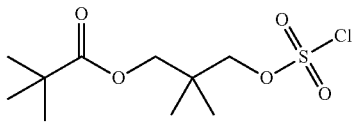 [SMILES: CC(C)(COC(=O)C(C)(C)C)COS(=O)(=O)Cl]

Step 1: Synthesis of 3-hydroxy-2,2-dimethylpropyl pivalate (43a)

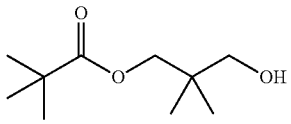

To a stirred solution of 2,2-dimethylpropane-1,3-diol (5.07 g, 48.7 mmol) in DCM (50 mL) at 0° C. under an atmosphere of argon was added trimethylacetyl chloride (2.0 mL, 16.2 mmol), pyridine (2.63 mL, 32.5 mmol) and N,N-4-dimethylaminopyridine (0.4 g, 3.2 mmol). The mixture was allowed to warm to room temperature and stirred at room temperature overnight. The mixture was cooled to 0° C. and the reaction was quenched with the addition of 1N HCl (50 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 1:5) as eluent to give the product (43a) as an oil. $^1$H-NMR (300 MHz, CDCl$_3$): δ 3.92 (s, 2H), 3.27 (s, 2H), 1.22 (s, 9H), 0.92 (s, 6H).

Step 2: Synthesis of 3-((chlorosulfonyl)oxy)-2,2-dimethylpropyl pivalate (43)

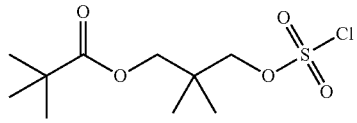 [SMILES: CC(C)(COC(=O)C(C)(C)C)COS(=O)(=O)Cl]

Pyridine (0.75 mL, 9.3 mmol) was added to a stirred mixture of 3-hydroxy-2,2-dimethylpropyl pivalate (43a) (1.17 g, 6.2 mmol) and Et$_2$O (20 mL) under an atmosphere of argon. The solution was cooled to −78° C. and sulfuryl chloride (0.75 mL, 9.3 mmol) in Et$_2$O (8 mL) was slowly added at −78° C. The mixture was stirred at −78° C. for 1 h and then warmed to room temperature and stirred for 1 h. The reaction mixture was filtered to remove the pyridine salt, and the filtrate was concentrated under vacuum to give the product (43) as an oil, that was used directly in the next step without further purification (yield assumed quantitative).

Example 44

Synthesis of 3-((chlorosulfonyl)oxy)-2,2-dimethylpropyl 3-chloro-2,6-dimethoxybenzoate (44)

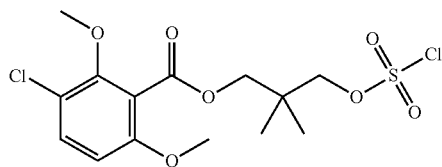 [SMILES: COc1ccc(Cl)c(OC)c1C(=O)OCC(C)(C)COS(=O)(=O)Cl]

Step 1: Synthesis of 3-hydroxy-2,2-dimethylpropyl 2,6-dimethoxybenzoate (44a)

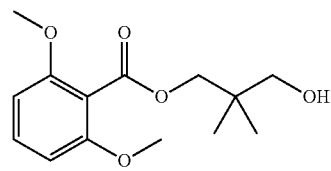 [SMILES: COc1cccc(OC)c1C(=O)OCC(C)(C)CO]

To a stirred solution of 2,2-dimethylpropane-1,3-diol (3.89 g, 37.4 mmol) in DCM (40 mL) at 0° C. under an atmosphere of argon was added 2,6-dimethoxybenzoyl chloride (80% purity; 3.13 g, 12.5 mmol), pyridine (2.02 mL, 24.9 mmol), and N,N-4-dimethylaminopyridine (0.3 g, 2.5 mmol). The mixture was allowed to warm to room temperature and stirred at room temperature overnight. The mixture was cooled to 0° C. and the reaction was quenched by the addition of 1N HCl (50 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 1:5) as eluent to give the product (44a) as an oil. $^1$H-NMR (300 MHz, CDCl$_3$): δ 7.19 (t, J=5.0 Hz, 1H), 6.48 (d, J=8.1 Hz, 2H), 4.09 (s, 2H), 3.71 (s, 6H), 3.33 (s, 2H), 0.89 (s, 6H).

Step 2: Synthesis of 3-((chlorosulfonyl)oxy)-2,2-dimethylpropyl 3-chloro-2,6-dimethoxybenzoate (44)

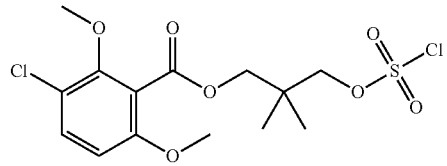 [SMILES: COc1ccc(Cl)c(OC)c1C(=O)OCC(C)(C)COS(=O)(=O)Cl]

Pyridine (0.16 mL, 2.0 mmol) was added to a stirred mixture of 3-hydroxy-2,2-dimethylpropyl 2,6-dimethoxybenzoate (44a) (0.35 g, 1.3 mmol) and Et$_2$O (10 mL) under an atmosphere of argon. The solution was cooled to −78° C. and sulfuryl chloride (0.16 mL, 2.0 mmol) in Et$_2$O (8 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (44) as an oil, that was used directly in the next step without further purification (yield assumed quantitative). $^1$H-NMR (300 MHz, CDCl$_3$): δ 7.36 (d, J=8.7 Hz, 1H), 6.66 (d, J=8.7 Hz, 1H), 4.35 (s, 2H), 4.21 (s, 2H), 3.89 (s, 3H), 3.81 (s, 3H), 1.13 (s, 6H).

Example 45

Synthesis of 4-hydroxy-2,2,3,3-tetramethylbutyl 2,6-dimethylbenzoate (45)

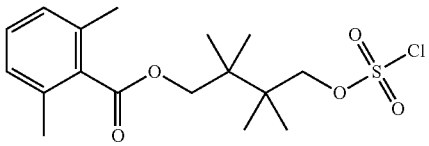 [SMILES: Cc1cccc(C)c1C(=O)OCC(C)(C)C(C)(C)COS(=O)(=O)Cl]

Step 1: Synthesis of 2,2,3,3-tetramethylbutane-1,4-diol (45a)

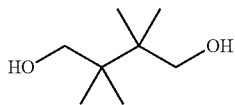

A solution of 3,3,4,4-tetramethyldihydrofuran-2(3H)-one (prepared according to U.S. Pat. No. 3,658,849) (1.0 g, 7.0 mmol) in Et$_2$O (28 mL) was added to a stirring slurry of LiAlH$_4$ (95%; 0.32 g, 8.1 mmol) in Et$_2$O (28 mL) at 0° C. under an atmosphere of argon. The mixture was warmed to room temperature and stirred overnight. Sodium sulfate decahydrate was slowly added until effervescence in the flask ceased. The solid was filtered through a pad of Celite®, and the pad was washed with EtOAc. The filtrate was concentrated under vacuum, and the residue was purified by column chromatography on silica gel using EtOAc/hexanes (0:1 to 7:3) as eluent to give the product (45a) (0.7 g) as a solid. $^1$H-NMR (300 MHz, CDCl$_3$): δ 3.41 (s, 4H), 0.88 (s, 12H).

Step 2: Synthesis of 4-hydroxy-2,2,3,3-tetramethylbutyl 2,6-dimethylbenzoate (45b)

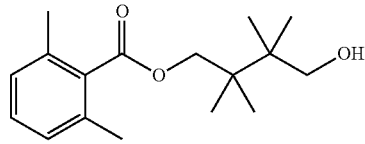 [SMILES: Cc1cccc(C)c1C(=O)OCC(C)(C)C(C)(C)CO]

To a stirred solution of 2,2,3,3-tetramethylbutane-1,4-diol (45a) (0.71 g, 4.9 mmol) in DCM (15 mL) at 0° C. under an atmosphere of argon was added 2,6-dimethylbenzoyl chloride (0.2 mL, 1.6 mmol), pyridine (0.26 mL, 3.2 mmol) and N,N-4-dimethylaminopyridine (0.04 g, 0.3 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (45b) as an oil (266 mg). $^1$H-NMR (300 MHz, CDCl$_3$): δ 7.18 (t, J=8.4 Hz, 1H), 7.02 (d, J=6.9 Hz, 2H), 4.25 (s, 2H), 3.51 (s, 2H), 2.31 (s, 6H), 0.98 (s, 6H), 0.93 (s, 6H).

Step 3: Synthesis of 4-((chlorosulfonyl)oxy)-2,2,3,3-tetramethylbutyl 2,6-dimethylbenzoate (45)

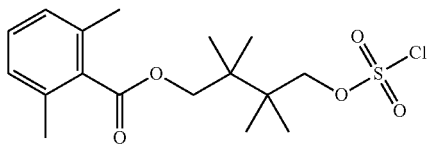 [SMILES: Cc1cccc(C)c1C(=O)OCC(C)(C)C(C)(C)COS(=O)(=O)Cl]

Pyridine (0.11 mL, 1.3 mmol) was added to a stirred mixture of 4-hydroxy-2,2,3,3-tetramethylbutyl 2,6-dimethylbenzoate (45b) (0.26 g, 0.9 mmol) and Et$_2$O (10 mL) under an atmosphere of argon. The solution was cooled to −78° C. and sulfuryl chloride (0.11 mL, 1.3 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (45) as an oil, that was used directly in the next step without further purification (yield assumed quantitative).

Example 46

Synthesis of 4-((chlorosulfonyl)oxy)-2,2,3,3-tetramethylbutyl benzoate (46)

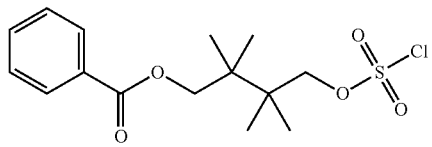 [SMILES: CC(C)(COC(=O)c1ccccc1)C(C)(C)COS(=O)(=O)Cl]

Step 1: Synthesis of 4-hydroxy-2,2,3,3-tetramethylbutyl benzoate (46a)

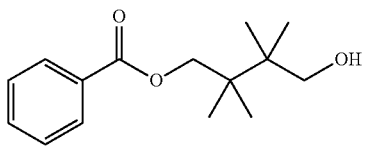 [SMILES: CC(C)(CO)C(C)(C)COC(=O)c1ccccc1]

To a stirred solution of 2,2,3,3-tetramethylbutane-1,4-diol (45a) (0.74 g, 5.0 mmol) in DCM (15 mL) at 0° C. under an atmosphere of argon was added benzoyl chloride (0.25 mL, 2.0 mmol), pyridine (0.33 mL, 4.0 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give the product (46a) as an oil. $^1$H-NMR (300 MHz, CDCl$_3$): δ 8.05 (d, J=7.2 Hz, 2H), 7.58 (t, J=7.4 Hz, 1H), 7.46 (t, J=7.4 Hz, 2H), 4.27 (s, 2H), 3.59 (s, 2H), 1.05 (s, 6H), 0.99 (s, 6H).

Step 2: Synthesis of 4-((chlorosulfonyl)oxy)-2,2,3,3-tetramethylbutyl benzoate (46)

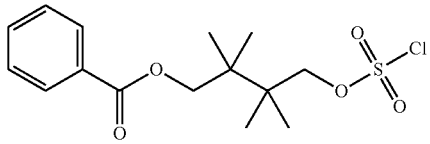 [SMILES: CC(C)(COC(=O)c1ccccc1)C(C)(C)COS(=O)(=O)Cl]

Pyridine (0.29 mL, 3.6 mmol) was added to a stirred mixture of 4-hydroxy-2,2,3,3-tetramethylbutyl benzoate (46a) (0.70 g, 2.8 mmol) and Et$_2$O (10 mL) under an atmosphere of argon. The solution was cooled to −78° C. and sulfuryl chloride (0.29 mL, 3.6 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (46) as an oil, that was used directly in the next step without further purification (yield assumed quantitative).

Example 47

Synthesis of 4-((chlorosulfonyl)oxy)-2,2,3,3-tetramethylbutyl propionate (47)

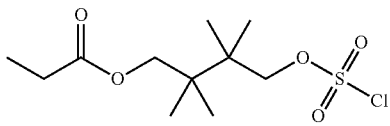 [SMILES: CCC(=O)OCC(C)(C)C(C)(C)COS(=O)(=O)Cl]

Step 1: Synthesis of 4-hydroxy-2,2,3,3-tetramethylbutyl propionate (47a)

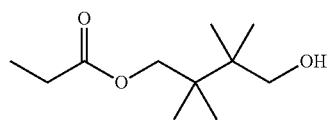

To a stirred solution of 2,2,3,3-tetramethylbutane-1,4-diol (45a) (0.59 g, 4.0 mmol) in DCM (15 mL) at 0° C. under an atmosphere of argon was added propionyl chloride (0.25 mL, 3.1 mmol), pyridine (0.33 mL, 4.0 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried (Na$_2$SO$_4$), and concentrated under vacuum. The residue was purified by column chromatography on silica gel using EtOAc/hexanes (0:1 to 3:2) as eluent to give di-acylated material, followed by the product (47a) (300 mg) as an oil. $^1$H-NMR (300 MHz, CDCl$_3$): δ 3.99 (s, 2H), 3.49 (s, 2H), 2.38-2.31 (q, 2H), 1.15 (t, J=7.8 Hz, 3H), 0.91 (d, J=4.8 Hz, 12H).

Step 2: Synthesis of 4-((chlorosulfonyl)oxy)-2,2,3,3-tetramethylbutyl propionate (47)

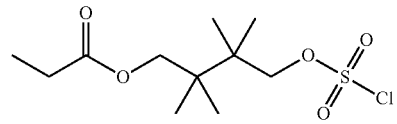 [SMILES: CCC(=O)OCC(C)(C)C(C)(C)COS(=O)(=O)Cl]

Pyridine (0.16 mL, 1.9 mmol) was added to a stirred mixture of 4-hydroxy-2,2,3,3-tetramethylbutyl propionate (47a) (0.30 g, 1.5 mmol) and Et$_2$O (10 mL) under an atmosphere of argon. The solution was cooled to −78° C. and sulfuryl chloride (0.16 mL, 1.9 mmol) in Et$_2$O (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the product (54) as an oil, that was used directly in the next step without further purification (yield assumed quantitative).

Example 48

Synthesis of (3-methyl-2-oxotetrahydro-2H-pyran-3-yl)methyl sulfochloridate (48)

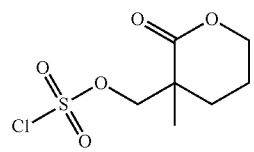

Step 1: Synthesis of 3-((benzyloxy)methyl)-3-methyltetrahydro-2H-pyran-2-one (48a)

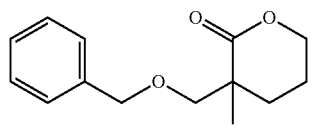 [SMILES: CC1(COCc2ccccc2)CCCOC1=O]

δ-Valerolactone (5.23 g, 52.2 mmol) was dissolved in a mixture of THF (120 mL) and HMPA (9.2 mL) under an atmosphere of argon. The reaction mixture was cooled to −78° C. and stirred for 10 min. A solution of lithium diisopropylamide, 2.0M in THF (28.7 mL, 57.5 mmol) was added dropwise over 5 min. The reaction was stirred at −78° C. for 30 min and then neat MeI (3.3 mL, 52.8 mmol) was added to the reaction over 5 min. The mixture was stirred at −78° C. for 30 min then removed from the cooling bath and allowed to warm to 0° C. and stirred for 30 min (note: the mixture gradually became yellow during this time). The mixture was re-cooled to −78° C. and stirred for 10 min, and then an additional amount of lithium diisopropylamide, 2.0 M in THF (28.7 mL, 57.5 mmol) was added over 5 min. The reaction was stirred at −78° C. for 30 min, then neat benzyl chloromethyl ether (70%; 10.5 mL, 52.8 mmol) was added over 5 min. The mixture was left to warm to room temperature and stirred for 16 h. The solvent was then removed under vacuum and the residue was partitioned between saturated ammonium chloride (200 mL) and EtOAc (200 mL). The aqueous layer was extracted with EtOAc (2×100 mL) and the combined organic layers were washed with brine (2×100 mL), dried (Na$_2$SO$_4$), filtered, and concentrated under vacuum (19 g). The residue was dry-loaded onto silica gel and purified by column chromatography on silica gel (120 g cartridge) using EtOAc/hexanes as eluent to give the product contaminated with an impurity (6.9 g). The residue was re-purified by column chromatography on silica gel using DCM/hexanes (0:1 to 4:1) as eluent to give the product (48a) (1.76 g) as a liquid. $^1$H-NMR (300 MHz, CDCl$_3$): δ 7.29-7.37 (m, 5H), 4.61 (dd, J=21.0, 12.3 Hz, 2H), 4.32-4.38 (m, 2H), 3.26-3.81 (dd, J=15.8, 8.1 Hz, 2H), 2.21-2.30 (m, 1H), 1.87-1.94 (m, 2H), 1.59-1.66 (m, 1H), 1.23 (s, 3H).

Step 2: Synthesis of 3-(hydroxymethyl)-3-methyl-tetrahydro-2H-pyran-2-one (48b)

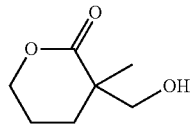

3-((Benzyloxy)methyl)-3-methyltetrahydro-2H-pyran-2-one (48a) (0.52 g, 2.2 mmol) was dissolved in 2-propanol (25 mL) and the solution was degassed and back-flushed with argon. (Note: do not use MeOH as solvent, as it may ring-open the lactone during hydrogenation). Palladium on carbon, 10% (0.26 g, 0.2 mmol), was added to the mixture and the system was sealed. The reaction was degassed and back-flushed with hydrogen (3 times) and stirred under an atmosphere of hydrogen for 2 h. The suspension was filtered through a pad of Celite®, and the filter cake washed with fresh 2-propanol (2×50 mL). The filtrate was concentrated under vacuum, and the product (48b) was used without further purification. $^1$H-NMR (300 MHz, CDCl$_3$): δ 4.27-4.45 (m, 2H), 3.67 (d, J=11.4 Hz, 1H), 3.52 (d, J=11.1 Hz, 1H), 1.84-2.03 (m, 2H), 1.58-1.64 (m, 1H), 1.29 (s, 3H).

Step 3: Synthesis of (3-methyl-2-oxotetrahydro-2H-pyran-3-yl)methyl sulfochloridate (48)

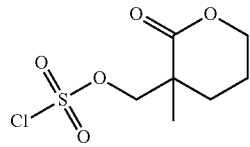

A solution of 3-(hydroxymethyl)-3-methyltetrahydro-2H-pyran-2-one (48b) (0.32 g, 2.2 mmol) and pyridine (0.21 mL, 2.6 mmol) in Et$_2$O (10 mL) was cooled to −78° C. under an atmosphere of argon. Neat sulfuryl chloride (0.21 mL, 2.6 mmol) was added dropwise to the above solution via a syringe. The mixture was stirred at −78° C. for 10 min, then the flask was warmed to room temperature and stirred for 1 h (monitored by TLC EtOAc/hexanes, 3:7). A precipitate formed to give a thick suspension. The suspension was filtered through a 0.45 μM Teflon® filter, and the filter cake rinsed with fresh Et$_2$O (2×5 mL). An aliquot (0.5 mL) was taken and concentrated, and an NMR was obtained for the mixture. The remaining solution containing the product (48) was used directly in the next step. $^1$H-NMR (300 MHz, CDCl$_3$): δ 4.87 (d, J=9.3 Hz, 1H), 4.25-4.50 (m, 2H), 4.32 (d, J=8.7 Hz, 1H), 2.00-2.20 (m, 2H), 1.75-2.00 (m, 2H), 1.39 (s, 3H).

Example 49

Synthesis of 2-(3-((chlorosulfonyl)oxy)-2,2-dimethylpropyl)phenyl acetate (49)

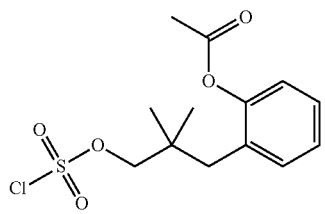 [SMILES: CC(=O)Oc1ccccc1CC(C)(C)COS(=O)(=O)Cl]

Step 1: Synthesis of ethyl 3-(2-methoxyphenyl)-2,2-dimethylpropanoate (49a)

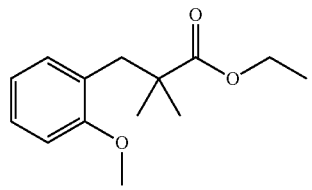 [SMILES: CCOC(=O)C(C)(C)Cc1ccccc1OC]

A stirred solution of lithium diisopropylamide, 2.0 M in THF (26.6 mL, 53.2 mmol) was diluted with THF (100 mL) was cooled to −78° C. under an atmosphere of argon, and stirred for 5 min. Neat ethyl isobutyrate (6.68 mL, 49.7 mmol) was added dropwise over 15 min, and the mixture allowed to stir at −78° C. for 1 h. A solution of 1-(bromomethyl)-2-methoxybenzene (prepared according to *J. Am. Chem. Soc.* 2013, 135, 11951) (12.0 g, 59.7 mmol) in THF (100 mL) was added dropwise over 30 min. The mixture was allowed to warm to room temperature and stirred for 20 h. The reaction was quenched with brine (100 mL) and extracted with Et$_2$O (4×100 mL). The combined organic layers were dried (MgSO$_4$), filtered, and concentrated under vacuum. The crude residue was purified by column chromatography on silica gel (120 g column) using EtOAc/hexanes (0:1 to 5:95) as eluent to give the product (49a) as a liquid (8.06 g, 68%). $^1$H-NMR (300 MHz, CDCl$_3$): δ 7.18 (dt, J=1.8, 8.1 Hz, 1H), 7.06 (dd, J=1.5, 8.1 Hz, 1H), 6.82-6.87 (m, 2H), 4.12 (q, J=6.9 Hz, 2H), 3.77 (s, 3H), 2.92 (s, 2H), 1.26 (t, J=6.9 Hz, 3H), 1.15 (s, 6H).

Step 2: Synthesis of 3,3-dimethylchroman-2-one (49b)

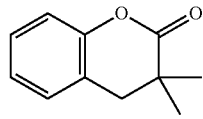

Ethyl 3-(2-methoxyphenyl)-2,2-dimethylpropanoate (49a) (8.1 g, 34.2 mmol) was dissolved in DCM (200 mL) and cooled to 0° C. under an atmosphere of argon. A solution of BBr$_3$ (3.6 mL, 37.7 mmol) in DCM (100 mL) was added dropwise to the cold solution. The mixture was warmed to room temperature and stirred overnight (a solid formed during the reaction). The colored suspension was cooled in an ice water bath and water (150 mL) was added to the mixture. The organic and aqueous layers were separated, and the aqueous layer was extracted with DCM (3×75 mL). The combined organic layers were dried (MgSO$_4$; note: the solution became darker), filtered, and concentrated under vacuum to give the product (49b) (4.85 g, 80%) as an oil. This material was used without further purification. $^1$H-NMR (300 MHz, CDCl$_3$): δ 7.01-7.25 (m, 3H), 2.85 (s, 2H), 1.29 (s, 6H).

Step 3: Synthesis of 2-(3-hydroxy-2,2-dimethylpropyl)phenol (49c)

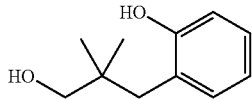

LiAlH$_4$ (1.94 g, 51.1 mmol) was suspended in Et$_2$O (52.5 mL) under an atmosphere of argon and the mixture was cooled to 0° C. in an ice water bath. A solution of 3,3-dimethylchroman-2-one (49b) (4.85 g, 27.5 mmol) in Et$_2$O (50 mL) and added dropwise to the suspension over 30 min. The mixture was warmed to room temperature and stirred for 20 h. The mixture was cooled in an ice water bath and water (2 mL), 15% aqueous sodium hydroxide (2 mL), and water (6 mL), were sequentially added by slow addition. The mixture was warmed to room temperature and stirred for 15 min. Anhydrous MgSO$_4$ was added to the suspension and the mixture stirred for 15 min. The mixture was filtered, and the filter cake washed with Et$_2$O (3×50 mL). The filtrate was concentrated under vacuum to give the product (49c) (4.34 g, 88%) as a solid. This material was used without further purification. $^1$H-NMR (300 MHz, CDCl$_3$): δ 7.15 (dt, J=8.1, 1.5 Hz, 1H), 7.04 (dd, J=7.5, 1.8 Hz, 1H), 6.82-7.01 (m, 2H), 3.22 (s, 2H), 2.61 (s, 2H), 0.98 (s, 6H).

Step 4: Synthesis of 2-(3-((tert-butyldimethylsilyl)oxy)-2,2-dimethylpropyl)phenol (49d)

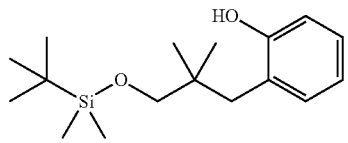 [SMILES: CC(C)(CO[Si](C)(C)C(C)(C)C)Cc1ccccc1O]

A solution of 2-(3-hydroxy-2,2-dimethylpropyl)phenol (49c) (4.0 g, 22.2 mmol) and imidazole (3.8 g, 56.0 mmol) was dissolved in DMF (50 mL) and tert-butyldimethylsilyl chloride (4.0 g, 26.6 mmol) was added to the solution and stirred for 2 h. The solvent was removed under high vacuum and the residue was purified by column chromatography on silica gel (40 g cartridge) with hexanes (5:95 to 2:3) as eluent to give the product (49d) as an oil (7.34 g, >100%). The compound was approximately 90% pure and was used directly in the next step without further purification. $^1$H-NMR (300 MHz, CDCl$_3$): δ 7.11 (dt, J=7.5, 1.8 Hz, 1H), 7.10 (dd, J=7.5, 1.8 Hz, 1H), 6.90 (dd, J=8.1, 1.5 Hz, 1H), 6.79 (dt, J=6.9, 0.9 Hz, 1H), 3.17 (s, 2H), 2.57 (s, 2H), 0.97 (s, 9H), 0.92 (s, 6H), 0.13 (s, 6H).

Step 5: Synthesis of 2-(3-((tert-butyldimethylsilyl)oxy)-2,2-dimethylpropyl)phenyl acetate (49e)

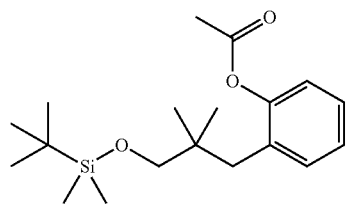 [SMILES: CC(=O)Oc1ccccc1CC(C)(C)CO[Si](C)(C)C(C)(C)C]

A solution of 2-(3-((tert-butyldimethylsilyl)oxy)-2,2-dimethylpropyl)phenol (49d) (ca. 90% purity; 2.5 g, 7.6 mmol) and Et$_3$N (2.3 g, 22.9 mmol) in THF (90 mL) was cooled to 0° C. in an ice bath under an atmosphere of argon. Acetyl chloride (0.65 mL, 9.2 mmol) was added dropwise to the mixture, and after complete addition the ice bath was removed. The reaction was allowed to warm to room temperature and stirred for 2 h. The suspension was filtered and the solid washed with fresh THF (2×20 mL). The filtrate was concentrated under vacuum and the residue dry-loaded onto silica gel, then purified by column chromatography on silica gel (40 g cartridge) using 0-8% EtOAc/hexanes (0:1 to 8:92) as eluent to give the product (49e) (2.16 g, 84%) as an oil. $^1$H-NMR (300 MHz, CDCl$_3$): δ 7.11-7.27 (m, 3H), 7.04 (d, J=7.5 Hz, 1H), 3.25 (s, 2H), 2.51 (s, 2H), 2.30 (s, 3H), 0.93 (s, 9H), 0.81 (s, 6H), 0.06 (s, 6H).

Step 6: Synthesis of 2-(3-hydroxy-2,2-dimethylpropyl)phenyl acetate and 3-(2-hydroxyphenyl)-2,2-dimethylpropyl acetate (49f)

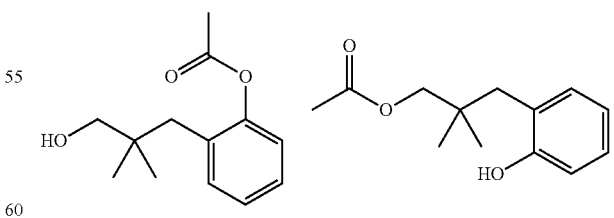

Pyridine hydrofluoride (70%, 1.3 mL, 10.4 mmol) was added to a stirred solution of 2-(3-((tert-butyldimethylsilyl)oxy)-2,2-dimethylpropyl)phenyl acetate (49e) (0.70 g, 2.1 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL), washed with brine (3×75 mL), dried (Na₂SO₄), filtered, and concentrated under vacuum to give a mixture of the desired alcohol and 3-(2-hydroxyphenyl)-2,2-dimethylpropyl acetate in a 65:35. NMR analysis showed the presence of both esters of the product (49f). This material was used directly in the next step without further purification. ¹H-NMR (300 MHz, CDCl₃) of desired product: δ 6.8-7.26 (m, 4H), 3.79 (s, 2H), 3.27 (s, 2H), 2.62 (s, 2H), 2.53 (s, 2H), 2.33 (s, 3H), 2.13 (s, 3H), 0.974 (s, 6H), 0.90 (s, 6H).

Step 7: Synthesis of 2-(3-((chlorosulfonyl)oxy)-2,2-dimethylpropyl)phenyl acetate (49)

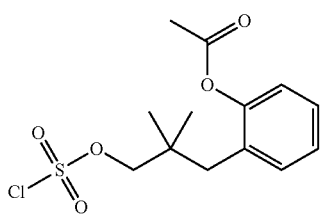 [SMILES: CC(=O)Oc1ccccc1CC(C)(C)COS(=O)(=O)Cl]

A solution of sulfuryl chloride (172 µL, 2.1 mmol) in Et₂O (6.8 mL) was cooled to −78° C. under an atmosphere of argon. A solution of 2-(3-hydroxy-2,2-dimethylpropyl)phenyl acetate (49f) (0.43 g, 1.9 mmol) and pyridine (172 µL, 2.1 mmol) in Et₂O (2.0 mL) was added dropwise to the sulfuryl chloride solution via cannula. The mixture was stirred at −78° C. for 10 min, then the flask was warmed to room temperature and stirred for 1.5 h (monitored by TLC 30% EtOAc/hexanes). The suspension was filtered through a 0.45 µm PTFE syringe filter, and the syringe filter was rinsed with fresh Et₂O (10 mL) to provide the product (49). The filtrate was used immediately in the next step without further purification. The yield was assumed to be quantitative.

Example 50

Synthesis of 2-(3-((chlorosulfonyl)oxy)-2,2-dimethylpropyl)phenyl pivalate (50)

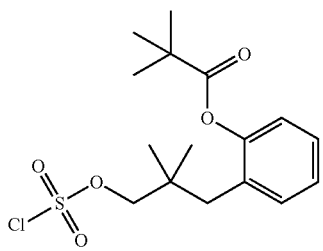 [SMILES: CC(C)(COS(=O)(=O)Cl)Cc1ccccc1OC(=O)C(C)(C)C]

Step 1: Synthesis of 2-(3-((tert-butyldimethylsilyl)oxy)-2,2-dimethylpropyl)phenyl pivalate (50a)

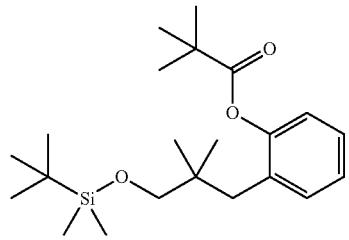 [SMILES: CC(C)(CO[Si](C)(C)C(C)(C)C)Cc1ccccc1OC(=O)C(C)(C)C]

2-(3-((tert-Butyldimethylsilyl)oxy)-2,2-dimethylpropyl)phenol (0.9 g, 3.1 mmol) and N,N-4-dimethylaminopyridine (0.93 g, 7.6 mmol) were dissolved in THF (50 mL) under an atmosphere of argon. Trimethylacetyl chloride (0.45 mL, 3.7 mmol) was added dropwise to the mixture at room temperature to immediately form a white solid, and the addition was continued until a suspension was formed. The reaction was stirred at room temperature for 2 h, and then filtered and the filter cake washed with THF (10 mL). The filtrate was dry-loaded on to silica gel (15 g) and purified by column chromatography on silica gel using EtOAc/hexanes (0:1 to 6:94) as eluent to give the product (50a) contaminated with ca. 3% of starting material by NMR analysis. This material was used without further purification. ¹H-NMR (300 MHz, CDCl₃): δ 7.27 (dd, J=7.2, 2.1 Hz, 1H), 7.21 (dt, J=7.5, 1.8 Hz, 1H), 7.15 (dt, J=7.8, 1.8 Hz, 1H), 6.97 (dd, J=8.1, 1.8 Hz, 1H), 3.25 (s, 2H), 2.49 (s, 2H), 1.38 (s, 9H), 0.92 (s, 9H), 0.82 (s, 6H), 0.05 (s 6H).

Step 2: Synthesis of 2-(3-hydroxy-2,2-dimethylpropyl)phenyl pivalate (50b)

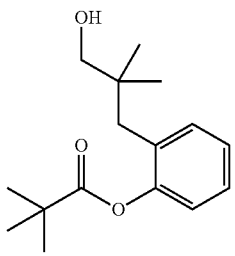 [SMILES: CC(C)(CO)Cc1ccccc1OC(=O)C(C)(C)C]

Pyridine hydrofluoride (70%, 1.3 mL, 10.4 mmol) was added to a stirred solution of 2-(3-((tert-butyldimethylsilyl)oxy)-2,2-dimethylpropyl)phenyl pivalate (50a) (0.70 g, 1.8 mmol) and pyridine (2.5 mL, 31.2 mmol) in THF (25 mL) at room temperature under an atmosphere of argon, and the mixture was stirred for 24 h. The solvent was removed under vacuum (bath temperature set to 25° C.), and the residue was dissolved in EtOAc (100 mL) and washed with brine (3×75 mL), dried (Na₂SO₄), filtered, and concentrated under vacuum to give the desired product (50b) as an oil. This material was used directly in the next step without further purification. ¹H-NMR (300 MHz, CDCl₃): δ 7.12-7.26 (m, 3H), 6.98 (m, 1H), 3.31 (s, 2H), 2.51 (s, 2H), 1.39 (s, 9H), 0.89 (s, 9H).

Step 3: Synthesis of 2-(3-((chlorosulfonyl)oxy)-2,2-dimethylpropyl)phenyl pivalate (50)

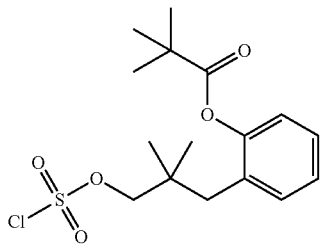 [SMILES: CC(C)(COS(=O)(=O)Cl)Cc1ccccc1OC(=O)C(C)(C)C]

A solution of sulfuryl chloride (173 μL, 2.1 mmol) in Et$_2$O (7.5 mL) was cooled to −78° C. under an argon atmosphere. A solution of 2-(3-hydroxy-2,2-dimethylpropyl)phenyl pivalate (50b) (0.47 g, 1.8 mmol) and pyridine (173 μL, 2.1 mmol) in Et$_2$O (2.2 mL) was added dropwise to the sulfuryl chloride solution via cannula. The mixture was stirred at −78° C. for 10 min, and then the flask was warmed to room temperature and stirred for 1.5 h (monitored by TLC 30% EtOAc/hexanes). The suspension was filtered through a 0.45-μm PTFE syringe filter, and the syringe filter was rinsed with fresh Et$_2$O to provide the product (50). The filtrate was used immediately in the next step without further purification. The yield was assumed to be quantitative.

Example 51

Synthesis of S-(4-((chlorosulfonyl)oxy)-3,3-dimethylbutyl) ethanethioate (51)

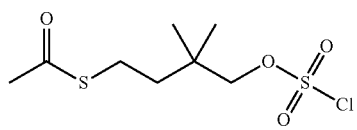

A solution of freshly distilled sulfuryl chloride (271 μL, 3.7 mmol) in Et$_2$O (5 mL) was cooled to −78° C. under an atmosphere of argon. A solution of S-(4-hydroxy-3,3-dimethylbutyl) ethanethioate (prepared according to *Chem. Commun.* 2011, 47, 2038) (500 mg, 2.8 mmol) and pyridine (267 μL, 3.3 mmol) in Et$_2$O (3 mL) was added dropwise to the sulfuryl chloride solution over the course of 5 min. The flask was rinsed with diethyl ether (2×5 mL) and the rinse was also added to the reaction mixture. The mixture was stirred at −78° C. for 1 h and allowed to warm to room temperature and stirred at room temperature for another 20 min. The precipitate was filtered (quickly) and the filter cake rinsed with Et$_2$O (12 mL). The filtrate was concentrated under vacuum at room temperature to afford the title compound (51) as an oil which was used immediately for the next step without further purification.

Example 52

Synthesis of S-(5-((chlorosulfonyl)oxy)-4,4-dimethylpentyl) ethanethioate (52)

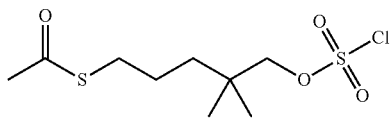 [SMILES: CC(=O)SCCCC(C)(C)COS(=O)(=O)Cl]

Step 1: Synthesis of 5-bromo-2,2-dimethylpentan-1-ol (52a)

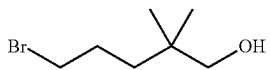

DCM (18 mL) was added to LiBH$_4$ (0.66 g, 30.4 mmol) followed by dropwise addition of anhydrous MeOH (1.2 ml, 30.4 mmol) over 20 min under an atmosphere of argon. After the H$_2$ effervescence had ceased, a solution of ethyl 5-bromo-2,2-dimethylpentanoate (prepared according to PCT Application Publication No. 2011046771) (4.5 g, 19.0 mmol) in DCM (10 mL) was added dropwise over 20 min. The reaction mixture was heated to reflux for 16 h, cooled to room temperature, and carefully hydrolyzed with a saturated NH$_4$Cl solution (30 mL). The suspension was extracted with DCM (3×50 mL). The combined organic layers were washed with 1N HCl (26 mL) and brine (40 mL), dried, and concentrated under vacuum to give the product (52a) (3.61 g, 97%) as an oil. $^1$H-NMR (300 MHz, CDCl$_3$): δ 3.39 (t, J=6.9 Hz, 2H), 3.24 (s, 2H), 1.90-1.76 (m, 2H), 1.48 (br. s, 1H), 1.41-1.36 (m, 2H), 0.88 (s, 6H).

Step 2: Synthesis of S-(5-hydroxy-4,4-dimethylpentyl) ethanethioate (52b)

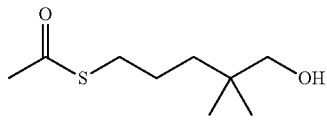

A solution of 5-bromo-2,2-dimethylpentan-1-ol (59a) (2.0 g, 10.3 mmol) and potassium thioacetate (2.34 g, 20.5 mmol) in acetone (22 mL) was stirred under an inert atmosphere at room temperature for 23 h. After removing the solvents under vacuum at room temperature, the residue was purified by column chromatography on silica gel column using EtOAc/hexanes (0:1 to 2:3) as eluent to give the product (52b) (1.2 g, 61%) as an oil. $^1$H-NMR (300 MHz, CDCl$_3$): δ 3.31 (s, 2H), 2.85 (t, J=7.8 Hz, 2H), 2.32 (s, 3H), 1.62-1.48 (m, 2H), 1.32-1.21 (m, 2H), 0.86 (s, 6H).

Step 3: Synthesis of S-(5-((chlorosulfonyl)oxy)-4,4-dimethylpentyl) ethanethioate (52)

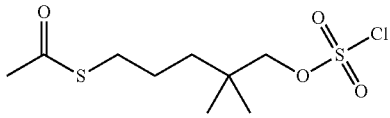 [SMILES: CC(=O)SCCCC(C)(C)COS(=O)(=O)Cl]

A solution of freshly distilled sulfuryl chloride (379 µL, 5.2 mmol) in Et$_2$O (8 mL) was cooled to −78° C. under an atmosphere of argon. A solution of S-(5-hydroxy-4,4-dimethylpentyl) ethanethioate (52b) (700 mg, 3.6 mmol) and pyridine (374 µL, 4.6 mmol) in Et$_2$O (4 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with Et$_2$O (10 mL). The filtrate was concentrated under vacuum at room temperature to afford the title compound (52) as an oil which was used immediately for the next step without further purification.

Example 53

Synthesis of S-(3-((chlorosulfonyl)oxy)-2,2-dimethylpropyl) ethanethioate (53)

Step 1: Synthesis of S-(3-hydroxy-2,2-dimethylpropyl) ethanethioate (53a)

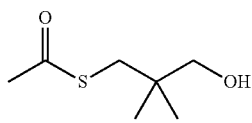

Potassium thioacetate (4.1 g, 35.8 mmol) was dissolved in DMF (20 mL) under an atmosphere of argon. 3-Hydroxy-2,2-dimethylpropyl 4-methylbenzenesulfonate (prepared according to PCT Application Publication No. 2012165648) (4.2 g, 16.3 mmol) was added, and the mixture was stirred at 80° C. for 2.5 h. After cooling, brine (100 mL) was added, and the mixture was extracted with Et$_2$O (3×100 mL). The combined organic layers were washed with brine (5×50 mL), dried (Na$_2$SO$_4$), filtered, and concentrated under vacuum (residual DMF was removed by high vacuum). The residue was purified by column chromatography on silica gel using EtOAc/hexanes (0:1 to 15:85) as eluent to provide the product (53a) (1.06 g, 40%) as an oil. $^1$H-NMR (300 MHz, CDCl$_3$): δ 3.23 (br. s, 2H), 2.89 (s, 2H), 2.62 (br. s, 1H), 2.37 (s, 3H), 0.94 (s, 6H).

Step 2: Synthesis of S-(3-((chlorosulfonyl)oxy)-2,2-dimethylpropyl) ethanethioate (53)

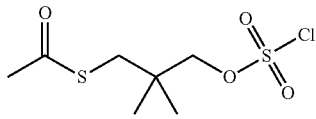

A solution of freshly distilled sulfuryl chloride (283 µL, 3.9 mmol) in Et$_2$O (4 mL) was cooled to −78° C. under an argon atmosphere. A solution of S-(3-hydroxy-2,2-dimethylpropyl) ethanethioate (53a) (520 mg, 3.1 mmol) and pyridine (327 µL, 4.0 mmol) in Et$_2$O (6 mL) was added dropwise to the sulfuryl chloride solution over the course of 5 min. The mixture was stirred at −78° C. for 1 h, then allowed to warm to room temperature. The precipitate was filtered (quickly) and the filter cake rinsed with Et$_2$O (10 mL). The filtrate was concentrated under vacuum at room temperature to afford the title compound (53) as an oil which was used immediately for the next step without further purification.

Example 54

Synthesis of 3-((chlorosulfonyl)oxy)-2,2-dimethylpropyl 2,6-dimethylbenzoate (54)

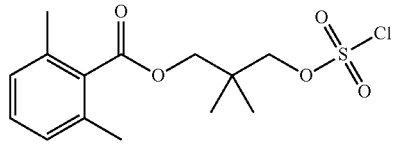

Step 1: Synthesis of 3-hydroxy-2,2-dimethylpropyl 2,6-dimethylbenzoate (54a)

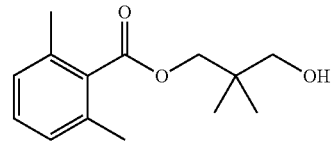 [SMILES: Cc1cccc(C)c1C(=O)OCC(C)(C)CO]

To a stirred solution of 2,2-dimethylpropane-1,3-diol (2.5 g, 24.3 mmol) in DCM (60 mL) at ca. 0° C. (ice bath) under an atmosphere of argon, was added 2,6-dimethylbenzoyl chloride (1.2 mL, 8.1 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of NaHCO$_3$ and brine, dried (MgSO$_4$), filtered and concentrated under vacuum. The residue was purified by column chromatography on silica gel using EtOAc/hexanes (1:9 to 2:3) as eluent to give the product (54a) (1.5 g, 78%) as an oil. $^1$H-NMR (300 MHz, CDCl$_3$): δ 7.21 (m, 1H), 7.04 (m, 2H), 4.18 (s, 2H), 3.41 (s, 2H), 2.32 (s, 6H), 2.20 (br. s, 1H), 0.99 (s, 6H).

Step 2: Synthesis of 3-((chlorosulfonyl)oxy)-2,2-dimethylpropyl 2,6-dimethylbenzoate (54)

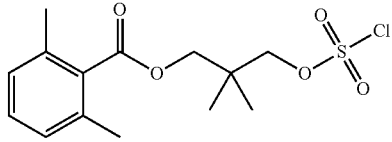 [SMILES: Cc1cccc(C)c1C(=O)OCC(C)(C)COS(=O)(=O)Cl]

A solution of freshly distilled sulfuryl chloride (0.25 mL, 3.9 mmol) in Et$_2$O (6 mL) was cooled to −78° C. under an argon atmosphere. A solution of 3-hydroxy-2,2-dimethylpropyl 2,6-dimethylbenzoate (54a) (500 mg, 2.1 mmol) and pyridine (0.26 mL, 3.3 mmol) in Et$_2$O (6 mL) was added dropwise to the sulfuryl chloride solution over the course of 5 min. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (54) as an oil, which was used immediately in the next step without further purification.

Example 55

Synthesis of 3-((chlorosulfonyl)oxy)-2,2-dimethylpropyl (3r,5r,7r)-adamantane-1-carboxylate (55)

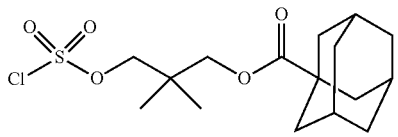 [SMILES: CC(C)(COC(=O)C12CC3CC(CC(C3)C1)C2)COS(=O)(=O)Cl]

Step 1: Synthesis of 3-hydroxy-2,2-dimethylpropyl (3r,5r,7r)-adamantane-1-carboxylate (62a)

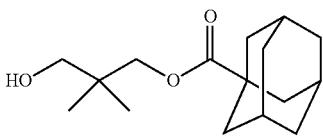 [SMILES: CC(C)(CO)COC(=O)C12CC3CC(CC(C3)C1)C2]

To a stirred solution of 2,2-dimethylpropane-1,3-diol (2.5 g, 24.3 mmol) in DCM (60 mL) at ca. 0° C. (ice bath) under an argon atmosphere, was added 1-adamantane-carbonyl chloride (1.36 g, 6.9 mmol), pyridine (1.1 mL, 13.7 mmol), and N,N-4-dimethylaminopyridine (99 mg, 0.8 mmol). The reaction mixture was allowed to gradually warm to room temperature and the mixture was stirred overnight. The reaction was quenched by the addition of 1N HCl, and the mixture was extracted with DCM (twice). The combined organic extracts were washed with a saturated aqueous solution of NaHCO$_3$ and brine, dried (MgSO$_4$), filtered, and concentrated under vacuum to give the product (55a) (1.82 g, 100%) as an oil. $^1$H-NMR (300 MHz, CDCl$_3$): δ 3.91 (s, 2H), 3.25 (s, 2H), 2.01 (br. s, 3H), 1.89 (br. s, 6H), 1.71 (br. s, 7H), 0.91 (s, 6H).

Step 2: Synthesis of 3-((chlorosulfonyl)oxy)-2,2-dimethylpropyl (3r,5r,7r)-adamantane-1-carboxylate (55)

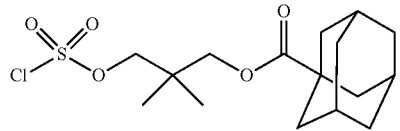

A solution of freshly distilled sulfuryl chloride (266 µL, 3.3 mmol) in Et$_2$O (4 mL) was cooled to −78° C. under an argon atmosphere. A solution of 3-hydroxy-2,2-dimethylpropyl-adamantane-1-carboxylate (55a) (600 mg, 2.2 mmol) and pyridine (0.28 mL, 3.5 mmol) in Et$_2$O (4 mL) was added dropwise to the sulfuryl chloride solution over the course of 5 min. The flask was rinsed with Et$_2$O (5 mL), and the rinse was also added to the reaction mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (55) as an oil, which was used immediately in the next step without further purification.

Example 56

Synthesis of diethyl 2-(((chlorosulfonyl)oxy) methyl)-2-methylmalonate (56)

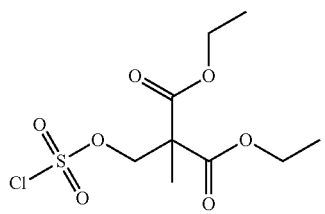 [SMILES: CCOC(=O)C(C)(COS(=O)(=O)Cl)C(=O)OCC]

Step 1: Synthesis of diethyl 2-(hydroxymethyl)-2-methylmalonate (56a)

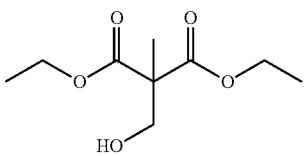

To a suspension of paraformaldehyde (1.3 g, 43.3 mmol) and K$_2$CO$_3$ (11 g, 79 mmol) in EtOH (150 mL) was added diethyl 2-methylmalonate (4.5 mL, 26.3 mmol). The mixture was stirred at room temperature for 17 h, then filtered through a pad of Celite®, and the filter cake washed with EtOH (2×30 mL). The filtrate was concentrated under vacuum and the residue was purified by column chromatography on silica gel using EtOAc/hexanes (0:1 to 3:2) as eluent to afford the product (56a) (4.0 g, 74%) as an oil.

$^1$H-NMR (300 MHz, CDCl$_3$): δ 4.22 (q, J=6.9 Hz, 4H), 3.83 (d, J=6.9 Hz, 2H), 2.90 (t, J=7.8 Hz, 1H), 1.42 (s, 3H), 1.26 (t, J=6.9 Hz, 6H).

Step 2: Synthesis of diethyl 2-(((chlorosulfonyl)oxy)methyl)-2-methylmalonate (56)

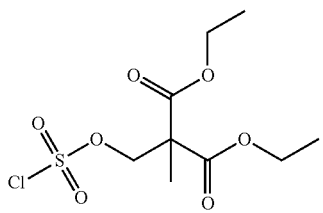 [SMILES: CCOC(=O)C(C)(COS(=O)(=O)Cl)C(=O)OCC]

A solution of freshly distilled sulfuryl chloride (248 μL, 3.0 mmol) in Et$_2$O (8 mL) was cooled to −78° C. under an atmosphere of argon. A solution of diethyl 2-(hydroxymethyl)-2-methylmalonate (56a) (500 mg, 2.4 mmol) and pyridine (0.26 mL, 3.2 mmol) in Et$_2$O (4 mL) was added dropwise to the sulfuryl chloride solution over the course of 5 min. The flask was rinsed with Et$_2$O (5 mL), and the rinse was also added to the reaction mixture. The mixture was stirred at −78° C. for 1 h, and then allowed to warm to room temperature. The precipitate was filtered (quickly) and the filter cake rinsed with Et$_2$O (12 mL). The filtrate was concentrated under vacuum at room temperature to afford the title compound (56) as an oil which was used immediately in the next step without further purification.

Example 57

Synthesis of propyl 3-((chlorosulfonyl)oxy)-2,2-dimethylpropanoate (57)

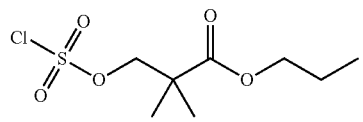

Step 1: Synthesis of propyl 3-hydroxy-2,2-dimethylpropanoate (57a)

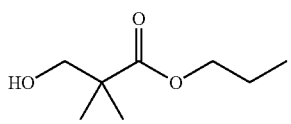

A mixture of 3-hydroxy-2,2-dimethylpropanoic acid (1.15 g, 9.7 mmol) was charged and 1-propanol (15 mL) and conc. H$_2$SO$_4$ (70 μL, 1.3 mmol) in a 20 mL-microwave vial was stirred at room temperature and then heated in a microwave at 80° C. for 2 h and stirred at room temperature overnight. When the desired product was identified by TLC (EtOAc/hexanes; 3:7) the mixture was concentrated under vacuum (40° C.) and diluted with EtOAc (80 mL) and H$_2$O (30 mL). The organic layer was washed with H$_2$O (twice), and brine, then dried (Na$_2$SO$_4$), filtered, and concentrated to give the product (57a) (1.18 g, 76%) as an oil. The material was used next step directly without purification. $^1$H-NMR (300 MHz, CDCl$_3$): δ 4.07 (t, J=6.6 Hz, 2H), 3.55 (s, 2H), 2.42 (br. s, 1H), 1.70-1.61 (m, 2H), 1.19 (s, 6H), 0.95 (t, J=7.5 Hz, 3H).

Step 2: Synthesis of propyl 3-((chlorosulfonyl)oxy)-2,2-dimethylpropanoate (57)

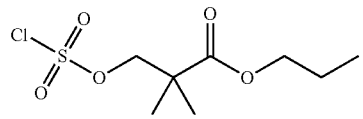

A solution of freshly distilled sulfuryl chloride (194 μL, 2.7 mmol) in Et$_2$O (1.0 mL) was cooled to −78° C. under an atmosphere of argon. A solution of propyl 3-hydroxy-2,2-dimethylpropanoate (57a) (0.42 g, 2.6 mmol) and pyridine (215 μL, 2.7 mmol) in Et$_2$O was added dropwise to the sulfuryl chloride solution over the course of 5 min. The flask was rinsed with Et$_2$O (3×1 mL), and the rinse was added to the reaction mixture. The mixture was stirred at −78° C. for 5 min and then allowed to warm to room temperature and stirred for 1 h. The mixture was filtered and the filtrate was concentrated under vacuum to afford the title compound (57) (0.56 g, 83%) as an oil, which was used immediately in the next step without further purification. $^1$H-NMR (300 MHz, CDCl$_3$): δ 4.50 (s, 2H), 4.10 (t, J=6.6 Hz, 2H), 1.72-1.64 (m, 2H), 1.32 (s, 6H), 0.95 (t, J=7.2 Hz, 3H).

Example 58

Synthesis of butyl 3-((chlorosulfonyl)oxy)-2,2-dimethylpropanoate (58)

Step 1: Synthesis of butyl 3-hydroxy-2,2-dimethylpropanoate (58a)

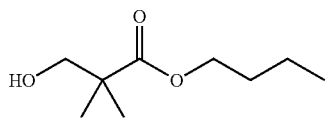

A mixture of 3-hydroxy-2,2-dimethylpropanoic acid (1.15 g, 9.7 mmol) was charged and 1-butanol (15 mL) and conc. H$_2$SO$_4$ (70 μL, 1.3 mmol) in a 20 mL-microwave vial was stirred at room temperature then heated in a microwave at 80° C. for 2 h, then stirred at room temperature overnight. When the desired product was identified by TLC (EtOAc/hexanes; 3:7) the mixture was concentrated under vacuum (40° C.; co-evaporated with toluene×3) and diluted with EtOAc (80 mL) and H$_2$O (30 mL). The organic layer was washed with H$_2$O (twice), and brine, then dried (Na$_2$SO$_4$), filtered and concentrated to give the product (58a) (1.24 g, 81%) as an oil. The material was used next step directly without purification. $^1$H-NMR (300 MHz, CDCl$_3$): δ 4.11 (t, J=6.5 Hz, 2H), 3.55 (s, 2H), 2.42 (br. s, 1H), 1.65-1.58 (m, 2H), 1.43-1.35 (m, 2H), 1.19 (s, 6H), 0.94 (t, J=7.5 Hz, 3H).

Step 2: Synthesis of butyl 3-((chlorosulfonyl)oxy)-2,2-dimethylpropanoate (58)

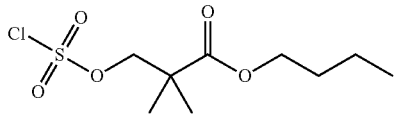 [SMILES: CCCCOC(=O)C(C)(C)COS(=O)(=O)Cl]

A solution of freshly distilled sulfuryl chloride (198 µL, 2.7 mmol) in Et$_2$O (1.0 mL) was cooled to −78° C. under an atmosphere of argon. A solution of propyl 3-hydroxy-2,2-dimethylpropanoate (58a) (0.47 g, 2.7 mmol) and pyridine (219 µL, 2.7 mmol) in Et$_2$O was added dropwise to the sulfuryl chloride solution over the course of 5 min. The flask was rinsed with Et$_2$O (3×1 mL), which was added to the reaction mixture. The mixture was stirred at −78° C. for 5 min and then allowed to warm to room temperature and stirred for 1 h. The mixture was filtered, and the filtrate was concentrated under vacuum to afford the title compound (58) (0.52 g, 72%) as an oil, which was used immediately in the next step without further purification. $^1$H-NMR (300 MHz, CDCl$_3$): δ 4.50 (s, 2H), 4.14 (t, J=6.8 Hz, 2H), 1.66-1.59 (m, 2H), 1.43-1.35 (m, 2H), 1.32 (s, 6H), 0.94 (t, J=7.4 Hz, 3H).

Example 59

Synthesis of 4-((chlorosulfonyl)oxy)-3,3-dimethylbutyl pivalate (59)

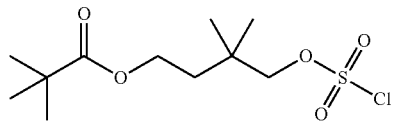 [SMILES: CC(C)(CCOC(=O)C(C)(C)C)COS(=O)(=O)Cl]

Step 1: Synthesis of 4-hydroxy-3,3-dimethylbutyl pivalate (59a)

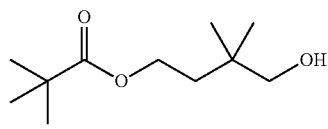

To a stirred solution of 2,2-dimethylbutane-1,4-diol (0.86 g, 7.3 mmol) in DCM (9 mL) at ca. 0° C. (ice bath) under an argon atmosphere, was added trimethylacetyl chloride (0.89 mL, 7.3 mmol), Et$_3$N (1.17 mL, 14.5 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$ and brine, then dried (Na$_2$SO$_4$), and concentrated under vacuum. The residue was purified by column chromatography on silica gel using EtOAc/hexanes (0:1 to 3:7) as eluent to give the desired product (59a) (0.42 g, 28%). $^1$H-NMR (300 MHz, CDCl$_3$): δ 4.13 (t, J=7.1 Hz, 2H), 3.35 (s, 2H), 1.61 (q, J=6.9 Hz, 2H), 1.19 (s, 9H), 0.93 (s, 6H).

Step 2: Synthesis of 4-((chlorosulfonyl)oxy)-3,3-dimethylbutyl pivalate (59)

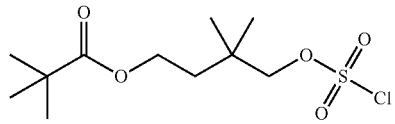 [SMILES: CC(C)(CCOC(=O)C(C)(C)C)COS(=O)(=O)Cl]

A solution of freshly distilled sulfuryl chloride (153 µL, 2.1 mmol) in Et$_2$O (4.5 mL) was cooled to −78° C. under an argon atmosphere. A solution of 4-hydroxy-3,3-dimethylbutyl pivalate (59a) (0.42 g, 2.1 mmol) and pyridine (203 µL, 2.5 mmol) in Et$_2$O (3 mL) was added dropwise to the sulfuryl chloride solution over the course of 60 min. The mixture was allowed to warm to room temperature and stirred for 30 min. The mixture was filtered, and the filtrate was concentrated under vacuum to afford the title compound (59) as an oil, which was used immediately in the next step without further purification. $^1$H-NMR (300 MHz, CDCl$_3$): δ 4.23 (s, 2H), 4.13 (t, J=6.8 Hz, 2H), 1.71 (t, J=6.6 Hz, 2H), 1.19 (s, 9H), 1.08 (s, 6H).

Example 60

Synthesis of ethyl 2-(((chlorosulfonyl)oxy)methyl)-2-ethylbutanoate (60)

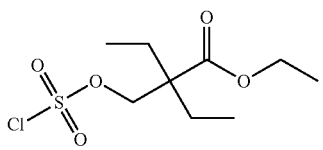 [SMILES: CCOC(=O)C(CC)(CC)COS(=O)(=O)Cl]

A solution of freshly distilled sulfuryl chloride (126 µL, 1.7 mmol) in Et$_2$O (3.2 mL) was cooled to −78° C. under an argon atmosphere. A solution of ethyl 2-ethyl-2-(hydroxymethyl)butanoate (ex-enamine) (0.30 g, 1.7 mmol) and pyridine (153 µL, 1.9 mmol) in Et$_2$O (2.1 mL) was added dropwise to the sulfuryl chloride solution over the course of 60 min. The mixture was allowed to warm to room temperature and stirred for 30 min. The mixture was re-cooled to −78° C. and sulfuryl chloride (20 µL) was added, and the reaction allowed to warm to room temperature and stirred for a further 30 min. Et$_2$O (5 mL) was added and the mixture stirred for 5 min, then filtered, and the filtrate was concentrated under vacuum to afford the title compound (60), which was used immediately in the next step without further purification. $^1$H-NMR (300 MHz, CDCl$_3$): δ 4.62 (s, 2H), 4.21 (q, J=7.3 Hz, 2H), 1.78-1.58 (m, 4H), 1.28 (t, J=7.1 Hz, 3H), 0.88 (t, J=7.7 Hz, 6H).

Example 61

Synthesis of 4-((chlorosulfonyl)oxy)-3,3-dimethylbutyl 2,6-dimethylbenzoate (61)

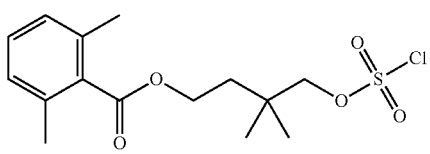 [SMILES: Cc1cccc(C)c1C(=O)OCCC(C)(C)COS(=O)(=O)Cl]

Step 1: Synthesis of 4-hydroxy-3,3-dimethylbutyl 2,6-dimethylbenzoate (61a)

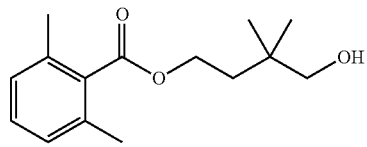 [SMILES: Cc1cccc(C)c1C(=O)OCCC(C)(C)CO]

To a stirred solution of 2,2-dimethylbutane-1,4-diol (0.84 g, 7.1 mmol) in DCM (9 mL) at ca. 0° C. (ice bath) under an argon atmosphere, was added 2,6-dimethylbenzoyl chloride (1.0 g, 5.9 mmol), pyridine (0.96 mL, 11.9 mmol), and N,N-4-dimethylaminopyridine (catalytic amount). The reaction mixture was allowed to gradually warm to room temperature and the mixture was stirred overnight. The mixture was quenched by the addition of 1N HCl (50 mL). The organic and aqueous layers were partitioned and the aqueous layer was extracted with DCM (twice). The combined organic layers were washed with saturated NaHCO$_3$, and then dried (Na$_2$SO$_4$), and concentrated under vacuum. The residue was purified by column chromatography on silica gel using EtOAc/hexanes (0:1 to 3:7) as eluent to give the desired product (61a) (0.42 g, 28%). $^1$H-NMR (300 MHz, CDCl$_3$): δ 7.18 (t, J=7.6 Hz, 1H), 7.04-7.01 (m, 2H), 4.41 (t, J=7.6 Hz, 2H), 3.37 (s, 2H), 2.31 (s, 6H), 1.76 (t, J=7.5 Hz, 2H), 0.97 (s, 6H).

Step 2: Synthesis of 4-((chlorosulfonyl)oxy)-3,3-dimethylbutyl 2,6-dimethylbenzoate (61)

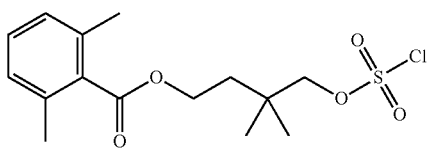 [SMILES: Cc1cccc(C)c1C(=O)OCCC(C)(C)COS(=O)(=O)Cl]

A solution of freshly distilled sulfuryl chloride (122 μL, 1.7 mmol) in Et$_2$O (1.0 mL) was cooled to −78° C. under an atmosphere of argon. A solution of 4-hydroxy-3,3-dimethylbutyl 2,6-dimethylbenzoate (61a) (0.42 g, 1.7 mmol) and pyridine (136 μL, 1.7 mmol) in Et$_2$O (1.5 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (61) as an oil, which was used immediately in the next step without further purification (not pure). $^1$H-NMR (300 MHz, CDCl$_3$): δ 7.19 (t, J=7.7 Hz, 1H), 7.03 (d, J=7.5 Hz, 2H), 4.41 (t, J=7.4 Hz, 2H), 4.23 (s, 2H), 2.31 (s, 6H), 1.84 (t, J=6.9 Hz, 2H), 1.11 (s, 6H).

Example 62

Synthesis of 4-((chlorosulfonyl)oxy)-3,3-dimethylbutyl adamantane-1-carboxylate (62)

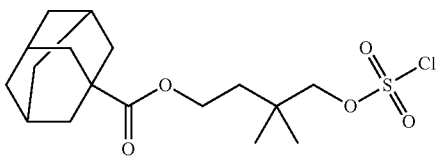 [SMILES: CC(C)(CCOC(=O)C12CC3CC(CC(C3)C1)C2)COS(=O)(=O)Cl]

Step 1: Synthesis of 4-hydroxy-3,3-dimethylbutyl adamantane-1-carboxylate (62a)

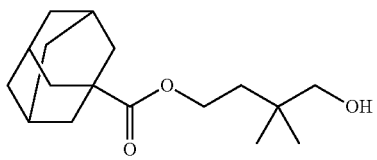 [SMILES: CC(C)(CO)CCOC(=O)C12CC3CC(CC(C3)C1)C2]

To a stirred solution of 2,2-dimethylbutane-1,4-diol (0.72 g, 6.1 mmol) in DCM (20 mL) at ca. 0° C. (ice bath) under an atmosphere of argon, was added 1-adamantane-carbonyl chloride (1.1 g, 10.1 mmol), pyridine (0.82 mL, 10.1 mmol), and N,N-4-dimethylaminopyridine (0.03 g, 0.3 mmol). The reaction mixture was allowed to gradually warm to room temperature and the mixture was stirred overnight. The mixture was quenched by the addition of 1N HCl. The organic and aqueous layers were partitioned, and the aqueous layer was extracted with DCM (twice). The combined organic layers were washed with saturated NaHCO$_3$ and brine, and then dried (MgSO$_4$), and concentrated under vacuum. The residue was purified by column chromatography on silica gel using EtOAc/hexanes (0:1 to 1:1) as eluent to give the desired product (62a) (0.49 g, 35%). $^1$H-NMR (300 MHz, CDCl$_3$): δ 4.14-4.09 (m, 2H), 3.34 (s, 2H), 2.00 (m, 3H), 1.90-1.86 (m, 6H), 1.75-1.59 (m, 6H), 1.59 (t, J=7.1 Hz, 2H), 0.92 (s, 6H).

Step 2: Synthesis of 4-((chlorosulfonyl)oxy)-3,3-dimethylbutyl adamantane-1-carboxylate (62)

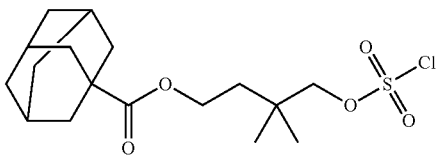 [SMILES: CC(C)(CCOC(=O)C12CC3CC(CC(C3)C1)C2)COS(=O)(=O)Cl]

A solution of freshly distilled sulfuryl chloride (127 μL, 1.7 mmol) in Et$_2$O (1.2 mL) was cooled to −78° C. under an atmosphere of argon. A solution of 4-hydroxy-3,3-dimethylbutyl adamantane-1-carboxylate (62a) (0.48 g, 1.7 mmol) and pyridine (141 μL, 1.7 mmol) in Et$_2$O (1.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (62) as an oil, which was used immediately in the next step without further purification (not pure). $^1$H-NMR (300 MHz, CDCl$_3$): δ 4.25 (s, 2H), 4.13 (t, J=6.8 Hz, 2H), 2.01 (m, 3H), 1.90-1.85 (m, 6H), 1.73-1.69 (m, 8H), 1.08 (s, 6H).

Example 63

Synthesis of 4-((chlorosulfonyl)oxy)-3,3-dimethylbutyl 2,6-dimethoxybenzoate (63)

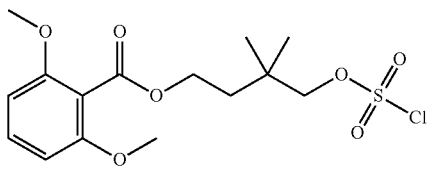 [SMILES: COc1cccc(OC)c1C(=O)OCCC(C)(C)COS(=O)(=O)Cl]

Step 1: Synthesis of 4-hydroxy-3,3-dimethylbutyl 2,6-dimethoxybenzoate (63a)

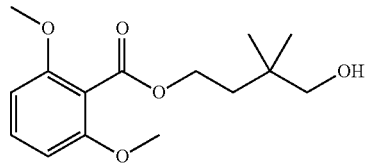 [SMILES: COc1cccc(OC)c1C(=O)OCCC(C)(C)CO]

To a stirred solution of 2,2-dimethylbutane-1,4-diol (1.85 g, 15.7 mmol) in DCM (28 mL) at ca. 0° C. (ice bath) under an atmosphere of argon, was added 2,6-dimethoxybenzoyl chloride (80%; 3.93 g, 15.7 mmol), Et$_3$N (2.5 mL, 31.3 mmol), and N,N-4-dimethylaminopyridine (catalytic amount). The reaction mixture was allowed to gradually warm to room temperature and the mixture was stirred overnight. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 2:3) as eluent to give the desired product (63a) (ca. 80% purity; 0.92 g). $^1$H-NMR (300 MHz, CDCl$_3$): δ 7.29-7.26 (m, 1H), 6.57-6.53 (m, 3H), 4.43-4.39 (m, 2H), 3.83 (s, 6H), 3.36 (s, 2H), 1.74 (t, J=6.5 Hz, 2H), 0.95 (s, 6H).

Step 2: Synthesis of 4-((chlorosulfonyl)oxy)-3,3-dimethylbutyl 2,6-dimethoxybenzoate (63)

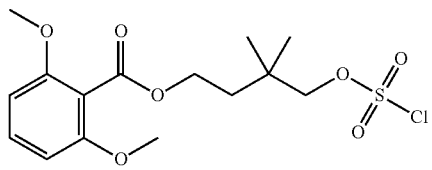 [SMILES: COc1cccc(OC)c1C(=O)OCCC(C)(C)COS(=O)(=O)Cl]

A solution of freshly distilled sulfuryl chloride (0.2 mL, 2.7 mmol) in Et$_2$O (1.9 mL) was cooled to −78° C. under an argon atmosphere. A solution of 4-hydroxy-3,3-dimethylbutyl 2,6-dimethoxybenzoate (63a) (ca. 80% purity; 0.97 g, 2.7 mmol) and pyridine (222 μL, 2.7 mmol) in Et$_2$O (2.7 mL) was added dropwise to the sulfuryl chloride solution over the course of 15 min. The flask was rinsed with Et$_2$O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (63) as an oil, which was used immediately in the next step without further purification (not pure).

Example 64

Synthesis of 5-((chlorosulfonyl)oxy)-4,4-dimethylpentyl benzoate (64)

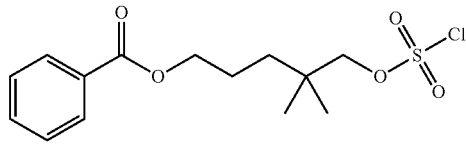 [SMILES: CC(C)(CCCOC(=O)c1ccccc1)COS(=O)(=O)Cl]

Step 1: Synthesis of 5-hydroxy-4,4-dimethylpentyl benzoate (64a)

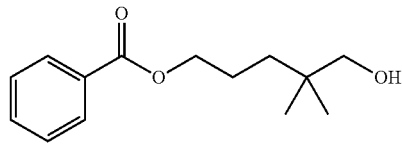 [SMILES: CC(C)(CO)CCCOC(=O)c1ccccc1]

To a stirred solution of 2,2-dimethylpentane-1,5-diol (*J. Org. Chem.* 2010, 75, 1892-1897; PCT International Publication No. WO 2002092606) (1.55 g, 11.7 mmol) in DCM (20 mL) at ca. 0° C. (ice bath) under an argon atmosphere, was added benzoyl chloride (1.5 mL, 12.9 mmol). The reaction mixture was stirred at room temperature for 2.5 h and concentrated under vacuum. EtOAc was added to the residue and the mixture was stirred. The filtrate was concentrated under the residue purified by column chromatography on silica gel using EtOAc/hexanes (0:1 to 1:4) as eluent to give the product (64a) (1.38 g, 50%) as an oil.

¹H-NMR (300 MHz, CDCl₃): δ 8.04 (d, J=6.9 Hz, 2H), 7.56 (t, J=7.5 Hz, 1H), 7.44 (t, J=7.5 Hz, 2H), 4.31 (t, J=6.8 Hz, 2H), 3.36 (s, 2H), 1.81-1.71 (m, 2H), 1.42-1.36 (m, 2H), 0.92 (s, 6H).

Step 2: Synthesis of
5-((chlorosulfonyl)oxy)-4,4-dimethylpentyl benzoate (64)

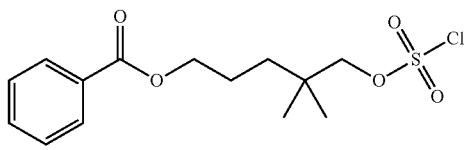 [SMILES: CC(C)(CCCOC(=O)c1ccccc1)COS(=O)(=O)Cl]

A solution of freshly distilled sulfuryl chloride (0.2 mL, 2.7 mmol) in Et₂O (1.9 mL) was cooled to −78° C. under an argon atmosphere. A solution of 4-hydroxy-3,3-dimethylpentyl benzoate (64a) (0.76 g, 3.2 mmol) and pyridine (218 µL, 2.7 mmol) in Et₂O (2.7 mL) was added dropwise to the sulfuryl chloride solution over the course of 15 min. The flask was rinsed with Et₂O (2×20 mL), and the rinse was added to the reaction mixture. The mixture was stirred at −78° C. for 10 min then allowed to warm to room temperature and stirred for 1 h. The mixture was filtered, and the filtrate was concentrated under vacuum to afford the title compound (64) as an oil, which was used immediately in the next step without further purification (not pure). ¹H-NMR (300 MHz, CDCl₃): δ 8.04 (d, J=7.5 Hz, 2H), 7.57-7.55 (m, 1H), 7.48-7.33 (m, 1H), 4.35-4.29 (m, 2H), 4.23 (s, 2H), 1.81-1.74 (m, 2H), 1.53-1.21 (m, 2H), 1.06 (s, 6H).

Example 65

Synthesis of
5-((chlorosulfonyl)oxy)-4,4-dimethylpentyl 2,6-dimethoxybenzoate (65)

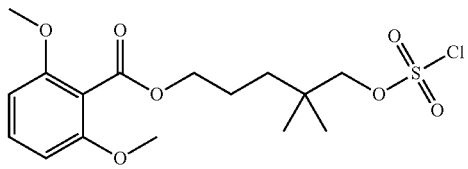 [SMILES: COc1cccc(OC)c1C(=O)OCCCC(C)(C)COS(=O)(=O)Cl]

Step 1: Synthesis of 5-hydroxy-4,4-dimethylpentyl 2,6-dimethoxybenzoate (65a)

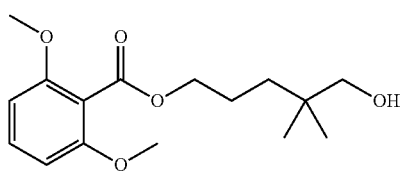 [SMILES: COc1cccc(OC)c1C(=O)OCCCC(C)(C)CO]

To a stirred solution of 2,2-dimethylpentane-1,5-diol (1.5 g, 11.3 mmol) in pyridine (8.3 mL) at 0° C. under an argon atmosphere was added 2,6-dimethoxybenzoyl chloride (80%; 1.4 g, 5.6 mmol) in one portion. The reaction mixture was allowed to warm to room temperature and for 3 h. The reaction mixture was concentrated to dryness and EtOAc was added. The mixture was filtered and the filtrate was concentrated under vacuum. The residue was purified by column chromatography on silica gel using EtOAc/hexanes (0:1 to 3:7) as eluent to give the product (65a) (0.65 g, 39%) as an oil. ¹H-NMR (300 MHz, CDCl₃): δ 7.31-7.26 (m, 2H), 6.55 (d, J=8.1 Hz, 2H), 4.33 (t, J=6.2 Hz, 2H), 3.82 (s, 6H), 3.33 (s, 2H), 1.77-1.67 (m, 2H), 1.41-1.35 (m, 2H), 0.92 (s, 6H).

Step 2: Synthesis of
5-((chlorosulfonyl)oxy)-4,4-dimethylpentyl 2,6-dimethoxybenzoate (65)

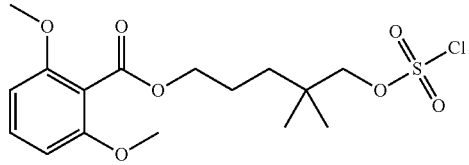 [SMILES: COc1cccc(OC)c1C(=O)OCCCC(C)(C)COS(=O)(=O)Cl]

A solution of freshly distilled sulfuryl chloride (0.16 mL, 2.2 mmol) in Et₂O was cooled to −78° C. under an atmosphere of argon. A solution of 5-hydroxy-4,4-dimethylpentyl 2,6-dimethoxybenzoate (65a) (0.65 g, 2.2 mmol) and pyridine (177 µL, 2.2 mmol) in Et₂O was added dropwise to the sulfuryl chloride solution over the course of 15 min. The flask was rinsed with Et₂O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (65) as an oil, which was used immediately in the next step without further purification (not pure). ¹H-NMR (300 MHz, CDCl₃): δ 7.32-7.26 (m, 1H), 6.56 (d, J=8.7 Hz, 2H), 4.34 (t, J=6.2 Hz, 2H), 4.21 (s, 2H), 3.81 (s, 6H), 1.77-1.71 (m, 2H), 1.52-1.46 (m, 2H), 1.03 (s, 6H).

Example 66

Synthesis of
5-((chlorosulfonyl)oxy)-4,4-dimethylpentyl 2,6-dimethylbenzoate (66)

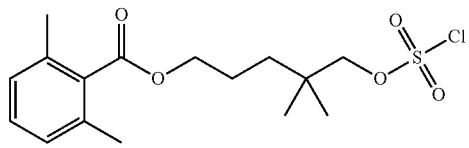 [SMILES: Cc1cccc(C)c1C(=O)OCCCC(C)(C)COS(=O)(=O)Cl]

Step 1: Synthesis of 5-hydroxy-3,3-dimethylpentyl 2,6-dimethylbenzoate (66a)

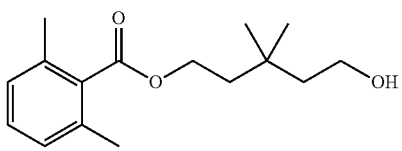 [SMILES: Cc1cccc(C)c1C(=O)OCCC(C)(C)CCO]

To a stirred solution of 2,2-dimethylpentane-1,5-diol (1.1 g, 8.3 mmol) in pyridine (8.3 mL) at 0° C. under an argon atmosphere was added 2,6-dimethylbenzoyl chloride in one portion. The reaction mixture was allowed to warm to room temperature for 3 h. The reaction was concentrated to dryness and EtOAc was added. The mixture was filtered and the filtrate was concentrated under vacuum. The residue was purified by column chromatography on silica gel using EtOAc/hexanes (0:1 to 1:4) as eluent to give the product (66a) (0.44 g, 25%) as an oil. ¹H-NMR (300 MHz, CDCl₃): δ 7.18 (t, J=7.7 Hz, 1H), 7.03 (d, J=7.5 Hz, 2H), 4.32 (t, J=6.3 Hz, 2H), 3.34 (s, 2H), 2.32 (s, 6H), 1.78-1.68 (m, 2H), 1.40-1.34 (m, 2H), 0.90 (s, 6H).

Step 2: Synthesis of 5-((chlorosulfonyl)oxy)-4,4-dimethylpentyl 2,6-dimethylbenzoate (66)

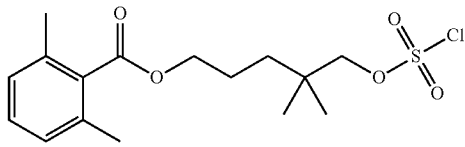 [SMILES: Cc1cccc(C)c1C(=O)OCCCC(C)(C)COS(=O)(=O)Cl]

A solution of freshly distilled sulfuryl chloride (122 µL, 1.7 mmol) in Et₂O was cooled to −78° C. under an atmosphere of argon. A solution of 5-hydroxy-4,4-dimethylpentyl 2,6-dimethylbenzoate (66a) (0.44 g, 1.7 mmol) and pyridine (135 µL, 1.7 mmol) in Et₂O was added dropwise to the sulfuryl chloride solution over the course of 15 min. The flask was rinsed with Et₂O (2×20 mL), and the rinse was added to the reaction mixture. The mixture was stirred at −78° C. for 10 min and then allowed to warm to room temperature and stirred for 1 h. The mixture was filtered, and the filtrate was concentrated under vacuum to afford the title compound (66), which was used immediately in the next step without further purification. ¹H-NMR (300 MHz, CDCl₃): δ 7.19 (t, J=7.5 Hz, 1H), 7.03 (d, J=7.5 Hz, 2H), 4.33 (t, J=6.2 Hz, 2H), 4.20 (s, 2H), 2.32 (s, 6H), 1.81-1.71 (m, 2H), 1.51-1.45 (m, 2H), 1.04 (s, 6H).

Example 67

Synthesis of 4-((chlorosulfonyl)oxy)-3,3-dimethylbutyl 2-methylbenzoate (67)

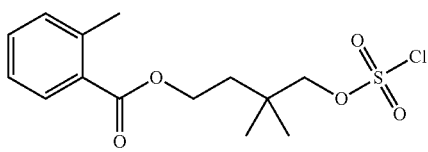 [SMILES: Cc1ccccc1C(=O)OCCC(C)(C)COS(=O)(=O)Cl]

Step 1: Synthesis of 4-hydroxy-3,3-dimethylbutyl 2-methylbenzoate (67a)

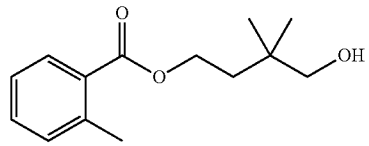 [SMILES: Cc1ccccc1C(=O)OCCC(C)(C)CO]

To a stirred solution of 2,2-dimethylbutane-1,4-diol (0.80 g, 6.8 mmol) in pyridine (5 mL) at ca. 0° C. (ice bath) under an argon atmosphere, was added toluoyl chloride (0.89 mL, 6.8 mmol) dropwise. The reaction mixture was allowed to gradually warm to room temperature and the mixture was stirred for 4 h. The mixture was concentrated under vacuum and suspended in EtOAc, and then filtered and the filter cake washed with EtOAc. The filtrate was concentrated under vacuum and the residue purified by column chromatography on silica gel using EtOAc/hexanes (0:1 to 3:7) as eluent to give the desired product (67a) (0.7 g, 44%). ¹H-NMR (300 MHz, CDCl₃): δ 7.88 (d, J=8.4 Hz, 1H), 7.40 (t, J=7.1 Hz, 1H), 7.26-7.24 (m, 2H), 4.38 (t, J=7.3 Hz, 2H), 3.41 (s, 3H), 2.60 (s, 3H), 1.78 (t, J=7.5 Hz, 2H), 0.98 (s, 6H).

Step 2: Synthesis of 4-((chlorosulfonyl)oxy)-3,3-dimethylbutyl 2-methylbenzoate (67)

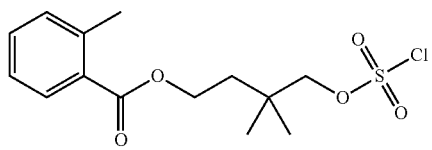 [SMILES: Cc1ccccc1C(=O)OCCC(C)(C)COS(=O)(=O)Cl]

A solution of freshly distilled sulfuryl chloride (96 µL, 1.3 mmol) in Et₂O (0.8 mL) was cooled to −78° C. under an atmosphere of argon. A solution of 4-hydroxy-3,3-dimethylbutyl 2-methylbenzoate (67a) (0.31 g, 1.3 mmol) and pyridine (106 µL, 1.3 mmol) in Et₂O (1.1 mL) was added dropwise to the sulfuryl chloride solution over the course of 15 min. The flask was rinsed with Et₂O (2×20 mL), which was added to the reaction mixture. The mixture was stirred at −78° C. for 10 min then allowed to warm to room temperature and stirred for 30 min. The mixture was filtered, and the product (67) was used immediately in the next step without further purification. ¹H-NMR (300 MHz, CDCl₃): δ 7.89 (d, J=8.1 Hz, 1H), 7.41-7.39 (m, 1H), 7.26-7.25 (m, 2H), 4.41-4.35 (m, 2H), 4.28 (s, 2H), 2.61 (s, 3H), 1.87 (t, J=7.2 Hz, 2H), 1.13 (s, 6H).

Example 68

Synthesis of 4-((chlorosulfonyl)oxy)-2,2,3,3-tetramethylbutyl 3-chloro-2,6-dimethoxybenzoate (68)

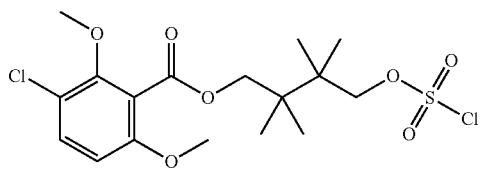 [SMILES: COc1ccc(Cl)c(OC)c1C(=O)OCC(C)(C)C(C)(C)COS(=O)(=O)Cl]

Step 1: Synthesis of 4-hydroxy-2,2,3,3-tetramethylbutyl 2,6-dimethoxybenzoate (68a)

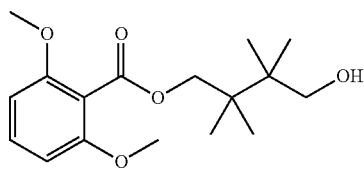 [SMILES: COc1cccc(OC)c1C(=O)OCC(C)(C)C(C)(C)CO]

To a stirred solution of 2,2,3,3-tetramethylbutane-1,4-diol (45a) (0.7 g, 4.8 mmol) in DCM (20 mL) at 0° C. under an atmosphere of argon was added 2,6-dimethoxybenzoyl chloride (80%; 0.55 g, 2.2 mmol), pyridine (0.36 mL, 4.4 mmol) and N,N-4-dimethylaminopyridine (0.05 g, 0.4 mmol). The mixture was allowed to warm to room temperature and stirred at room temperature overnight. The mixture was cooled to 0° C. and the reaction was quenched by the addition of 1N HCl (15 mL), and then extracted with DCM (twice). The combined organic layers were washed with sat. sodium bicarbonate and brine, then dried ($Na_2SO_4$), and concentrated under vacuum. The residue was purified by column chromatography on silica gel using EtOAc/hexanes (0:1 to 3:2) as eluent to give the product (68a) as an oil.
$^1$H-NMR (300 MHz, $CDCl_3$): δ 7.29 (t, J=8.4 Hz, 1H), 6.56 (d, J=8.1 Hz, 2H), 4.24 (s, 2H), 3.81 (s, 6H), 3.49 (s, 2H), 0.98 (s, 6H), 0.92 (s, 6H).

Step 2: Synthesis of 4-((chlorosulfonyl)oxy)-2,2,3,3-tetramethylbutyl 3-chloro-2,6-dimethoxybenzoate (68)

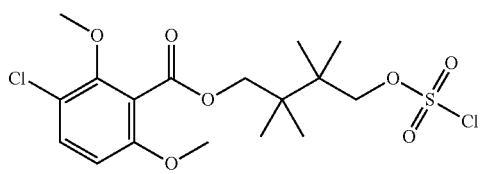 [SMILES: COc1ccc(Cl)c(OC)c1C(=O)OCC(C)(C)C(C)(C)COS(=O)(=O)Cl]

Pyridine (0.15 mL, 1.8 mmol) was added to a stirred mixture of 4-hydroxy-2,2,3,3-tetramethylbutyl propionate (68a) (0.30 g, 1.5 mmol) and $Et_2O$ (10 mL) under an atmosphere of argon. The solution was cooled to −78° C. and sulfuryl chloride (0.15 mL, 1.8 mmol) in $Et_2O$ (3 mL) was slowly added at −78° C. The mixture was stirred at −78° C. for 1 h and then warmed to room temperature, and stirred for 1 h. The reaction mixture was filtered to remove the pyridine salt, and the filtrate was concentrated under vacuum to give the title compound (68) as an oil, that was used directly in the next step without further purification (yield assumed quantitative).

Example 69

Synthesis of 2-(((chlorosulfonyl)oxy)methyl)-2-methylpropane-1,3-diyl dibenzoate (69)

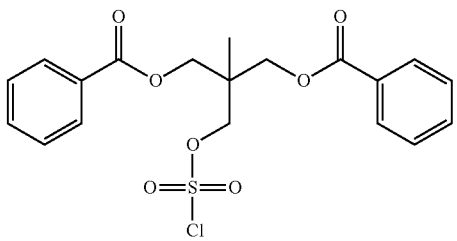 [SMILES: CC(COC(=O)c1ccccc1)(COC(=O)c1ccccc1)COS(=O)(=O)Cl]

Step 1: Synthesis of 2-(hydroxymethyl)-2-methylpropane-1,3-diyl dibenzoate (69a)

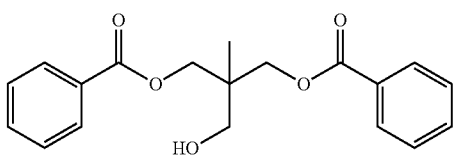 [SMILES: CC(CO)(COC(=O)c1ccccc1)COC(=O)c1ccccc1]

Benzoyl chloride (2.46 mL, 20.0 mmol) was added dropwise to a mixture of 2-(hydroxymethyl)-2-methylpropane-1,3-diol (1.2 g, 10.0 mmol), pyridine (2.02 mL, 25.0 mmol), and N,N-4-dimethylaminopyridine (0.06 g, 0.4 mmol) in DCM (30 mL) at room temperature. After stirring at room temperature overnight, the organic phase was washed with 1 M HCl, water, and brine, dried ($MgSO_4$), and concentrated under vacuum. The residue was purified by column chromatography on silica gel using EtOAc/hexanes (0:1 to 2:3) as eluent to give the product (69a) (1.3 g, 40%) as an oil.
$^1$H-NMR (300 MHz, $CDCl_3$): δ 8.06-8.02 (m, 4H), 7.62-7.56 (m, 2H), 7.49-7.42 (m, 4H), 4.39 (s, 2H), 4.38 (s, 2H), 3.59 (s, 2H), 1.16 (s, 3H).

Step 2: Synthesis of 2-(((chlorosulfonyl)oxy)methyl)-2-methylpropane-1,3-diyl dibenzoate (69)

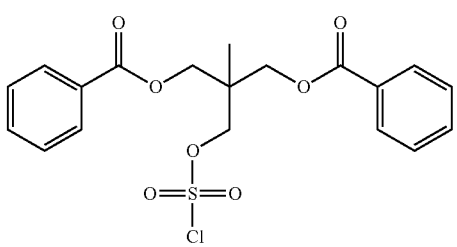 [SMILES: CC(COC(=O)c1ccccc1)(COC(=O)c1ccccc1)COS(=O)(=O)Cl]

A solution of freshly distilled sulfuryl chloride (0.3 mL, 3.7 mmol) in Et₂O (5 mL) was cooled to −78° C. under an atmosphere of argon. A solution of 2-(hydroxymethyl)-2-methylpropane-1,3-diyl dibenzoate (69a) (800 mg, 2.4 mmol) and pyridine (0.32 mL, 3.9 mmol) in Et₂O (5 mL) was added dropwise to the sulfuryl chloride solution over the course of 5 min. The flask was rinsed with Et₂O (3 mL), which was also added to the mixture. The mixture was stirred at −78° C. for 1 h, and then allowed to warm to room temperature. The precipitate was filtered (quickly) and the filter cake rinsed with Et₂O (12 mL). The filtrate was concentrated under vacuum at room temperature to afford the title compound (69) as an oil which was used immediately in the next step without further purification.

Example 70

Synthesis of 2-(((chlorosulfonyl)oxy)methyl)-2-methylpropane-1,3-diyl diacetate (70)

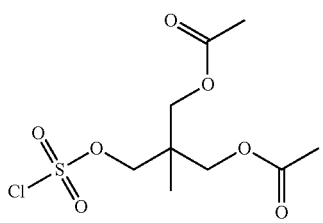 [SMILES: CC(=O)OCC(C)(COC(C)=O)COS(=O)(=O)Cl]

Step 1: Synthesis of 2-(hydroxymethyl)-2-methylpropane-1,3-diyl diacetate (70a)

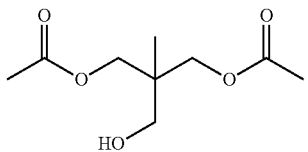

Acetic anhydride (3.46 mL, 36.6 mmol) was added dropwise to a mixture of 2-(hydroxymethyl)-2-methylpropane-1,3-diol (2.2 g, 18.0 mmol), pyridine (12 mL, 25.0 mmol), and N,N-4-dimethylaminopyridine (0.05 g) at room temperature. After stirring at room temperature overnight, the mixture was concentrated under vacuum. The mixture was suspended in EtOAc (100 mL), and H₂O (20 mL) was slowly added at 0° C. The aqueous and organic layers were partitioned, and the organic layer was washed with and brine, dried (Na₂SO₄), then concentrated under vacuum. The residue was purified by column chromatography on silica gel using EtOAc/hexanes (0:1 to 3:2) as eluent to give the product (70a) (1.0 g, 26%). ¹H-NMR (300 MHz, CDCl₃): δ 4.02 (s, 4H), 3.41 (s, 2H), 2.08 (s, 6H), 0.96 (s, 3H).

Step 2: Synthesis of 2-(((chlorosulfonyl)oxy)methyl)-2-methylpropane-1,3-diyl diacetate (70)

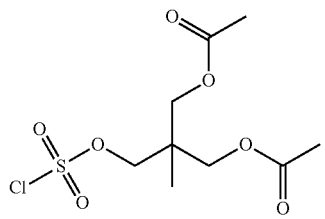 [SMILES: CC(=O)OCC(C)(COC(C)=O)COS(=O)(=O)Cl]

A solution of freshly distilled sulfuryl chloride (0.33 mL, 4.0 mmol) in Et₂O (4 mL) was cooled to −78° C. under an atmosphere of argon. A solution of 2-(hydroxymethyl)-2-methylpropane-1,3-diyl diacetate (70a) (550 mg, 2.7 mmol) and pyridine (0.35 mL, 4.3 mmol) in Et₂O (4 mL) was added dropwise to the sulfuryl chloride solution over the course of 5 min. The flask was rinsed with Et₂O (5 mL), which was also added to the mixture. The mixture was stirred at −78° C. for 1 h, then allowed to warm to room temperature. The precipitate was filtered (quickly) and the filter cake rinsed with Et₂O (12 mL). The filtrate was concentrated under vacuum at room temperature to afford the title compound (70) as an oil which was used immediately for the next step without further purification.

Example 71

Synthesis of 5-((chlorosulfonyl)oxy)-2,2,4,4-tetramethylpentyl 2,6-dimethoxybenzoate (71)

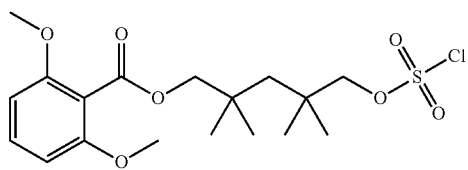 [SMILES: COc1cccc(OC)c1C(=O)OCC(C)(C)CC(C)(C)COS(=O)(=O)Cl]

Step 1: Synthesis of 5-hydroxy-2,2,4,4-tetramethylpentyl 2,6-dimethoxybenzoate (71a)

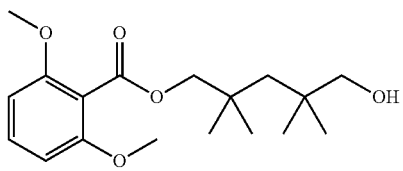 [SMILES: COc1cccc(OC)c1C(=O)OCC(C)(C)CC(C)(C)CO]

To a stirred solution of 2,2,4,4-tetramethylpentane-1,5-diol (39c) (0.64 g, 4.0 mmol) and pyridine (0.32 mL, 4.0 mmol) in DCM (27 mL) was added 2,6-dimethoxybenzoyl chloride (80%; 1.0 g, 4.0 mmol) in DCM (10 mL) dropwise over the course of 30 min at 0° C. (ice bath) under an atmosphere of argon. The reaction mixture was allowed to warm to room temperature and stirred overnight. The mixture was diluted with H₂O (30 mL), and the layers were separated. The aqueous layer was extracted with DCM (2×30 mL), and the combined organic layers were washed with brine (30 mL), dried (Na₂SO₄), and concentrated under vacuum. The residue was purified by column chromatography on silica gel using EtOAc/hexanes (0:1 to 2:98) as eluent to give the product (71a) (927 mg, 71%) as an oil. The compound was contaminated, presumably with the diacylated byproduct. The material was used in the next step without further purification.

Step 2: Synthesis of 5-((chlorosulfonyl)oxy)-2,2,4,4-tetramethylpentyl 2,6-dimethoxybenzoate (71)

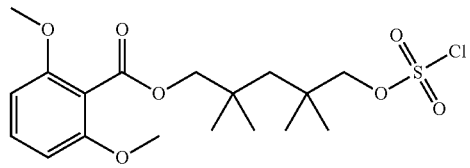 [SMILES: COc1cccc(OC)c1C(=O)OCC(C)(C)CC(C)(C)COS(=O)(=O)Cl]

A solution of sulfuryl chloride (0.21 mL, 2.8 mmol) in Et₂O (13 mL) was cooled to −78° C. under an argon atmosphere. A solution of 5-hydroxy-2,2,4,4-tetramethylpentyl 2,6-dimethoxybenzoate (71a) (921 mg, 2.8 mmol) and pyridine (0.23 mL, 2.8 mmol) in Et₂O (13 mL) was added dropwise to the sulfuryl chloride solution over the course of 10 min. The mixture was stirred at −78° C. for 5 h. The mixture was filtered and the filtrate stored to give a solution of the product (71) in Et₂O (ca. 20 mL). The yield was assumed to be quantitative. This mixture was used in the next step without further purification.

Example 72

Synthesis of R/S-ethyl 3-((chlorosulfonyl)oxy)-2,2-dimethylbutanoate (72)

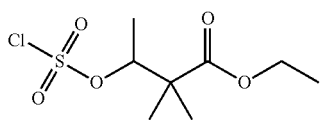

A solution of freshly distilled sulfuryl chloride (148 μL, 2.0 mmol) in Et₂O (0.2 mL) was cooled to −78° C. under an argon atmosphere. A solution of ethyl 3-hydroxy-2,2-dimethylbutanoate (prepared according to *J. Med. Chem.* 1987, 30, 366-374 and *Ad. Synth. Catal.* 2009, 351, 3128-3132) (324 mg, 2.0 mmol) and pyridine (164 μL, 2.0 mmol) in Et₂O (0.2 mL) was added dropwise to the sulfuryl chloride solution over the course of 15 min. The flask was rinsed with Et₂O (2×20 mL), which was added to the reaction mixture. The mixture was stirred at −78° C. for 30 min. The mixture was filtered and the product (72) was used directly in the next step with an assumed quantitative yield. ¹H-NMR (300 MHz, CDCl₃): δ 5.34-5.29 (m, 1H), 4.22-4.14 (m, 2H), 1.55-1.52 (m, 3H), 1.35-1.08 (m, 9H).

Example 74

Synthesis of (3,5,5-trimethyl-2-oxotetrahydrofuran-3-yl)methyl sulfochloridate (74)

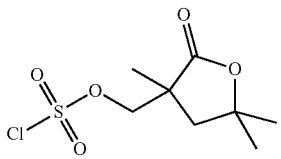

Step 1: Synthesis of 3,5,5-trimethyldihydrofuran-2(3H)-one (74a)

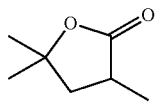

5,5-Dimethyldihydrofuran-2(3H)-one (4.7 g, 41.2 mmol) was dissolved in THF (94 mL) and the mixture was cooled to −78° C. under an atmosphere of argon. A solution of lithium diisopropylamide, 2.0 M solution in THF (22.6 mL, 45.2 mmol) was added dropwise over 10 min. The reaction was stirred at −78° C. for 2 h, and then neat MeI (2.6 mL, 41.6 mmol) was added to the reaction over 5 min. The reaction was stirred at −78° C. for 45 min, and then the mixture was allowed to warm to room temperature and stirred for 16 h. The reaction was quenched with saturated NH₄Cl (25 mL) and the mixture concentrated to remove THF. The aqueous residue was diluted with H₂O to dissolve solid and then extracted with ethyl acetate (3×40 mL). The combined organic layer was concentrated under vacuum, and the residue was purified by column chromatography on silica gel using EtOAc/hexanes (0:1 to 2:3) as eluent to provide a liquid which solidified on standing. This solid was purified further via Kugelrohr distillation to give the product (74a) (3.2 g) as an oil. ¹H-NMR (300 MHz, CDCl₃): δ 2.78-2.87 (m, 1H), 2.33 (dd, J=9.3, 12.3 Hz, 1H), 1.71 (t, J=12.3 Hz, 1H), 1.45 (s, 3H), 1.38 (s, 3H), 1.29 (d, J=6.9 Hz, 3H).

Step 2: Synthesis of 3-((benzyloxy)methyl)-3,5,5-trimethyldihydrofuran-2(3H)-one (74b)

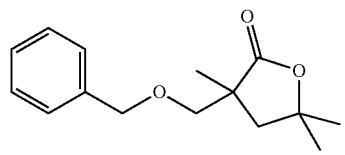 [SMILES: CC1(C)CC(C)(COCc2ccccc2)C(=O)O1]

3,5,5-Trimethyldihydrofuran-2(3H)-one (74a) (3.2 g, 25.0 mmol) was dissolved in THF (60 mL) and the mixture was cooled to −78° C. under an atmosphere of argon. A solution of lithium diisopropylamide, 2.0 M in THF (13.7 mL, 27.5 mmol) was added dropwise over 10 min. The mixture was stirred at −78° C. for 30 min, then neat benzyl chloromethyl ether (90%; 4.2 mL, 27.5 mmol) was added over 5 min. The mixture was allowed to warm to room temperature and was stirred for 16 h. Saturated NH$_4$Cl (10 mL) and H$_2$O (10 mL) was added and the solvent was removed under vacuum. The residue was extracted with EtOAc (2×75 mL) and the combined organic layers were washed with brine (2×75 mL), dried (Na$_2$SO$_4$), filtered and concentrated under vacuum (5.8 g). The residue was purified by column chromatography on silica gel using EtOAc/hexanes (0:1 to 2:3) as eluent to give the product (2.27 g) and impure fractions (1.35 g). The impure fractions were re-purified by column chromatography on silica gel using EtOAc/hexanes (0:1 to 1:4) as eluent to give additional pure product (74b) (1.39 g). The product (3.66 g) was an oil. $^1$H-NMR (300 MHz, CDCl$_3$): δ 7.28-7.34 (m, 5H), 4.62 (dd, J=11.7, 35.1 Hz, 2H), 3.61 (d, J=11.7 Hz, 1H), 3.32 (d, J=11.7 Hz, 1H), 2.48 (d, J=12.9 Hz, 1H), 1.89 (d, J=12.9 Hz, 1H), 1.45 (d, J=6.9 Hz, 6H), 1.26 (s, 3H).

Step 3: Synthesis of 3-(hydroxymethyl)-3,5,5-trimethyldihydrofuran-2(3H)-one (74c)

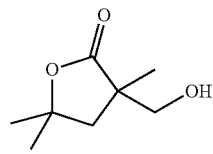

3-((Benzyloxy)methyl)-3,5,5-trimethyldihydrofuran-2(3H)-one (74b) (1.8 g, 7.2 mmol) was dissolved in 2-propanol (60 mL) and the solution was degassed with argon. Solid 10.0% palladium on carbon (0.31 g, 0.3 mmol) was added to the flask. The flask was sealed and vacuum degassed, and then back flushed with hydrogen (3 times). The reaction was stirred for 6 h. The suspension was filtered through Celite® and the filter cake washed with 2-propanol (15 mL). The filtrate was concentrated under vacuum to provide the product (74c) as a crude oil. $^1$H-NMR (300 MHz, CDCl$_3$): δ 3.75 (dd, J=6.9, 11.1 Hz, 1H), 3.51 (dd, J=5.7, 11.1 Hz, 1H), 2.33 (d, J=12.9 Hz, 1H), 2.23 (t, J=6 Hz, 1H), 1.94 (d, J=12.9 Hz, 1H), 1.48 (d, J=6.9 Hz, 6H), 1.32 (s, 3H).

Step 4: Synthesis of (3,5,5-trimethyl-2-oxotetrahydrofuran-3-yl)methyl sulfochloridate (74)

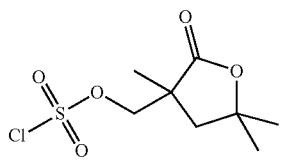

A solution of 3-(hydroxymethyl)-3,5,5-trimethyldihydrofuran-2(3H)-one (74c) (0.50 g, 3.2 mmol) and pyridine (0.28 mL, 3.5 mmol) in Et$_2$O (10 mL) was cooled to −78° C. under an atmosphere of argon. Neat sulfuryl chloride (0.28 mL, 3.5 mmol) was added dropwise to the above solution via syringe. The mixture was stirred at −78° C. for 10 min, then the flask was warmed to room temperature and stirred for 1 h (monitored by TLC 30% EA/hexanes). A precipitate formed to give a thick suspension. The suspension was filtered through a 0.45-µM Teflon® filter and the filter cake rinsed with fresh Et$_2$O (2×5 mL). An aliquot (0.5 mL) was taken and concentrated and an NMR was obtained for the mixture. The remaining solution containing the product (74) was used directly in the next step. $^1$H-NMR (300 MHz, CDCl$_3$): δ 4.60 (d, J=9.3 Hz, 1H), 4.36 (d, J=9.3 Hz, 1H), 2.37 (d, J=14.1 Hz, 1H), 2.09 (d, J=13.5 Hz, 1H), 1.51 (d, J=8.4 Hz, 6H), 1.44 (s, 3H).

Example 75

Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (75)

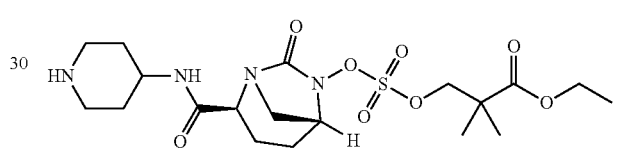

Step 1: Synthesis of (2S,5R)-6-(benzyloxy)-7-oxo-1,6-diazabicyclo[3.2.1]octane-2-carboxylic acid (75a)

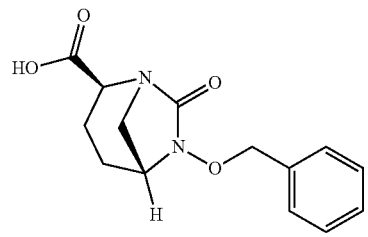 [SMILES: O=C(O)[C@@H]1CC[C@@H]2CN1C(=O)N2OCc1ccccc1]

A solution of distilled sulfuryl chloride (0.61 mL, 7.5 mmol) in Et$_2$O (10 mL) was cooled to −78° C. under nitrogen. A solution of ethyl 3-hydroxy-2,2-dimethylpropanoate (1.0 g, 6.8 mmol) and pyridine (0.55 mL, 6.8 mmol) in Et$_2$O (2.0 mL) was then added dropwise over 1 h via a syringe. The reaction was stirred at −78° C. for 1 h, and the mixture was allowed to warm to room temperature and stirred for additional 2 h. After the mixture was filtered, the filtrate was concentrated under vacuum to give the product (75a) as a colorless liquid (1.46 g, yield 87%). $^1$H NMR (300 MHz, CDCl$_3$): δ 4.50 (s, 2H), 4.19 (q, J=6.9 Hz, 2H), 1.31 (s, 6H), 1.28 (t, J=6.9 Hz, 3H).

Step 2: Synthesis of tert-butyl 4-((2S,5R)-6-(benzyloxy)-7-oxo-1,6-diazabicyclo[3.2.1]octane-2-carboxamido)piperidine-1-carboxylate (75b)

Step 3: Synthesis of tert-butyl 4-((2S,5R)-6-hydroxy-7-oxo-1,6-diazabicyclo[3.2.1]octane-2-carboxamido)piperidine-1-carboxylate (75c)

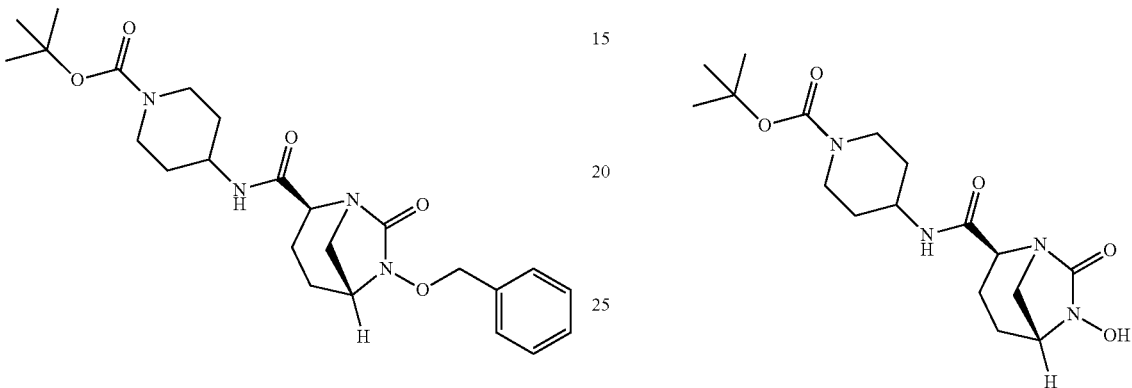

To a mixture of (2S,5R)-6-(benzyloxy)-7-oxo-1,6-diazabicyclo[3.2.1]octane-2-carboxylic acid (75a) (10 g, 36.2 mmol), tert-butyl 4-aminopiperidine-1-carboxylate (7.26 g, 36.2 mmol) in DCM (200 mL) was added HATU (13.76 g, 36.2 mmol) and DIPEA (6.31 mL, 36.2 mmol). The reaction was stirred at room temperature overnight. The mixture was washed with saturated NH$_4$Cl solution, water and brine. The organic layer was dried with anhydrous Na$_2$SO$_4$, filtered, and concentrated under vacuum to give a crude residue. The residue was purified by silica gel column chromatography using EtOAc/hexane (1:1) as eluent to give the product (75b) (10.3 g, yield 62%) as a white solid. $^1$H NMR (300 MHz, CDCl$_3$): δ 7.36-7.44 (m, 5H), 6.55 (d, 1H, J=8.1 Hz), 5.05 (d, 1H, J=11.7 Hz), 4.90 (d, 1H, J=11.1 Hz), 4.02 (br, s, 1H), 3.87-3.99 (m, 2H), 3.29 (s, 1H), 3.01 (d, 1H), 2.85 (t, 2H), 2.64 (d, 1H), 2.37 (dd, 1H), 1.84-2.05 (m, 4H), 1.55-1.67 (m, 2H), 1.45 (s, 9H), 1.23-1.36 (m, 2H). MS (ESI) C$_{24}$H$_{34}$N$_4$O$_5$=459.1 (M+1)$^+$.

To a solution of tert-butyl 4-((2S,5R)-6-(benzyloxy)-7-oxo-1,6-diazabicyclo[3.2.1]octane-2-carboxamido)piperidine-1-carboxylate (75b) (0.6 g, 1.31 mmol) in MeOH (6 mL) was added 10% palladium on carbon (0.2 g). The reaction mixture was stirred under 1 atm hydrogen pressure for 1 h. After the mixture was filtered through a pad of Celite®, the filtrate was concentrated under vacuum to give a crude product (75c) (0.48 g, yield 100%) that was used directly for the next step. $^1$H NMR (300 MHz, CDCl$_3$): δ 6.62 (d, 1H, J=7.8 Hz), 3.86-4.01 (m, 4H), 3.75 (s, 1H), 3.17 (d, 1H), 2.91 (t, 2H), 2.81 (d, 1H), 2.42 (m, 1H), 2.13 (m, 1H), 1.88 (m, 4H), 1.74 (m, 1H), 1.45 s, 9H), 1.31 (m, 2H).

Step 4: Synthesis of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (75d)

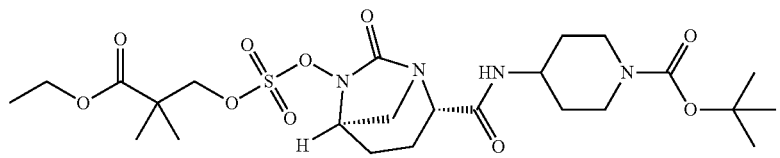 [SMILES: CCOC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (75c) (1.31 mmol) was dissolved in THF (7.0 mL) and 1,3-dimethyltetrahydropyrimidin-2(1H)-one (3 mL), and the resulting solution was cooled to −78° C. under a nitrogen atmosphere. A solution of NaHMDS in THF (1M, 1.31 mL, 1.31 mmol) was added dropwise, and the mixture was stirred at −78° C. for 10 min. A solution of ethyl 3-((chlorosulfonyl)oxy)-2,2-dimethylpropanoate (3a) (352 mg, 1.44 mmol) in THF (1 mL) was then added to the reaction mixture via syringe. After 10 min at −78° C., the reaction mixture was allowed to warm to room temperature and stirred overnight. The reaction mixture was diluted with EtOAc and washed with saturated NaHCO₃, water, and brine. The organic layer was dried with anhydrous Na₂SO₄, filtered, and concentrated under vacuum to give a crude residue. The residue was purified by silica gel column chromatography using EtOAc/hexane (1:1) as eluent to give the product (75d) (330 mg, yield 44%) as a white foam. ¹H NMR (300 MHz, CDCl₃): δ 6.44 (d, 1H, J=8.1 Hz), 4.59-4.73 (dd, 2H, J=8.7 Hz), 3.89-4.23 (m, 7H), 3.28 (d, 1H), 2.83-2.92 (m, 3H), 2.42-2.49 (m, 1H), 2.14-2.17 (m, 1H), 1.80-1.97 (m, 4H), 1.46 (s, 9H), 1.58-1.23 (m, 11H). MS (ESI) C₂₄H₄₀N₄O₁₀S=577 (M+1)⁺.

Step 5: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (75)

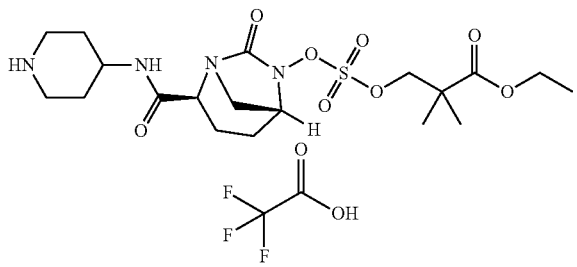

To a mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (75d) (240 mg, 0.42 mmol) in DCM (1.4 mL) was added trifluoroacetic acid (1.4 mL) at −10° C. The reaction was stirred at −10° C. for 30 min. LC/MS analysis indicated that the stating material was completely consumed. The mixture was concentrated under vacuum to give a crude residue. The residue was purified by prep-HPLC on C18 column eluting with MeCN/H₂O containing 0.1% TFA (5-100%) to give the title compound (75) (103 mg, yield 42%) as an off-white powder. ¹H NMR (300 MHz, CDCl₃): δ 9.42 (br s, 1H), 9.06 (br s, 1H), 6.71 (d, 1H, J=7.8 Hz), 4.57-4.73 (dd, 2H, J=9.0 Hz), 3.99-4.19 (m, 5H), 3.48 (d, 2H), 3.26 (d, 1H), 3.00 (m, 2H), 2.88 (d, 1H), 1.82-2.39 (m, 7H), 1.23-1.30 (m, 9H). ¹³C NMR (75 MHz, CDCl₃): δ 174.5, 168.9, 167.3, 80.8, 62.0, 61.6, 60.4, 46.8, 44.9, 43.6, 43.3, 28.7, 22.3, 21.9, 20.9, 18.0, 14.4. ¹⁹F NMR (282 MHz, CDCl₃): δ −75.8. MS (ESI) C₁₉H₃₂N₄O₈S=477 (M+1)⁺.

Analytical HPLC was performed on Agilent 1200 system using a Phenomenex® C18 column (150×4.6 mm i.d.). The mobile phase was a linear gradient of MeCN and water (0.1% TFA, 5% MeCN to 100% MeCN in 15 min). The flow rate was maintained at 1 mL/min and the eluent was monitored with UV detector at 220 and 254 nm. HPLC retention time: 7.31 min.

Example 76

Synthesis of 2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (76)

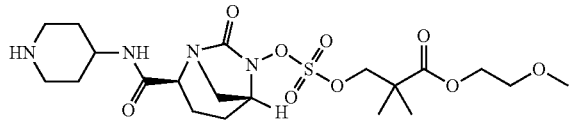 [SMILES: COCCOC(=O)C(C)(C)COS(=O)(=O)ON1C(=O)N2C[C@H]1CC[C@H]2C(=O)NC1CCNCC1]

Step 1: Synthesis of 2-methoxyethyl 3-((chlorosulfonyl)oxy)-2,2-dimethylpropanoate (76a)

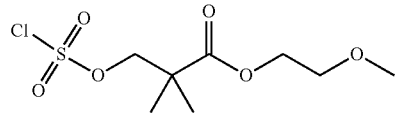 [SMILES: COCCOC(=O)C(C)(C)COS(=O)(=O)Cl]

A solution of distilled sulfuryl chloride (0.51 mL, 6.2 mmol) in Et₂O (10 mL) was cooled to −78° C. under nitrogen. A solution of 2-methoxyethyl 3-hydroxy-2,2-dimethylpropanoate (15a) (1.0 g, 5.68 mmol) and pyridine (0.46 mL, 5.68 mmol) in Et₂O (2.0 mL) was then added dropwise over 1 h via a syringe. The reaction was stirred at −78° C. for 1 h, and then the mixture was allowed to warm to room temperature and stirred for 2 h. After the mixture was filtered, the filtrate was concentrated under vacuum to give the product (76a) as a colorless liquid (1.5 g, yield 96%). ¹H NMR (300 MHz, CDCl₃): δ 4.40 (s, 2H), 4.29 (t, 3H), 3.59 (t, 3H), 3.37 (s, 3H), 1.32 (s, 6H).

Step 2: Synthesis of tert-butyl 4-((2S,5R)-6-(((3-(2-methoxyethoxy)-2,2-dimethyl-3-oxopropoxy)sulfonyl)oxy)-7-oxo-1,6-diazabicyclo[3.2.1]octane-2-carboxamido)piperidine-1-carboxylate (76b)

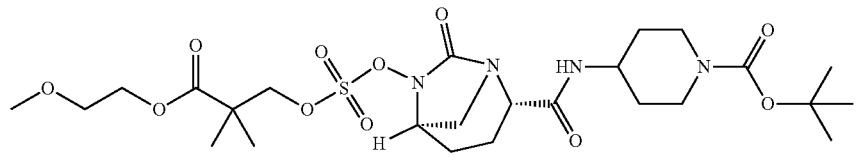 [SMILES: COCCOC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (76b) (3.26 mmol) was dissolved in THF (14 mL) and 1,3-dimethyltetrahydropyrimidin-2(1H)-one (6 mL), and the resulting solution was cooled to −78° C. under a nitrogen atmosphere. A solution of NaHMDS in THF (1M, 3.59 mL, 3.59 mmol) was added dropwise, and the mixture was stirred at −78° C. for 10 min. A solution of 2-methoxyethyl 3-((chlorosulfonyl)oxy)-2,2-dimethylpropanoate (21a) (878 mg, 3.59 mmol) in THF (2 mL) was then added to the 20.9, 18.0. 19F NMR (282 MHz, CDCl$_3$): δ −75.8. MS (ESI) $C_{20}H_{34}N_4O_9S$=507 (M+1)$^+$. HPLC retention time (MeCN/H$_2$O in 0.1% TFA): 6.75 min.

Example 77

Synthesis of 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (77)

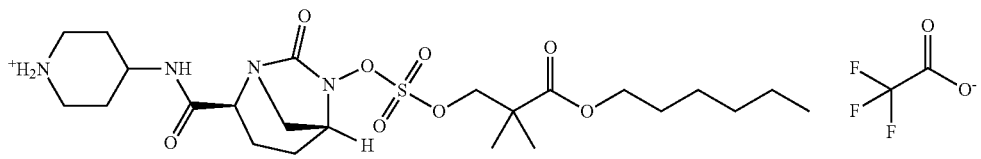 [SMILES: CCCCCCOC(=O)C(C)(C)COS(=O)(=O)ON1C(=O)N2C[C@H]1CC[C@H]2C(=O)NC1CC[NH2+]CC1 ; O=C([O-])C(F)(F)F]

reaction mixture via a syringe. After 10 min at −78° C., the reaction mixture was allowed to warm to room temperature and stirred overnight. The reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:1) as eluent to give the product (76c) (0.96 g, yield 48%) as a white foam. MS (ESI) $C_{25}H_{42}N_4O_{11}S$=607.0 (M+1)$^+$.

Step 3: Synthesis of 2-methoxyethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (76)

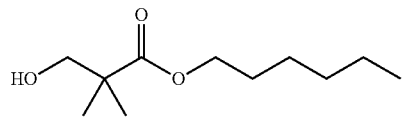

To a mixture of tert-butyl 4-((2S,5R)-6-(((3-(2-methoxyethoxy)-2,2-dimethyl-3-oxopropoxy)sulfonyl)oxy)-7-oxo-1,6-diazabicyclo[3.2.1]octane-2-carboxamido)piperidine-1-carboxylate (76c) (0.86 g, 1.42 mmol) in DCM (4.3 mL) was added trifluoroacetic acid (4.3 mL) at −10° C. The reaction mixture was stirred at −10° C. for 30 min. LC/MS analysis indicated that the stating material was completely consumed. The mixture was concentrated under vacuum to give a crude residue. The residue was purified by prep-HPLC on a C18 column eluting with MeCN/H$_2$O containing 0.1% TFA (5-75%) to give the title compound (76) (513 mg, yield 58%) as a yellow powder. $^1$H NMR (300 MHz, CDCl$_3$): δ 9.09 (br s, 1H), 8.75 (br s, 1H), 6.83 (d, 1H, J=7.8 Hz), 4.59-4.71 (dd, 2H, J=9.3 Hz), 3.99-4.36 (m, 5H), 3.60 (m, 2H), 3.50 (d, 2H), 3.39 (s, 3H), 3.30 (d, 1H), 3.02 (m, 2H), 2.89 (d, 1H), 1.87-2.40 (m, 7H), 1.25-1.30 (m, 9H). $^{13}$C NMR (75 MHz, CDCl$_3$): δ 174.4, 168.9, 167.4, 80.6, 70.6, 64.5, 62.0, 60.4, 59.3, 46.8, 44.9, 43.6, 43.2, 28.7, 22.4, 21.8, Step 1: Synthesis of hexyl 3-hydroxy-2,2-dimethylpropanoate (77a)

A mixture of 3-hydroxy-2,2-dimethylpropionic acid (4.7 g, 40 mmol), 1-hexanol (70 mL) and concentrated sulfuric acid (or fuming sulfuric acid, 1 mL) was heated to 80° C. and stirred overnight. After allowing to cool, the mixture was concentrated under vacuum (high vacuum pump required) and the residue was then partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried over anhydrous Na$_2$SO$_4$, filtered and concentrated under vacuum to provide the product as an oil. The product was difficult to purify using silica gel chromatography; and therefore the product was distilled under high vacuum at 47° C. to provide 4.92 g of the pure ester product (77a) (yield 61%). H NMR (300 MHz, CDCl$_3$) δ 4.10 (td, J=6.7, 1.3 Hz, 2H), 3.55 (d, J=5.1 Hz, 2H), 2.42 (s, 1H), 1.64 (s, 1H), 1.72-1.56 (m, 1H), 1.35 (s, 1H), 1.31 (s, 6H), 1.27-1.11 (m, 6H), 0.95-0.84 (m, 3H). MS (ESI) $C_{11}H_{22}O_3$=203 (M+1)$^+$.

Step 2: Synthesis of hexyl 3-((chlorosulfonyl)oxy)-2,2-dimethylpropanoate (77b)

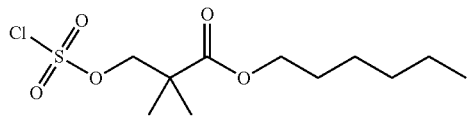 [SMILES: CCCCCCOC(=O)C(C)(C)COS(=O)(=O)Cl]

A solution of freshly distilled sulfuryl chloride (0.60 mL, 7.4 mmol) in Et$_2$O (10 mL) was cooled to −78° C. under an atmosphere of N$_2$. A solution of hexyl 3-hydroxy-2,2-dimethylpropanoate (77a) (1.0 g, 4.94 mmol) and pyridine (0.48 mL, 5.93 mmol) in Et$_2$O (5 mL) was added dropwise to the sulfuryl chloride solution over the course of 20 min. The flask was rinsed with Et₂O (3×1 mL) and the rinse added to the reaction mixture. The mixture was stirred at −78° C. until completion by TLC (30 min; 30% EA/hexane). The precipitate was filtered, and the filtrate was concentrated under vacuum to afford the crude product (77b) as a solid foam and was used in the next step without further purification. ¹H-NMR (300 MHz, CDCl₃): δ 4.50 (s, 2H), 4.13 (t, J=6.8 Hz, 2H), 1.69-1.60 (m, 2H), 1.40-1.27 (m, 12H), 0.91-0.87 (m, 3H).

Step 3: Synthesis of tert-butyl 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidine-1-carboxylate (77c)

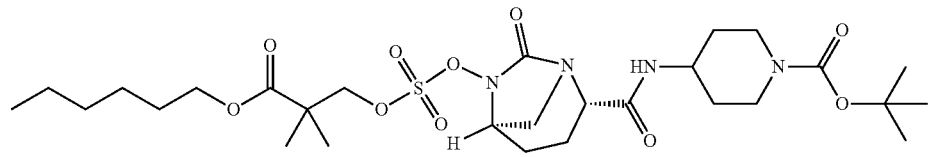 [SMILES: CCCCCCOC(=O)C(C)(C)COS(=O)(=O)ON1C(=O)N2C[C@H]1CC[C@H]2C(=O)NC1CCN(C(=O)OC(C)(C)C)CC1]

The hydroxamic acid (2.39 mmol) was dissolved in THF (12 mL) and 1,3-dimethyltetrahydropyrimidin-2(1H)-one (3.4 mL), and the resulting solution was cooled to −78° C. under an atmosphere of N₂. A solution of NaHMDS in THF (2.4 mL, 1.0 M, 2.4 mmol) was added dropwise to and the mixture stirred for 20 min. Neat hexyl 3-((chlorosulfonyl)oxy)-2,2-dimethylpropanoate (77b) (0.973 g, 2.64 mmol) was added quickly to the reaction mixture. The syringe was rinsed with THF (3×4 mL) and the rinse was also added to the mixture. After 10 min, the reaction mixture was warmed to room temperature and stirred until complete as determined by TLC and LC-MS. EtOAc (30 mL) and saturated aqueous NaHCO₃ (30 mL) were added to the mixture. The layers were partitioned, and the organic layer was washed with saturated aqueous NaHCO₃ (30 mL), water (3×20 mL), and brine (30 mL), and then dried (Na₂SO₄), filtered and concentrated under vacuum to leave a crude residue. The residue was purified by silica gel column chromatography using EtOAc/hexane (1:9 to 1:0) as eluent, followed by high-performance liquid chromatography to give the product (77c) (740 mg, yield 49% for 3 steps) as a solid foam. ¹H-NMR (300 MHz, CDCl₃) δ 6.43 (d, J=8.2 Hz, 1H), 4.76-4.64 (m, 1H), 4.60 (d, J=9.0 Hz, 1H), 4.19-4.03 (m, 5H), 3.98 (d, J=7.5 Hz, 2H), 3.28 (d, J=12.0 Hz, 1H), 2.90 (d, J=12.0 Hz, 2H), 2.45 (dd, J=14.8, 6.2 Hz, 1H), 2.14 (s, 1H), 1.97-1.84 (m, 3H), 1.62 (q, J=7.0 Hz, 11H), 1.46 (s, 9H), 1.34-1.19 (m, 14H), 0.88 (d, J=7.0 Hz, 3H). MS (ESI) $C_{28}H_{48}N_4O_{10}S$=633 (M+1)⁺.

Step 4: Synthesis of 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (77)

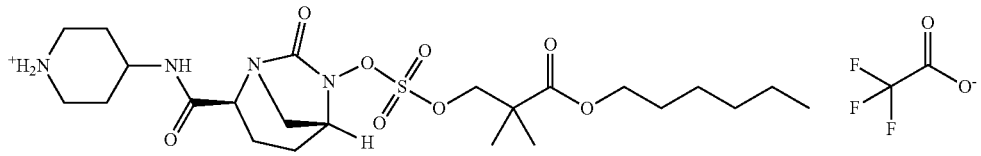 [SMILES: CCCCCCOC(=O)C(C)(C)COS(=O)(=O)ON1C(=O)N2C[C@H]1CC[C@H]2C(=O)NC1CC[NH2+]CC1 ; O=C([O-])C(F)(F)F]

tert-Butyl 4-((2S,5R)-6-(((3-(hexyloxy)-2,2-dimethyl-3-oxopropoxy)sulfonyl)oxy)-7-oxo-1,6-diazabicyclo[3.2.1]octane-2-carboxamido)piperidine-1-carboxylate (77c) (300 mg, 0.474 mmol) was dissolved in DCM (2 mL) and cooled to −10° C. To the solution was added TFA (2 mL) dropwise. The reaction was monitored with LCMS or TLC until completion (ca. 10 min). The solvent was removed in vacuo and the residue was purified using prep-HPLC with MeCN/H$_2$O containing 0.1% TFA (20-100%) as an eluent to provide, after lyophilization, the title compound (77) (212.4 mg, yield 84%) as a foam. $^1$H NMR (300 MHz, CDCl$_3$) δ 9.08 (s, 1H), 8.74 (s, 1H), 6.88 (d, J=7.9 Hz, 1H), 4.70-4.51 (m, 2H), 4.23-3.92 (m, 6H), 3.47 (d, J=12.6 Hz, 2H), 3.31-3.19 (m, 1H), 2.95 (dd, J=19.6, 11.0 Hz, 3H), 2.34 (dd, J=15.0, 6.2 Hz, 1H), 2.10 (s, 2H), 1.91 (ddd, J=15.8, 12.6, 8.0 Hz, 1H), 1.61 (ddd, J=12.5, 8.1, 6.3 Hz, 3H), 1.40-1.16 (m, 14H), 0.91-0.80 (m, 3H). $^{13}$C NMR (75 MHz, CDCl$_3$) δ 174.2, 168.6, 167.1, 80.4, 65.5, 61.7, 60.1, 46.6, 44.7, 43.3, 42.9, 42.9, 31.4, 31.4, 28.5, 25.6, 25.5, 22.2, 22.2, 21.6, 20.7, 17.8, 14.0. $^{19}$F NMR (282 MHz, CDCl$_3$) δ −75.6. MS (ESI) C$_{23}$H$_{40}$N$_4$O$_8$S=533 (M+1)$^+$. HPLC retention time (MeCN/H$_2$O in 0.1% TFA): 8.18 min.

Example 78

Synthesis of 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (78)

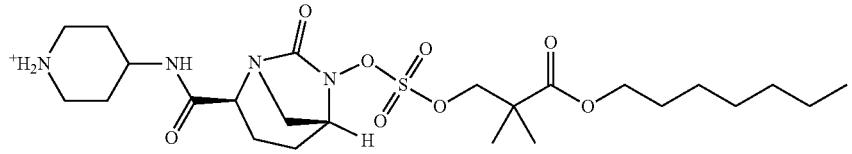

Step 1: Synthesis of heptyl 3-hydroxy-2,2-dimethylpropanoate (78a)

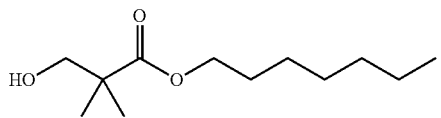

A mixture of 3-hydroxy-2,2-dimethylpropionic acid (4.7 g, 40 mmol), 1-heptanol (70 mL) and concentrated sulfuric acid (1 mL) was heated to 80° C. and stirred overnight. After allowing to cool, the mixture was concentrated under vacuum (high vacuum pump required) and the residue partitioned between EtOAc (100 mL) and saturated aqueous NaHCO$_3$ (100 mL). The aqueous phase was washed with H$_2$O (50 mL), saturated NaHCO$_3$ (50 mL) and brine (50 mL), and then dried (Na$_2$SO$_4$), filtered and concentrated under vacuum to provide the product as an oil. The product was distilled under high vacuum at 65° C. to provide the title compound (78a) as an oil (6.7 g, 77% yield). $^1$H NMR (300 MHz, CDCl$_3$) δ 4.09 (td, J=6.7, 0.9 Hz, 2H), 3.55 (d, J=6.1 Hz, 2H), 2.43 (t, J=6.7 Hz, 1H), 1.60 (d, J=22.8 Hz, 4H), 1.3-1.58 (m, 6H), 1.27-1.14 (m, 6H), 0.92-0.83 (m, 3H).

Step 2: Synthesis of heptyl 3-((chlorosulfonyl)oxy)-2,2-dimethylpropanoate (78b)

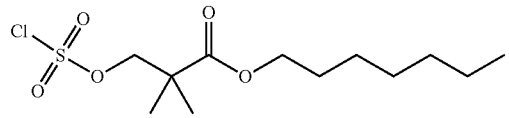 [SMILES: CCCCCCCOC(=O)C(C)(C)COS(=O)(=O)Cl]

A solution of sulfuryl chloride (0.6 mL, 7.4 mmol) in Et$_2$O (15 mL) was cooled to −78° C. under an atmosphere of N$_2$. A solution of heptyl 3-hydroxy-2,2-dimethylpropanoate (78a) (1.0 g, 4.94 mmol) and pyridine (479 μL, 5.93 mmol) in Et$_2$O (1 mL) was added dropwise to the sulfuryl chloride solution over the course of 30 min. The flask was rinsed with Et$_2$O (3×1 mL) and the rinse added to the reaction mixture. The mixture was stirred at −78° C. until completion as monitored by TLC (30 min; 30% EA/hexane). The precipitate was filtered, and the filtrate was concentrated under vacuum to afford heptyl 3-((chlorosulfonyl)oxy)-2,2-dimethylpropanoate (78b) (1.37 g, yield 92%). The mixture was stored at −78° C. and used in the next step without further purification. $^1$H NMR (300 MHz, CDCl$_3$) δ 4.50 (s, 2H), 4.20-4.02 (m, 2H), 1.68 (m, 2H), 1.31 (d, J=3.1 Hz, 13H), 1.23 (s, 1H), 0.95-0.83 (m, 3H).

Step 3: Synthesis of tert-butyl 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidine-1-carboxylate (78c)

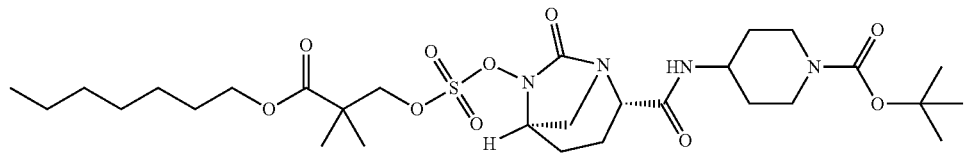 [SMILES: CCCCCCCOC(=O)C(C)(C)COS(=O)(=O)ON1C(=O)N2C[C@H]1CC[C@H]2C(=O)NC1CCN(C(=O)OC(C)(C)C)CC1]

Hydroxamic acid (1) (2.399 mmol, from hydrogenation, without further purification) was dissolved in THF (12 mL) and 1,3-dimethyltetrahydropyrimidin-2(1H)-one (3 mL) and the resulting solution was cooled to −78° C. under a nitrogen atmosphere. A 1.0 M solution of NaHMDS in THF (2.4 mL, 2.4 mmol) was added dropwise to the cooled solution and stirred for 20 min. Heptyl 3-((chlorosulfonyl)oxy)-2,2-dimethylpropanoate (78b) (0.79 g, 2.63 mmol) in THF (5 mL) was rapidly added to the reaction mixture. The syringe was rinsed with THF (3×2 mL) and the rinse was also added to the mixture. After 10 min, the reaction mixture was warmed to room temperature and stirred until completion as determined by TLC and LC-MS. EtOAc (50 mL) and saturated aqueous NaHCO$_3$ (50 mL) were added to the mixture. The aqueous and organic layers were partitioned, and the organic layer was washed with saturated aqueous NaHCO$_3$ (10 mL), water (3×10 mL), brine (20 mL), and then dried (Na$_2$SO$_4$), filtered and concentrated under vacuum to provide a crude residue. The residue was purified by silica gel column chromatography using EtOAc/hexane (5% to 95%) as eluent, to give 740.0 mg (49% yield) of the product (78c).

Step 4: Synthesis of 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidin-1-ium 2,2,2-trifluoroacetate (78)

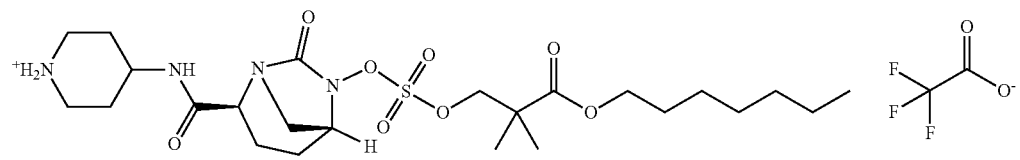 [SMILES: CCCCCCCOC(=O)C(C)(C)COS(=O)(=O)ON1C(=O)N2C[C@H]1CC[C@H]2C(=O)NC1CC[NH2+]CC1 ; O=C([O-])C(F)(F)F]

tert-Butyl 4-((2S,5R)-6-(((3-(heptyloxy)-2,2-dimethyl-3-oxopropoxy)sulfonyl)oxy)-7-oxo-1,6-diazabicyclo[3.2.1]octane-2-carboxamido)piperidine-1-carboxylate (78c) (472.1 mg, 0.73 mmol) dissolved in DCM (5 mL) was cooled to −10° C., to which was added TFA (5 mL) dropwise. After completion, the solvent was evaporated in vacuo and the residue was purified with prep-HPLC using MeCN/H$_2$O containing 0.1% TFA (20-100%) to give the title compound (78) (390 mg, 81% yield) as a solid foam. $^1$H NMR (300 MHz, CDCl$_3$) δ 8.93 (d, J=10.4 Hz, 1H), 8.62 (s, 1H), 6.90 (d, J=7.8 Hz, 1H), 4.70-4.51 (m, 2H), 4.18-3.92 (m, 6H), 3.48 (d, J=12.2 Hz, 2H), 3.26 (d, J=11.5 Hz, 1H), 2.98 (dt, J=24.4, 11.7 Hz, 3H), 2.34 (dd, J=15.1, 6.3 Hz, 1H), 2.10 (s, 2H), 1.60 (h, J=6.6 Hz, 3H), 1.24 (q, J=11.1, 9.8 Hz, 18H), 0.90-0.79 (m, 4H). $^{13}$C NMR (75 MHz, CDCl$_3$) δ 174.2, 168.6, 167.1, 80.3, 73.9, 65.4, 61.6, 60.1, 46.5, 44.6, 43.4, 42.8, 42.8, 31.6, 28.8, 28.4, 28.3, 25.8, 25.7, 22.5, 22.1, 22.1, 21.5, 20.6, 17.8, 14.0. $^{19}$F NMR (282 MHz, CDCl$_3$) δ −75.7. MS (ESI) C$_{24}$H$_{42}$N$_4$O$_8$S=547 (M+1)$^+$. HPLC retention time (MeCN/H$_2$O in 0.1% TFA): 9.59 min.

Example 79

Synthesis of 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (79)

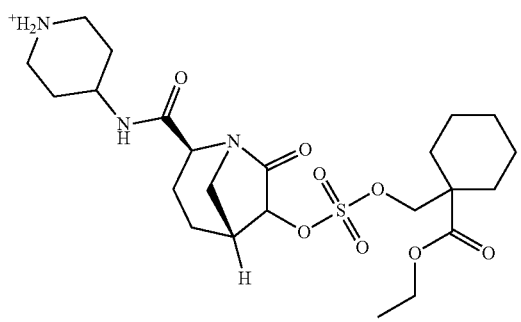

-continued

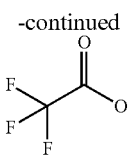

Step 1: Synthesis of ethyl 1-(hydroxymethyl)cyclohexanecarboxylate (79a)

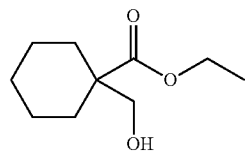

Diethyl cyclohexane-1,1-dicarboxylate (2.12 g, 9.29 mmol) was dissolved in THF (50 mL) and to which was added LiAl(OtBu)$_3$ (5.9 g, 23.2 mmol) in portions. The reaction mixture was stirred at reflux overnight. The reaction was cooled in an ice bath and treated carefully with 10% KHSO$_4$ aq. solution (30 mL) with stirring for 10 min. The precipitate formed was filtered out through a pad of Celite®. The filtrate was extracted with EtOAc (3×40 mL) and the organic phase was combined and washed with brine (50 mL), dried over NaSO$_4$, filtered and concentrated in vacuo. The residue was purified with CombiFlash (SiO$_2$) in 0-5% MeOH/DCM to obtain the desired product (79a) as an oil (1.23 g, 71% yield). $^1$H NMR (300 MHz, CDCl$_3$) δ 4.19 (qd, J=7.1, 0.8 Hz, 2H), 3.62 (d, J=6.4 Hz, 2H), 3.46 (s, 1H), 2.00 (dt, J=11.5, 6.4 Hz, 4H), 1.57-1.22 (m, 9H).

Step 2: Synthesis of ethyl 1-(((chlorosulfonyl)oxy)methyl)cyclohexanecarboxylate (79b)

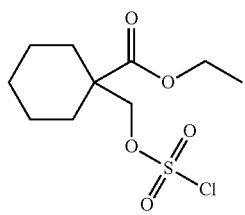 [SMILES: CCOC(=O)C1(COS(=O)(=O)Cl)CCCCC1]

A solution of freshly distilled sulfuryl chloride (294 µL, 3.63 mmol) in Et$_2$O (10 mL) was cooled to −78° C. under an atmosphere of nitrogen. A solution of ethyl 1-(hydroxymethyl)cyclohexanecarboxylate (79a) (0.615 g, 3.3 mmol) and pyridine (294 µL, 3.63 mmol) in Et$_2$O (6 mL) was added dropwise to the sulfuryl chloride solution during 15 min. The flask was rinsed with Et$_2$O (3×1 mL) and the rinse added to the reaction. The mixture was stirred at −78° C. until completion (ca. 30 min; monitored by TLC, 30% EtOAc/hexane). The precipitate was filtered, and the filtrate was concentrated under vacuum to afford the title compound (79b) as an oil, 0.94 g in quantitative yield, which was used directly in the next step without purification. $^1$H-NMR (300 MHz, CDCl$_3$): δ 4.52 (s, 2H), 4.21 (q, J=7.1 Hz, 2H), 2.04 (s, 2H), 1.53-1.39 (m, 8H), 1.39-1.21 (m, 3H).

Step 3: Synthesis of tert-Butyl 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidine-1-carboxylate (79c)

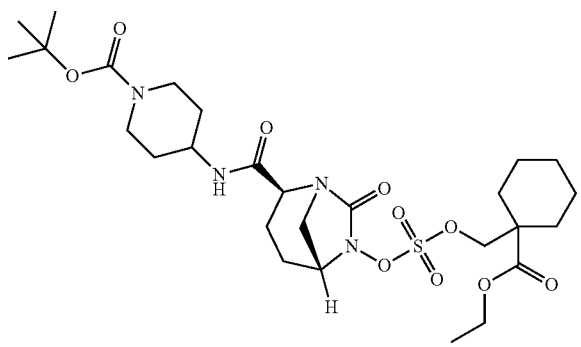 [SMILES: CCOC(=O)C1(COS(=O)(=O)ON2C(=O)N3C[C@H]2CC[C@H]3C(=O)NC2CCN(C(=O)OC(C)(C)C)CC2)CCCCC1]

Hydroxamic acid (2.73 mmol) was dissolved in THF (14 mL) and 1,3-dimethyltetrahydropyrimidin-2(1H)-one (7 mL), and the resulting solution was cooled to −78° C. under an atmosphere of nitrogen. A 1.0 M solution of NaHMDS in THF (2.73 mL, 2.73 mmol) was added dropwise over 20 min, and the mixture stirred for 10 min. Ethyl 1-(((chlorosulfonyl)oxy)methyl)cyclohexanecarboxylate (79b) (0.94 g, 3.3 mmol) in THF (2 mL) was rapidly added to the reaction mixture. After 10 min stirring at −78° C., the mixture was allowed to warm to room temperature and stirred for 1 h. The reaction mixture was diluted with EtOAc (60 mL) and H$_2$O at −60° C. The aqueous and organic layers were partitioned, and the organic layer was washed with H$_2$O (3×30 mL), and brine (50 mL), then dried (Na$_2$SO$_4$), filtered and concentrated under vacuum to give the crude residue (330 mg). The oil was purified by silica gel column chromatography using EtOAc/hexane (3:7 to 1:0) as eluent to give the product (79c) (0.98 g, yield 59%) as a solid. $^1$H-NMR (300 MHz, CDCl$_3$): δ 6.43 (d, J=8.2 Hz, 1H), 4.75 (d, J=9.2 Hz, 1H), 4.59 (d, J=9.1 Hz, 1H), 4.28-4.05 (m, 5H), 4.04-3.90 (m, 3H), 2.87 (t, J=12.4 Hz, 3H), 2.45 (dd, J=15.0, 5.7 Hz, 1H), 2.08-1.84 (m, 4H), 1.56 (d, J=10.6 Hz, 3H), 1.46 (s, 9H), 1.46-1.34 (m, 5H), 1.37-1.20 (m, 8H). MS (ESI) C$_{27}$H$_{44}$N$_4$O$_{10}$S: 617 (M+H)$^+$.

Step 4: 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidin-1-ium 2,2,2-trifluoroacetate (79)

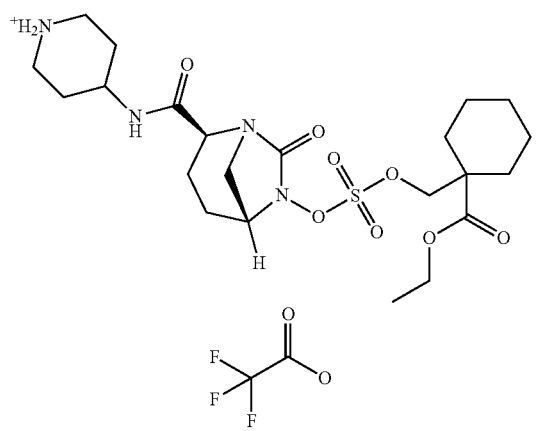

tert-Butyl 4-((2S,5R)-6-((((1-(ethoxycarbonyl)cyclohexyl)methoxy)sulfonyl)oxy)-7-oxo-1,6-diazabicyclo[3.2.1]octane-2-carboxamido)piperidine-1-carboxylate (79c) (403.3 mg, 0.65 mmol) dissolved in DCM (4 mL) was cooled to −10° C. (salt ice bath) to which was added TFA (4 mL) dropwise. The reaction monitored by LCMS. After 30 min, it was complete. The solvent was removed in vacuo and the residue was purified with prep-HPLC in MeCN/H2O containing 0.1% TFA (20-100%) to give the title compound (79) (263.7 mg, yield 78%) as a solid foam. $^1$H NMR (300 MHz, CDCl$_3$) δ 9.02 (d, J=10.6 Hz, 1H), 8.66 (s, 1H), 6.87 (d, J=7.8 Hz, 1H), 4.70 (d, J=9.1 Hz, 1H), 4.54 (d, J=9.0 Hz, 1H), 4.16 (dtd, J=12.9, 6.7, 6.3, 3.1 Hz, 4H), 4.00 (q, J=8.7, 7.2 Hz, 3H), 3.47 (d, J=12.3 Hz, 2H), 3.26 (d, J=11.5 Hz, 1H), 2.95 (dd, J=25.8, 11.9 Hz, 3H), 2.35 (dd, J=15.3, 6.3 Hz, 1H), 2.11 (t, J=10.3 Hz, 4H), 1.99 (s, 2H), 2.08-1.87 (m, 2H), 1.89-1.72 (m, 4H), 1.54 (d, J=8.0 Hz, 5H), 1.25 (dd, J=14.4, 3.8 Hz, 2H). $^{13}$C NMR (75 MHz, CDCl$_3$) δ 173.2, 168.5, 167.0, 80.2, 61.7, 61.1, 60.0, 47.0, 46.6, 44.6, 43.3, 30.4, 29.9, 28.3, 25.3, 22.4, 22.2, 22.0, 20.6, 17.7, 14.1. $^{19}$F NMR (282 MHz, CDCl$_3$) δ −75.7. MS (ESI) C$_{22}$H$_{36}$N$_4$O$_8$S=517 (M+1)$^+$. HPLC retention time (MeCN/H$_2$O in 0.1% TFA): 8.15 min.

Example 80

Synthesis of (5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (80)

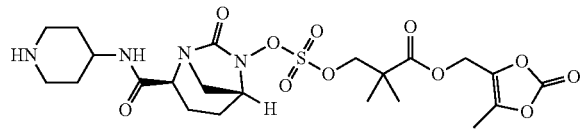 [SMILES: Cc1oc(=O)oc1COC(=O)C(C)(C)COS(=O)(=O)ON1C(=O)N2C[C@H]1CC[C@H]2C(=O)NC1CCNCC1]

Step 1: Synthesis of (5-methyl-2-oxo-1,3-dioxol-4-yl)methyl 3-hydroxy-2,2-dimethylpropanoate (80a)

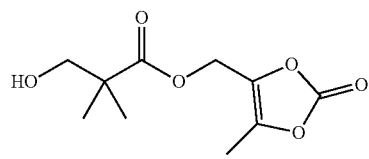

To a stirred solution of 3-hydroxy-2,2-dimethylpropanoic acid (4.0 g, 33.9 mmol) and potassium carbonate (4.68 g, 33.9 mmol) in DMF (45 mL) at 0° C. was added 4-(hydroxymethyl)-5-methyl-1,3-dioxol-2-one (5.03 g, 33.9 mmol) in DMF (5 mL) dropwise over 1 h. The reaction was stirred at room temperature overnight. The reaction mixture was diluted with EtOAc and washed with water and brine. The organic layer was dried with anhydrous Na$_2$SO$_4$, filtered, and concentrated under vacuum to give a crude residue. The residue was purified by silica gel column chromatography using EtOAc/hexane (1:4 to 2:3) as eluent to give the product (80a) as a yellow liquid (1.6 g, yield 21%). $^1$H NMR (300 MHz, CDCl$_3$): δ 4.86 (s, 2H), 3.58 (s, 2H), 2.18 (s, 3H), 1.20 (s, 6H).

Step 2: Synthesis of (5-methyl-2-oxo-1,3-dioxol-4-yl)methyl 3-((chlorosulfonyl)oxy)-2,2-dimethylpropanoate (80b)

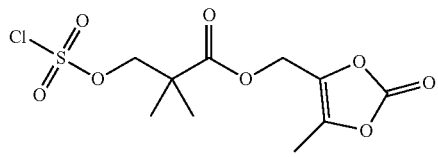 [SMILES: Cc1oc(=O)oc1COC(=O)C(C)(C)COS(=O)(=O)Cl]

A solution of distilled sulfuryl chloride (0.61 mL, 7.53 mmol) in Et$_2$O (15 mL) was cooled to −78C under nitrogen. A solution of (5-methyl-2-oxo-1,3-dioxol-4-yl)methyl 3-hydroxy-2,2-dimethylpropanoate (80a) (1.48 g, 6.43 mmol) in Et$_2$O (1 mL) was added. Subsequently, a solution of pyridine (0.55 mL, 6.86 mmol) in Et$_2$O (1 mL) was added over a period of 1 h. The reaction was stirred at −78° C. for 1 h. After the mixture was filtered, the filtrate was concentrated under vacuum to give the product (80b) as a yellow oil (1.6 g, yield 76%). $^1$H NMR (300 MHz, CDCl$_3$): δ 4.90 (s, 2H), 4.49 (s, 2H), 2.19 (s, 3H), 1.33 (s, 6H).

Step 3: Synthesis of tert-butyl 4-((2S,5R)-6-(((2,2-dimethyl-3-((5-methyl-2-oxo-1,3-dioxol-4-yl)methoxy)-3-oxopropoxy)sulfonyl)oxy)-7-oxo-1,6-diazabicyclo[3.2.1]octane-2-carboxamido)piperidine-1-carboxylate (80c)

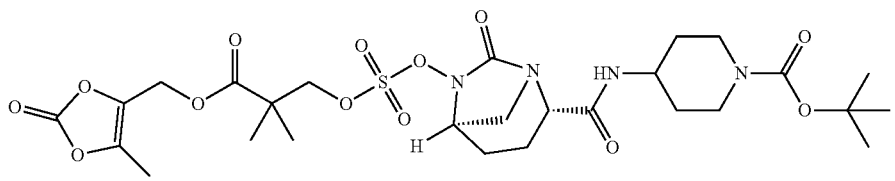 [SMILES: Cc1oc(=O)oc1COC(=O)C(C)(C)COS(=O)(=O)ON1C(=O)N2C[C@H]1CC[C@H]2C(=O)NC1CCN(C(=O)OC(C)(C)C)CC1]

tert-Butyl 4-((2S,5R)-6-hydroxy-7-oxo-1,6-diazabicyclo[3.2.1]octane-2-carboxamido)piperidine-1-carboxylate (80b) (2.18 mmol) was dissolved in THF (14 mL) and 1,3-dimethyltetrahydropyrimidin-2(1H)-one (6 mL), and the resulting solution was cooled to −78° C. under nitrogen. A solution of NaHMDS in THF (1M, 2.62 mL, 2.62 mmol) was added dropwise, and the mixture was stirred at −78° C. for 10 min. A solution of (5-methyl-2-oxo-1,3-dioxol-4-yl)methyl 3-((chlorosulfonyl)oxy)-2,2-dimethylpropanoate (25b) (106b) (0.86 g, 2.62 mmol) in THF (1 mL) was then added to the reaction mixture via a syringe. After stirring for 1 h at −78° C., the reaction mixture was diluted with EtOAc and washed with saturated NaHCO$_3$, water, and brine. The organic layer was dried with anhydrous Na$_2$SO$_4$, filtered, and concentrated under vacuum to give a crude residue. The residue was purified by silica gel column chromatography using EtOAc/hexane (1:3 to 1:1) as eluent to give the product (80c) as a yellow paste (0.44 g, yield 31%). $^1$H NMR (300 MHz, CDCl$_3$): δ 6.73 (d, 1H, J=8.1 Hz), 4.78-4.98 (m, 3H), 4.47 (d, 1H, J=8.7 Hz), 3.93-4.15 (m, 5H), 3.27 (d, 1H), 2.83-2.92 (m, 3H), 2.41-2.45 (m, 1H), 2.18 (s, 3H), 2.15 (m, 1H), 1.78-1.92 (m, 4H), 1.45 (s, 9H), 1.23-1.58 (m, 8H). MS (ESI) C$_{27}$H$_{40}$N$_4$O$_{13}$S=661 (M+1)$^+$.

Step 5: Synthesis of (5-methyl-2-oxo-1,3-dioxol-4-yl)methyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (TFA salt) (80)

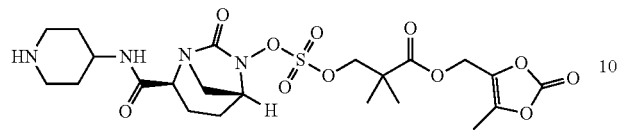

To a solution of tert-butyl 4-((2S,5R)-6-(((2,2-dimethyl-3-((5-methyl-2-oxo-1,3-dioxol-4-yl)methoxy)-3-oxopropoxy)sulfonyl)oxy)-7-oxo-1,6-diazabicyclo[3.2.1]octane-2-carboxamido)piperidine-1-carboxylate (80c) (100 mg, 0.15 mmol) in DCM (3 mL) was added trifluoroacetic acid (0.4 mL) at −10° C. The reaction was stirred at −10° C. for 1 h. LC/MS analysis indicated that the stating material was consumed. The mixture was concentrated under vacuum to give a crude residue. The residue was purified by prep-HPLC on a C18 column eluting using MeCN/H$_2$O containing 0.1% TFA (5-80%) to give the title compound (80) as off-white powder (55.2 mg, yield 55%). $^1$H NMR (300 MHz, CDCl$_3$): δ 9.43 (br s, 1H), 9.05 (br s, 1H), 7.14 (d, 1H, J=6.9 Hz), 4.99 (d, 1H, J=13.5 Hz), 4.95 (d, 1H, J=8.1 Hz), 4.78 (d, 1H, J=14.1 Hz), 4.41 (d, 1H, J=9.3 Hz), 4.14 (s, 1H), 4.06 (m, 1H), 3.98 (d, 1H, J=6.3 Hz), 3.47 (d, 2H), 3.29 (d, 1H), 3.04 (m, 2H), 2.86 (d, 1H), 1.82-2.40 (m, 11H), 1.29-1.33 (ds, 6H). $^{13}$C NMR (75 MHz, CDCl$_3$): δ 173.9, 169.1, 167.3, 152.9, 141.0, 133.7, 80.3, 62.0, 60.4, 54.8, 46.8, 44.7, 43.4, 43.3, 28.5, 22.3, 22.0, 20.8, 18.0, 9.6. $^{19}$F NMR (282 MHz, CDCl$_3$): δ −75.9. MS (ESI) C$_{22}$H$_{32}$N$_4$O$_{11}$S=561 (M+1)$^+$.

Analytical HPLC was performed on an Agilent 1200 system using a Phenomenex® C18 column (150×4.6 mm i.d.). The mobile phase was a linear gradient of MeCN and water (0.1% TFA, 5% MeCN to 100% MeCN in 15 min). The flow rate was maintained at 1 mL/min and the eluent was monitored with UV detector at 220 nm and 254 nm. HPLC retention time: 7.25 min.

Example 81

Synthesis of tert-butyl 4-((2S,5R)-6-(benzyloxy)-7-oxo-1,6-diazabicyclo[3.2.1]octane-2-carboxamido)piperidine-1-carboxylate (81)

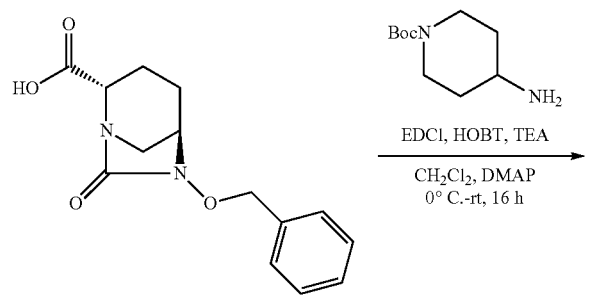

(2S,5R)-6-(benzyloxy)-7-oxo-1,6-diazabicyclo[3.2.1]octane-2-carboxylic acid (32.0 g, 113 mmol), Et$_3$N (50 mL, 359 mmol) and 1-hydroxybenzotriazole (24.4 g, 181 mmol) in DCM (500 mL) was cooled to 0° C., and the resulting solution was stirred at 0° C. for 30 min. Tert-butyl 4-aminopiperidine-1-carboxylate (25.2 g, 120 mmol) and N,N-4-dimethylaminopyridine (3.0 g, 25 mmol) was added to the reaction mixture, warmed to 25° C., and stirred for 16 h. The mixture was washed with H$_2$O (2×300 mL), 10% aqueous citric acid solution (2×300 mL), saturated Na$_2$CO$_3$ solution (2×250 mL), H$_2$O (2×300 mL), dried (Na$_2$SO$_4$), and concentrated to give a pale foam. The solid was stirred with ether (300 mL) for 2 h and filtered to give the product (81) as a solid. The filtrate was concentrated and purified by column chromatography on silica gel using EtOAc/hexanes (1:1 to 6:4) as eluent to give additional product (81). Combined yield: 43.1 g, 83%. LC-MS: m/z=459.2 [M+H]$^+$; $^1$H-NMR (300 MHz, CDCl$_3$): δ 7.43-7.36 (m, 5H), 6.55 (d, J=8.1 Hz, 1H), 5.06 (d, J=11.1 Hz, 1H), 4.91 (d, J=11.4 Hz, 1H), 4.01-3.93 (m, 2H), 3.89 (d, J=7.2 Hz, 2H), 3.29 (br. s, 1H), 3.00 (d, J=8.7 Hz, 1H), 2.86 (t, J=12.0 Hz, 2H), 2.64 (d, J=11.1 Hz, 1H), 2.41-2.34 (m, 1H), 2.01-1.85 (m, 4H), 1.45 (s, 9H), 1.35-1.28 (m, 2H).

Example 82

Synthesis of tert-butyl 4-((2S,5R)-6-hydroxy-7-oxo-1,6-diazabicyclo[3.2.1]octane-2-carboxamido)piperidine-1-carboxylate hydrate (82)

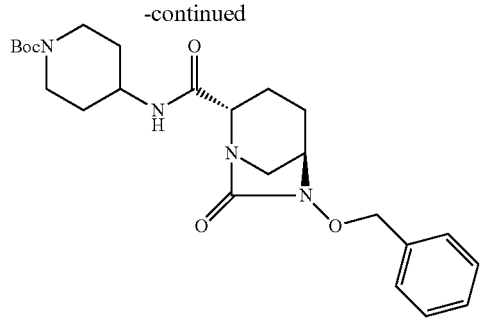

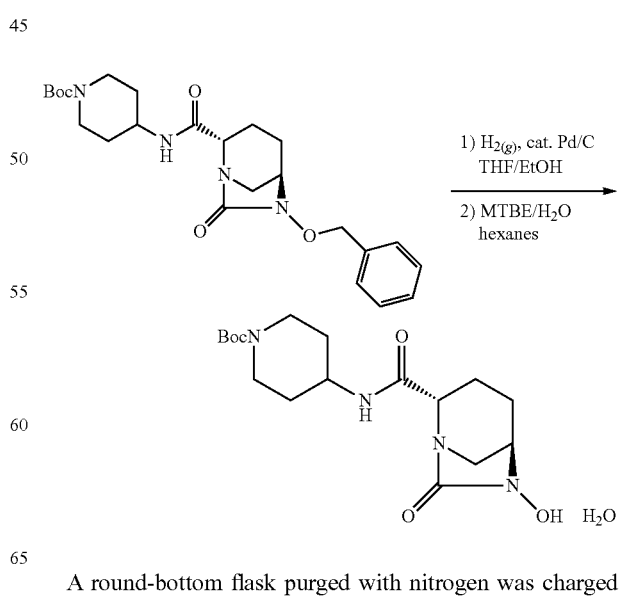

A round-bottom flask purged with nitrogen was charged with tert-butyl 4-((2S,5R)-6-(benzyloxy)-7-oxo-1,6-diazabicyclo[3.2.1]octane-2-carboxamido)piperidine-1-carboxylate (81) (5.0 g, 11 mmol), palladium on carbon (10 wt % loading dry basis; ~50% wet; 750 mg, 0.7 mmol), followed by EtOH (30 mL), and THF (60 mL). The round bottom flask was charged with hydrogen, and the reaction mixture was stirred at 25° C. for 90 min. The hydrogenation flask and a receiving vessel were cooled to −10° C. (dry ice/brine bath). The catalyst was filtered-off over a pad of Celite® into the receiving vessel, and the pad was rinsed with 3:1 THF/EtOH (20 mL). The filtrate was charged with tert-butyl methyl ether (100 mL) followed by distilled $H_2O$ (8 mL) and the mixture was stirred at −10° C. for several min. The mixture was charged with hexanes 100 mL and stirred at −10° C. for 1 h under an inert atmosphere of nitrogen. The suspension was concentrated, the residue was sonicated for several minutes in hexanes (50 mL), and the mixture concentrated. This was repeated once more to give the product (82) (3.9 g, 93% yield) as a solid [Note: This solid appeared to be stable to prolonged storage at 25° C.]. LC-MS: m/z=369.1 [M+H]$^+$; $^1$H-NMR (300 MHz, CDCl$_3$): δ 6.69 (d, J=8.1 Hz, 1H), 4.04-3.91 (m, 3H), 3.85 (d, J=7.8 Hz, 1H), 3.74 (s, 1H), 3.16 (d, J=11.1 Hz, 1H), 2.87 (t, J=12.2 Hz, 2H), 2.78 (d, J=11.1 Hz, 1H), 2.41 (dd, J=14.7, 6.6 Hz, 1H), 2.10 (m, 1H), 1.99-1.88 (m, 3H), 1.76-1.65 (m, 1H), 1.44 (s, 9H), 1.40-1.31 (m, 2H); $^1$H-NMR (300 MHz, d$_6$-DMSO): δ 9.70 (s, 1H), 7.87 (d, J=8.1 Hz, 1H), 3.87-3.72 (m, 3H), 3.64 (d, J=6.6 Hz, 1H), 3.56 (s, 1H), 2.98-2.94 (m, 1H), 2.87-2.83 (m, 1H), 2.77 (m, 2H), 2.06-2.00 (m, 1H), 1.86 (m, 1H), 1.77-1.60 (m, 4H), 1.37-1.27 (m, 11H); $^{13}$C-NMR (75 MHz, d$_6$-DMSO): δ 168.8, 167.0, 153.9, 78.6, 58.8, 58.7, 46.8, 46.1, 31.1, 31.0, 28.1, 20.3, 18.2.

Example 83

Synthesis of ethyl 3-((chlorosulfonyl)oxy)-2,2-dimethylpropanoate (83)

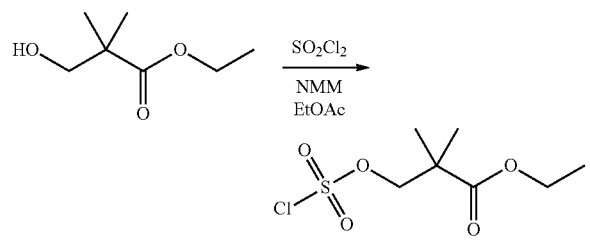

A round-bottom flask was charged with 17.6 g of ethyl 3-hydroxy-2,2-dimethylpropanoate. $H_2O$ was removed by co-evaporating the alcohol with hexanes (4×100 mL). The residue of ethyl 3-hydroxy-2,2-dimethylpropanoate (16.1 g, 110 mmol) was dissolved in anhydrous EtOAc (80 mL) and stirred at 0° C. for 10 min. 4-methylmorpholine (13.5 mL, 121 mmol) was added dropwise to the mixture and stirred at 0° C. for 10 min. Sulfuryl chloride (10.1 mL, 121 mmol) in anhydrous EtOAc (40 mL) was added dropwise over the course of 10 min, and the reaction mixture was stirred at 0° C. for 40 min. The solids were removed by filtration, and the filtrate was recovered in a receiving vessel that was cooled to 0° C. The filter cake was then rinsed with EtOAc (2×50 mL) giving the product (83) as a solution in EtOAc. This was used in the next step without further purification or concentration. Yield was assumed to be quantitative. $^1$H-NMR (300 MHz, CDCl$_3$): δ 4.50 (s, 2H), 4.19 (q, J=7.1 Hz, 2H), 1.31-1.25 (m, 9H).

Example 84

Synthesis of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84)

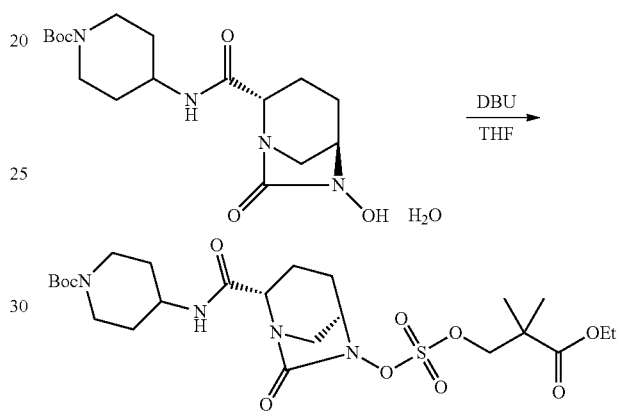

A flask was charged with tert-butyl 4-((2S,5R)-6-hydroxy-7-oxo-1,6-diazabicyclo[3.2.1]octane-2-carboxamido)piperidine-1-carboxylate hydrate (82) (3.7 g, 9.6 mmol) dissolved in THF (150 mL) and cooled to −78° C. A solution of ethyl 3-((chlorosulfonyl)oxy)-2,2-dimethylpropanoate (83) (ca. 0.67 M, 29 mL, 19 mmol) in EtOAc was added dropwise to the reaction mixture at a rate such that the reaction temperature did not exceed −55° C., and this was stirred for 15 min. 1,8-diazabicyclo[5.4.0]undec-7-ene (4.4 mL, 29 mmol) was added dropwise to the reaction mixture at such a rate that the reaction temperature did not exceed −58° C., and this was stirred for 10 min. The mixture was warmed to 0° C. at a rate not exceeding 20° C. per min. The reaction mixture was stirred at 0° C. (ice/water bath) until the starting material was consumed (within 1 h; reaction was followed by HPLC at 196 nm). The mixture was poured into ice cold $H_2O$ (300 mL), extracted with EtOAc (200 mL), and the organic layer was washed with brine (200 mL), dried (Na$_2$SO$_4$), and concentrated under vacuum. The residue was purified by column chromatography on silica gel using EtOAc/hexanes (0:1 to 7:3) as eluent to give the product (84) (4.4 g, 80% yield) as a white foam. LC-MS: m/z=577.1 [M+H]$^+$; $^1$H-NMR (300 MHz, CDCl$_3$): δ 6.43 (d, J=8.7 Hz, 1H), 4.71 (d, J=9.3 Hz, 1H), 4.60 (d, J=8.7 Hz, 1H), 4.21-3.93 (m, 7H), 3.29-3.26 (m, 1H), 2.92-2.83 (m, 3H), 2.48-2.41 (m, 1H), 2.17-2.14 (m, 1H), 1.94-1.83 (m, 4H), 1.46 (s, 9H), 1.40-1.25 (m, 11H); $^{13}$C-NMR (75 MHz, CDCl$_3$): δ 174.1, 167.9, 167.1, 154.7, 80.4, 79.9, 62.0, 61.3, 60.1, 47.1, 46.8, 42.8, 42.6, 32.1, 31.9, 28.5, 22.1, 21.7, 20.8, 17.6, 14.1.

Example 85

Synthesis of (5-methyl-2-oxo-1,3-dioxol-4-yl) methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (85)

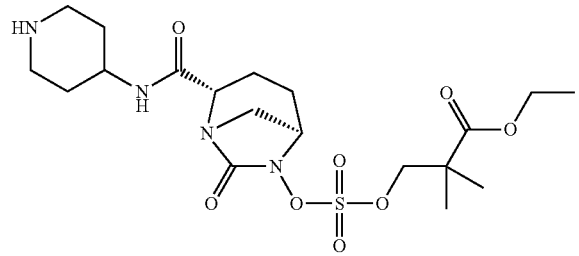

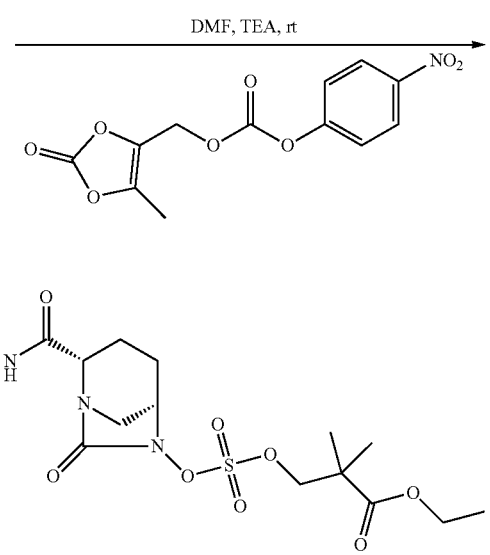

Step 1. Synthesis of (5-methyl-2-oxo-1,3-dioxol-4-yl)methyl (4-nitrophenyl) carbonate (85a)

To a stirred mixture of 4-nitrophenyl chloroformate (3.0 g, 14.9 mmol) in DCM (30 mL) at 0° C. was added pyridine (1.4 ml, 16.4 mmol). 4-(Hydroxymethyl)-5-methyl-1,3-dioxol-2-one (203 g, 15.6 mmol) in DCM (15 mL) was then added to the mixture. The mixture was stirred at 0° C. for 30 min, then allowed to warm to 25° C. and stirred for 18 h. Additional DCM was added, and the mixture was washed with $H_2O$ (×1), 0.5 N NaOH (×1), $H_2O$ (×2), and brine (×1), then dried ($Na_2SO_4$), filtered and concentrated under vacuum. The residue was purified by column chromatography on silica gel (40 g column) using EtOAc/hexanes as eluent (0:1 to 3:2) to give the desired product (85a) as an off-white solid (3.7 g). $^1$HNMR (300 MHz, $CDCl_3$) δ 8.30 (d, J=8.7 Hz, 2H), 7.40 (d, J=8.7 Hz, 2H), 5.03 (s, 2H), 2.22 (s, 3H); $^{13}$CNMR (75 MHz, $CDCl_3$), δ 155.1, 152.3, 151.7, 145.7, 141.5, 132.2, 125.4, 121.7, 58.1, 9.5.

Step 2: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (85b)

TFA (5.8 mL, 76.2 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (1.0 g, 1.7 mmol) in DCM (10 mL) at −10° C. The reaction mixture was stirred at −10° C. for 30 min. LC-MS indicated that the starting material was completely consumed (m/z=477.3 [M+H]$^+$ for desired product). The mixture was concentrated under vacuum to give the crude product (85b) containing a small amount of TFA. The compound was used directly in the next step without further purification. m/z=477.3 [M+H]$^+$.

Step 3: Synthesis of (5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (85)

To a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (85b) (0.82 g, 1.7 mmol) in DMF (20 mL) was added $Et_3N$ (2.9 mL, 20.6 mmol), followed by (5-methyl-2-oxo-1,3-dioxol-4-yl)methyl (4-nitrophenyl) carbonate (85a) (0.61 g, 2.1 mmol). The reaction mixture was stirred at room temperature overnight, then diluted with EtOAc and washed with $H_2O$. The organic layer was dried ($Na_2SO_4$), filtered and concentrated under vacuum. The residue was purified by column chromatography on silica gel (40 g column) using EtOAc/hexanes as eluent (0:1 to 1:0) to give the desired product (85) (100 mg) as a solid (foam). Also obtained from the column was the desired product with a small amount of impurity (130 mg). Data for pure product m/z=633.3 [M+H]$^+$; $^1$HNMR (300 MHz, $CDCl_3$) δ 6.46 (d, J=7.8 Hz, 1H), 4.84 (s, 2H), 4.71 (d, J=8.7 Hz, 1H), 4.60 (d, J=9.3 Hz, 1H), 4.21-3.98 (m, 7H), 3.27 (d, J=11.7 Hz, 1H), 2.95-2.87 (m, 3H), 2.44-2.40 (m, 1H), 2.18 (s, 3H), 2.15-2.14 (m, 1H), 1.96-1.85 (m, 4H), 1.40-1.24 (m, 11H); $^{13}$CNMR (75 MHz, $CDCl_3$) δ 174.4, 168.3, 167.3, 154.6, 140.3, 134.3, 80.8, 62.2, 61.6, 60.4, 55.2, 47.1, 43.3, 43.1, 32.0, 22.4, 22.0, 21.0, 17.8, 14.4, 9.8.

Example 86

Synthesis of acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (86)

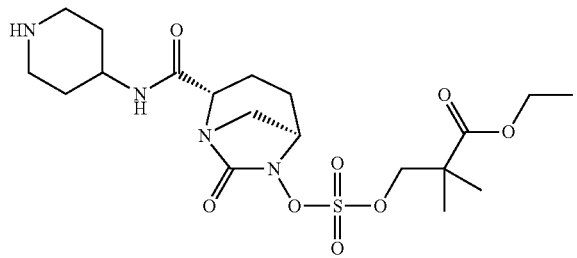
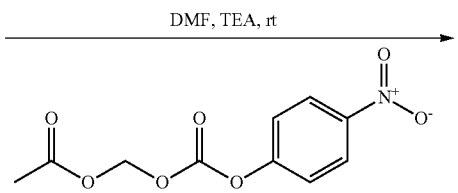
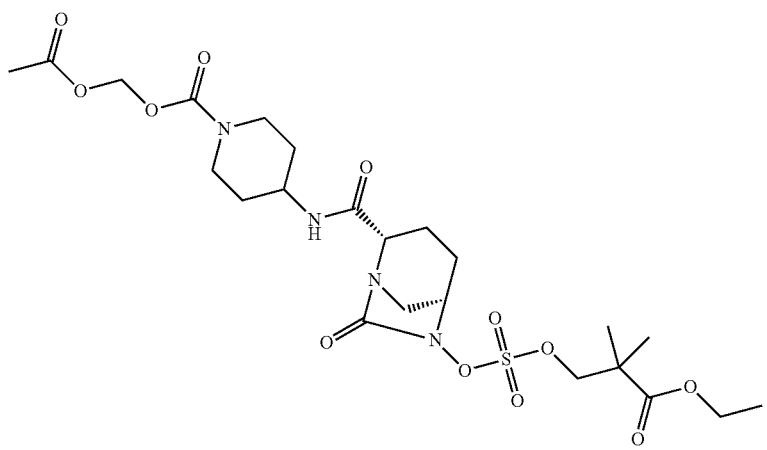

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (86a)

TFA (5.8 mL, 76.2 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (1.0 g, 1.7 mmol) in DCM (10 mL) at −10° C. The reaction mixture was stirred at −10° C. for 30 min. LC-MS indicated that the starting material was completely consumed (m/z=477.3 [M+H]$^+$ for desired product). The mixture was concentrated under vacuum to give the crude product (86a) containing a small amount of TFA. The compound was used directly in the next step without further purification. m/z=477.3 [M+H]$^+$

Step 2: Synthesis of acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (86)

Et$_3$N (2.9 mL, 20.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (86a) (0.82 g, 1.7 mmol) in DMF (20 mL) under an atmosphere of nitrogen. (((4-nitrophenoxy)carbonyl)oxy)methyl acetate, prepared according to PCT International Publication No. WO 2009151392, (527 mg, 2.1 mmol) was added and the mixture was stirred at rt overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give the product (86) (300 mg) as a white foam. NMR and LCMS indicated that the product was pure, but HPLC showed the presence of an unknown impurity. A portion of the white foam (90 mg) was purified again by reverse phase HPLC using MeCN/H$_2$O (1:9 to 95:5) as eluent to give the product (70 mg) as a solid. m/z=593.1 [M+H]$^+$; $^1$H-NMR (300 MHz, CDCl$_3$) δ 6.44 (d, J=8.1 Hz, 1H), 5.75 (s, 2H), 4.71 (d, J=9.0 Hz, 1H), 4.60 (d, J=8.7 Hz, 1H), 4.21-3.97 (m, 7H), 3.27 (d, J=11.7 Hz, 1H), 3.10-2.87 (m, 3H), 2.46-2.41 (m, 1H), 2.17-2.11 (m, 4H), 2.00-1.88 (m, 4H), 1.38-1.25 (m, 11H); $^{13}$C-NMR (75 MHz, CDCl$_3$) δ 174.0, 169.9, 168.0, 166.9, 153.4, 80.4, 61.9, 61.2, 60.0, 46.8, 42.9, 42.9, 42.8, 32.0, 31.8, 31.5, 22.1, 21.6, 20.9, 20.7, 17.4, 14.1.

Example 87

Synthesis of 1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (87)

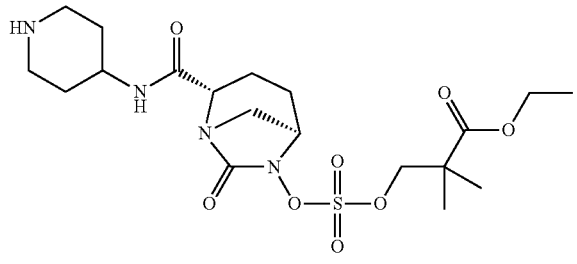
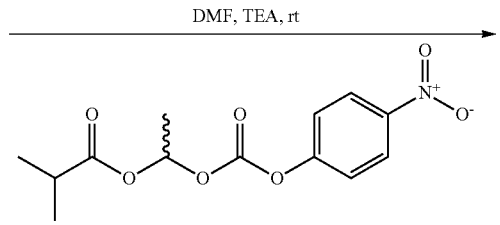
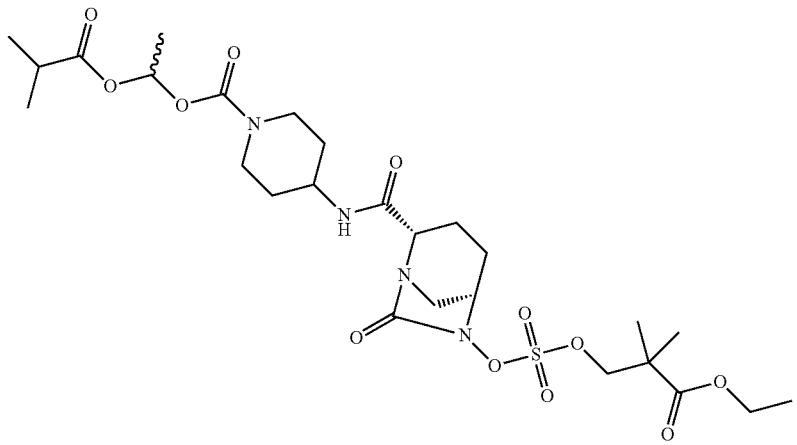

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (87a)

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (0.8 g, 1.4 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude product containing a small amount of TFA. The compound was used directly in the next step without further purification. m/z=477.3 [M+H]$^+$

Step 2: Synthesis of 1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (87)

Et$_3$N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (87a) (0.66 g, 1.4 mmol) in DMF (20 mL) under an atmosphere of nitrogen. 1-(((4-nitrophenoxy)carbonyl)oxy)ethyl isobutyrate (ex-ChemScene Catalog No. CS-B0942) (494 mg, 1.7 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give the product (290 mg) as a white foam. NMR and LCMS indicated that the product was pure, but HPLC showed the presence of an unknown impurity. The white foam was purified again by reverse phase HPLC using MeCN/H$_2$O (1:9 to 95:5) as eluent to give the product (220 mg) as a white foam. m/z=635.1 [M+H]$^+$; $^1$H-NMR (300 MHz, CDCl$_3$) δ 6.82-6.76 (q, 1H), 6.45 (d, J=7.5 Hz, 1H), 4.71 (d, J=8.7 Hz, 1H), 4.60 (d, J=9.3 Hz, 1H), 4.23-3.97 (m, 7H), 3.27 (d, J=11.7 Hz, 1H), 2.94-2.87 (m, 3H), 2.56-2.41 (m, 2H), 2.17-2.14 (m, 1H), 2.00-1.77 (m, 4H), 1.48 (d, J=5.1 Hz, 3H), 1.47-1.24 (m, 11H), 1.16 (d, J=7.2 Hz, 6H); $^{13}$C-NMR (75 MHz, CDCl$_3$) δ 175.2, 174.1, 167.9, 166.9, 153.0, 90.0, 80.4, 61.9, 61.2, 60.0, 46.8, 46.7, 42.8, 42.8, 33.8, 31.8, 22.1, 21.6, 20.7, 19.8, 18.7, 18.7, 17.5, 14.1.

Example 88

Synthesis of (pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (88)

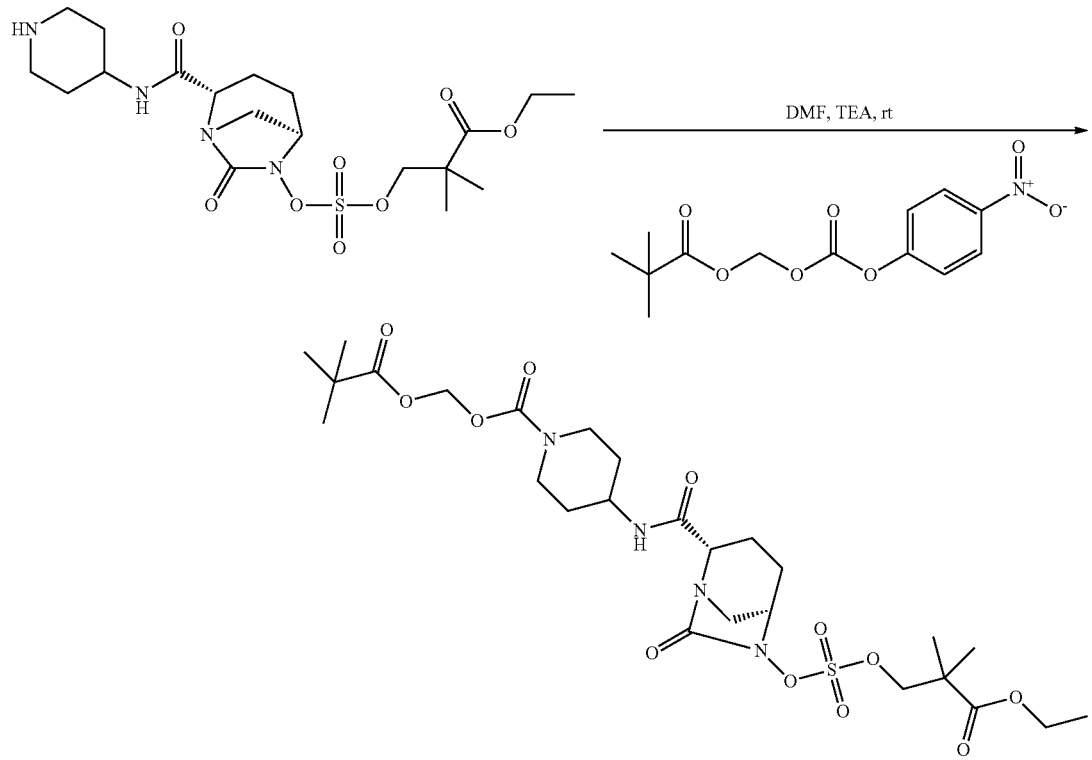

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (88a)

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (0.8 g, 1.4 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude product (88a) containing a small amount of TFA. The compound was used directly in the next step without further purification. m/z=477.3 [M+H]$^+$ [Note: excess TFA present]

Step 2: Synthesis of (pivaloyloxy)methyl 4-((2S, 5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (88)

Et$_3$N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (88a) (0.66 g, 1.4 mmol) in DMF (20 mL) under a nitrogen atmosphere. (((4-nitrophenoxy)carbonyl)oxy)methyl pivalate (494 mg, 1.7 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give impure product (88). The impure product was purified again by reverse phase HPLC using MeCN/H$_2$O (1:9 to 95:5) as eluent to give the product (88) (100 mg) as a white foam. LC/MS: m/z=635.2 [M+H]$^+$; $^1$H-NMR (300 MHz, CDCl$_3$): δ 6.43 (d, J=7.5 Hz, 1H), 5.77 (s, 2H), 4.71 (d, J=8.7 Hz, 1H), 4.60 (d, J=8.7 Hz, 1H), 4.22-3.97 (m, 7H), 3.27 (d, J=11.7 Hz, 1H), 2.97-2.87 (m, 3H), 2.46-2.40 (m, 1H), 2.18-2.14 (m, 1H), 1.97-1.83 (m, 4H), 1.42-1.24 (m, 11H), 1.22 (s, 9H); $^{13}$C-NMR (75 MHz, CDCl$_3$): δ 177.5, 174.0, 167.9, 166.9, 153.4, 80.6, 80.4, 61.9, 61.2, 60.0, 46.8, 46.7, 42.9, 42.9, 42.8, 38.8, 31.8, 31.6, 26.9, 22.1, 21.6, 20.7, 17.4, 14.1.

Example 89

Synthesis of (isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (89)

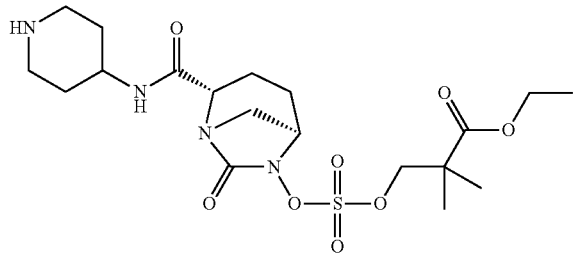
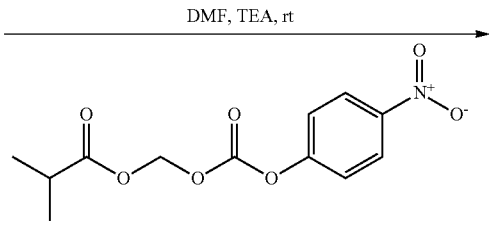
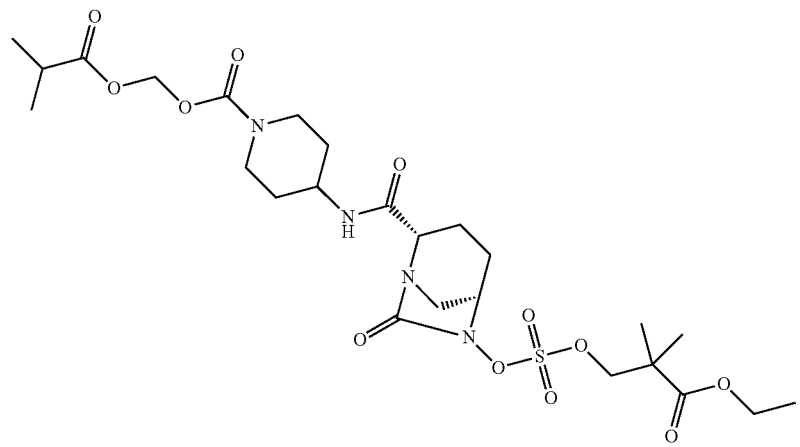

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (89a)

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (0.8 g, 1.4 mmol) in DCM (10 mL) at −10° C. The reaction mixture was stirred at −10° C. for 60 min. LC-MS indicated that the starting material was completely consumed (m/z=477.3 [M+H]+ for desired product). The mixture was concentrated under vacuum to give the crude product (89a) containing a small amount of TFA. The compound was used directly in the next step without further purification. m/z=477.3 [M+H]+ [Note: excess TFA present]

Step 2: Synthesis of (isobutryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (89)

Et₃N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (89a) (0.66 g, 1.4 mmol) in DMF (20 mL) under an atmosphere of nitrogen. (((4-nitrophenoxy)carbonyl)oxy)methyl isobutyrate (471 mg, 1.7 mmol) was added and the mixture was stirred at 25° C. overnight. The reaction mixture was diluted with EtOAc and H₂O, and the aqueous and organic layers were partitioned. The organic layer was dried (Na₂SO₄), filtered and concentrated under vacuum to leave a crude residue. The residue was purified by column chromatography on silica gel (40 g column) using EtOAc/hexanes (0:1 t 1:0) as eluent to give impure product. The impure product (89) was purified again by reverse phase HPLC using MeCN/H₂O (1:9 to 95:5) as eluent to give the product (89) (100 mg) as a white foam. LC/MS: m/z=621.2 [M+H]+; ¹H-NMR (300 MHz, CDCl₃): δ 6.43 (d, J=8.1 Hz, 1H), 5.77 (s, 2H), 4.71 (d, J=8.7 Hz, 1H), 4.60 (d, J=8.7 Hz, 1H), 4.22-3.97 (m, 7H), 3.27 (d, J=11.1 Hz, 1H), 2.96-2.87 (m, 3H), 2.64-2.55 (m, 1H), 2.46-2.41 (m, 1H), 2.18-2.14 (m, 1H), 1.99-1.78 (m, 4H), 1.37-1.25 (m, 11H), 1.18 (d, J=6.9 Hz, 6H); ¹³C-NMR (75 MHz, CDCl₃): δ 176.7, 174.7, 168.6, 167.5, 154.1, 81.0, 62.5, 61.9, 60.6, 47.4, 47.4, 43.6, 43.5, 43.4, 34.4, 32.4, 22.7, 22.2, 21.3, 19.3, 18.1, 14.7.

Example 90

Synthesis of 1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (90)

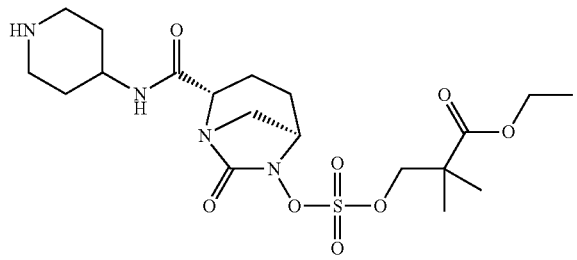
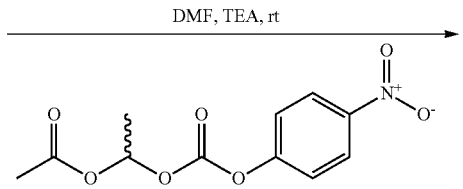

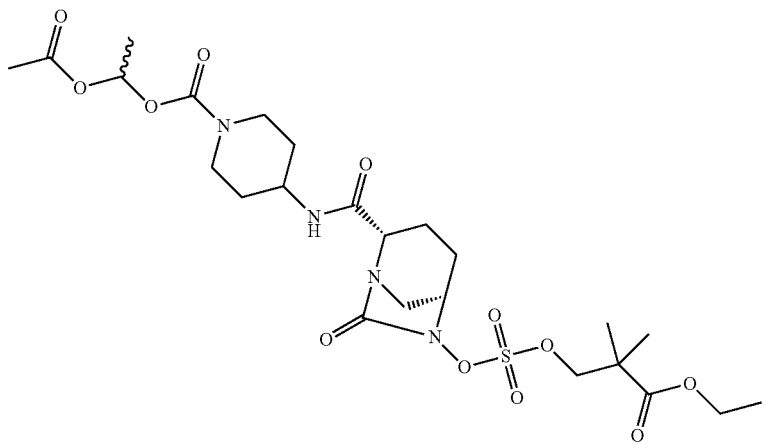

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (90a)

TFA (4.7 mL, 60.9 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (0.8 g, 1.4 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude product (90a) containing a small amount of TFA. The compound was used directly in the next step without further purification. m/z=477.3 [M+H]$^+$ [Note: excess TFA present]

Step 2: Synthesis of 1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (90)

Et$_3$N (2.3 mL, 16.6 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (90a) (0.66 g, 1.4 mmol) in DMF (20 mL) under a nitrogen atmosphere. 1-(((4-Nitrophenoxy)carbonyl)oxy)ethyl acetate (450 mg, 1.7 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:0) as eluent to give impure product (90). The impure product was purified again by reverse phase HPLC using MeCN/H$_2$O (1:9 to 95:5) as eluent to give the product (90) (160 mg) as a white gel. LC/MS: m/z=607.1 [M+H]$^+$; $^1$H-NMR (300 MHz, CDCl$_3$): δ 6.82-6.76 (m, 1H), 6.45 (d, J=8.1 Hz, 1H), 4.70 (d, J=9.6 Hz, 1H), 4.58 (d, J=9.3 Hz, 1H), 4.22-3.96 (m, 7H), 3.26 (d, J=12.0 Hz, 1H), 3.01-2.87 (m, 3H), 2.46-2.39 (m, 1H), 2.16-2.11 (m, 1H), 2.05 (s, 3H), 2.03-1.77 (m, 4H), 1.47 (d, J=5.1 Hz, 3H), 1.38-1.24 (m, 11H); $^{13}$C-NMR (75 MHz, CDCl$_3$): δ 174.0, 169.0, 167.9, 166.9, 152.9, 90.0, 80.4, 61.9, 61.2, 60.0, 46.8, 46.7, 42.8, 31.6, 22.0, 21.6, 21.0, 20.6, 19.8, 17.5, 14.1.

Example 91

Synthesis of 1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (91)

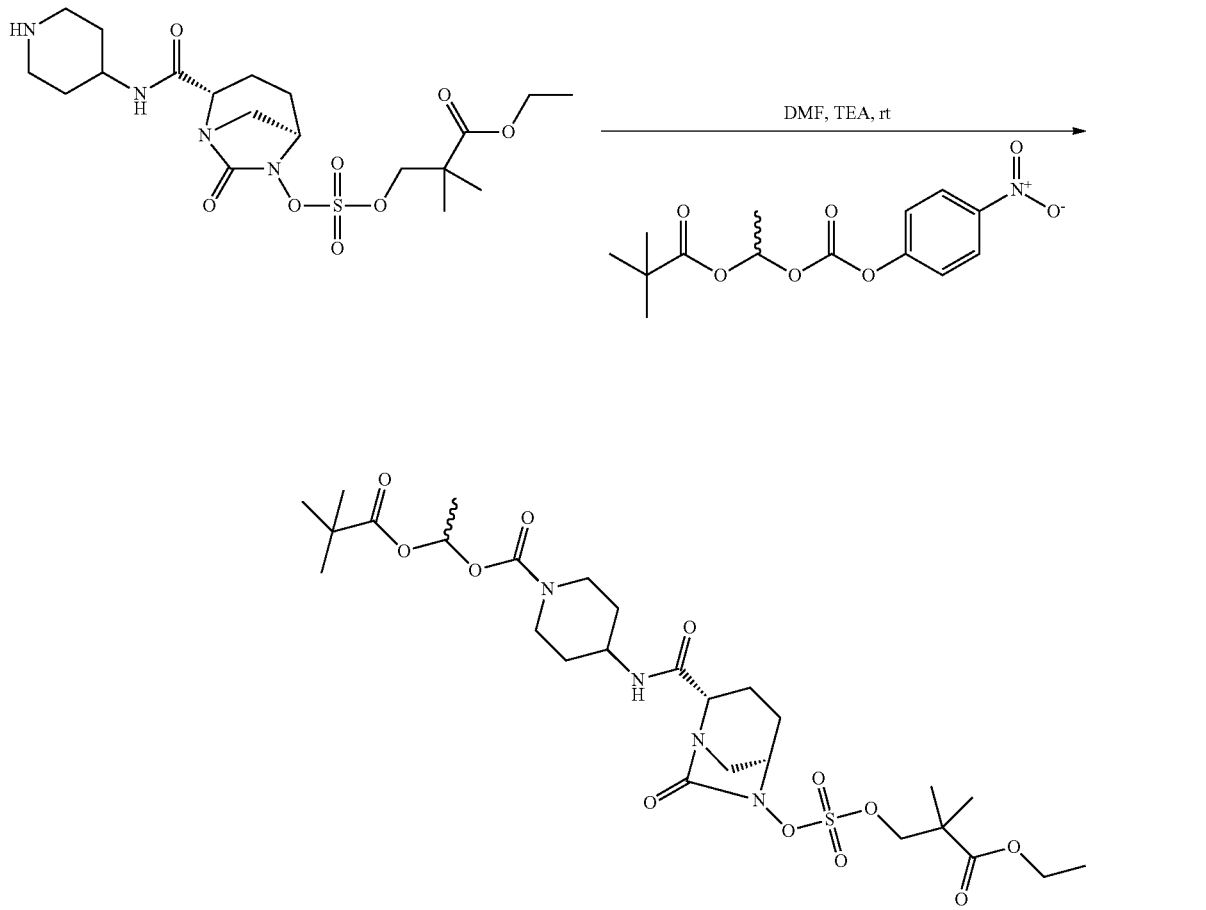

Step 1: Synthesis of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (91a)

TFA (4.1 mL, 53.3 mmol) was added to a stirred mixture of tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (84) (0.7 g, 1.2 mmol) in DCM (10 mL) at −10° C. The reaction mixture was stirred at −10° C. for 60 min. LC-MS indicated that the starting material was completely consumed (m/z=477.3 [M+H]$^+$ for desired product). The mixture was concentrated under vacuum to give the crude product (91a) containing a small amount of TFA. The compound was used directly in the next step without further purification. m/z=477.3 [M+H]$^+$ [Note: excess TFA present]

Step 2: Synthesis of 1-(pivaloyloxy)ethyl 4-((2S, 5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (91)

Et$_3$N (2.0 mL, 14.4 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate (0.57 g, 1.2 mmol) in DMF (20 mL) under a nitrogen atmosphere. 1-(((4-Nitrophenoxy)carbonyl)oxy)ethyl pivalate (450 mg, 1.4 mmol) was added and the mixture was stirred at 25° C. overnight. The reaction mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 t 1:0) as eluent to give impure product (91). The impure product was purified again by reverse phase HPLC using MeCN/H$_2$O (1:9 to 95:5) as eluent to give the product (91) (115 mg) as a white gel. LC/MS: m/z=649.1 [M+H]$^+$; $^1$H-NMR (300 MHz, CDCl$_3$): δ 6.79-6.74 (q, 1H), 6.45 (d, J=8.1 Hz, 1H), 4.71 (d, J=8.7 Hz, 1H), 4.59 (d, J=9.0 Hz, 1H), 4.21-3.91 (m, 7H), 3.26 (d, J=12.3 Hz, 1H), 3.00-2.87 (m, 3H), 2.48-2.40 (m, 1H), 2.17-2.12 (m, 1H), 1.97-1.80 (m, 4H), 1.48 (d, J=5.4 Hz, 3H), 1.42-1.26 (m, 11H), 1.24 (s, 9H); $^{13}$C-NMR (75 MHz, CDCl$_3$): δ $^{13}$C-NMR (75 MHz, CDCl$_3$): δ 176.6, 174.1, 167.89, 166.9, 153.0, 110.0, 90.1, 80.4, 61.9, 61.2, 60.0, 46.9, 46.7, 42.8, 42.8, 38.7, 31.7, 26.9, 22.1, 21.6, 20.7, 19.7, 17.4, 14.1.

Example 92

Synthesis of ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (92)

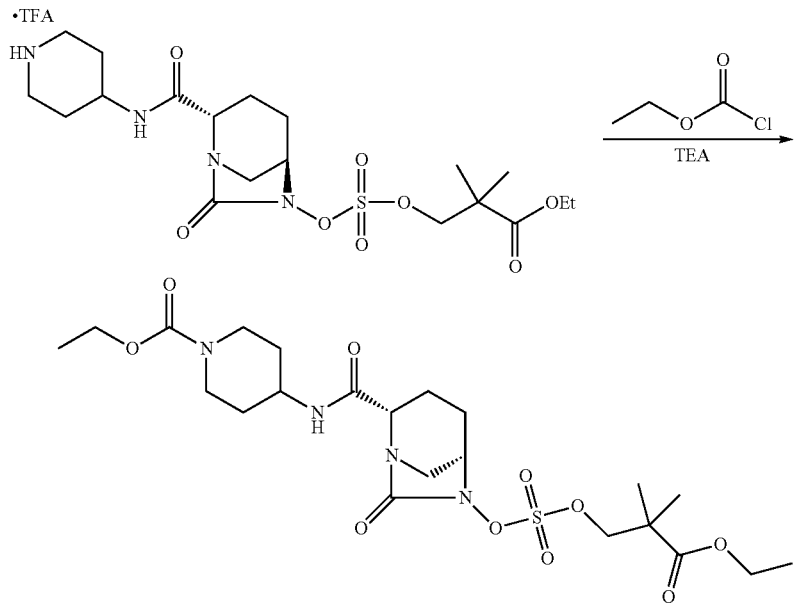

Et$_3$N (5.1 mL, 36.6 mmol) was slowly added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate TFA salt (91a TFA salt) (1.8 g, 3.0 mmol) in DCM (50 mL) at 0° C. Ethyl chloroformate (0.32 mL, 3.4 mmol) was then added, and the mixture was allowed to warm to rt and stirred for 50 min. The mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:9) as eluent to give the title compound (92) (1.2 g) as a solid. LC/MS: m/z=549.37 [M+H]$^+$; $^1$H-NMR (300 MHz, CDCl$_3$) δ 6.45 (d, J=7.5 Hz, 1H), 4.70 (d, J=8.7 Hz, 1H), 4.59 (d, J=8.7 Hz, 1H), 4.20-3.93 (m, 9H), 3.27 (d, J=11.7 Hz 1H), 3.00-2.87 (m, 3H), 2.50-2.40 (m, 1H), 2.16-2.13 (m, 1H), 1.99-1.77 (m, 4H), 1.40-1.23 (m, 14H); $^{13}$C-NMR (75 MHz, CDCl$_3$) δ 174.0, 167.8, 166.9, 155.4, 80.4, 61.9, 61.4, 61.2, 60.0, 46.9, 46.7, 42.8, 42.6, 42.6, 32.0, 31.7, 22.0, 21.6, 20.7, 17.4, 14.7, 14.0.

Example 93

Synthesis of (((S)-2-amino-3-methylbutanoyl)oxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (TFA salt) (93)

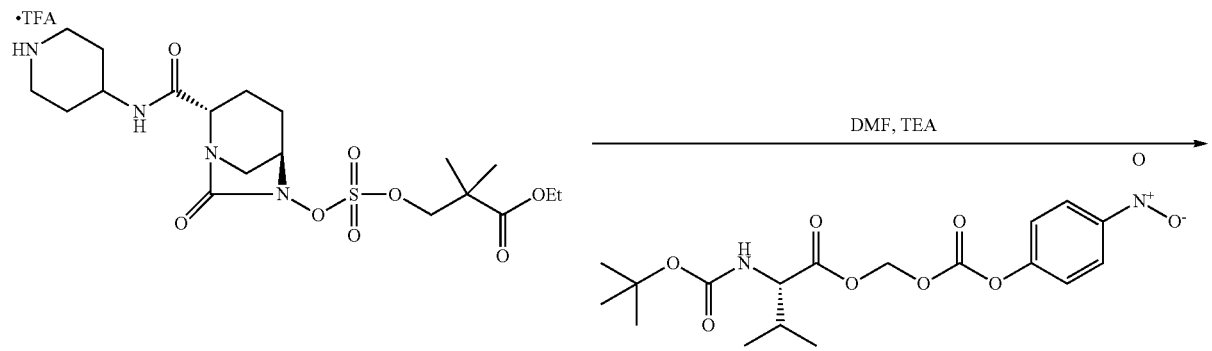

-continued

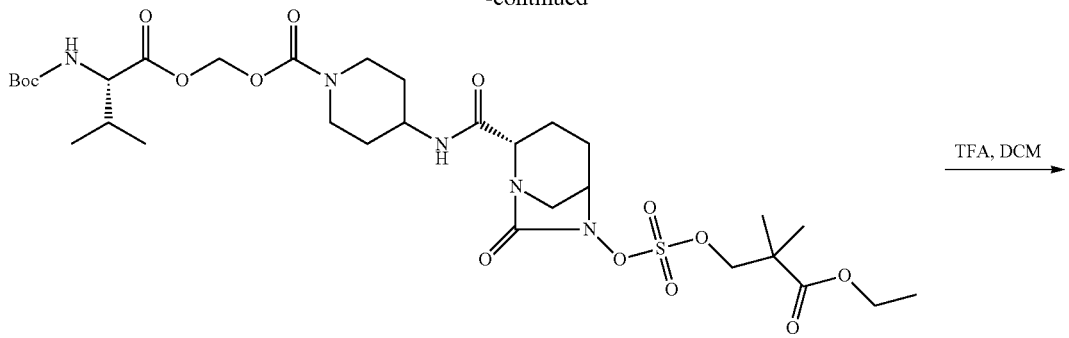

→ TFA, DCM

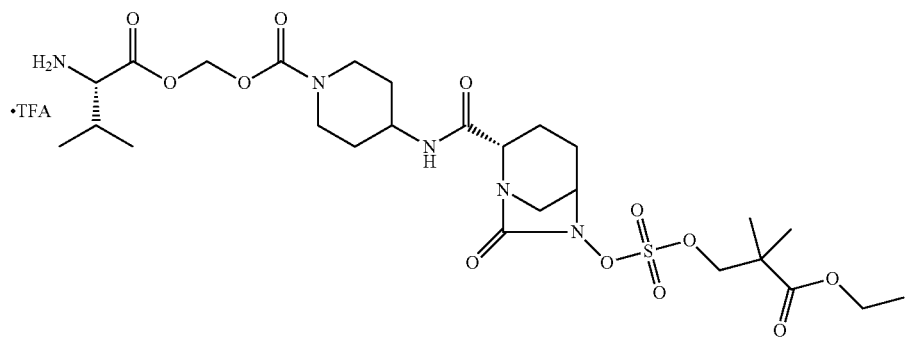

Step 1: Synthesis of (((S)-2-((tert-butoxycarbonyl)amino)-3-methylbutanoyl)oxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (93a)

Et$_3$N (15.8 mL, 113.3 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate TFA salt (91a TFA salt) [Note: excess TFA present] (4.5 g, 9.4 mmol) in DMF (30 mL). (S)-(((4-nitrophenoxy)carbonyl)oxy)methyl 2-((tert-butoxycarbonyl)amino)-3-methylbutanoate (5.6 g, 9.4 mmol; note: 70% purity) in DMF (20 mL) was added and the mixture was stirred at 25° C. overnight. The mixture was diluted with EtOAc and H$_2$O, and the aqueous and organic layers were partitioned. The organic layer was dried (Na$_2$SO$_4$), filtered and concentrated under vacuum to leave a crude residue. The residue was purified by column chromatography on silica gel (40 g column) using EtOAc/hexanes (0:1 to 1:4) as eluent to give the title compound (93a) (1.2 g) as an oil [Note: an additional 1.4 g of less pure product (93a) was also obtained]. LC/MS: m/z=750.08 [M+H]$^+$; $^1$H-NMR (300 MHz, CDCl$_3$) δ 6.47 (s, 1H), 5.84-5.78 (dd, J=5.4 Hz, 4.2 Hz, 2H), 4.98 (d, J=12.0 Hz, 1H), 4.70 (d, J=8.7 Hz, 1H), 4.59 (d, J=8.7 Hz, 1H), 4.29-3.97 (m, 8H), 3.28 (d, J=14.7 Hz, 1H), 3.30-2.87 (m, 3H), 2.48-2.41 (dd, J=6.6, 5.4 Hz, 1H), 2.16-2.07 (m, 2H), 1.97-1.77 (m, 4H), 1.44-1.23 (m, 20H), 0.96 (d, J=6.9 Hz, 3H), 0.87 (d, J=7.2 Hz, 3H).

Step 2: Synthesis of (((S)-2-amino-3-methylbutanoyl)oxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (TFA salt) (93)

TFA (5.7 mL, 74.7 mmol) was added to a stirred mixture of (((S)-2-((tert-butoxycarbonyl)amino)-3-methylbutanoyl)oxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (93a) (1.4 g, 1.9 mmol) in DCM (40 mL) at −10° C. The mixture was warmed to 25° C. and stirred for 90 min. The mixture was concentrated under vacuum and purified by reverse-phase HPLC (MeCN/H$_2$O (+0.1% TFA); 1:9 to 7:3) to give the title compound (93) (1.62 g; TFA salt) as a solid. LC/MS: m/z=650.30 [M+H]$^+$.

Example 94

Synthesis of 1-(((S)-2-amino-3-methylbutanoyl)oxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (TFA salt) (94)

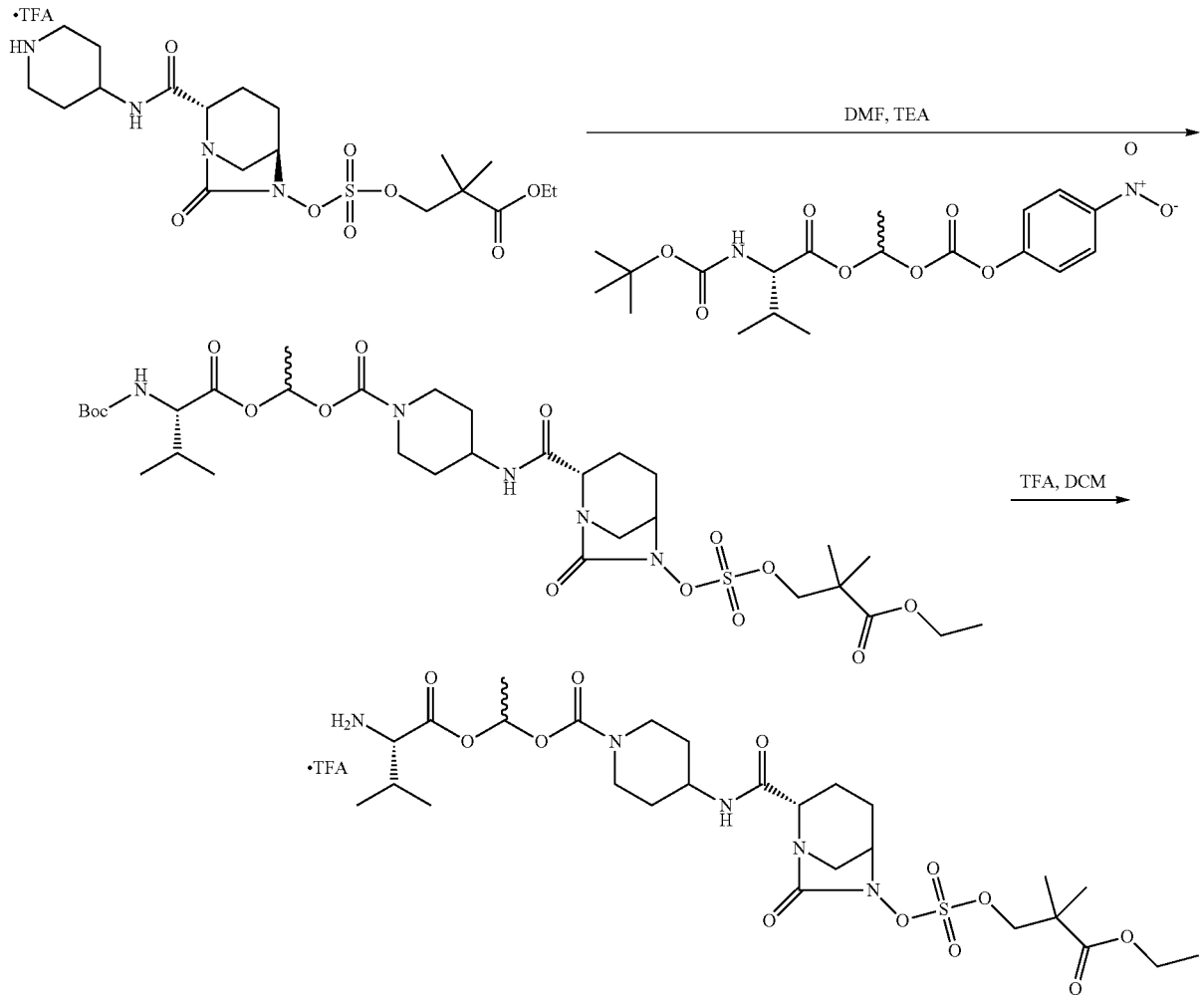

Step 1: Synthesis of 1-(((S)-2-((tert-butoxycarbonyl)amino)-3-methylbutanoyl)oxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (94a)

Et₃N (6.2 mL, 44.7 mmol) was added to a stirred mixture of ethyl 2,2-dimethyl-3-(((((2S,5R)-7-oxo-2-(piperidin-4-ylcarbamoyl)-1,6-diazabicyclo[3.2.1]octan-6-yl)oxy)sulfonyl)oxy)propanoate TFA salt (91a) [note: excess TFA present] (2.2 g, 3.7 mmol) in DMF (11 mL). (2S)-1-(((4-nitrophenoxy)carbonyl)oxy)ethyl 2-((tert-butoxycarbonyl)amino)-3-methylbutanoate (3.9 g, 4.6 mmol; note: 50% purity) in DMF (11 mL) was added and the mixture was stirred at 25° C. overnight. The mixture was diluted with EtOAc and H₂O, and the aqueous and organic layers were partitioned. The organic layer was dried (Na₂SO₄), filtered and concentrated under vacuum to leave a crude residue. The residue was purified by column chromatography on silica gel (40 g column) using EtOAc/hexanes (0:1 t 1:0) as eluent to give the title compound (94a) as an oil. LC/MS: m/z=764 [M+H]⁺; ¹H-NMR (300 MHz, CDCl₃) 6.88-6.82 (m, 1H), 6.47-6.44 (m, 1H), 5.02 (d, J=8.1 Hz, 1H), 4.71 (d, J=9.3 Hz, 1H), 4.59 (d, J=11.7 Hz, 1H), 4.22-3.98 (m, 8H), 3.30-3.26 (m, 1H), 2.95-2.87 (m, 3H), 2.45-2.41 (m, 1H), 2.17-2.06 (m, 2H), 2.00-1.77 (m, 5H), 1.52 (m, 3H), 1.44 (s, 9H), 1.28-1.24 (m, 10H), 0.97-0.87 (m, 6H).

Step 2: Synthesis of 1-(((S)-2-amino-3-methylbutanoyl)oxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (TFA salt) (94)

TFA (11.2 mL, 146.6 mmol) was added to a stirred mixture of 1-(((S)-2-((tert-butoxycarbonyl)amino)-3-methylbutanoyl)oxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate (94a) in DCM (80 mL) at −10° C. The mixture was warmed to 25° C. and stirred for 90 min. The mixture was concentrated under vacuum, combined with a previous run of this experiment and purified by reverse-phase HPLC (MeCN/H$_2$O (+0.1% TFA); 1:9 to 9:1) to give the title compound (94) (1.56 g; TFA salt). LC/MS: m/z=664.29 [M+H]$^+$.

Example 95

Oral Bioavailability in Rats

A pharmacokinetic (PK) study was performed in three male Sprague-Dawley (SD) rats following intravenous (IV) and oral (PO) administrations of relebactam at 2 mg/kg and test compounds at 10 mg/kg, respectively and relebactam measured in plasma.

Relebactam was dissolved in phosphate buffered saline (PBS) (pH 7.5) at 0.4 mg/mL for intravenous (IV) injection. Compounds for oral administration were formulated in 10% ethanol/40% polyethylene glycol (PEG) 400/50% water for injection (WFI) (pH 6.5) at 1 mg/mL. The dosing volumes are 5 mL/kg for IV and 10 mL/kg for PO. All aspects of this work including housing, experimentation, and animal disposal were performed in general accordance with the "Guide for the Care and Use of Laboratory Animals: Eighth Edition" (National Academies Press, Washington, D.C., 2011); and Suckow et al., Ed. The Laboratory Rat. 2nd Edition. Academic Press. New York. 2005. Animals had access to standard lab diet and autoclaved tap water ad libitum.

Blood aliquots (300 µL to 400 µL) were collected from jugular vein-catheterized rats into tubes coated with lithium heparin at various times. The tubes were mixed gently and kept on ice and then centrifuged at 2,500 rpm for 15 min at 4° C., within 1 h after collection. For animals in the control groups, blood was collected by cardiac puncture and the plasma was harvested and kept frozen at −70° C. until further analysis. Beaudoin et al., Bioanalytical method validation for the simultaneous determination of ceftazidime and avibactam in rat plasma. *Bioanalysis.* 2016 8:111-22.

Plasma samples were processed using acetonitrile precipitation and analyzed by LC-MS/MS. A plasma calibration curve was generated with aliquots of drug-free plasma spiked with the test substance at the specified concentration levels. The spiked plasma samples were processed together with the unknown plasma samples using the same procedure. The processed plasma samples were stored at −70° C. until receiving LC-MS/MS analysis, at which time peak areas are recorded, and the concentrations of the test substance in the unknown plasma samples were determined using the respective calibration curve. The reportable linear range of the assay was determined, along with the lower limit of quantitation (LLQ). Plots of plasma concentration of compound versus time were constructed. The pharmacokinetic parameters of compound after IV and PO dosing (AUC$_{last}$, AUC$_{INF}$, T$_{1/2}$, T$_{max}$, and C$_{max}$) were obtained from the non-compartmental analysis (NCA) of the plasma data using WinNonlin. WinNonlin® Certara L. P. Pharsight, St. Louis, Mo.

In these tests, relebactam exhibited an oral bioavailability (% F) of 1.8%, and compounds (75), (77), (78), and (80) exhibited an oral bioavailability (% F) of relebactam greater than 5%.

Example 96

Minimum Inhibitory Concentration

Minimum inhibitor concentration (MIC) values of the investigational monobactams and β-lactamase inhibitors are determined by broth microdilution susceptibility testing conducted in accordance with guidelines from the Clinical and Laboratory Standards Institute (Clinical and Laboratory Standards Institute (CLSI). Methods for Dilution Antimicrobial Susceptibility Tests for Bacteria That Grow Aerobically; Approved Standard-Tenth Edition. CLSI document M07-A10. CLSI, 950 West Valley Road, Suite 2500, Wayne, Pa. 19087-1898 USA, 2015; CLSI. Performance Standards for Antimicrobial Susceptibility Testing: Twenty-Sixth Informational Supplement. CLSI document M100-S26, CLSI, 950 West Valley Road, Suite 2500, Wayne, Pa. 19087 USA, 2016) against a panel of bacterial strains expressing characterized β-lactamases that confer resistance to β-lactams. Zasowski et al., The β-Lactams Strike Back: Ceftazidime-Avibactam. *Pharmacotherapy,* 2015 35:755-70; Levasseur et al., In vitro antibacterial activity of the ceftazidime-avibactam combination against enterobacteriaceae, including strains with well-characterized β-lactamases. *Antimicrob Agents Chemother,* 2015 59:1931-4. Compounds are stored as dry powder and stored at −20° C. prior to testing. These compounds and comparator drugs are solubilized in the appropriate solvent on the day of the assay. All drugs are tested using a drug concentration range of 0.001 µg/mL to 64 µg/mL. β-lactamase inhibitors are tested at a constant concentration of 4 µg/mL. Isolates are streaked onto appropriate media and incubated overnight at 35° C. The MIC values are determined using cation-adjusted Mueller Hinton broth (MHBII; BD, Sparks, Md.) in accordance with CLSI guidelines in 96-well format plates. MICs are recorded after 18 h incubation at 35° C. The MIC is read and recorded as the lowest concentration of drug that inhibits visible growth of the organism.

Example 97

Oral Bioavailability in Dogs

The oral bioavailability of certain relebactam prodrugs provided by the present disclosure in dogs is evaluated.

Dosing formulations are prepared on the day of dosing. Intravenous formulations are prepared under aseptic conditions, sterile filtered, and brought to room temperature prior to dosing. The intravenous formulation can include relebactam at a final concentration of 2.0 mg/mL in PBS at pH 7.5.

The oral dosing formulations can have a final concentration of either relebactam or a relebactam prodrug of 2 mg/mL in a solution of 1 mL ethanol, 4 mL PEG400, and 5 mL water for injection, with the pH adjusted to 7 with 1N NaOH.

The formulations are administered to male Beagle dogs weighing from 8 kg to 410 kg. The animals are maintained in accordance with the Guide for the Care and Use of Laboratory Animals, National Research Council, The National Academies Press, Washington, DC, 2011.

The dogs receive either an IV bolus dose of 10 mg/kg, or a peroral dose of 20 mg/kg. The dose levels are selected to bridge the gap between primary historical control data and the NHP study (American Veterinary Medial Association. AVMA Guidelines on Euthanasia. 2013) to accurately predict the prodrug activity in humans. Intravenous administration is into the cephalic vein followed by a 0.5 mL flush with sterile saline. Oral administration is via to the stomach using an 18-French catheter followed by a 15-mL flush with deionized water. Two dogs are used for each arm of the study.

The plasma concentration of relebactam is measured at intervals following administration. Within 2 minutes of collection, 100 μL of whole blood is transferred to K₂EDTA tubes containing 300 μL acetonitrile. Each vial with the blood/acetonitrile mixture is vortexed for about 30 seconds and immediately frozen on dry ice and maintained frozen (−55° C. to −85° C.) until analysis. The relebactam concentration is determined using LC/MS/MS.

The area under the concentration vs. time curves (AUC) is calculated using the linear trapezoidal method with linear interpolation. The percent oral bioavailability (% F) of relebactam is determined by comparing the AUC following oral administration with the AUC following IV administration on a dose normalized basis.

Example 98

Oral Bioavailability in Monkeys

The oral bioavailability of certain relebactam prodrugs provided by the present disclosure in male Cynomolgus monkeys is evaluated.

Dosing formulations are prepared on the day of dosing. Intravenous formulations are prepared under aseptic conditions, sterile filtered, and brought to room temperature prior to dosing. The intravenous formulation can include relebactam at a final concentration of 2.0 mg/mL in PBS at pH 7.5.

The oral dosing formulations can have a final concentration of either relebactam or a relebactam prodrug of 2 mg/mL in a solution of 1 mL ethanol, 4 mL PEG400, and 5 mL water for injection, with the pH adjusted to 7 with 1N NaOH.

The formulations are administered to male Cynomolgus monkeys weighing from 2 kg to 4 kg. The animals are maintained in accordance with the Guide for the Care and Use of Laboratory Animals, National Research Council, The National Academies Press, Washington, DC, 2011.

The monkeys receive either an IV bolus dose of 10 mg/kg, or a peroral dose of 20 mg/kg. The dosing levels are selected to mimic therapeutically effective systemic concentrations in humans. Intravenous administration is into the saphenous vein. Oral administration is via oral intubation via a flexible oral tube. Two monkeys are used for each arm of the study.

The plasma concentration of relebactam is measured at intervals following administration. Within 2 minutes of collection, 100 μL of whole blood is transferred to K₂EDTA tubes containing 300 μL acetonitrile. Each vial with the blood/acetonitrile mixture is vortexed for about 30 seconds and immediately frozen on dry ice and maintained frozen (−55° C. to −85° C.) until analysis. The relebactam concentration is determined using LC/MS/MS.

The area under the concentration vs. time curves (AUC) is calculated using the linear trapezoidal method with linear interpolation. The percent oral bioavailability (% F) of relebactam is determined by comparing the AUC following oral administration with the AUC following IV administration on a dose normalized basis.

Example 99

Oral Bioavailability in Beagle Dogs

The oral bioavailability of certain relebactam prodrugs provided by the present disclosure in Beagle dogs was evaluated.

Dosing formulations are prepared on the day of dosing. Intravenous formulations are prepared under aseptic conditions, sterile filtered, and brought to room temperature prior to dosing. The intravenous formulation included relebactam at a final concentration of 2.8 mg/mL in PBS at pH 7.5.

The oral dosing formulations of the relebactam prodrugs had a final concentration of a relebactam prodrug of 10 mg/mL in a solution of 15% (v/v) Campul MCM C8, 15% (v/v) Gelucire 44/14, and 10% (v/v) ethanol in purified water.

The formulations were administered to male Beagle dogs weighing about 10 kg. The animals were maintained in accordance with the Guide for the Care and Use of Laboratory Animals, National Research Council, The National Academies Press, Washington, DC, 2011.

The dogs received either an IV bolus dose of 9.9 mg/kg, or a peroral dose of 22 mg/kg (Compound 87) or 20.0 mg/kg (Compound 88). The dose levels were selected to bridge the gap between primary historical control data and the NHP study (American Veterinary Medial Association. AVMA Guidelines on Euthanasia. 2013) to accurately predict the prodrug activity in humans. Intravenous administration was into the cephalic vein followed by a 0.5 mL flush with sterile saline. Oral administration was via the stomach using an 18-French catheter followed by a 15-mL flush with deionized water. Two dogs were used for each arm of the study.

The plasma concentration of relebactam was measured at intervals following administration. Within 2 minutes of collection, 100 μL of whole blood ws transferred to K₂EDTA tubes containing 300 μL acetonitrile. Each vial with the blood/acetonitrile mixture was vortexed for about 30 sec and immediately frozen on dry ice and maintained frozen (−55° C. to −85° C.) until analysis. The relebactam concentration was determined using LC/MS/MS.

The area under the concentration vs. time curves (AUC) was calculated using the linear/log trapezoidal method with linear interpolation. The percent oral bioavailability (% F) of relebactam was determined by comparing the AUC following oral administration with the AUC following IV administration on a dose normalized basis.

The mean plasma concentration following IV administration of relebactam or peroral administration of Compound (86) or Compound (87) is shown in the FIGURE. A summary of the results is shown in Table 1.

TABLE 1

Experimental summary.

| | Relebactam | Compound (87) | Compound (88) |
|---|---|---|---|
| Administration | IV | PO | PO |
| Nominal dose (mg/kg) | 10.0 | 20.0 | 20.0 |
| Administered dose (mg/kg) | 9.88 | 22.0 | 20.4 |
| MW | 348.38 | 634.7 | 634.7 |
| Relebactam-equivalent dose (mg/kg) (NOMINAL) | 10 | 11.0 | 11.0 |
| Relebactam-equivalent dose (mg/kg) (ACTUAL) | 9.88 | 12.1 | 11.2 |
| $AUC_{0-inf}$ (ng · h/mL) | 29379 (3734)[1] | 12523 (1136) | 4914 (2509) |
| $AUC_{0-inf}/D$ | 2974 (580) | 1037 (94) | 439 (224) |
| F % | — | 35.4 (4) | 15.0 (7) |

[1]Mean (SD).

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A compound of Formula (1):

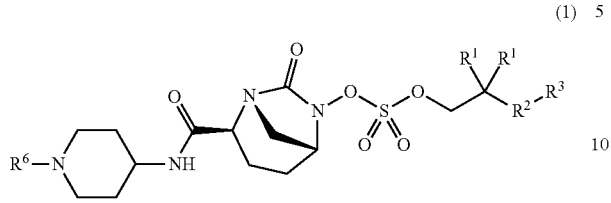

or a pharmaceutically acceptable salt thereof, wherein,
each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^6$ is selected from a moiety of Formula (2), a moiety of Formula (3), a moiety of Formula (4), and a moiety of Formula (5):

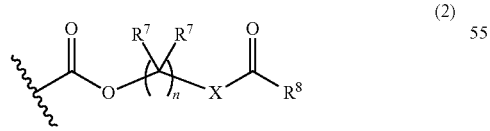

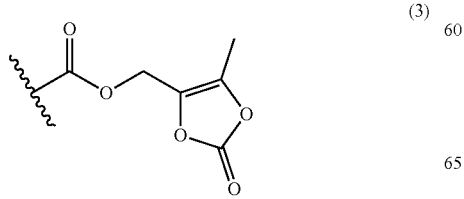

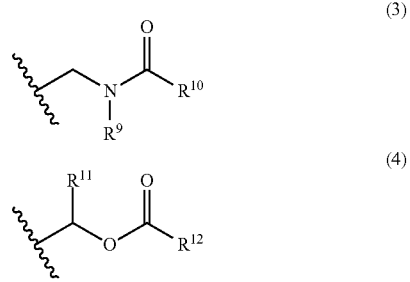

wherein,
each $R^7$ is independently selected from hydrogen, $C_{1-8}$ alkyl, or each $R^7$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

n is an integer from 1 to 4;

X is selected from O and NH;

$R^8$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^9$ is selected from hydrogen and $C_{1-6}$ alkyl;

$R^{10}$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^{11}$ is selected from hydrogen and $C_{1-6}$ alkyl; and $R^{12}$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

2. The compound of claim 1, or a pharmaceutically acceptable salt thereof, wherein
each $R^1$ is independently $C_{1-6}$ alkyl;
$R^2$ is a single bond; and
$R^3$ is —C(O)—O—$R^4$, wherein $R^4$ is selected from $C_{1-8}$ alkyl, $C_{1-8}$ heteroalkyl, $C_{7-9}$ arylalkyl, and $C_{5-7}$ heterocycloalkyl.

3. The compound of claim 1, or a pharmaceutically acceptable salt thereof, wherein $R^6$ is a moiety of Formula (2):

(2)

wherein,
- each $R^1$ is independently $C_{1-6}$ alkyl;
- $R^2$ is a single bond;
- $R^3$ is —C(O)—O—$R^4$;
- $R^4$ is $C_{1-6}$ alkyl;
- n is 1;
- each $R^7$ is independently selected from hydrogen and $C_{1-6}$ alkyl; and
- $R^8$ is selected from $C_{1-6}$ alkyl and —CH(—$R^{13}$)—NH$_2$, wherein $R^{13}$ is selected from $C_{1-6}$ alkyl.

4. The compound of claim 1, or a pharmaceutically acceptable salt thereof, wherein $R^6$ is a moiety of Formula (3):

(3)

wherein,
- each $R^1$ is independently $C_{1-6}$ alkyl;
- $R^2$ is a single bond;
- $R^3$ is —C(O)—O—$R^4$; and
- $R^4$ is $C_{1-6}$ alkyl.

5. The compound of claim 1, or a pharmaceutically acceptable salt thereof, wherein $R^6$ is a moiety of Formula (4):

(4)

wherein,
- each $R^1$ is independently $C_{1-6}$ alkyl;
- $R^2$ is a single bond;
- $R^3$ is —C(O)—O—$R^4$;
- $R^4$ is $C_{1-6}$ alkyl;
- $R^9$ is selected from hydrogen, methyl, ethyl, and isopropyl; and
- $R^{10}$ is selected from methyl, ethyl, n-propyl, isopropyl, n-butyl, iso-butyl, sec-butyl, and tert-butyl.

6. The compound of claim 1, or a pharmaceutically acceptable salt thereof, wherein $R^6$ is a moiety of Formula (5):

(5)

wherein,
- each $R^1$ is independently $C_{1-6}$ alkyl;
- $R^2$ is a single bond;
- $R^3$ is —C(O)—O—$R^4$;
- $R^4$ is $C_{1-6}$ alkyl;
- $R^{11}$ is selected from hydrogen, methyl, ethyl, and isopropyl; and
- $R^{12}$ is selected from methyl, ethyl, n-propyl, isopropyl, n-butyl, iso-butyl, sec-butyl, and tert-butyl.

7. The compound of claim 1, wherein the compound is selected from:
- tert-butyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- (5-methyl-2-oxo-1,3-dioxol-4-yl)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- acetoxymethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- 1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- (pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- (isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- 1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
- 1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate, or a pharmaceutically acceptable salt of any of the foregoing.

8. The compound of claim 1, wherein the compound has the structure of Formula (13):

(13)

or a pharmaceutically acceptable salt thereof, wherein,
each $R^1$ is independently $C_{1-3}$ alkyl;
$R^2$ is a single bond;
$R^3$ is —C(O)—O—$R^4$, wherein $R^4$ is $C_{1-4}$ alkyl;
$R^7$ is selected from hydrogen and $C_{1-4}$ alkyl; and
$R^8$ is $C_{1-4}$ alkyl.

9. The compound of claim 8, or a pharmaceutically acceptable salt thereof, wherein
each $R^1$ is independently selected from methyl, ethyl, n-propyl, and iso-propyl;
$R^4$ is selected from methyl, ethyl, n-propyl, and iso-propyl;
$R^7$ is selected from hydrogen, methyl, ethyl, n-propyl, and iso-propyl; and
$R^8$ is selected from methyl, ethyl, n-propyl, iso-propyl, n-butyl, iso-butyl, and tert-butyl.

10. The compound of claim 8, selected from:
acetoxymethyl 4-((2S,5R)-6-(((3-ethoxy-2,2-dimethyl-3-oxoprop oxy)sulfonyl)oxy)-7-oxo-1,6-diazabicyclo[3.2.1]octane-2-carboxamido)piperidine-1-carboxylate;
1-(isobutyryloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(pivaloyloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
(isobutyryloxy)methyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
1-acetoxyethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
1-(pivaloyloxy)ethyl 4-((2S,5R)-6-(((3-ethoxy-2,2-dimethyl-3-oxopropoxy)sulfonyl)oxy)-7-oxo-1,6-diazabicyclo[3.2.1]octane-2-carboxamido)piperidine-1-carboxylate;
or a pharmaceutically acceptable salt of any of the foregoing.

11. A pharmaceutical composition comprising the compound of claim 1, or a pharmaceutically acceptable salt thereof, and a pharmaceutically acceptable vehicle.

12. A method of inhibiting a β-lactamase enzyme in a patient comprising administering to the patient an effective amount of the compound of claim 1 or a pharmaceutically acceptable salt thereof, or a pharmaceutical composition thereof, wherein the β-lactamase enzyme is a Class A β-lactamase enzyme or a Class C β-lactamase enzyme.

13. The method of claim 12, wherein administering comprises orally administering.

14. The method of claim 12, wherein administering comprises administering an oral dosage form.

\* \* \* \* \*